US012747452B2

(12) United States Patent
Dimidschstein et al.

(10) Patent No.: US 12,747,452 B2
(45) Date of Patent: Sep. 29, 2026

(54) INTERNEURON-SPECIFIC THERAPEUTICS FOR NORMALIZING NEURONAL CELL EXCITABILITY AND TREATING DRAVET SYNDROME

(71) Applicants: THE BROAD INSTITUTE, INC., Cambridge, MA (US); PRESIDENT AND FELLOWS OF HARVARD COLLEGE, Cambridge, MA (US); NEW YORK UNIVERSITY, New York, NY (US)

(72) Inventors: Jordane Dimidschstein, Cambridge, MA (US); Gordon Fishell, Cambridge, MA (US); Orrin Devinsky, New York, NY (US)

(73) Assignees: THE BROAD INSTITUTE, INC., Cambridge, MA (US); PRESIDENT AND FELLOWS OF HARVARD COLLEGE, Cambridge, MA (US); NEW YORK UNIVERSITY, New York, NY (US)

( * ) Notice: Subject to any disclaimer, the term of this patent is extended or adjusted under 35 U.S.C. 154(b) by 776 days.

(21) Appl. No.: 17/428,538

(22) PCT Filed: Jan. 27, 2020

(86) PCT No.: PCT/US2020/015183

§ 371 (c)(1),
(2) Date: Aug. 4, 2021

(87) PCT Pub. No.: WO2020/163102

PCT Pub. Date: Aug. 13, 2020

(65) Prior Publication Data

US 2022/0195457 A1 Jun. 23, 2022

Related U.S. Application Data

(60) Provisional application No. 62/916,477, filed on Oct. 17, 2019, provisional application No. 62/823,281, filed on Mar. 25, 2019, provisional application No. 62/801,483, filed on Feb. 5, 2019.

(51) Int. Cl.

| | |
|---|---|
| ***C12N 15/86*** | (2006.01) |
| ***A61K 48/00*** | (2006.01) |
| *A61K 38/00* | (2006.01) |
| *C07K 14/705* | (2006.01) |

(52) U.S. Cl.

CPC .......... *C12N 15/86* (2013.01); *A61K 48/0058* (2013.01); *A61K 38/00* (2013.01); *C07K 14/705* (2013.01); *C12N 2750/14143* (2013.01); *C12N 2830/008* (2013.01); *C12N 2830/48* (2013.01)

(58) Field of Classification Search

CPC .......... C12N 15/86; C12N 2750/14143; C12N 2830/008; A61K 48/0058; A61K 38/00; C07K 14/705

See application file for complete search history.

(56) References Cited

U.S. PATENT DOCUMENTS

| | | | | |
|---|---|---|---|---|
| 2013/0347137 | A1* | 12/2013 | Deisseroth | G01N 33/5091 800/9 |
| 2018/0078658 | A1* | 3/2018 | Fishell | C12N 7/00 |
| 2019/0024119 | A1 | 1/2019 | Tagliatela et al. | |
| 2019/0024120 | A1* | 1/2019 | Tagliatela | C12N 15/8645 |

FOREIGN PATENT DOCUMENTS

| | | | |
|---|---|---|---|
| CN | 101255424 | A | 9/2008 |
| WO | 2018187363 | A1 | 10/2018 |

OTHER PUBLICATIONS

Long, Yue-Sheng, et al. "Identification of the promoter region and the 5'-untranslated exons of the human voltage-gated sodium channel Nav1. 1 gene (SCN1A) and enhancement of gene expression by the 5'-untranslated exons." Journal of neuroscience research 86.15 (2008): 3375-3381. (Year: 2008).*

Encode Search Results for CCREs mapped to SCN1A. Encode Database. ENCODE Project Consortium. "An integrated encyclopedia of DNA elements in the human genome." Nature 489.7414 (2012): 57. (Year: 2012).*

Vormstein-Schneider, Douglas, et al. "Viral manipulation of functionally distinct interneurons in mice, non-human primates and humans." Nature neuroscience 23.12 (2020): 1629-1636. (Year: 2020).*

(Continued)

*Primary Examiner* — Teresa E Knight
*Assistant Examiner* — Michael Angelo Riga
(74) *Attorney, Agent, or Firm* — Greenberg Traurig, LLP; Melissa Hunter-Ensor; Leslie Serunian

(57) ABSTRACT

Provided are therapeutic virus vectors, particularly, recombinant adeno-associated virus (rAAV) vectors, designed to contain an enhancer sequence that specifically restricts expression of an effector gene (e.g., an SCN1A-encoding polynucleotide, Gq-DREADD-encoding polynucleotide, or PSAM-encoding polynucleotide) contained in the vector to PV-expressing GABAergic interneuron or to neuron cell populations in the brain. The rAAV vectors, compositions and methods thereof are useful for treating subjects afflicted with neuropathologies, seizures, pharmacologically-intractable forms of epilepsy including Dravet syndrome (DS), a form of infantile epilepsy associated with severe seizures, cognitive impairment and premature death, as the cause of DS involves loss of function of a sodium channel encoded by the SCN1A gene. The described vectors restore expression of effector genes to the appropriate interneuron or neuron cell populations with specificity and sensitivity, advantageously to address the root cause of the disease by restoring the excitation-inhibition balance by means of gene-therapy (with SCN1A) or pharmacogenetics.

14 Claims, 46 Drawing Sheets

Specification includes a Sequence Listing.

(56) References Cited

OTHER PUBLICATIONS

Aguet et al., “Genetic effects on gene expression across human tissues,” Nature, Oct. 12, 2017, vol. 550, pp. 204-213.
Armbruster et al., “Evolving the lock to fit the key to create a family of G protein-coupled receptors potently activated by an inert ligand,” Proceedings of the National Academy of Sciences of the United States of America, Mar. 20, 2007, vol. 104, No. 12, pp. 5163-5168.
Blomer et al., “Highly Efficient and Sustained Gene Transfer in Adult Neurons with a Lentivirus Vector,” Journal of Virology, Sep. 1997, vol. 71, No. 9, pp. 6641-6649.
Buenrostro et al., “Single-cell chromatin accessibility reveals principles of regulatory variation,” Nature, Jul. 23, 2015, vol. 523, No. 7561, pp. 486-490.
Cayouette et al., “Adenovirus-Mediated Gene Transfer of Ciliary Neurotrophic Factor Can Prevent Photoreceptor Degeneration in the Retinal Degeneration (rd) Mouse,” Human Gene Therapy, 1997, vol. 8, pp. 423-430,.
Chan et al., “Engineered AAVs for efficient noninvasive gene delivery to the central and peripheral nervous systems,” Nature Neuroscience, Aug. 2017, vol. 20, No. 8, pp. 1172-1179.
Chen et al., “Ultra-sensitive fluorescent proteins for imaging neuronal activity,” Nature, Jul. 18, 2013, vol. 499, No. 7458, pp. 295-300.
Chi, Kelly Rae, “Remote Mind Control. Using chemogenetic tools to spur the brain into action,” The Scientist, Nov. 1, 2015, 7 pages.
Choi et al., “Optimization of AAV expression cassettes to improve packaging capacity and transgene expression in neurons,” Molecular Brain, 2014, vol. 7, Article No. 17, pp. 1-10.
Cusanovich et al., “Multiplex Single Cell Profiling of Chromatin Accessibility by Combinatorial Cellular Indexing,” Science, May 22, 2015, vol. 348, No. 6237, pp. 910-914.
Daya et al., “Gene Therapy Using Adeno-Associated Virus Vectors,” Clinical Microbiology Reviews, Oct. 2008, vol. 21, No. 4, pp. 583-593.
Dimidschstein et al., “A viral strategy for targeting and manipulating interneurons across vertebrate species,” Nature Neuroscience, Dec. 2016, vol. 19, No. 12, pp. 1743-1749.
Hermening et al., “Increased protein expression from adenoviral shuttle plasmids and vectors by insertion of a small chimeric intron sequence,” Journal of Virological Methods, 2004, vol. 122, No. 1, pp. 73-77.
Hirsch et al., “Delivering Transgenic DNA Exceeding the Carrying Capacity of AAV Vectors,” Methods in Molecular Biology, 2016, vol. 1382, pp. 21-39.
Hirsch et al., “Little Vector, Big Gene Transduction: Fragmented Genome Reassembly of Adeno-associated Virus,” Molecular Therapy, Jan. 2010, vol. 18, No. 1, pp. 6-8.
Hu et al., “A G Protein-biased Designer G Protein-coupled Receptor Useful for Studying the Physiological Relevance of Gq/11-dependent Signaling Pathways,” The Journal of Biological Chemistry, Apr. 8, 2016, vol. 291, No. 15, pp. 7809-7820.
Kelsom et al., “Development and specification of GABAergic cortical interneurons,” Cell & Bioscience, 2013, vol. 3, Article No. 19, pp. 1-19.
Kido et al., “Use of a retroviral vector with an internal opsin promoter to direct gene expression to retinal photoreceptor cells,” Current Eye Research, 1996, vol. 15, pp. 833-844.
Kotterman et al., “Engineering adeno-associated viruses for clinical gene therapy,” Nature Reviews Genetics, Jul. 2014, vol. 15, No. 7, pp. 445-451.
Madisen et al., “A toolbox of Cre-dependent optogenetic transgenic mice for light-induced activation and silencing,” Nature Neuroscience, 2012, vol. 15, No. 5, pp. 793-802.
Magnus et al., “Chemical and genetic engineering of selective ligand-ion channel interactions,” Science, Sep. 2, 2011, vol. 333, No. 6047, pp. 1292-1296.
Magnus et al., “Ultrapotent chemogenetics for research and potential clinical applications,” Science, Apr. 12, 2019, vol. 364, No. 6436, eaav5282, pp. 1-8.
Mainen et al., “Influence of dendritic structure on firing pattern in model neocortical neurons,” Nature, Jul. 25, 1996, vol. 382, pp. 363-366.
Miyoshi et al., “Stable and efficient gene transfer into the retina using an HIV-based lentiviral vector,” Proceedings of the National Academy of Sciences of the United States of America, Sep. 1997, vol. 94, pp. 10319-10323.
Mo et al., “Epigenomic Signatures of Neuronal Diversity in the Mammalian Brain,” Neuron, Jun. 17, 2015, vol. 86, pp. 1369-1384.
Naldini et al., “In Vivo Gene Delivery and Stable Transduction of Nondividing Cells by a Lentiviral Vector,” Science, Apr. 12, 1996, vol. 272, pp. 263-267.
NCBI GenBank Accession No. AC010127.12, “*Homo sapiens* BAC cione RP11-218 from 2, complete sequence,” Apr. 8, 2005.
Needleman et al., “A General Method Applicable to the Search for Similarities in the Amino Acid Sequence of Two Proteins,” Journal of Molecular Biology, 1970, vol. 48, pp. 443-453.
Ong et al., “Enhancer function: new insights into the regulation of tissue-specific gene expression,” Nature Reviews Genetics, Apr. 2011, vol. 12, No. 4, pp. 283-293.
Rivera et al., “Long-term pharmacologically regulated expression of erythropoietin in primates following AAV-mediated gene transfer,” Blood, Feb. 15, 2005, vol. 105, No. 4, pp. 1424-1430.
Shapiro et al., “Unparalleled Control of Neural Activity Using Orthogonal Pharmacogenetics,” ACS Chemical Neuroscience, 2012, vol. 3, No. 8, pp. 619-629.
Spruston, Nelson, “Pyramidal neuron,” Scholarpedia, 2009, vol. 4, Iss. 5, Article No. 6130, pp. 1-13.
Spruston, Nelson, “Pyramidal neurons: dendritic structure and synaptic integration,” Nature Reviews Neuroscience, Mar. 2008, vol. 9, pp. 206-221.
Sternson et al., “Chemogenetic Tools to Interrogate Brain Functions,” Annual Review of Neuroscience, 2014, vol. 37, pp. 387-407.
Tricoire et al., “A Blueprint for the Spatiotemporal Origins of Mouse Hippocampal Interneuron Diversity,” The Journal of Neuroscience, Jul. 27, 2011, vol. 31, No. 30, pp. 10948-10970.
Walker et al., “Optogenetic and chemogenetic therapies for epilepsy,” Neuropharmacology, 2019, Article No. 107751, pp. 1-8.
Yu et al., “Reduced sodium current in GABAergic interneurons in a mouse model of severe myoclonic epilepsy in Infancy,” Nature Neuroscience, Sep. 2006, vol. 9, No. 9, pp. 1142-1149.
Zhao et al., “Adeno-associated virus 2-mediated gene transfer: role of a cellular serine/threonine protein phosphatase in augmenting transduction efficiency,” Gene Therapy, 2007, vol. 14, pp. 545-550.
International Search Report and Written Opinion in corresponding International Patent ApplicationPCT/US20/15183, mailed Jul. 17, 2020 (18 pages).
Written Opinion dated Feb. 28, 2024 in corresponding Singaporean Patent Application No. 11202107813R (7 pages).
Office Action dated Apr. 1, 2024 in corresponding Chinese Patent Application No. 202080027324.8 (6 pages).
English translation of Office Action dated Apr. 1, 2024 in corresponding Chinese Patent Application No. 202080027324.8 (7 pages).
Meyer et al., “In Vivo Labeling of Parvalbumin-Positive Interneurons and Analysis of Electrical Coupling in Identified Neurons,” The Journal of Neuroscience, Aug. 15, 2002, vol. 22, No. 16, pp. 7055-7064.
Van Den Pol et al., “Selective Neuronal Expression of Green Fluorescent Protein with Cytomegalovirus Promoter Reveals Entire Neuronal Arbor in Transgenic Mice,” The Journal of Neuroscience, Dec. 15, 1998, vol. 18, No. 24, pp. 10640-10651.
Wykes et al., “Gene therapy and editing: Novel potential treatments for neuronal channelopathies,” Neuropharmacology, 2018, vol. 132, pp. 108-117.
Extended European Search Report dated Nov. 11, 2022 in corresponding European Patent Application No. 20752944.7 (9 pages).
Sone, Masamitsu, “Genome-wide analysis of gene expression regulated by three dimensional chromatin structure,” Grants-in-Aid for Scientific Research Report on the Research Achievements, 2016, pp. 1-4 [English Abstract].
Search Report and Written Opinion dated Mar. 23, 2023 in corresponding Singaporean Patent Application No. 11202107813R (12 pages).

(56) References Cited

OTHER PUBLICATIONS

Office Action dated Sep. 15, 2023 in corresponding Chinese Patent Application No. 202080027324.8 (12 pages).
English translation of Office Action dated Sep. 15, 2023 in corresponding Chinese Patent Application No. 202080027324.8 (13 pages).
Office Action dated Oct. 20, 2023 in corresponding Canadian Patent Application No. 3,128,525 (6 pages).
Office Action dated Dec. 25, 2023 in corresponding Japanese Patent Application No. 2021-545659 (6 pages).
English translation of Office Action dated Dec. 25, 2023 in corresponding Japanese Patent Application No. 2021-545659 (6 pages).
Office Action dated Dec. 23, 2024, received in counterpart Chinese Patent Application No. 202080027324.8 (10 pages).
English translation of Office Action dated Dec. 23, 2024, received in counterpart Chinese Patent Application No. 202080027324.8 (10 pages).
Office Action and English Translation of Office Action dated Aug. 6, 2024 in corresponding Chinese Patent Application No. 202080027324.8 (17 pages).
Office Action and English Translation of Office Action dated Sep. 2, 2024 in corresponding Japanese Patent Application No. 2021-545659 (5 pages).
Office Action dated Jan. 24, 2025, received in counterpart Singaporean Patent Application No. 11202107813R (8 pages).
Office Action dated Feb. 3, 2025, received in counterpart Japanese Patent Application No. 2021-545659 (4 pages).
English translation of Office Action dated Feb. 3, 2025, received in counterpart Japanese Patent Application No. 2021-545659 (3 pages).
Office Action dated Apr. 28, 2025, received in corresponding Canadian Patent Application No. 3, 128,525 (6 pages).
Office Action dated Sep. 22, 2025, in corresponding Korean Patent Application No. 10-2021-7028274 (5 pages).
English Translation of the Office Action dated Sep. 22, 2025, in corresponding Korean Patent Application No. 10-2021-7028274 (3 pages).
Office Action dated Apr. 20, 2026, in corresponding Japanese Patent Application No. 2025-076698 (3 pages).
English Translation of the Office Action dated Apr. 20, 2026, in corresponding Japanese Patent Application No. 2025-076698 (3 pages).
Office Action dated Nov. 20, 2025, in corresponding Israeli Patent Application No. 284909 (7 pages).

* cited by examiner

| Enhancer | Gene | Target | Specificity | Position | Mouse_mr | Mouse_mm10 |
|---|---|---|---|---|---|---|
| E1 | Scn1a | PV | 0.22 | intergenic | chr2 | 66256056 |
| E2 | Scn1a | PV | 0.9 | intronic | chr2 | 66364036 |
| E3 | Scn1a | PV | 0.57 | intronic | chr2 | 66383190 |
| E4 | Scn1a | PV | 0.14 | intronic | chr2 | 66387764 |
| E5 | Scn1a | PYR | 0.2 | intronic | chr2 | 66392447 |
| E6 | Scn1a | VIP | 0.88 | intronic | chr2 | 66401767 |
| E7 | Scn1a | PV | 0.33 | intronic | chr2 | 66407834 |
| E8 | Scn1a | PV | 0.61 | intronic | chr2 | 66439814 |
| E9 | Scn1a | PV | 0.47 | intergenic | chr2 | 66441748 |
| E10 | Scn1a | PV | 0.23 | intergenic | chr2 | 66450594 |
| E11 | Pvalb | PV | 0.9 | intronic | chr15 | 78204152 |
| E12 | Pvalb | PV | 0.59 | intronic | chr15 | 78204583 |
| E13 | Pvalb | PV | 0.67 | intronic | chr15 | 78205234 |
| E14 | Acan | PV | 0.94 | intergenic | chr7 | 79052127 |
| E15 | Acan | PV | 0.79 | intergenic | chr7 | 79053118 |
| E16 | Acan | PV | 0.58 | intronic | chr7 | 79056553 |
| E17 | Acan | PV | 0.54 | intronic | chr7 | 79079999 |
| E18 | Tmem132c | PV | 0.57 | intronic | chr5 | 127243448 |
| E19 | Tmem132c | PV | 0.57 | intronic | chr5 | 127257256 |
| E20 | Tmem132c | PV | 0.66 | intronic | chr5 | 127290515 |
| E21 | Tmem132c | PV | 0.71 | intronic | chr5 | 127300767 |
| E22 | Tmem132c | PV | 0.94 | intronic | chr5 | 127305150 |
| E23 | Tmem132c | PV | 0.64 | intronic | chr5 | 127323924 |
| E24 | Tmem132c | PV | 0.82 | intronic | chr5 | 127331966 |
| E25 | Tmem132c | PV | 0.73 | intronic | chr5 | 127355818 |
| E26 | Lrrc38 | PV | 0.72 | intergenic | chr4 | 143348892 |
| E27 | Lrrc38 | PV | 0.66 | intronic | chr4 | 143361408 |
| E28 | Inpp5j | PV | 0.83 | intergenic | chr11 | 3504821 |
| E29 | Inpp5j | PV | 0.94 | intergenic | chr11 | 3509025 |
| E30 | Mef2c | PV | 0.77 | intergenic | chr13 | 83503268 |
| E31 | Mef2c | PV | 0.63 | intronic | chr13 | 83507235 |
| E32 | Mef2c | PV | 0.7 | intronic | chr13 | 83515122 |
| E33 | Mef2c | PV | 0.82 | intronic | chr13 | 83518268 |
| E34 | Pthlh | PV | 0.48 | intronic | chr6 | 147263395 |
| E35 | Pthlh | PV | 0.86 | intergenic | chr6 | 147266874 |

*FIG. 1A-1*

| Mouse_mm10_ | Size (bp) | mouse_mm10_DAS_Link |
|---|---|---|
| 66257335 | 1279 | http://genome.ucsc.edu/cgi-bin/das/mm10/dna?segment=chr2:66256056,66257335 |
| 66364653 | 617 | http://genome.ucsc.edu/cgi-bin/das/mm10/dna?segment=chr2:66364036,66364653 |
| 66384021 | 831 | http://genome.ucsc.edu/cgi-bin/das/mm10/dna?segment=chr2:66383190,66384021 |
| 66388024 | 260 | http://genome.ucsc.edu/cgi-bin/das/mm10/dna?segment=chr2:66387764,66388024 |
| 66393109 | 662 | http://genome.ucsc.edu/cgi-bin/das/mm10/dna?segment=chr2:66392447,66393109 |
| 66402372 | 605 | http://genome.ucsc.edu/cgi-bin/das/mm10/dna?segment=chr2:66401767,66402372 |
| 66410263 | 2429 | http://genome.ucsc.edu/cgi-bin/das/mm10/dna?segment=chr2:66407834,66410263 |
| 66441457 | 1643 | http://genome.ucsc.edu/cgi-bin/das/mm10/dna?segment=chr2:66439814,66441457 |
| 66442268 | 520 | http://genome.ucsc.edu/cgi-bin/das/mm10/dna?segment=chr2:66441748,66442268 |
| 66451140 | 546 | http://genome.ucsc.edu/cgi-bin/das/mm10/dna?segment=chr2:66450594,66451140 |
| 78204655 | 503 | http://genome.ucsc.edu/cgi-bin/das/mm10/dna?segment=chr15:78204152,78204655 |
| 78204784 | 201 | http://genome.ucsc.edu/cgi-bin/das/mm10/dna?segment=chr15:78204583,78204784 |
| 78205766 | 532 | http://genome.ucsc.edu/cgi-bin/das/mm10/dna?segment=chr15:78205234,78205766 |
| 79052622 | 495 | http://genome.ucsc.edu/cgi-bin/das/mm10/dna?segment=chr7:79052127,79052622 |
| 79053435 | 317 | http://genome.ucsc.edu/cgi-bin/das/mm10/dna?segment=chr7:79053118,79053435 |
| 79057054 | 501 | http://genome.ucsc.edu/cgi-bin/das/mm10/dna?segment=chr7:79056553,79057054 |
| 79080472 | 473 | http://genome.ucsc.edu/cgi-bin/das/mm10/dna?segment=chr7:79079999,79080472 |
| 127244121 | 673 | http://genome.ucsc.edu/cgi-bin/das/mm10/dna?segment=chr5:127243448,127244121 |
| 127257594 | 338 | http://genome.ucsc.edu/cgi-bin/das/mm10/dna?segment=chr5:127257256,127257594 |
| 127291016 | 501 | http://genome.ucsc.edu/cgi-bin/das/mm10/dna?segment=chr5:127290515,127291016 |
| 127301107 | 340 | http://genome.ucsc.edu/cgi-bin/das/mm10/dna?segment=chr5:127300767,127301107 |
| 127305592 | 442 | http://genome.ucsc.edu/cgi-bin/das/mm10/dna?segment=chr5:127305150,127305592 |
| 127324468 | 544 | http://genome.ucsc.edu/cgi-bin/das/mm10/dna?segment=chr5:127323924,127324468 |
| 127332522 | 556 | http://genome.ucsc.edu/cgi-bin/das/mm10/dna?segment=chr5:127331966,127332522 |
| 127356133 | 315 | http://genome.ucsc.edu/cgi-bin/das/mm10/dna?segment=chr5:127355818,127356133 |
| 143349749 | 857 | http://genome.ucsc.edu/cgi-bin/das/mm10/dna?segment=chr4:143348892,143349749 |
| 143362362 | 954 | http://genome.ucsc.edu/cgi-bin/das/mm10/dna?segment=chr4:143361408,143362362 |
| 3505244 | 423 | http://genome.ucsc.edu/cgi-bin/das/mm10/dna?segment=chr11:3504821,3505244 |
| 3509652 | 627 | http://genome.ucsc.edu/cgi-bin/das/mm10/dna?segment=chr11:3509025,3509652 |
| 83504033 | 765 | http://genome.ucsc.edu/cgi-bin/das/mm10/dna?segment=chr13:83503268,83504033 |
| 83507457 | 222 | http://genome.ucsc.edu/cgi-bin/das/mm10/dna?segment=chr13:83507235,83507457 |
| 83515409 | 287 | http://genome.ucsc.edu/cgi-bin/das/mm10/dna?segment=chr13:83515122,83515409 |
| 83519179 | 911 | http://genome.ucsc.edu/cgi-bin/das/mm10/dna?segment=chr13:83518268,83519179 |
| 147263584 | 189 | http://genome.ucsc.edu/cgi-bin/das/mm10/dna?segment=chr6:147263395,147263584 |
| 147267390 | 516 | http://genome.ucsc.edu/cgi-bin/das/mm10/dna?segment=chr6:147266874,147267390 |

*FIG. 1A-1 (cont.)*

| Enhancer | Gene | Target | Specificity | Position | Human_hg38_chr | Human_hg38_start | Human_hg38_stop |
|---|---|---|---|---|---|---|---|
| E1 | Scn1a | PV | 22% | intergenic | chr2 | 165953030 | 165954796 |
| E2 | Scn1a | PV | 90% | intronic | chr2 | 166084035 | 166084884 |
| E3 | Scn1a | PV | 57% | intronic | chr2 | 166090876 | 166091720 |
| E4 | Scn1a | PV | 14% | intronic | chr2 | 166094366 | 166094633 |
| E5 | Scn1a | PYR | 20% | intronic | chr2 | 166103693 | 166104587 |
| E6 | Scn1a | VIP | 88% | intronic | chr2 | 166118214 | 166118879 |
| E7 | Scn1a | PV | 33% | intronic | chr2 | 165892760 | 165897884 |
| E8 | Scn1a | PV | 61% | intronic | chr2 | 166148156 | 166149792 |
| E9 | Scn1a | PV | 47% | intergenic | chr2 | 166150066 | 166150702 |
| E10 | Scn1a | PV | 23% | intergenic | chr2 | 166160023 | 166160609 |
| E11 | Pvalb | PV | 90% | intronic | chr22 | 36816984 | 36817612 |
| E12 | Pvalb | PV | 59% | intronic | chr22 | 36817484 | 36817720 |
| E13 | Pvalb | PV | 67% | intronic | chr22 | 36818134 | 36818727 |
| E14 | Acan | PV | 94% | intergenic | chr15 | 88802240 | 88802877 |
| E15 | Acan | PV | 79% | intergenic | chr15 | 88803290 | 88803678 |
| E16 | Acan | PV | 58% | intronic | chr15 | 88807290 | 88807962 |
| E17 | Acan | PV | 54% | intronic | chr15 | 88833390 | 88833984 |
| E18 | Tmem132c | PV | 57% | intronic | chr12 | 128377753 | 128378783 |
| E19 | Tmem132c | PV | 57% | intronic | chr12 | 128289803 | 128290279 |

*FIG. 1A-2*

| Human_hg38_size_(bp) | human_hg38_DAS_link | % Conservation between mouse and human |
|---|---|---|
| 1766 | http://genome.ucsc.edu/cgi-bin/das/hg38/dna?segment=chr2:165953030,165954796 | 69% |
| 849 | http://genome.ucsc.edu/cgi-bin/das/hg38/dna?segment=chr2:166084035,166084884 | 71% |
| 844 | http://genome.ucsc.edu/cgi-bin/das/hg38/dna?segment=chr2:166090876,166091720 | 67% |
| 267 | http://genome.ucsc.edu/cgi-bin/das/hg38/dna?segment=chr2:166094366,166094633 | 78% |
| 894 | http://genome.ucsc.edu/cgi-bin/das/hg38/dna?segment=chr2:166103693,166104587 | 72% |
| 665 | http://genome.ucsc.edu/cgi-bin/das/hg38/dna?segment=chr2:166118214,166118879 | 72% |
| 5124 | http://genome.ucsc.edu/cgi-bin/das/hg38/dna?segment=chr2:165892760,165897884 | 74% |
| 1636 | http://genome.ucsc.edu/cgi-bin/das/hg38/dna?segment=chr2:166148156,166149792 | 75% |
| 636 | http://genome.ucsc.edu/cgi-bin/das/hg38/dna?segment=chr2:166150066,166150702 | 72% |
| 586 | http://genome.ucsc.edu/cgi-bin/das/hg38/dna?segment=chr2:166160023,166160609 | 75% |
| 628 | http://genome.ucsc.edu/cgi-bin/das/hg38/dna?segment=chr22:36816984,36817612 | 78% |
| 236 | http://genome.ucsc.edu/cgi-bin/das/hg38/dna?segment=chr22:36817484,36817720 | 74% |
| 593 | http://genome.ucsc.edu/cgi-bin/das/hg38/dna?segment=chr22:36818134,36818727 | 73% |
| 637 | http://genome.ucsc.edu/cgi-bin/das/hg38/dna?segment=chr15:88802240,88802877 | 72% |
| 388 | http://genome.ucsc.edu/cgi-bin/das/hg38/dna?segment=chr15:88803290,88803678 | 84% |
| 672 | http://genome.ucsc.edu/cgi-bin/das/hg38/dna?segment=chr15:88807290,88807962 | 82% |
| 594 | http://genome.ucsc.edu/cgi-bin/das/hg38/dna?segment=chr15:88833390,88833984 | 86% |
| 1030 | http://genome.ucsc.edu/cgi-bin/das/hg38/dna?segment=chr12:128377753,128378783 | 70% |
| 476 | http://genome.ucsc.edu/cgi-bin/das/hg38/dna?segment=chr12:128289803,128290279 | 78% |

*FIG. 1A-2 (cont.)*

| | | | | | | | |
|---|---|---|---|---|---|---|---|
| E20 | Tmem132c | PV | 66% | intronic | chr12 | 128323153 | 128323718 |
| E21 | Tmem132c | PV | 71% | intronic | chr12 | 128332503 | 128332974 |
| E22 | Tmem132c | PV | 94% | intronic | chr12 | 128336003 | 128336491 |
| E23 | Tmem132c | PV | 64% | intronic | chr12 | 128365603 | 128366181 |
| E24 | Tmem132c | PV | 82% | intronic | chr12 | 128375853 | 128376606 |
| E25 | Tmem132c | PV | 73% | intronic | chr12 | 128408553 | 128408930 |
| E26 | Lrrc38 | PV | 72% | intergenic | chr1 | 13388723 | 13390212 |
| E27 | Lrrc38 | PV | 66% | intronic | chr1 | 13469123 | 13470861 |
| E28 | Inpp5j | PV | 83% | intergenic | chr22 | 31124894 | 31125629 |
| E29 | Inpp5j | PV | 94% | intergenic | chr22 | 31132544 | 31133831 |
| E30 | Mef2c | PV | 77% | intergenic | chr5 | 88655733 | 88657379 |
| E31 | Mef2c | PV | 63% | intronic | chr5 | 88872683 | 88872997 |
| E32 | Mef2c | PV | 70% | intronic | chr5 | 88745133 | 88745535 |
| E33 | Mef2c | PV | 82% | intronic | chr5 | 88799783 | 88801354 |
| E34 | Pthlh | PV | 48% | intronic | chr12 | 27969472 | 27969690 |
| E35 | Pthlh | PV | 86% | intergenic | chr12 | 27973822 | 27974489 |

*FIG. 1A-3*

| | | |
|---|---|---|
| 565 | http://genome.ucsc.edu/cgi-bin/das/hg38/dna?segment=chr12:128323153,128323718 | 77% |
| 471 | http://genome.ucsc.edu/cgi-bin/das/hg38/dna?segment=chr12:128332503,128332974 | 74% |
| 488 | http://genome.ucsc.edu/cgi-bin/das/hg38/dna?segment=chr12:128336003,128336491 | 75% |
| 578 | http://genome.ucsc.edu/cgi-bin/das/hg38/dna?segment=chr12:128365603,128366181 | 85% |
| 753 | http://genome.ucsc.edu/cgi-bin/das/hg38/dna?segment=chr12:128375853,128376606 | 74% |
| 377 | http://genome.ucsc.edu/cgi-bin/das/hg38/dna?segment=chr12:128408553,128408930 | 77% |
| 1489 | http://genome.ucsc.edu/cgi-bin/das/hg38/dna?segment=chr1:13388723,13390212 | 70% |
| 1738 | http://genome.ucsc.edu/cgi-bin/das/hg38/dna?segment=chr1:13469123,13470861 | 71% |
| 735 | http://genome.ucsc.edu/cgi-bin/das/hg38/dna?segment=chr22:31124894,31125629 | 77% |
| 1287 | http://genome.ucsc.edu/cgi-bin/das/hg38/dna?segment=chr22:31132544,31133831 | 74% |
| 1646 | http://genome.ucsc.edu/cgi-bin/das/hg38/dna?segment=chr5:88655733,88657379 | - |
| 314 | http://genome.ucsc.edu/cgi-bin/das/hg38/dna?segment=chr5:88872683,88872997 | 68% |
| 402 | http://genome.ucsc.edu/cgi-bin/das/hg38/dna?segment=chr5:88745133,88745535 | 70% |
| 1571 | http://genome.ucsc.edu/cgi-bin/das/hg38/dna?segment=chr5:88799783,88801354 | - |
| 218 | http://genome.ucsc.edu/cgi-bin/das/hg38/dna?segment=chr12:27969472,27969690 | 68% |
| 667 | http://genome.ucsc.edu/cgi-bin/das/hg38/dna?segment=chr12:27973822,27974489 | 69% |

*FIG. 1A-3 (cont.)*

AAV-S5E2-dTomato

| FIG. | Panel | Enhancer | Marker | Layer | No. | Mean | s.e.m |
|---|---|---|---|---|---|---|---|
| 3 | B | E1 | Reporter | 1-6 | 3 | 17.1 | 4.7 |
| 3 | B | E2 | Reporter | 1-6 | 3 | 78.7 | 11.4 |
| 3 | B | E3 | Reporter | 1-6 | 3 | 49.1 | 5.5 |
| 3 | B | E4 | Reporter | 1-6 | 3 | 16 | 2.6 |
| 3 | B | E5 | Reporter | 1-6 | 3 | 38.3 | 17 |
| 3 | B | E6 | Reporter | 1-6 | 3 | 8.1 | 0.2 |
| 3 | B | E7 | Reporter | 1-6 | 3 | 10.4 | 1.4 |
| 3 | B | E8 | Reporter | 1-6 | 3 | 41.9 | 9.2 |
| 3 | B | E9 | Reporter | 1-6 | 3 | 28.2 | 5.6 |
| 3 | B | E10 | Reporter | 1-6 | 3 | 22.3 | 7.2 |
| 3 | B | Dlx | Reporter | 1-6 | 3 | 100.1 | 7.9 |
| 3 | B | E1 | Reporter / Gad1 | 1-6 | 2 | 95.1 | 4.3 |
| 3 | B | E2 | Reporter / Gad1 | 1-6 | 2 | 97.8 | 0 |
| 3 | B | E3 | Reporter / Gad1 | 1-6 | 2 | 95 | 2.8 |
| 3 | B | E4 | Reporter / Gad1 | 1-6 | 2 | 97.6 | 2.4 |
| 3 | B | E5 | Reporter / Gad1 | 1-6 | 2 | 63.7 | 1.5 |

*FIG. 11*

| FIG. | Panel | Enhancer | Marker | Layer | No. | Mean | s.e.m |
|---|---|---|---|---|---|---|---|
| 3 | B | E6 | Reporter / Gad1 | 1-6 | 2 | 98.7 | 1.3 |
| 3 | B | E7 | Reporter / Gad1 | 1-6 | 2 | 89.5 | 4 |
| 3 | B | E8 | Reporter / Gad1 | 1-6 | 2 | 85.4 | 0.5 |
| 3 | B | E9 | Reporter / Gad1 | 1-6 | 2 | 98.6 | 1.4 |
| 3 | B | E10 | Reporter / Gad1 | 1-6 | 2 | 96.7 | 2.4 |
| 3 | B | Dlx | Reporter / Gad1 | 1-6 | 4 | 93.4 | 1.3 |
| 3 | B | E1 | Reporter / PV | 1-6 | 6 | 50.3 | 5.6 |
| 3 | B | E2 | Reporter / PV | 1-6 | 6 | 74 | 2.5 |
| 3 | B | E3 | Reporter / PV | 1-6 | 4 | 45.5 | 2.1 |
| 3 | B | E4 | Reporter / PV | 1-6 | 6 | 30.7 | 3.8 |
| 3 | B | E5 | Reporter / PV | 1-6 | 6 | 22.8 | 2.4 |
| 3 | B | E6 | Reporter / PV | 1-6 | 2 | 16 | 2 |
| 3 | B | E7 | Reporter / PV | 1-6 | 6 | 50.8 | 2.1 |
| 3 | B | E8 | Reporter / PV | 1-6 | 4 | 47.5 | 3.4 |
| 3 | B | E9 | Reporter / PV | 1-6 | 6 | 52.8 | 6.3 |
| 3 | B | E10 | Reporter / PV | 1-6 | 4 | 29 | 2.7 |

*FIG. 11 (cont.)*

| FIG. | Panel | Enhancer | Marker | Layer | No. | Mean | s.e.m |
|---|---|---|---|---|---|---|---|
| 3 | C | E2 | Reporter / Gad1 | 1 | 3 | 0 | 0 |
| 3 | C | E2 | Reporter / Gad1 | 2/3 | 3 | 94.7 | 0.9 |
| 3 | C | E2 | Reporter / Gad1 | 4 | 3 | 100 | 0 |
| 3 | C | E2 | Reporter / Gad1 | 5 | 3 | 97.1 | 1 |
| 3 | C | E2 | Reporter / Gad1 | 6 | 3 | 97.2 | 2.8 |
| 3 | C | E2 | Reporter / PV | 1 | 3 | 0 | 0 |
| 3 | C | E2 | Reporter / PV | 2/3 | 3 | 86.5 | 2.8 |
| 3 | C | E2 | Reporter / PV | 4 | 3 | 93.5 | 1.7 |
| 3 | C | E2 | Reporter / PV | 5 | 3 | 87.3 | 2.1 |
| 3 | C | E2 | Reporter / PV | 6 | 3 | 87.3 | 2.1 |
| 3 | C | E2 | Reporter / SST | 1 | 3 | 0 | 0 |
| 3 | C | E2 | Reporter / SST | 2/3 | 3 | 0 | 0 |
| 3 | C | E2 | Reporter / SST | 4 | 3 | 6.1 | 0.8 |
| 3 | C | E2 | Reporter / SST | 5 | 3 | 3.3 | 1 |
| 3 | C | E2 | Reporter / SST | 6 | 3 | 7.6 | 1 |
| 3 | C | E2 | Reporter / VIP | 1 | 3 | na | na |

*FIG. 11 (cont.)*

| FIG. | Panel | Enhancer | Marker | Layer | No. | Mean | s.e.m |
|---|---|---|---|---|---|---|---|
| 3 | C | E2 | Reporter / VIP | 2/3 | 3 | na | na |
| 3 | C | E2 | Reporter / VIP | 4 | 3 | na | na |
| 3 | C | E2 | Reporter / VIP | 5 | 3 | na | na |
| 3 | C | E2 | Reporter / VIP | 6 | 3 | na | na |
| 3 | C | E5 | Reporter / Gad1 | 1 | 3 | 91.7 | 8.3 |
| 3 | C | E5 | Reporter / Gad1 | 2/3 | 3 | 98.9 | 1.1 |
| 3 | C | E5 | Reporter / Gad1 | 4 | 3 | 95.7 | 0 |
| 3 | C | E5 | Reporter / Gad1 | 5 | 3 | 35 | 1.7 |
| 3 | C | E5 | Reporter / Gad1 | 6 | 3 | 94.7 | 5.3 |
| 3 | C | E5 | Reporter / PV | 1 | 3 | 0 | 0 |
| 3 | C | E5 | Reporter / PV | 2/3 | 3 | 36.3 | 7.7 |
| 3 | C | E5 | Reporter / PV | 4 | 3 | 15.8 | 3.8 |
| 3 | C | E5 | Reporter / PV | 5 | 3 | 17.8 | 4.5 |
| 3 | C | E5 | Reporter / PV | 6 | 3 | 12.9 | 2.1 |
| 3 | C | E5 | Reporter / SST | 1 | 3 | 0 | 0 |
| 3 | C | E5 | Reporter / SST | 2/3 | 3 | 7.1 | 4.3 |

*FIG. 11 (cont.)*

| FIG. | Panel | Enhancer | Marker | Layer | No. | Mean | s.e.m |
|---|---|---|---|---|---|---|---|
| 3 | C | E5 | Reporter / SST | 4 | 3 | 22.4 | 10.3 |
| 3 | C | E5 | Reporter / SST | 5 | 3 | 13.1 | 4.3 |
| 3 | C | E5 | Reporter / SST | 6 | 3 | 12.3 | 12.3 |
| 3 | C | E5 | Reporter / VIP | 1 | 3 | na | na |
| 3 | C | E5 | Reporter / VIP | 2/3 | 3 | na | na |
| 3 | C | E5 | Reporter / VIP | 4 | 3 | na | na |
| 3 | C | E5 | Reporter / VIP | 5 | 3 | na | na |
| 3 | C | E5 | Reporter / VIP | 6 | 3 | na | na |
| 3 | C | E6 | Reporter / Gad1 | 1 | 3 | 0 | 0 |
| 3 | C | E6 | Reporter / Gad1 | 2/3 | 3 | 95.5 | 4.5 |
| 3 | C | E6 | Reporter / Gad1 | 4 | 3 | 100 | 0 |
| 3 | C | E6 | Reporter / Gad1 | 5 | 3 | 98.3 | 1.7 |
| 3 | C | E6 | Reporter / Gad1 | 6 | 3 | 100 | 0 |
| 3 | C | E6 | Reporter / PV | 1 | 3 | 0 | 0 |
| 3 | C | E6 | Reporter / PV | 2/3 | 3 | 5.4 | 1.4 |
| 3 | C | E6 | Reporter / PV | 4 | 3 | 3.4 | 0.6 |

*FIG. 11 (cont.)*

| FIG. | Panel | Enhancer | Marker | Layer | No. | Mean | s.e.m |
|---|---|---|---|---|---|---|---|
| 3 | C | E6 | Reporter / PV | 5 | 3 | 2.3 | 0.6 |
| 3 | C | E6 | Reporter / PV | 6 | 3 | 1.8 | 0.3 |
| 3 | C | E6 | Reporter / SST | 1 | 3 | 0 | 0 |
| 3 | C | E6 | Reporter / SST | 2/3 | 3 | 0 | 0 |
| 3 | C | E6 | Reporter / SST | 4 | 3 | 7.5 | 4.6 |
| 3 | C | E6 | Reporter / SST | 5 | 3 | 5.9 | 2.6 |
| 3 | C | E6 | Reporter / SST | 6 | 3 | 2.9 | 2.9 |
| 3 | C | E6 | Reporter / VIP | 1 | 3 | 0 | 0 |
| 3 | C | E6 | Reporter / VIP | 2/3 | 3 | 92.5 | 2.6 |
| 3 | C | E6 | Reporter / VIP | 4 | 3 | 76.3 | 8.8 |
| 3 | C | E6 | Reporter / VIP | 5 | 3 | 76.7 | 3.8 |
| 3 | C | E6 | Reporter / VIP | 6 | 3 | 96.2 | 3.8 |
| 3 | C | E2 | Density Gad1+ | 1 | 3 | 0.3 | 0.5 |
| 3 | C | E2 | Density Gad1+ | 2/3 | 3 | 12.5 | 1 |
| 3 | C | E2 | Density Gad1+ | 4 | 3 | 30.9 | 3.1 |
| 3 | C | E2 | Density Gad1+ | 5 | 3 | 35 | 1.4 |

*FIG. 11 (cont.)*

| FIG. | Panel | Enhancer | Marker | Layer | No. | Mean | s.e.m |
|---|---|---|---|---|---|---|---|
| 3 | C | E2 | Density Gad1+ | 6 | 3 | 18.8 | 4.8 |
| 3 | C | E2 | Density Gad1- | 1 | 3 | 0 | 0 |
| 3 | C | E2 | Density Gad1- | 2/3 | 3 | 0.7 | 0.1 |
| 3 | C | E2 | Density Gad1- | 4 | 3 | 0 | 0 |
| 3 | C | E2 | Density Gad1- | 5 | 3 | 1.1 | 0.6 |
| 3 | C | E2 | Density Gad1- | 6 | 3 | 0.7 | 0.9 |
| 3 | C | E2 | Density Gad1+ | 1 | 3 | 2.2 | 0.9 |
| 3 | C | E5 | Density Gad1+ | 2/3 | 3 | 22.2 | 1.5 |
| 3 | C | E5 | Density Gad1+ | 4 | 3 | 12.2 | 0.5 |
| 3 | C | E5 | Density Gad1+ | 5 | 3 | 18.6 | 0.3 |
| 3 | C | E5 | Density Gad1+ | 6 | 3 | 8.4 | 1.9 |
| 3 | C | E5 | Density Gad1- | 1 | 3 | 0.3 | 0.4 |
| 3 | C | E5 | Density Gad1- | 2/3 | 3 | 0.3 | 0.4 |
| 3 | C | E5 | Density Gad1- | 4 | 3 | 0.6 | 0 |
| 3 | C | E5 | Density Gad1- | 5 | 3 | 34.7 | 3 |
| 3 | C | E5 | Density Gad1- | 6 | 3 | 0.6 | 0.8 |

*FIG. 11 (cont.)*

| FIG. | Panel | Enhancer | Marker | Layer | No. | Mean | s.e.m |
|---|---|---|---|---|---|---|---|
| 3 | C | E6 | Density Gad1+ | 1 | 3 | 0 | 0 |
| 3 | C | E6 | Density Gad1+ | 2/3 | 3 | 34.7 | 7.2 |
| 3 | C | E6 | Density Gad1+ | 4 | 3 | 36.8 | 1.3 |
| 3 | C | E6 | Density Gad1+ | 5 | 3 | 13.7 | 6.6 |
| 3 | C | E6 | Density Gad1+ | 6 | 3 | 13.6 | 1 |
| 3 | C | E6 | Density Gad1- | 1 | 3 | 0 | 0 |
| 3 | C | E6 | Density Gad1- | 2/3 | 3 | 0 | 0 |
| 3 | C | E6 | Density Gad1- | 4 | 3 | 0.6 | 0.9 |
| 3 | C | E6 | Density Gad1- | 5 | 3 | 0 | 0 |
| 3 | C | E6 | Density Gad1- | 6 | 3 | 0.6 | 0.9 |
| 4 | B | E2 | Reporter / PV | 1-6 | 4 | 91.6 | 0.9 |
| 4 | B | E2 | Reporter / PV | 1-6 | 8 | 90.8 | 1.1 |
| 4 | B | E2 | PV / reporter | 1-6 | 19 | 75.7 | 2.9 |
| 4 | D | E2 | Reporter at .5 | 1-6 | 3 | 10 | 1.1 |
| 4 | D | E2 | Reporter at 2 | 1-6 | 3 | 33 | 10.6 |
| 4 | D | E2 | Reporter at 5 | 1-6 | 3 | 96.5 | 8.4 |

*FIG. 11 (cont.)*

| FIG. | Panel | Enhancer | Marker | Layer | No. | Mean | s.e.m |
|---|---|---|---|---|---|---|---|
| 4 | D | E2 | Reporter / PV at .5 | 1-6 | 3 | 86.4 | 0.5 |
| 4 | D | E2 | Reporter / PV at 2 | 1-6 | 3 | 86.6 | 0.6 |
| 4 | D | E2 | Reporter / PV at 5 | 1-6 | 3 | 91.3 | 0.8 |
| 4 | E | E2 | Reporter / PV 1-15 | 1-6 | 4 | 56.7 | 2.3 |
| 4 | E | E2 | Reporter / PV 7-15 | 1-6 | 5 | 67.2 | 1.5 |
| 4 | E | E2 | Reporter / PV 10-15 | 1-6 | 3 | 81.7 | 1.1 |
| 4 | E | E2 | Reporter / PV 4-7 | 1-6 | 2 | 60.9 | 1.9 |
| 4 | E | E2 | Reporter / PV 7-10 | 1-6 | 5 | 78.1 | 1.8 |
| 5 | A | E2 | Reporter / PV | 1-6 | 4 | 85.3 | 0.6 |
| 5 | A | E2 | PV / reporter | 1-6 | 4 | 87.7 | 1.2 |
| 5 | B | E2 | Delta | 1-6 | 14 | 8.2 | 0.8 |
| 5 | A | E2 | Rat | 1-6 | 1 | 93 | na |

*FIG. 11 (cont.)*

| FIG. | Panel | Enhancer | Marker | Layer | No. | Mean | s.e.m |
|---|---|---|---|---|---|---|---|
| 5 | A | E2 | Marmoset | 1-6 | 4 | 91.8 | 3.1 |
| 5 | A | E2 | Macaque | 1-6 | 4 | 87.3 | 0.5 |
| 8 | A | E2 | IR | na | 10 | 119.1 | 11.8 |
| 8 | A | E2 | AHP | na | 10 | 15 | 0.9 |
| 8 | B | E2 | Reporter / PV V1 | 1-6 | 2 | 88.1 | 2.3 |
| 8 | B | E2 | Reporter / PV CG | na | 2 | 80.2 | 3.7 |
| 8 | B | E2 | Reporter / PV SUB | na | 3 | 91.1 | 2.1 |
| 8 | B | E2 | Reporter / PV CA1 | na | 6 | 80.5 | 1.9 |
| 8 | B | E2 | Reporter / PV STR | na | 3 | 54.8 | 5.8 |
| 8 | B | E2 | Reporter / PV BLA | na | 3 | 38.1 | 4.1 |
| 8 | B | E2 | Reporter / PV SNR | na | 2 | 84.2 | 1.1 |
| 10 | A | E2 | IR | na | 44 | 56.2 | 6.7 |
| 10 | A | E2 | AHP | na | 45 | 28.8 | 0.8 |

*FIG. 11 (cont.)*

| RE | Gene | Target | Specificity | Position | Chr | Start | Stop | Size (bp) | scATAC PV | scATAC SST | scATAC VIP | scATAC ID2 | bATAC Ex | Ms/Hm |
|---|---|---|---|---|---|---|---|---|---|---|---|---|---|---|
| E1 | Scn1a | PV | 22% | intergenic | chr2 | 66256056 | 66257335 | 1279 | 1 | 1 | 1 | 1 | 1 | 69% |
| E2 | Scn1a | PV | 90% | intronic | chr2 | 66364036 | 66364653 | 617 | 1 | 0 | 0 | 1 | 0 | 71% |
| E3 | Scn1a | PV | 57% | intronic | chr2 | 66383190 | 66384021 | 831 | 1 | 1 | 1 | 1 | 1 | 67% |
| E4 | Scn1a | PV | 14% | intronic | chr2 | 66387764 | 66388024 | 260 | 0 | 0 | 0 | 0 | 0 | 78% |
| E5 | Scn1a | PYR | 20% | intronic | chr2 | 66392447 | 66393109 | 662 | 1 | 1 | 1 | 1 | 1 | 72% |
| E6 | Scn1a | VIP | 88% | intronic | chr2 | 66401767 | 66402372 | 605 | 0 | 0 | 0 | 0 | 0 | 72% |
| E7 | Scn1a | PV | 33% | intronic | chr2 | 66407834 | 66410263 | 2429 | 1 | 1 | 1 | 1 | 1 | 74% |
| E8 | Scn1a | PV | 61% | intronic | chr2 | 66439814 | 66441457 | 1643 | 1 | 1 | 1 | 1 | 1 | 75% |
| E9 | Scn1a | PV | 47% | intergenic | chr2 | 66441748 | 66442268 | 520 | 1 | 0 | 0 | 0 | 1 | 72% |
| E10 | Scn1a | PV | 23% | intergenic | chr2 | 66450594 | 66451140 | 546 | 1 | 1 | 1 | 1 | 1 | 75% |
| E11 | Pvalb | PV | 90% | intronic | chr15 | 78204152 | 78204655 | 503 | 1 | 1 | 1 | 1 | 0 | 78% |
| E12 | Pvalb | PV | 59% | intronic | chr15 | 78204583 | 78204784 | 201 | 1 | 1 | 0 | 0 | 0 | 74% |
| E13 | Pvalb | PV | 67% | intronic | chr15 | 78205234 | 78205766 | 532 | 0 | 1 | 0 | 0 | 0 | 73% |
| E14 | Acan | PV | 94% | intergenic | chr7 | 79052127 | 79052622 | 495 | 1 | 0 | 0 | 0 | 0 | 72% |
| E15 | Acan | PV | 79% | intergenic | chr7 | 79053118 | 79053435 | 317 | 1 | 1 | 1 | 1 | 1 | 84% |
| E16 | Acan | PV | 58% | intronic | chr7 | 79056553 | 79057054 | 501 | 0 | 0 | 0 | 0 | 0 | 82% |
| E17 | Acan | PV | 54% | intronic | chr7 | 79079999 | 79080472 | 473 | 1 | 0 | 0 | 0 | 0 | 86% |

*FIG. 15A-1*

| RE | Gene | Target | Specificity | Position | Chr | Start | Stop | Size (bp) | scATAC PV | scATAC SST | scATAC VIP | scATAC ID2 | hATAC Ex | Ms/Hm |
|---|---|---|---|---|---|---|---|---|---|---|---|---|---|---|
| E18 | Tmem132c | PV | 57% | intronic | chr5 | 127243448 | 127244121 | 673 | 1 | 1 | 0 | 0 | 0 | 70% |
| E19 | Tmem132c | PV | 57% | intronic | chr5 | 127257256 | 127257594 | 338 | 0 | 1 | 0 | 0 | 0 | 78% |
| E20 | Tmem132c | PV | 66% | intronic | chr5 | 127290515 | 127291016 | 501 | 1 | 0 | 0 | 0 | 0 | 77% |
| E21 | Tmem132c | PV | 71% | intronic | chr5 | 127300767 | 127301107 | 340 | 0 | 0 | 0 | 0 | 0 | 74% |
| E22 | Tmem132c | PV | 94% | intronic | chr5 | 127305150 | 127305592 | 442 | 1 | 0 | 0 | 0 | 0 | 75% |
| E23 | Tmem132c | PV | 64% | intronic | chr5 | 127323924 | 127324468 | 544 | 1 | 1 | 1 | 1 | 0 | 85% |
| E24 | Tmem132c | PV | 82% | intronic | chr5 | 127331966 | 127332522 | 556 | 1 | 1 | 1 | 1 | 0 | 74% |
| E25 | Tmem132c | PV | 73% | intronic | chr5 | 127355818 | 127356133 | 315 | 1 | 0 | 0 | 0 | 0 | 77% |
| E26 | Lrrc38 | PV | 72% | intergenic | chr4 | 143348892 | 143349749 | 857 | 1 | 1 | 1 | 0 | 0 | 70% |
| E27 | Lrrc38 | PV | 66% | intronic | chr4 | 143361408 | 143362362 | 954 | 1 | 0 | 1 | 0 | 0 | 71% |
| E28 | Inpp5j | PV | 83% | intergenic | chr11 | 3504821 | 3505244 | 423 | 1 | 1 | 1 | 1 | 1 | 77% |
| E29 | Inpp5j | PV | 94% | intergenic | chr11 | 3509025 | 3509652 | 627 | 1 | 1 | 0 | 0 | 0 | 74% |
| E30 | Mef2c | PV | 77% | intergenic | chr13 | 83503268 | 83504033 | 765 | 0 | 0 | 0 | 0 | 0 | - |
| E31 | Mef2c | PV | 63% | intronic | chr13 | 83507235 | 83507457 | 222 | 0 | 0 | 0 | 0 | 0 | 68% |
| E32 | Mef2c | PV | 70% | intronic | chr13 | 83515122 | 83515409 | 287 | 0 | 0 | 0 | 0 | 0 | 70% |
| E33 | Mef2c | PV | 82% | intronic | chr13 | 83518268 | 83519179 | 911 | 1 | 1 | 1 | 1 | 1 | - |
| E34 | Pthlh | PV | 48% | intronic | chr6 | 147263395 | 147263584 | 189 | 1 | 1 | 1 | 1 | 1 | 68% |
| E35 | Pthlh | PV | 86% | intergenic | chr6 | 147266874 | 147267390 | 516 | 0 | 0 | 0 | 0 | 0 | 69% |

*FIG. 15A-2*

| RE | Gene | Target | Specificity | Position | Mouse_ mm10_Chr | Mouse_ mm10_Start | Mouse_ mm10_Stop | Size (bp) | Human_ hg38_Chr | Human_ hg38_Start | Human_ hg38_Stop | Human_hg38 _size_(bp) | Percentage of conservation Mouse vs Human |
|---|---|---|---|---|---|---|---|---|---|---|---|---|---|
| E1 | Scn1a | PV | 22% | intergenic | chr2 | 66256056 | 66257335 | 1279 | chr2 | 165953030 | 165954796 | 1766 | 69% |
| E2 | Scn1a | PV | 90% | intronic | chr2 | 66364036 | 66364653 | 617 | chr2 | 166084035 | 166084884 | 849 | 71% |
| E3 | Scn1a | PV | 57% | intronic | chr2 | 66383190 | 66384021 | 831 | chr2 | 166090876 | 166091720 | 844 | 67% |
| E4 | Scn1a | PV | 14% | intronic | chr2 | 66387764 | 66388024 | 260 | chr2 | 166094366 | 166094633 | 267 | 78% |
| E5 | Scn1a | PYR | 20% | intronic | chr2 | 66392447 | 66393109 | 662 | chr2 | 166103693 | 166104587 | 894 | 72% |
| E6 | Scn1a | VIP | 88% | intronic | chr2 | 66401767 | 66402372 | 605 | chr2 | 166118214 | 166118879 | 665 | 72% |
| E7 | Scn1a | PV | 33% | intronic | chr2 | 66407834 | 66410263 | 2429 | chr2 | 165892760 | 165897884 | 5124 | 74% |
| E8 | Scn1a | PV | 61% | intronic | chr2 | 66439814 | 66441457 | 1643 | chr2 | 166148156 | 166149792 | 1636 | 75% |
| E9 | Scn1a | PV | 47% | intergenic | chr2 | 66441748 | 66442268 | 520 | chr2 | 166150066 | 166150702 | 636 | 72% |
| E10 | Scn1a | PV | 23% | intergenic | chr2 | 66450594 | 66451140 | 546 | chr2 | 166160023 | 166160609 | 586 | 75% |
| E11 | Pvalb | PV | 90% | intronic | chr15 | 78204152 | 78204655 | 503 | chr22 | 36816984 | 36817612 | 628 | 78% |
| E12 | Pvalb | PV | 59% | intronic | chr15 | 78204583 | 78204784 | 201 | chr22 | 36817484 | 36817720 | 236 | 74% |
| E13 | Pvalb | PV | 67% | intronic | chr15 | 78205234 | 78205766 | 532 | chr22 | 36818134 | 36818727 | 593 | 73% |
| E14 | Acan | PV | 94% | intergenic | chr7 | 79052127 | 79052622 | 495 | chr15 | 88802240 | 88802877 | 637 | 72% |
| E15 | Acan | PV | 79% | intergenic | chr7 | 79053118 | 79053435 | 317 | chr15 | 88803290 | 88803678 | 388 | 84% |
| E16 | Acan | PV | 58% | intronic | chr7 | 79056553 | 79057054 | 501 | chr15 | 88807290 | 88807962 | 672 | 82% |
| E17 | Acan | PV | 54% | intronic | chr7 | 79079999 | 79080472 | 473 | chr15 | 88833390 | 88833984 | 594 | 86% |
| E18 | Tmem132c | PV | 57% | intronic | chr5 | 127243448 | 127244121 | 673 | chr12 | 128377753 | 128378783 | 1030 | 70% |

FIG. 16A-1

| RE | Gene | Target | Specificity | Position | Mouse_mm10_Chr | Mouse_mm10_Start | Mouse_mm10_Stop | Size (bp) | Human_hg38_Chr | Human_hg38_Start | Human_hg38_Stop | Human_hg38_size_(bp) | Percentage of conservation Mouse vs Human |
|---|---|---|---|---|---|---|---|---|---|---|---|---|---|
| E19 | Tmem132c | PV | 57% | intronic | chr5 | 127257256 | 127257594 | 338 | chr12 | 128289803 | 128290279 | 476 | 78% |
| E20 | Tmem132c | PV | 66% | intronic | chr5 | 127290515 | 127291016 | 501 | chr12 | 128323153 | 128323718 | 565 | 77% |
| E21 | Tmem132c | PV | 71% | intronic | chr5 | 127300767 | 127301107 | 340 | chr12 | 128332503 | 128332974 | 471 | 74% |
| E22 | Tmem132c | PV | 94% | intronic | chr5 | 127305150 | 127305592 | 442 | chr12 | 128336003 | 128336491 | 488 | 75% |
| E23 | Tmem132c | PV | 64% | intronic | chr5 | 127323924 | 127324468 | 544 | chr12 | 128365603 | 128366181 | 578 | 85% |
| E24 | Tmem132c | PV | 82% | intronic | chr5 | 127331966 | 127332522 | 556 | chr12 | 128375853 | 128376606 | 753 | 74% |
| E25 | Tmem132c | PV | 73% | intronic | chr5 | 127355818 | 127356133 | 315 | chr12 | 128408553 | 128408930 | 377 | 77% |
| E26 | Lrrc38 | PV | 72% | intergenic | chr4 | 143348892 | 143349749 | 857 | chr1 | 13388723 | 13390212 | 1489 | 70% |
| E27 | Lrrc38 | PV | 66% | intronic | chr4 | 143361408 | 143362362 | 954 | chr1 | 13469123 | 13470861 | 1738 | 71% |
| E28 | Inpp5j | PV | 83% | intergenic | chr11 | 3504821 | 3505244 | 423 | chr22 | 31124894 | 31125629 | 735 | 77% |
| E29 | Inpp5j | PV | 94% | intergenic | chr11 | 3509025 | 3509652 | 627 | chr22 | 31132544 | 31133831 | 1287 | 74% |
| E30 | Mef2c | PV | 77% | intergenic | chr13 | 83503268 | 83504033 | 765 | chr5 | 88655733 | 88657379 | 1646 | - |
| E31 | Mef2c | PV | 63% | intronic | chr13 | 83507235 | 83507457 | 222 | chr5 | 88872683 | 88872997 | 314 | 68% |
| E32 | Mef2c | PV | 70% | intronic | chr13 | 83515122 | 83515409 | 287 | chr5 | 88745133 | 88745535 | 402 | 70% |
| E33 | Mef2c | PV | 82% | intronic | chr13 | 83518268 | 83519179 | 911 | chr5 | 88799783 | 88801354 | 1571 | - |
| E34 | Pthlh | PV | 48% | intronic | chr6 | 147263395 | 147263584 | 189 | chr12 | 27969472 | 27969690 | 218 | 68% |
| E35 | Pthlh | PV | 86% | intergenic | chr6 | 147266874 | 147267390 | 516 | chr12 | 27973822 | 27974489 | 667 | 69% |

*FIG. 16A-2*

SEQUENCE LISTING

<160> NUMBER OF SEQ ID NOS: 69

<210> SEQ ID NO 1
<211> LENGTH: 2009
<212> TYPE: PRT
<213> ORGANISM: Homo sapiens

<400> SEQUENCE: 1

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365
```

```
Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
```

-continued

```
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                1005

Met Asn  Asn Leu Gln Ile Ala  Val Asp Arg Met His  Lys Gly Val
    1010                 1015                 1020

Ala Tyr  Val Lys Arg Lys Ile  Tyr Glu Phe Ile Gln  Gln Ser Phe
    1025                 1030                 1035

Ile Arg  Lys Gln Lys Ile Leu  Asp Glu Ile Lys Pro  Leu Asp Asp
    1040                 1045                 1050

Leu Asn  Asn Lys Lys Asp Ser  Cys Met Ser Asn His  Thr Ala Glu
    1055                 1060                 1065

Ile Gly  Lys Asp Leu Asp Tyr  Leu Lys Asp Val Asn  Gly Thr Thr
    1070                 1075                 1080

Ser Gly  Ile Gly Thr Gly Ser  Ser Val Glu Lys Tyr  Ile Ile Asp
    1085                 1090                 1095

Glu Ser  Asp Tyr Met Ser Phe  Ile Asn Asn Pro Ser  Leu Thr Val
    1100                 1105                 1110

Thr Val  Pro Ile Ala Val Gly  Glu Ser Asp Phe Glu  Asn Leu Asn
    1115                 1120                 1125

Thr Glu  Asp Phe Ser Ser Glu  Ser Asp Leu Glu Glu  Ser Lys Glu
    1130                 1135                 1140

Lys Leu  Asn Glu Ser Ser Ser  Ser Ser Glu Gly Ser  Thr Val Asp
    1145                 1150                 1155

Ile Gly  Ala Pro Val Glu Glu  Gln Pro Val Val Glu  Pro Glu Glu
    1160                 1165                 1170

Thr Leu  Glu Pro Glu Ala Cys  Phe Thr Glu Gly Cys  Val Gln Arg
    1175                 1180                 1185

Phe Lys  Cys Cys Gln Ile Asn  Val Glu Glu Gly Arg  Gly Lys Gln
    1190                 1195                 1200
```

```
Trp Trp  Asn Leu Arg Arg Thr  Cys Phe Arg Ile Val  Glu His Asn
    1205                 1210                 1215

Trp Phe  Glu Thr Phe Ile Val  Phe Met Ile Leu Leu  Ser Ser Gly
    1220                 1225                 1230

Ala Leu  Ala Phe Glu Asp Ile  Tyr Ile Asp Gln Arg  Lys Thr Ile
    1235                 1240                 1245

Lys Thr  Met Leu Glu Tyr Ala  Asp Lys Val Phe Thr  Tyr Ile Phe
    1250                 1255                 1260

Ile Leu  Glu Met Leu Leu Lys  Trp Val Ala Tyr Gly  Tyr Gln Thr
    1265                 1270                 1275

Tyr Phe  Thr Asn Ala Trp Cys  Trp Leu Asp Phe Leu  Ile Val Asp
    1280                 1285                 1290

Val Ser  Leu Val Ser Leu Thr  Ala Asn Ala Leu Gly  Tyr Ser Glu
    1295                 1300                 1305

Leu Gly  Ala Ile Lys Ser Leu  Arg Thr Leu Arg Ala  Leu Arg Pro
    1310                 1315                 1320

Leu Arg  Ala Leu Ser Arg Phe  Glu Gly Met Arg Val  Val Val Asn
    1325                 1330                 1335

Ala Leu  Leu Gly Ala Ile Pro  Ser Ile Met Asn Val  Leu Leu Val
    1340                 1345                 1350

Cys Leu  Ile Phe Trp Leu Ile  Phe Ser Ile Met Gly  Val Asn Leu
    1355                 1360                 1365

Phe Ala  Gly Lys Phe Tyr His  Cys Ile Asn Thr Thr  Thr Gly Asp
    1370                 1375                 1380

Arg Phe  Asp Ile Glu Asp Val  Asn Asn His Thr Asp  Cys Leu Lys
    1385                 1390                 1395

Leu Ile  Glu Arg Asn Glu Thr  Ala Arg Trp Lys Asn  Val Lys Val
    1400                 1405                 1410

Asn Phe  Asp Asn Val Gly Phe  Gly Tyr Leu Ser Leu  Leu Gln Val
    1415                 1420                 1425

Ala Thr  Phe Lys Gly Trp Met  Asp Ile Met Tyr Ala  Ala Val Asp
    1430                 1435                 1440

Ser Arg  Asn Val Glu Leu Gln  Pro Lys Tyr Glu Glu  Ser Leu Tyr
    1445                 1450                 1455

Met Tyr  Leu Tyr Phe Val Ile  Phe Ile Ile Phe Gly  Ser Phe Phe
    1460                 1465                 1470

Thr Leu  Asn Leu Phe Ile Gly  Val Ile Ile Asp Asn  Phe Asn Gln
    1475                 1480                 1485

Gln Lys  Lys Lys Phe Gly Gly  Gln Asp Ile Phe Met  Thr Glu Glu
    1490                 1495                 1500

Gln Lys  Lys Tyr Tyr Asn Ala  Met Lys Lys Leu Gly  Ser Lys Lys
    1505                 1510                 1515

Pro Gln  Lys Pro Ile Pro Arg  Pro Gly Asn Lys Phe  Gln Gly Met
    1520                 1525                 1530

Val Phe  Asp Phe Val Thr Arg  Gln Val Phe Asp Ile  Ser Ile Met
    1535                 1540                 1545

Ile Leu  Ile Cys Leu Asn Met  Val Thr Met Met Val  Glu Thr Asp
    1550                 1555                 1560

Asp Gln  Ser Glu Tyr Val Thr  Thr Ile Leu Ser Arg  Ile Asn Leu
    1565                 1570                 1575

Val Phe  Ile Val Leu Phe Thr  Gly Glu Cys Val Leu  Lys Leu Ile
    1580                 1585                 1590
```

```
Ser Leu  Arg His Tyr Tyr Phe  Thr Ile Gly Trp Asn  Ile Phe Asp
    1595                 1600                 1605

Phe Val  Val Val Ile Leu Ser  Ile Val Gly Met Phe  Leu Ala Glu
    1610                 1615                 1620

Leu Ile  Glu Lys Tyr Phe Val  Ser Pro Thr Leu Phe  Arg Val Ile
    1625                 1630                 1635

Arg Leu  Ala Arg Ile Gly Arg  Ile Leu Arg Leu Ile  Lys Gly Ala
    1640                 1645                 1650

Lys Gly  Ile Arg Thr Leu Leu  Phe Ala Leu Met Met  Ser Leu Pro
    1655                 1660                 1665

Ala Leu  Phe Asn Ile Gly Leu  Leu Leu Phe Leu Val  Met Phe Ile
    1670                 1675                 1680

Tyr Ala  Ile Phe Gly Met Ser  Asn Phe Ala Tyr Val  Lys Arg Glu
    1685                 1690                 1695

Val Gly  Ile Asp Asp Met Phe  Asn Phe Glu Thr Phe  Gly Asn Ser
    1700                 1705                 1710

Met Ile  Cys Leu Phe Gln Ile  Thr Thr Ser Ala Gly  Trp Asp Gly
    1715                 1720                 1725

Leu Leu  Ala Pro Ile Leu Asn  Ser Lys Pro Pro Asp  Cys Asp Pro
    1730                 1735                 1740

Asn Lys  Val Asn Pro Gly Ser  Ser Val Lys Gly Asp  Cys Gly Asn
    1745                 1750                 1755

Pro Ser  Val Gly Ile Phe Phe  Phe Val Ser Tyr Ile  Ile Ile Ser
    1760                 1765                 1770

Phe Leu  Val Val Val Asn Met  Tyr Ile Ala Val Ile  Leu Glu Asn
    1775                 1780                 1785

Phe Ser  Val Ala Thr Glu Glu  Ser Ala Glu Pro Leu  Ser Glu Asp
    1790                 1795                 1800

Asp Phe  Glu Met Phe Tyr Glu  Val Trp Glu Lys Phe  Asp Pro Asp
    1805                 1810                 1815

Ala Thr  Gln Phe Met Glu Phe  Glu Lys Leu Ser Gln  Phe Ala Ala
    1820                 1825                 1830

Ala Leu  Glu Pro Pro Leu Asn  Leu Pro Gln Pro Asn  Lys Leu Gln
    1835                 1840                 1845

Leu Ile  Ala Met Asp Leu Pro  Met Val Ser Gly Asp  Arg Ile His
    1850                 1855                 1860

Cys Leu  Asp Ile Leu Phe Ala  Phe Thr Lys Arg Val  Leu Gly Glu
    1865                 1870                 1875

Ser Gly  Glu Met Asp Ala Leu  Arg Ile Gln Met Glu  Glu Arg Phe
    1880                 1885                 1890

Met Ala  Ser Asn Pro Ser Lys  Val Ser Tyr Gln Pro  Ile Thr Thr
    1895                 1900                 1905

Thr Leu  Lys Arg Lys Gln Glu  Glu Val Ser Ala Val  Ile Ile Gln
    1910                 1915                 1920

Arg Ala  Tyr Arg Arg His Leu  Leu Lys Arg Thr Val  Lys Gln Ala
    1925                 1930                 1935

Ser Phe  Thr Tyr Asn Lys Asn  Lys Ile Lys Gly Gly  Ala Asn Leu
    1940                 1945                 1950

Leu Ile  Lys Glu Asp Met Ile  Ile Asp Arg Ile Asn  Glu Asn Ser
    1955                 1960                 1965

Ile Thr  Glu Lys Thr Asp Leu  Thr Met Ser Thr Ala  Ala Cys Pro
    1970                 1975                 1980

Pro Ser  Tyr Asp Arg Val Thr  Lys Pro Ile Val Glu  Lys His Glu
```

1985                1990                1995

Gln Glu  Gly Lys Asp Glu Lys  Ala Lys Gly Lys
    2000                2005

<210> SEQ ID NO 2
<211> LENGTH: 6030
<212> TYPE: DNA
<213> ORGANISM: Homo sapiens

<400> SEQUENCE: 2
atggagcaaa cagtgcttgt accaccagga cctgacagct tcaacttctt caccagagaa 60
tctcttgcgg ctattgaaag acgcattgca gaagaaaagg caaagaatcc caaaccagac 120
aaaaaagatg acgacgaaaa tggcccaaag ccaaatagtg acttggaagc tggaaagaac 180
cttccattta tttatggaga cattcctcca gagatggtgt cagagcccct ggaggacctg 240
gacccctact atatcaataa gaaaactttt atagtattga ataaagggaa ggccatcttc 300
cggttcagtg ccacctctgc cctgtacatt ttaactccct tcaatcctct taggaaaata 360
gctattaaga ttttggtaca ttcattattc agcatgctaa ttatgtgcac tattttgaca 420
aactgtgtgt ttatgacaat gagtaaccct cctgattgga caaagaatgt agaatacacc 480
ttcacaggaa tatatacttt tgaatcactt ataaaaatta ttgcaagggg attctgttta 540
gaagatttta ctttccttcg ggatccatgg aactggctcg atttcactgt cattacattt 600
gcgtacgtca cagagtttgt ggacctgggc aatgtctcgg cattgagaac attcagagtt 660
ctccgagcat tgaagacgat ttcagtcatt ccaggcctga aaaccattgt gggagccctg 720
atccagtctg tgaagaagct ctcagatgta atgatcctga ctgtgttctg tctgagcgta 780
tttgctctaa ttgggctgca gctgttcatg ggcaacctga ggaataaatg tatacaatgg 840
cctcccacca atgcttcctt ggaggaacat agtatagaaa agaatataac tgtgaattat 900
aatggtacac ttataaatga aactgtcttt gagtttgact ggaagtcata tattcaagat 960
tcaagatatc attatttcct ggagggtttt ttagatgcac tactatgtgg aaatagctct 1020
gatgcaggcc aatgtccaga gggatatatg tgtgtgaaag ctggtagaaa tcccaattat 1080
ggctacacaa gctttgatac cttcagttgg gctttttttgt ccttgtttcg actaatgact 1140
caggacttct gggaaaatct ttatcaactg acattacgtg ctgctgggaa aacgtacatg 1200
atattttttg tattggtcat tttcttgggc tcattctacc taataaattt gatcctggct 1260
gtggtggcca tggcctacga ggaacagaat caggccacct tggaagaagc agaacagaaa 1320
gaggccgaat ttcagcagat gattgaacag cttaaaaagc aacaggaggc agctcagcag 1380
gcagcaacgg caactgcctc agaacattcc agagagccca gtgcagcagg caggctctca 1440
gacagctcat ctgaagcctc taagttgagt tccaagagtg ctaaggaaag aagaaatcgg 1500
aggaagaaaa gaaaacagaa agagcagtct ggtggggaag agaaagatga ggatgaattc 1560
caaaaatctg aatctgagga cagcatcagg aggaaaggtt ttcgcttctc cattgaaggg 1620
aaccgattga catatgaaaa gaggtactcc tccccacacc agtctttgtt gagcatccgt 1680
ggctccctat tttcaccaag gcgaaatagc agaacaagcc ttttcagctt tagagggcga 1740
gcaaaggatg tgggatctga gaacgacttc gcagatgatg agcacagcac ctttgaggat 1800
aacgagagcc gtagagattc cttgtttgtg ccccgacgac acggagagag acgcaacagc 1860
aacctgagtc agaccagtag gtcatcccgg atgctggcag tgtttccagc gaatgggaag 1920
atgcacagca ctgtggattg caatggtgtg gtttccttgg ttggtggacc ttcagttcct 1980
acatcgcctg ttggacagct tctgccagag gtgataatag ataagccagc tactgatgac 2040
aatggaacaa ccactgaaac tgaaatgaga aagagaaggt caagttcttt ccacgtttcc 2100
atggactttc tagaagatcc ttcccaaagg caacgagcaa tgagtatagc cagcattcta 2160
acaaatacag tagaagaact tgaagaatcc aggcagaaat gcccaccctg ttggtataaa 2220
ttttccaaca tattcttaat ctgggactgt tctccatatt ggttaaaagt gaaacatgtt 2280
gtcaacctgg ttgtgatgga cccatttgtt gacctggcca tcaccatctg tattgtctta 2340
aatactcttt tcatggccat ggagcactat ccaatgacgg accatttcaa taatgtgctt 2400
acagtaggaa acttggtttt cactgggatc tttacagcag aaatgtttct gaaaattatt 2460
gccatggatc cttactatta tttccaagaa ggctggaata tctttgacgg ttttattgtg 2520
acgcttagcc tggtagaact tggactcgcc aatgtggaag gattatctgt tctccgttca 2580
tttcgattgc tgcgagtttt caagttggca aaatcttggc caacgttaaa tatgctaata 2640
aagatcatcg gcaattccgt gggggctctg ggaaatttaa ccctcgtctt ggccatcatc 2700
gtcttcattt ttgccgtggt cggcatgcag ctctttggta aaagctacaa agattgtgtc 2760
tgcaagatcg ccagtgattg tcaactccca cgctggcaca tgaatgactt cttccactcc 2820
ttcctgattg tgttccgcgt gctgtgtggg gagtggatag agaccatgtg ggactgtatg 2880
gaggttgctg gtcaagccat gtgccttact gtcttcatga tggtcatggt gattggaaac 2940
ctagtggtcc tgaatctctt tctggccttg cttctgagct catttagtgc agacaacctt 3000
gcagccactg atgatgataa tgaaatgaat aatctccaaa ttgctgtgga taggatgcac 3060
aaaggagtag cttatgtgaa aagaaaaata tatgaattta ttcaacagtc cttcattagg 3120
aaacaaaaga ttttagatga aattaaacca cttgatgatc taaacaacaa gaaagacagt 3180
tgtatgtcca atcatacagc agaaattggg aaagatcttg actatcttaa agatgtaaat 3240
ggaactacaa gtggtatagg aactggcagc agtgttgaaa aatacattat tgatgaaagt 3300
gattacatgt cattcataaa caaccccagt cttactgtga ctgtaccaat tgctgtagga 3360
gaatctgact ttgaaaattt aaacacggaa gactttagta gtgaatcgga tctggaagaa 3420
agcaaagaga aactgaatga aagcagtagc tcatcagaag gtagcactgt ggacatcggc 3480
gcacctgtag aagaacagcc cgtagtggaa cctgaagaaa ctcttgaacc agaagcttgt 3540
ttcactgaag gctgtgtaca aagattcaag tgttgtcaaa tcaatgtgga agaaggcaga 3600
ggaaaacaat ggtggaacct gagaaggacg tgtttccgaa tagttgaaca taactggttt 3660
gagaccttca ttgttttcat gattctcctt agtagtggtg ctctggcatt tgaagatata 3720
tatattgatc agcgaaagac gattaagacg atgttggaat atgctgacaa ggttttcact 3780
tacattttca ttctggaaat gcttctaaaa tgggtggcat atggctatca aacatatttc 3840
accaatgcct ggtgttggct ggacttctta attgttgatg tttcattggt cagtttaaca 3900
gcaaatgcct tgggttactc agaacttgga gccatcaaat ctctcaggac actaagagct 3960
ctgagacctc taagagcctt atctcgattt gaagggatga gggtggttgt gaatgccctt 4020
ttaggagcaa ttccatccat catgaatgtg cttctggttt gtcttatatt ctggctaatt 4080
ttcagcatca tgggcgtaaa tttgtttgct ggcaaattct accactgtat taacaccaca 4140
actggtgaca ggtttgacat cgaagacgtg aataatcata ctgattgcct aaaactaata 4200
gaaagaaatg agactgctcg atggaaaaat gtgaaagtaa actttgataa tgtaggattt 4260
gggtatctct ctttgcttca agttgccaca ttcaaaggat ggatggatat aatgtatgca 4320
gcagttgatt ccagaaatgt ggaactccag cctaagtatg aagaaagtct gtacatgtat 4380
ctttactttg ttattttcat catctttggg tccttcttca ccttgaacct gtttattggt 4440
gtcatcatag ataatttcaa ccagcagaaa aagaagtttg gaggtcaaga catctttatg 4500
acagaagaac agaagaaata ctataatgca atgaaaaaat taggatcgaa aaaaccgcaa 4560
aagcctatac ctcgaccagg aaacaaattt caaggaatgg tctttgactt cgtaaccaga 4620
caagtttttg acataagcat catgattctc atctgtctta acatggtcac aatgatggtg 4680
gaaacagatg accagagtga atatgtgact accattttgt cacgcatcaa tctggtgttc 4740
attgtgctat ttactggaga gtgtgtactg aaactcatct ctctacgcca ttattatttt 4800
accattggat ggaatatttt tgattttgtg gttgtcattc tctccattgt aggtatgttt 4860
cttgccgagc tgatagaaaa gtatttcgtg tcccctaccc tgttccgagt gatccgtctt 4920
gctaggattg gccgaatcct acgtctgatc aaaggagcaa aggggatccg cacgctgctc 4980
tttgctttga tgatgtccct tcctgcgttg tttaacatcg gcctcctact cttcctagtc 5040
atgttcatct acgccatctt tgggatgtcc aactttgcct atgttaagag ggaagttggg 5100
atcgatgaca tgttcaactt tgagaccttt ggcaacagca tgatctgcct attccaaatt 5160
acaacctctg ctggctggga tggattgcta gcacccattc tcaacagtaa gccacccgac 5220
tgtgacccta ataaagttaa ccctggaagc tcagttaagg gagactgtgg gaacccatct 5280
gttggaattt tctttttgt cagttacatc atcatatcct tcctggttgt ggtgaacatg 5340
tacatcgcgg tcatcctgga gaacttcagt gttgctactg aagaaagtgc agagcctctg 5400
agtgaggatg actttgagat gttctatgag gtttgggaga agtttgatcc cgatgcaact 5460
cagttcatgg aatttgaaaa attatctcag tttgcagctg cgcttgaacc gcctctcaat 5520
ctgccacaac caaacaaact ccagctcatt gccatggatt tgcccatggt gagtggtgac 5580
cggatccact gtcttgatat cttatttgct tttacaaagc gggttctagg agagagtgga 5640
gagatggatg ctctacgaat acagatggaa gagcgattca tggcttccaa tccttccaag 5700
gtctcctatc agccaatcac tactacttta aaacgaaaac aagaggaagt atctgctgtc 5760
attattcagc gtgcttacag acgccacctt ttaaagcgaa ctgtaaaaca agcttccttt 5820
acgtacaata aaaacaaaat caaaggtggg gctaatcttc ttataaaaga agacatgata 5880
attgacagaa taaatgaaaa ctctattaca gaaaaaactg atctgaccat gtccactgca 5940
gcttgtccac cttcctatga ccgggtgaca aagccaattg tggaaaaaca tgagcaagaa 6000
ggcaaagatg aaaaagccaa agggaaataa 6030

<210> SEQ ID NO 3
<211> LENGTH: 590
<212> TYPE: PRT
<213> ORGANISM: Homo sapiens

<400> SEQUENCE: 3

Met Thr Leu His Asn Asn Ser Thr Thr Ser Pro Leu Phe Pro Asn Ile
1 5 10 15

Ser Ser Ser Trp Ile His Ser Pro Ser Asp Ala Gly Leu Pro Pro Gly
20 25 30

Thr Val Thr His Phe Gly Ser Tyr Asn Val Ser Arg Ala Ala Gly Asn
35 40 45

Phe Ser Ser Pro Asp Gly Thr Thr Asp Asp Pro Leu Gly Gly His Thr
50 55 60

Val Trp Gln Val Val Phe Ile Ala Phe Leu Thr Gly Ile Leu Ala Leu
65 70 75 80

```
Val Thr Ile Ile Gly Asn Ile Leu Val Ile Val Ser Phe Lys Val Asn
                85                  90                  95

Lys Gln Leu Lys Thr Val Asn Asn Tyr Phe Leu Leu Ser Leu Ala Cys
            100                 105                 110

Ala Asp Leu Ile Ile Gly Val Ile Ser Met Asn Leu Phe Thr Thr Tyr
        115                 120                 125

Ile Ile Met Asn Arg Trp Ala Leu Gly Asn Leu Ala Cys Asp Leu Trp
    130                 135                 140

Leu Ala Ile Asp Tyr Val Ala Ser Asn Ala Ser Val Met Asn Leu Leu
145                 150                 155                 160

Val Ile Ser Phe Asp Arg Tyr Phe Ser Ile Thr Arg Pro Leu Thr Tyr
                165                 170                 175

Arg Ala Lys Arg Thr Thr Lys Arg Ala Gly Val Met Ile Gly Leu Ala
            180                 185                 190

Trp Val Ile Ser Phe Val Leu Trp Ala Pro Ala Ile Leu Phe Trp Gln
        195                 200                 205

Tyr Phe Val Gly Lys Arg Thr Val Pro Pro Gly Glu Cys Phe Ile Gln
    210                 215                 220

Phe Leu Ser Glu Pro Thr Ile Thr Phe Gly Thr Ala Ile Ala Ala Phe
225                 230                 235                 240

Tyr Met Pro Val Thr Ile Met Thr Ile Leu Tyr Trp Arg Ile Tyr Lys
                245                 250                 255

Glu Thr Glu Lys Arg Thr Lys Glu Leu Ala Gly Leu Gln Ala Ser Gly
            260                 265                 270

Thr Glu Ala Glu Thr Glu Asn Phe Val His Pro Thr Gly Ser Ser Arg
        275                 280                 285

Ser Cys Ser Ser Tyr Glu Leu Gln Gln Gln Ser Met Lys Arg Ser Asn
    290                 295                 300

Arg Arg Lys Tyr Gly Arg Cys His Phe Trp Phe Thr Thr Lys Ser Trp
305                 310                 315                 320

Lys Pro Ser Ser Glu Gln Met Asp Gln Asp His Ser Ser Ser Asp Ser
                325                 330                 335

Trp Asn Asn Asn Asp Ala Ala Ala Ser Leu Glu Asn Ser Ala Ser Ser
            340                 345                 350

Asp Glu Glu Asp Ile Gly Ser Glu Thr Arg Ala Ile Tyr Ser Ile Val
        355                 360                 365

Leu Lys Leu Pro Gly His Ser Thr Ile Leu Asn Ser Thr Lys Leu Pro
    370                 375                 380

Ser Ser Asp Asn Leu Gln Val Pro Glu Glu Glu Leu Gly Met Val Asp
385                 390                 395                 400

Leu Glu Arg Lys Ala Asp Lys Leu Gln Ala Gln Lys Ser Val Asp Asp
                405                 410                 415

Gly Gly Ser Phe Pro Lys Ser Phe Ser Lys Leu Pro Ile Gln Leu Glu
            420                 425                 430

Ser Ala Val Asp Thr Ala Lys Thr Ser Asp Val Asn Ser Ser Val Gly
        435                 440                 445

Lys Ser Thr Ala Thr Leu Pro Leu Ser Phe Lys Glu Ala Thr Leu Ala
    450                 455                 460

Lys Arg Phe Ala Leu Lys Thr Arg Ser Gln Ile Thr Lys Arg Lys Arg
465                 470                 475                 480

Met Ser Leu Val Lys Glu Lys Lys Ala Ala Gln Thr Leu Ser Ala Ile
                485                 490                 495
```

```
Leu Leu Ala Phe Ile Ile Thr Trp Thr Pro Tyr Asn Ile Met Val Leu
            500                 505                 510

Val Asn Thr Phe Cys Asp Ser Cys Ile Pro Lys Thr Phe Trp Asn Leu
        515                 520                 525

Gly Tyr Trp Leu Cys Tyr Ile Asn Ser Thr Val Asn Pro Val Cys Tyr
    530                 535                 540

Ala Leu Cys Asn Lys Thr Phe Arg Thr Thr Phe Lys Met Leu Leu Leu
545                 550                 555                 560

Cys Gln Cys Asp Lys Lys Lys Arg Arg Lys Gln Gln Tyr Gln Gln Arg
                565                 570                 575

Gln Ser Val Ile Phe His Lys Arg Ala Pro Glu Gln Ala Leu
            580                 585                 590


<210> SEQ ID NO 4
<211> LENGTH: 590
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Thr Leu His Asn Asn Ser Thr Thr Ser Pro Leu Phe Pro Asn Ile
1               5                   10                  15

Ser Ser Ser Trp Ile His Ser Pro Ser Asp Ala Gly Leu Pro Pro Gly
            20                  25                  30

Thr Val Thr His Phe Gly Ser Tyr Asn Val Ser Arg Ala Ala Gly Asn
        35                  40                  45

Phe Ser Ser Pro Asp Gly Thr Thr Asp Asp Pro Leu Gly Gly His Thr
    50                  55                  60

Val Trp Gln Val Val Phe Ile Ala Phe Leu Thr Gly Ile Leu Ala Leu
65                  70                  75                  80

Val Thr Ile Ile Gly Asn Ile Leu Val Ile Val Ser Phe Lys Val Asn
                85                  90                  95

Lys Gln Leu Lys Thr Val Asn Asn Tyr Phe Leu Leu Ser Leu Ala Cys
            100                 105                 110

Ala Asp Leu Ile Ile Gly Val Ile Ser Met Asn Leu Phe Thr Thr Tyr
        115                 120                 125

Ile Ile Met Asn Arg Trp Ala Leu Gly Asn Leu Ala Cys Asp Leu Trp
    130                 135                 140

Leu Ala Ile Asp Cys Val Ala Ser Asn Ala Ser Val Met Asn Leu Leu
145                 150                 155                 160

Val Ile Ser Phe Asp Arg Tyr Phe Ser Ile Thr Arg Pro Leu Thr Tyr
                165                 170                 175

Arg Ala Lys Arg Thr Thr Lys Arg Ala Gly Val Met Ile Gly Leu Ala
            180                 185                 190

Trp Val Ile Ser Phe Val Leu Trp Ala Pro Ala Ile Leu Phe Trp Gln
        195                 200                 205

Tyr Phe Val Gly Lys Arg Thr Val Pro Pro Gly Glu Cys Phe Ile Gln
    210                 215                 220

Phe Leu Ser Glu Pro Thr Ile Thr Phe Gly Thr Ala Ile Ala Gly Phe
225                 230                 235                 240

Tyr Met Pro Val Thr Ile Met Thr Ile Leu Tyr Trp Arg Ile Tyr Lys
                245                 250                 255

Glu Thr Glu Lys Arg Thr Lys Glu Leu Ala Gly Leu Gln Ala Ser Gly
            260                 265                 270
```

```
Thr Glu Ala Glu Thr Glu Asn Phe Val His Pro Thr Gly Ser Ser Arg
        275                 280                 285

Ser Cys Ser Ser Tyr Glu Leu Gln Gln Gln Ser Met Lys Arg Ser Asn
    290                 295                 300

Arg Arg Lys Tyr Gly Arg Cys His Phe Trp Phe Thr Thr Lys Ser Trp
305                 310                 315                 320

Lys Pro Ser Ser Glu Gln Met Asp Gln Asp His Ser Ser Ser Asp Ser
                325                 330                 335

Trp Asn Asn Asn Asp Ala Ala Ala Ser Leu Glu Asn Ser Ala Ser Ser
            340                 345                 350

Asp Glu Glu Asp Ile Gly Ser Glu Thr Arg Ala Ile Tyr Ser Ile Val
        355                 360                 365

Leu Lys Leu Pro Gly His Ser Thr Ile Leu Asn Ser Thr Lys Leu Pro
    370                 375                 380

Ser Ser Asp Asn Leu Gln Val Pro Glu Glu Glu Leu Gly Met Val Asp
385                 390                 395                 400

Leu Glu Arg Lys Ala Asp Lys Leu Gln Ala Gln Lys Ser Val Asp Asp
                405                 410                 415

Gly Gly Ser Phe Pro Lys Ser Phe Ser Lys Leu Pro Ile Gln Leu Glu
            420                 425                 430

Ser Ala Val Asp Thr Ala Lys Thr Ser Asp Val Asn Ser Ser Val Gly
        435                 440                 445

Lys Ser Thr Ala Thr Leu Pro Leu Ser Phe Lys Glu Ala Thr Leu Ala
    450                 455                 460

Lys Arg Phe Ala Leu Lys Thr Arg Ser Gln Ile Thr Lys Arg Lys Arg
465                 470                 475                 480

Met Ser Leu Val Lys Glu Lys Lys Ala Ala Gln Thr Leu Ser Ala Ile
                485                 490                 495

Leu Leu Ala Phe Ile Ile Thr Trp Thr Pro Tyr Asn Ile Met Val Leu
            500                 505                 510

Val Asn Thr Phe Cys Asp Ser Cys Ile Pro Lys Thr Phe Trp Asn Leu
        515                 520                 525

Gly Tyr Trp Leu Cys Tyr Ile Asn Ser Thr Val Asn Pro Val Cys Tyr
    530                 535                 540

Ala Leu Cys Asn Lys Thr Phe Arg Thr Thr Phe Lys Met Leu Leu Leu
545                 550                 555                 560

Cys Gln Cys Asp Lys Lys Lys Arg Arg Lys Gln Gln Tyr Gln Gln Arg
                565                 570                 575

Gln Ser Val Ile Phe His Lys Arg Ala Pro Glu Gln Ala Leu
            580                 585                 590
```

<210> SEQ ID NO 5
<211> LENGTH: 1280
<212> TYPE: DNA
<213> ORGANISM: Mus musculus

<400> SEQUENCE: 5

```
caaagtggac agaggggagg ggaggggatg cgaggggagg ggaggggaat gatcgcgaaa      60

ggcttccaaa ccttgtcctt gtttttcacc atttctgaaa tatatgctga gtgcaactat     120

gggaagacca ttttcataat ctataatact cctcctttta aaggactttc gttaaccgct     180

tgcaaaggtg agtgccgggt agaggacatt agctcgctaa gtccctagaa atcacacttg     240

gagactaagc aggctttccc aggagaagtc caaagccaac ataagcagga ggctgggggc     300
```

```
tggccgttaa ccgcaaggca gtggttgagc cctcgggatc atcccggcgg ggggcgcagc    360

atctccgcca aggccgcagg ctctcaccat cagctgcccg agccaccctg tacctcgcag    420

tccactcgcc ctgcccacgc cccgcgccgc ccgctcacct tcagcccctg ggagtccatg    480

gccgccggct acccggaggg tgcccaccgc tgcccgccgc agggttaggg gttcagaccc    540

acttcccggg ccctcaaacc ctaagggacg cggcgtgcag cacgaggggc gtggcccgat    600

ctccattggt tgtcggcgtg agggggcgga gcttagttgt aggactagga aggagggggc    660

caccggagca ggcgaggagg gaaccccgag ggaggaccgc gagggcgact ggggctggaa    720

tccgctgagc attgagtgct gccgagttgt ggggctagag gagggaggtc cagcctggaa    780

acggcgcgag gaggagggat tgggtggagc aagagatatg agattaaaga ataaagatga    840

tgaagcagca aataggaggg agagccatgc cgcttttcat ccctgcaaac aaaggccgac    900

tccattttct cagcattttt tgtggaagcc gatttgcgca atgcggctta gtacttgacc    960

agggaaaatg atttacctga cacgtgtagt aatcgtgtct gggccacaag gtggcgcaga   1020

aaaatcacag ttcggcaaaa accttgaagc ctggcttggg cttgttctaa atcttttcag   1080

gcgctgctgt aattttgcta ttcgagtgct tattaaactg ctccgccaga tttccacccc   1140

caaagtctta tttaaaaata tgtggttacc tcttttagat ttctatttct taagtgtttg   1200

ctgtagtttg gatctaaact gtccctcaaa gacacacgtg ctgaatgttc cccagcccgt   1260

gtgctgttgg gagtggtgga                                               1280


<210> SEQ ID NO 6
<211> LENGTH: 618
<212> TYPE: DNA
<213> ORGANISM: Mus musculus

<400> SEQUENCE: 6

aatctaacat ggctgctata gcttactgac tagaagttaa gtgcacactt cctaaaagaa     60

ggctttgaca caagccactt cagttccctc ctcattttct tgtccccatt cctctctctg    120

tagaattctg agatttcaat tcagttttat acagaaacca cattactgta agccctacaa    180

agttatggca atatagctat atggagtcaa gtaatgtagg ttattttttt cccaatggtg    240

ctggtgaagg tggcaattat gtagctatac ttagcagact gaggaaattc tgctagagtc    300

agcatttgtc tcttcattgc tatgaaacag taatggaaaa ataaacaaaa acaaaaggca    360

aacactatgc ataattccct cagatcatat taacatgtga tgttggagta aattgttata    420

accccatttt ggaaatactt accttaatta actatgattt ccttaaaata atgcagtatt    480

tacaatctat atgaaagcac tatatgggac acatggtatg atggaacagt gcacccaaga    540

gacaccaaga acattcctgt ctgtggcagt cttttctcta tacagaggca tttagtctca    600

attgctcaga gttatttt                                                 618


<210> SEQ ID NO 7
<211> LENGTH: 832
<212> TYPE: DNA
<213> ORGANISM: Mus musculus

<400> SEQUENCE: 7

ataaaatttt attttcctaa aatttacatt taaaagccat ccaacttacc aaagtgattt     60

caaaccacaa ttacatttta tctcaactac cagcatttta tttagccagg atctacatga    120

gacacatatc atgatgtgct atgtacatct tgttatacag tgttatattg ataacaaatg    180

tcatcaatat aacattgaat taatcttcca taatttatgg ggaaaaaagg agcagcctta    240
```

ctgaagggca aagttataca acagctttac agaagctgca tgcgagtgca gtaccgggac 300
acgggcacgg acggcggcac tataaccatt ttccgtggtg gtaatcttgc tttcatctga 360
cacagaaaag agaccgccgt tttgaaaact cacagaacta gcctcacggt tttgtgagtc 420
cattgagcgc tggctgcgaa gaacggtgtt taactcgaga aatcattgaa caagttttag 480
aaaataaaga tgcttatgac aatttcaaac ttgaaggtct ccaaagaagg actgagatat 540
tggtgagagg agtaaagaga atcctggtgc atttatttca tgcttccttc tgttcgaaga 600
tcattttgag gtttataaaa ggtggggtga tccaaaaatc tccaggctga gagtcctggc 660
tgaggctgtg aactgggctg cagagaaagg gccacgcctc cctcctctgc tcgcattact 720
cagcagcttt tctgcatgtg gctggctgca gacaatctaa acccttccgc tgtcgctccc 780
cccttatact gttctgccaa aaggaaggca gagaggaaat cagctacggg gc 832

<210> SEQ ID NO 8
<211> LENGTH: 261
<212> TYPE: DNA
<213> ORGANISM: Mus musculus

<400> SEQUENCE: 8
tctgacagag caagtcttga cctgcttaac attatgttat gctagtcatt ttaaaatgag 60
tctttatttc ccatagaagg tcagtttttt tacattatta tataatcttt tgacagaata 120
acaaataaca ttctgaatgt ctcatttcta aatacaaaac atcttagtat aaaattatgc 180
attgttttaa atgcttggaa gtaggtccac atgtagaaaa caaagtacgt atgataaaaa 240
atatcaaaat tgtatattca g 261

<210> SEQ ID NO 9
<211> LENGTH: 663
<212> TYPE: DNA
<213> ORGANISM: Mus musculus

<400> SEQUENCE: 9
aatgttttga tatttaggag aaaattgcaa aacaaaatga tgacagtgtt tgaaagtgtt 60
tgatcagtgc caagcatcac tttatgtact tggcaaacat gacttgaggc cttaagctgt 120
gatttgcaaa tgtagattgg aatcaagatc tttatagatg aggaagcaaa aatcagaaga 180
caaaataaca ttatcaactt gatctcatgt gcagccaggg ctgaactgca aatgctgatt 240
tgccccagtc tgggctcctc aaatcgttcc ttggaatcct attagttgga actttatctc 300
tgctcgtggc agggtgcctg ggaccatgtt tataaatatc tgctgaatga agaataagtg 360
agtcaatcga accagaactc actttggtta gttaatttca ttcgtggtat ttatggagag 420
cagaagaaag aattccagag acacgatttg tcaaaactct ctaaagaaaa tgatgacact 480
atatattgat gaaaatgaat gttcttgttc ttgctttatt tgattttctt gtccccccac 540
tccccatctg ctagggtctc attacagcat agttcttgaa tatcccaggt tgacctgaag 600
ttacaatata ttcttgattt agatggcaga cattgggaat attttgactc ttaaaattta 660
ata 663

<210> SEQ ID NO 10
<211> LENGTH: 606
<212> TYPE: DNA
<213> ORGANISM: Mus musculus

<400> SEQUENCE: 10
ttgtcacttt gttactctac agtgttgcct ggagttcgat acttcattac tctatagtgg 60
ggtgaagaag ttcaccttct tattttcatt tccttccctc aatgatttct tcagagctag 120
ctcttaccag ctagaaattc ttcaaacgac actcgtgcct tccttcacac aggttgaact 180
atttgtctct aatgccctaa agtactggtg ttcaatcttc caggcacttc caatgatctg 240
aaatctgacc tgcttaggtc agctggctct gagattatgg tattctagtc ctcaaaccaa 300
cctgttggct cgttggtttt gtaccaaaca cactgactta catagctcaa aataccactg 360
gccttttaaa aatggcatat cacattccag gggaggatca aaactgctgg ctggtgatat 420
ttgtcaagtc tctcaaagtt gcactttcca ggattttcaa ttcactgaat tcttagacag 480
acatgtttat gtgaaagaat tctttatata ttttttctcc tctttgagtg ggcaaatgaa 540
aatcttgacc tctgggttcc ttattttatt tgactctctg tagtatttaa atcttaaaat 600
tttcct 606

<210> SEQ ID NO 11
<211> LENGTH: 2430
<212> TYPE: DNA
<213> ORGANISM: Mus musculus

<400> SEQUENCE: 11
gatactgtat aattaattag gcctccaatc atgccttccc agcctccacg gatggagaaa 60
ccctctccgc catgccttaa agaggaattg ctgtaataaa tgagtctcct gatagcaaat 120
ttctcagcaa gggggaatcg cgtaaatgga gacatagtat tgacagcaaa gtccaatgtg 180
ttatttttac cagaacgaac tctccggttc aagcctttga aagagacatt tgaaaaccaa 240
aaacaaacaa tgtaatggag cgaggaaaaa agccacagaa gtgagtggca gggagtttaa 300
aagagcagat gccactgcca ggtctatggg acataaccag ccacttgtgc tgggtcttgg 360
cagtttataa tgctacctca tcttctccgc gaaattgttt tcccgtaaat ctctgtggcc 420
atccattcct gtctacacat tatgttccta aaatagacac catctaaaaa tcacttcaag 480
gagctttgtg gaggaaggcc taaattgcaa cactcctcca gcgaagatag atgcagtgtt 540
tgatggcatt accagtcggt agccaggaag gggagtttgt gaggagtttt tccaccacag 600
ttaatctgtt tctggaagga aagggaagtg tcagacttcc cgaggaggca aacgtgtgtg 660
gaagctctca tttgcatcac ccccggcctg tcaggtattg cagcaaaagg gagaggtgag 720
ctaccctggc tctccttggg caggagggac agaatcagga agcatcaacc tcagcatgga 780
attttcctat tcctgtttgg catcctcctc ttgggatgat ttacagcgcg ggttggagaa 840
acacgctctg ccactccact agcgcaccag atagacagtg cagacctgca gatccatacc 900
cgaggagaag ccacatttcc tacgtgtgat agcaacagcg tttggcaatt tgcgactttg 960
ctactgcagc ttagaaaata tttagtcaca tgcacatctg aacagaaaga cacccaggct 1020
tgactcagtc atttccgtca gacacacgaa agaaaaagcg tctctgctca caagcttatt 1080
tggactgctt tgttgaaagg aggggcggca gacactttgt agatgtggca agagggcttt 1140
atatccagac ctcaaacagg taggagagaa ggaagccagg agaggtaagg aaggggcgtg 1200
gaaaagcctc acagccacct cgaagaaaac agttttttg ccctgttcag aaagcaagag 1260
gttccacagt ggttttgtgt caatggagca catctgcagt atcattgccg ttggtgacct 1320
ctgtctaatt aaaagtaagt cagtccttcc cacccggcat tgtctgaaac ccgggactct 1380
ttatcacttt gctaaagttc atttgcaagt gtagttaagg aagagtcagg ggggaaacag 1440
catctgtccc ttctggtcct ggggaggagg cactcctttc caagagtcaa gcctctgccc 1500
aaagaagctg cctcccctgc aatgctagga tccaggagca gccccgctgc cttcttgctt 1560
cctctgtgag gtctaatttt tgcatcatct ttaggagcga tatgacctct attcacagcc 1620
atcgaatcca gttccaaagc accaatgaca gagggggctt caagacaaga ccttgcctag 1680
gaggatgcag gcaagcaaag gcaagagctg gcccgatgcc aagttatttt aggccaaaga 1740
atctcatcct tctatcaaaa tgctgaactg caaaacgaac ctgatttcag ttcatggaag 1800
gttgagagga ggaggagggg gaggggagga ggaggaagag aggaggaggg gaggaggagg 1860
gaggaggagg aggggaggag gagggggaca gttggtccga attcacatgc aaaaatagac 1920
ttcctgttct gccccaactc ttatttccgt gggctcttct ccccaaggat ttaccaggta 1980
agaattcacc accaaagaag atcacaatga gataatcaga tggcttacct gataaaaagg 2040
aaaattatcc atctgcagtg aggagcaaca tctccccacg acgagtccgc accttccgtt 2100
gcaacgattc agattccttc ttgcaaaagg tgaccaagtg cttcacaagg gctgcagcct 2160 catagggca gaacacacgt acacaaacac acgcacacac acacacacat gcaccagaga 2220
cctctgcagt atcctctcgg cttcatcctc gcctcactct atggtaccta atacaaatca 2280
gcaaatagct tgttttaaaa aaaaaagaaa gaaaaaaaag cggagacagc acctaacgtt 2340
acagtgccat ctagtggcta catcgtaaat aggttctcac agcctggatt tctgtgttct 2400
ttctcaaccg cttccttctg gttccttttt 2430

<210> SEQ ID NO 12
<211> LENGTH: 1644
<212> TYPE: DNA
<213> ORGANISM: Mus musculus

<400> SEQUENCE: 12
attgatctcc aactttttaa atccctctgt cattttaaat gaggtgcact cggttgtgtc 60
atcatctcgg ttttaattgt gtgaaaattt cctgccaatc tcacaccgct gcggcaacct 120
caccttgcta cttgccctgc aagttctgca gtgtgccgtt ctgagtatgc cgttttaact 180
agttcttgca gcaggacaca aagcgagata gtctgataga accagttctc ctctggtttt 240
acctttactc ttagatgagt taagggtcac atcaaaccag ggctcagccc gccagatctc 300
ctaagcacag cccctcctga cccaatgcag ttaacccaac ctcattcagc gctagtatca 360
aatgacactg gagctgctgc agtatgcatc ccgagactaa gtaggcagga tttattatca 420
gcagaagtcc cctaactacc aggttattca agctccgttc ttgtcacaaa caggcgcggc 480
ggaagacaca gtgcagcaga ctcagagctc atttacaaga caagcgaatt ctcagttaga 540
gacaagggca gcgcggcagc gaactgcagt aaatcttttc acgctcacag caacatctaa 600
caatgctctc ctgcaacgcc tcagatcaaa cgaatcctac ttggtttaaa catcaaatca 660
acaccataaa aaaggcttca ttagcaaagt tcaatttagg atgtttttaa tcgtgtctta 720
attctagaac cagtgcgaga ctttccatgc ttattcaagc atgctgacag aattggaacc 780
tcttagaatt gcctacctgc acctatcagc ctggctgaca ggagcccgcc aaaggattaa 840
aaaaaaacaa aacccaaaac ataaaatcat gcaaaaaaat atttaccccc gaaagatgta 900
tgtagttaaa gctcagcttc ctgcagcctc gatagcccct gaagtgttaa tctgaagaaa 960
cagttccatg agtttccaca ggccggtagt gagtctccta cacttgacct agacagactt 1020
acataatgaa gcatcagtgc tggggagctt gcacgatgtc atcaccagca agagtaagaa 1080
gtattggcag cagcaagcag gcgggcaggc tgagatcttg catggaaatc atgaaccagg 1140

```
tcttgctttt cgtttttgaa acgttttgga aggagagtta tgaatagccc agaaataggt   1200

ctcattttgt gggtaggaag aatgaccaga agcatgaaag ctaaatctcc tggcaagtgc   1260

aggggacctc tcttggagtg tgcagtaaac ccgaggggac gacttctcct gctgtcaact   1320

cctgaaccat cacatctgga gtgaaggaag gggctggtga agccttgtaa taaatgcaaa   1380

ggatgctgct gagagctttg gtctgccttt aactcattgt ggtgagtaga ggggatgtgg   1440

cagtatgcaa tgagagttgg ttgtgtaggt tgctttgcag agtaataacc aaaaaaaaaa   1500

aaatctgtga agtgctcaat actttagaca cattttaata aacaagatga tagtaaaatt   1560

actcttctcc atcaaattga gactgtgctg ggttaaactg ttttaatgca ttttaactcc   1620

tgatgttcat ccaagtaata agag                                          1644
```

<210> SEQ ID NO 13
<211> LENGTH: 521
<212> TYPE: DNA
<213> ORGANISM: Mus musculus

<400> SEQUENCE: 13

```
atctcaagtg tatgtaacat gagctacagt cttaaaacct acaaacagta catccagtct     60

cctaccatga ttctgagtgt gatgatttca tatgagcaca agatgacatc atactattta    120

gttatatgta aaatcatggt cttacatggg ttgtggacaa aaccatctag ttttggaggt    180

gacagaaata gagaggacgc catgcactac ttaaaaataa tcgcagcctt cttttcttag    240

ctagggagtt tgctgctatg agccacatta agaccagggt gaggagatga gacgatacag    300

gggcatgaaa gaacacggtg atctactttc tcctgttaat taacgagtaa ggaaatagac    360

attaaaagaa gttaaatgtg tctgagccaa cgtaggtgag gtttccccca aattcacctg    420

gtagttttgc tactgcagta tagtaaatac ttgttttcat ttgttttttt tttttgtttt    480

tttttgtttt tttgtttttt tgtctttttg tttttttttt t                         521
```

<210> SEQ ID NO 14
<211> LENGTH: 547
<212> TYPE: DNA
<213> ORGANISM: Mus musculus

<400> SEQUENCE: 14

```
tattgcaaaa ggaaggaatg agacagttta tgcagagcta agggtttgtg cgttattatg     60

attaatcaca aggacagctg ccaagcttcc atcatgacaa tattctctgg gagaattcat    120

caggttctac tgtctattaa tttctgttga tgtatcttat ctggcatctt caatgacaga    180

ggacacttgt tagttttttt ttttaagtga aggttaaaag acaaagttca ttaaagaaat    240

gatttatata tgacatttaa gaactagcaa tgtcattgct tcaagaaaat tatgagaatt    300

tagtcttggt aggagtttac accatgtcct tgaagtgtct aattatgtga cttgatagtt    360

ttacttagta catatcgatt aggctgtatc tattatttat caagaaatta tggaaggagg    420

caatgtggca taggcataca cattctgatt ttaaaataat cctgctttta ccattaactc    480

cttctcagat aattctgaat acatatcttg tctatgaatc tgtgtaatca tggaaaaaga    540

aaaaatc                                                              547
```

<210> SEQ ID NO 15
<211> LENGTH: 1760
<212> TYPE: DNA
<213> ORGANISM: Homo sapiens

<400> SEQUENCE: 15
tctaatggac atacagtaac ccttcataaa tatttgctga acgagtgatt cagtgaacaa 60
atgaatagag aagaccaaca tccgaaaagt tattttattt tcaagcctca tgtctttaac 120
tgttttatat cagccttttct taagttgacc gtcattaata tttgctgaat gaatgagtca 180
gtgataaaca gagaagacca tcaccctaaa ataacgaccc ctccactttt aagtcttacg 240
tctttaatgg gtttcatata atctttctgc gctcttttta ctgtccagtg tgggagctga 300
cactagtttg ccttaagtcc ttaaaaatcg cacccggagg cgcagtgtca taggtaaccc 360
aagctttcct agtaaacatg atacaaaagt aaacacaacc aacagcatgg ggaccagcaa 420
ttcagaaaca ccgagcgggc gggctgccca gacctgggct tccccagcag ggcccgcgga 480
gaccggccgt gagcagaggc tgcaggccca ccccgcaacc cgagcagccg gggcaccgca 540
gggaaacagc ggcctagcga agccacccga gctccctccg cgcccccggg ccaaaaggcc 600
gcaaaggaac tccgcccgcc cgcccgctca cccgctcacc cgctcacccg ctcaccttca 660
attcctgcga gtccatggct gccccgaggc cgggccgcgg ggctctgggg attgtctcgc 720
cgcagcctaa aggaagacgc agaattcagc tcccctagcc tcccggagcg ctctagcgcc 780
ccgggcccca gcgggagggg cggggtcgcg ccgcgattgg ctgtcggagg gagaggcggg 840
cctgtgtggc ggggatcgtg ctgtaatgga gcaggggcgg cggggacccg gaggtgaggg 900
ctgcgagggc cgcccgggag ggtccgggct gggaaaaggg cctccgccgg agagtgcagc 960
tggaaaagga ggtcacactg ggaaacggct gtctgaggac agtgggtggg cgggccgagg 1020
aaatggaatt caggaataaa ggaaacggag tatgaagaag ggaagtctg tttcctgtca 1080 ctggttgtaa aggaagacac cattttctgc acgtttgtct ggaggcggat tcccgcagtg 1140
cggctctcag caaggctctg ccggcgcggg aaaaagcggt caactttcac gtgggcaagt 1200
tgttttacgg ccacaaggtg gcgcagaaaa aaaaaatcac acgttcttaa cagaaatacg 1260
gtgcgcttgg gcccgtcttt gcaggcgttg ctgcaatctt tgttagaatg tgtgttcaat 1320
tagccctttt ttaccagccc cgataataag agggacaaat aaattaaact tccagaaaat 1380
tagtgtcttg ttttcaatga tactactgat tttaaactga gaataaaatg aatcccaatg 1440
caaattttta tgtttgcacc ccattaggca actcaatcag tcacacatag atttcttaag 1500
tccaggaaat taaatggaaa tataatagac taagattttc tatttctgct taaataaata 1560
tttaaaatag tgcataaggt ctgagattta agtgatcttt gcagaatctt tcacgtggat 1620
tccaaatttt gatcctagtg ttaattatct tactttagtt gacatgatac gtagttgcct 1680
tttccagatt ttaagtttct taaggagttt ataaacattg actttttccc catgccaata 1740
ggttatgtaa ggacagtctt 1760

<210> SEQ ID NO 16
<211> LENGTH: 850
<212> TYPE: DNA
<213> ORGANISM: Homo sapiens

<400> SEQUENCE: 16
agtgtgggcc tcccagggct gtttagctag caatgagaga ggcactgcct atatccaagt 60
tgtatatggc aggttttgca caaagtggat tactcgaaga gaaagcctaa tggccagtct 120
attcatcttc ccctttctcg atgttcatct tttctctccc agctctcctt tattctcaat 180 tttcttttttt ttttttttt tgctcagcct ccatctcact tccgttgctg tcctctcccc 240
accccttccc actctggact gtgcctctcc tttgtagaca cttcaagtcc attctatttc 300
attcaaaaac catggtctag aagtaactta atgtaaaccc acaaagatgg agacagaatg 360
aatgccattc ttcttgctgc tctctcagac aatgcaggtc atttttgcct atggtgctgg 420
taaagccagg agttatgtag ctataagtag cagccagagg aaatagtgcc tgagtcagca 480
attgtctttt tattgctgtg gggcaataat gggagaaaaa atcaggcttg gtacaattcc 540
ctttgaagga aaaagatgcc aacactagca ttttaacaca aaatgctggt tgggggttgg 600
gaggaaggat gcttacattc cttctttgga aatatctact ttgataacca ttttggtaaa 660
ataatgcagt gttttcagtg tgcaaatcct ttcaggactc atggttgtat ggcagacgca 720
cctgacagca ataatttaag ggtaccctga gaatgactct gtggtctaaa aagaatgtgt 780
gtttggaagt ctgaggtaag aaatctggct ggaagtggcc aacctggaaa tttgctcctt 840
attattaagg 850

<210> SEQ ID NO 17
<211> LENGTH: 845
<212> TYPE: DNA
<213> ORGANISM: Homo sapiens

<400> SEQUENCE: 17
atagtgcaaa gtttaaattt cattttccta agatttgttt taaaataaca cgatttaccc 60
aagtgatttc aaaccacaat tacattctgt ttaaattact aatattttat tgcatcacaa 120
tctgcatgaa acagatgtca ggatataatg aactaacctg cattgtattt ttatttttgt 180
ctcctgtggc ataacgattt cataggaaag agaactacac agctgactga ctgatgggga 240
aagttacaca atggatagct ttgcagcaac atactaatgc ggtagggaga tgctgcagag 300
aggctagaaa taaaatcatt tctttccgga gcagcactgc ttgctgtcgg ctgagacaaa 360
aaagagattt cctttttttc ctttcttttt tttgaaaact cacataacat taattctgtt 420
aagcactgga tacacggaaa ggtgtttacc ttagaaaatc atttagcaat ttttagaaac 480
tagacatata gcaattttaa atctttttaa ctatctaatg accaaagcag agggtcctca 540
caagagggat ttagatgcta ctgaattgaa taaagaaaat atggatacat ttattgtatg 600
ccttattcag tttgaggttc attttgagtt tagaaatagg gatataaaaa catcaggggt 660
taaatagcat gggtaaagga catgaaccaa gctgcagaga agaggctgac tgcctgctat 720
atttgcaggc attactcagc acttttctta aaccgataca tcttgctggc tgcataagca 780
agacaagacc cttttcccta tggctcagga aggcagagaa gtcaacttca gccttgaaaa 840
aggca 845

<210> SEQ ID NO 18
<211> LENGTH: 268
<212> TYPE: DNA
<213> ORGANISM: Homo sapiens

<400> SEQUENCE: 18
tgccagacag aacaagtttt agtgtagttg atagtaagtt gtgcccagaa tattaaattg 60
agtcaaattt attttccaca taaagtcaca gttttatatg tcattatata atctcttggc 120
agaaataagg aataacattc tgaatgttgc actccaaaat tcaaagaatc ttagtataaa 180
aatatctagc attttagatg tttcaaagta gggccaaatg cagaaaataa gttggatatg 240
ataaaaatac cagaaagttc tattcagt 268

<210> SEQ ID NO 19
<211> LENGTH: 895

<212> TYPE: DNA
<213> ORGANISM: Homo sapiens

<400> SEQUENCE: 19
catgtaaaat taatatgatc ttttagtcac ttagaaaaaa taccataaag aacactaata 60
gtgtttaaaa gcatctaccc agtgccaaga actgcattat gtattggtga acataacttt 120
agactttacc atacaacgtg aaaatatata ttattatcac tattttacag atgaagcaat 180
aaaagtcaga aaaaatgtag ctaattaaag tgatactgtg tatagctaga gcagtgtata 240
gctagagctg atttgtctga ctctagccct agtttctttc cattatatca atttcctgga 300
aatgtatctc tgttcatggc atagtgcctg acactatgct tattaatatc ttttgaataa 360
aagaaccact gagtgatttg aaataaaact aaatttagtt agttaatttt attggtggta 420
tatagagata gtaggaaaaa taattgaaaa gagacataaa cagatttgcc aatactttct 480
aagaaaaatt atggaactag agtttagtca aaatgaatgc tttcattgtt agaattcaac 540
tttaatcttt gcagaataca aacaaagacc cattttctag aagaagtaac agggaagaga 600
gagtaagaaa gagataatga tgaacattgt ctaatgttac agcataatct agtaaggtaa 660
gaacagaaga gagttcattg acttaccaac atagttgtcc ctaatcacct ctgtgaacct 720
agagtgctac gatataataa tgattgtggt ggtttaaaaa gtaaatgggg ctgggcatgg 780
tggctcacat ctgtaatccc atcactttgg aaggctgagg caggtgtatt gcttgagctc 840
acaagctcga caccagcctg ggcaacatgg caaaaccccg tctctacaaa aaata 895

<210> SEQ ID NO 20
<211> LENGTH: 666
<212> TYPE: DNA
<213> ORGANISM: Homo sapiens

<400> SEQUENCE: 20
tccacttttt gctattccac agagatttca ggaagaaaaa tcacactcct attttctttt 60
tctttgctta ctgatttcta tttagtttct tttttttttt tttttttttt tttttttgag 120
aaagcgtctc actctcttgc gcaggctgga gtgcagtggc tagattcttc ttgagtatgc 180
tcaaacttcc tttttggaat gtcttccaaa ggcactcttg ccttcatttg tacaagttga 240
ttgacccttt aaaggcctta aatattattg tgcgacctca cagactcctc aaatcacctg 300
aaacctgaaa tgctgaggcc caggtggcac tgaaatgatg gtattctaga cctgacaccg 360
gactgttttc tccttggttt tgtcccaaca cactgacata catagcccaa aatactactg 420
gcctttttaa gtggcatatc acattccagg gtaatatcaa aactgctgcc tggtagcatt 480
tgtgaagtct caaagtaact ctttccagga ttttcaaatc cactgaattt cttagattga 540
aatatgtatg tgacagaatt ctcttagctt tctttcctct atgaatatgt aattggaaac 600
tctgagatcc ggtttctcat ctttattgga ttttttcttt aatcttaaaa ttatgaatat 660
ttgctt 666

<210> SEQ ID NO 21
<211> LENGTH: 5125
<212> TYPE: DNA
<213> ORGANISM: Homo sapiens

<400> SEQUENCE: 21
tggcaaaaac gcaaaacgtt gatggataac ggtgatgact tacacaacaa tgcgaatgca 60
tttaatgcca ctgaacagta cacttaaaaa tggttaagat gatgaatttt gtgttatata 120

-continued

```
tgtttcacca caatacaaaa tattctttaa aaaagacttt tggaaatact gtatctactt    180
aattacagga tgtcaaacta atacaggctg atagtatcat ttgtcccctt gacacacaat    240
cttgggtcca gagattttgt tcaccacacc ttttagcatc actaaaaagg gcacaataag    300
aatatggttt cagaaaaaga caattcaaat attggtcttg tcctttagct atgtgaattc    360
aatcaaatta ctcaaattct ttgagtccaa tatacttatt ttcttaaaat aggattataa    420
tattgactgt aggagtgcta cagaaataaa ggcatgaaaa atatttataa attacaaatg    480
ttattaataa tatttatact tccaaaaatg ttgacaagaa atagagtaac taccccataa    540
taaagccaca gcatctggaa gctatattgg attaagcaag aactaaaggt taaaatttcg    600
gattaaattt tttttgcatg atactgctag tattatcaac attgggaagg caatttcttg    660
aatatttctt atatactatt gaaatgtatt cattattagt tcaagttata attaccagtg    720
acagattaaa ttacattcac ttgtctttgg ttaaccatga catttgacag aaggcaaatt    780
tctgcactta agaaatgtat taaaaactaa aatgtatatt accttctaaa aaacttagct    840
ggtccatctt tattgatgaa tagtaggaag atatcaaaat agttataggg tgatgagatg    900
tggcaagcat gcagtgctat ggtatggtat tacaaagcac aggattctta actttgcctg    960
gaggagttgg gaaatttcac ataggagttg acctttgagc agcctcaagg ataggaggaa   1020
gatcttacta gacggacaaa ggcattccaa gtagcagaag gcatgcgcca agagggaagc   1080
agagaacagt gtggggagtg ttggtaactt tgatattatt aaagcggagg aagaaggata   1140
agaaatataa atggccaaat aatttgcggc catattatta ttaaaataat gctatgattt   1200
tagactttat cctgaagcac taacttaaat tttaagcaaa gggtaggttt tgatttttag   1260
aactgatatg ctagtcctat gatgacctgg agcagccaga acctagaagc tggaagatga   1320
gttgggaatc tgcactagtt cagatgagag gtgataaggg tcttcattag agcagtgggt   1380
taggatacga cagactggat gtgttagcta gctatcaagc aaacagagct gaggagacat   1440
gttaaccaat tagtatgaag gaaggggaaa gctcaaggcg atctggagat tctgagagag   1500
aaaaggggca atctgtcgtg agagcagtaa ttagatctag aagaggaatt tttcaactac   1560
ttaaattagg tcaaatttgt atggtacatt tctgaaataa gctaaaatag agccttaatc   1620
taaagtacaa gatgagttac tgaggataac caataatgta cacataaaat gaacggagat   1680
gcatgtttta gagtaattcc aacaaaatag atctgtggat aagtatgtaa ggtactagta   1740
agaataaagc atacaacaca agattaaaaa ctcttaagat taaaaatatc acatagacaa   1800
taaaaattta cttaaaattt tgtggttgtt tttgagacca agtctcactc tgtcaccgag   1860
gctggagtgc agtggtgtga tcttggctca cggcaacctc cacctcccag gttcaagcga   1920
ttctcctgct gtgtttttaa ttgacttggt gttttacagt cattcactga tccattcaac   1980
caataaacat ctatgttgcc acatccatgt gtgtggcatt ttgtctgata ttgggaatat   2040
ggtgtgatcc ctgaactcga ggagtctaca gtgtaataaa gaacacaaat atgcacataa   2100
atatttttag taaaatacta taagtaataa agacgtatgg acaaagtaac cgaggattag   2160
ggttaccaac tcatcccagt ttgcctgtga ctttctgtta gcatgggaag tcctgcatcc   2220
aggaaaaccc tttgctccga ggcaaatcta ggatggttgg tcatgctacc cagcaccaca   2280
taagacattt tttaatgtag gtggtggtag tgggatgcag atttactttt ttattttccc   2340
ccaagaggga tatattttag attatgtgtt tggaaagaga aaagggataa ggaagctaaa   2400
gttcatttta ggcaaaagga aaaaacccaa gcaaagactt ggaagcatgg ttgtatgtca   2460
tttggtgttg ctggagtaca agatccttat attgcattta taaaaaattg cttttatatt   2520
```

tgtttacaaa cagtccaaag cagccagtct actaagccaa ttttttttggg aaaaaggctg 2580
ctgccaagca acagaaactt acgtgaaaca aaacccacaa gacacatgaa gacttcttca 2640
aatcttagaa aactataatg tgtgagattc ttcaaatctt agaaaactat aatactttta 2700
atgacttaaa atattcacag tggaagaagt ctgtttttta aagaaataaa gttagatcat 2760
tgtctcaaag ggaaagactg tgaaatggga acagcttgag atagaatgaa tatattatgt 2820
atattacttt taaatggtag tttagagaag aggaataaga gaaaacagtg tggaacacaa 2880
ggtagaaatg gcagggaaaa aaacgataca ggcctgaaga aaataaaagt aggtttgggc 2940
aatgtgggtg gcaagatgag cccatatttt ggacccagag tgagtggaag aggtgagatg 3000
gtcaagtagt tcacagcatt cttttaaata acatctgagt atactctgga atagacaggg 3060
caaaaaacaa atgaaattgc ctgtggtagt ccccatatta aataaattta atttatttaa 3120
ttaaaaaact caaagagtaa aaataataaa gagaaagtgt tgatattact gtaaaaaaca 3180
gaccatattt tctcctttca atttttgtgc tcgctgggga tattttattt ttaaatacaa 3240
actgatgttc tctaaattca aacatctttt tattaaaagc gttactagag gtagcctgca 3300
gagcatatct agttctttga gttgccctgc ttgaaggatt gccacctctg tgtctctgag 3360
gctctgagca cagatgccta gggcatcagc ctgagatgaa ggtggtgggg tttagaagaa 3420
ctgaaacaca gctctaggac ttcctctgcc atttcaaact ctttttagta acacaggtag 3480
taacatacag tcatgtatta gtcaaacagt tcccacctct ttctttttct ctttcctctc 3540
ctccctccat ccctgcttcc ctttcttcct tttctccctc actcttcttt ccatctagta 3600
tttgttgagt actaactagg ccagatattc ttctaaattc tggaaacaca gcagtgaagg 3660
acaacgtttc tggtcacttg atgcttccat tctatgattt gtagtttttt gcttttgttt 3720
cacaagggct acacaaaacc caaaaatcct aaagccaaac cccaaaaact caactgaaca 3780
gaaaacagga taaagggaca gagagcaaga agtggtgcta cttgatgtag gccagtgagg 3840
gaggggcatt ctaaggaaga agcagcacca gagcaaaggc acaaaagaaa atgaggcagc 3900
agccagatag acctgtggga gcagcatatt ccgggaagta gaaacagcaa acaaaaaggc 3960
tcaaggctgt aattggcttg ggcttttgcc tacctagttt ctgttgtccc tttcttcttt 4020
actatcagaa ttctgatttt attctacagg gtattagatt cagctaaaag ataacatttc 4080
ccaccttctt ttgcagccac ggaggtgata ctactaaggg ttttttttgtt tgtttgtttg 4140
ttttgttttt aataaaacga tgatttgctg gttgggaagc ccttttgccc agctctgcac 4200
ccaccttccc cacctgggcc ctggaacatc aatgcccagc actgcggtgg tcatcttgaa 4260
ccatgaggtg atgctcaggc aagtcagggt aacaacgtag aacaaaaaga gagaaggctc 4320
tggtttcctg atgatactgt ggaaccgcca caccagtccc tacacagtgt acttttcatt 4380
tcttttacag agagaaaact aaaaaccgtg atttttagcc tagaattttc aggggtatct 4440
ctgccatttt caatgaaagt atttctaaat tcttcatagg ctagggatgg aaacacagat 4500
gagttatgac gacgctgcaa taatctatgt ggaagatggc aatgccttag accagggtgg 4560
cactaacaga ggtggtaaaa agtgatggca ttctaggtat actttgaatg tagcactaac 4620
aaggatttgc tgatagactg gaggtgatat atgagagaaa gatgagacaa aggttaactg 4680
tgaggtctgg gccggcacaa cagtgagcag tgatgccagt cactgaggtg agaggtgggg 4740
gtggagcaaa cttagaggcg agggaaagtt caggtgttct attttggaca tgttaagctt 4800
gagttactcc tagacatctg agtgggaatg caaagaggca gaggtgtaca tgagtaaggg 4860
ctgcagataa atgtttagga cacatctgca catacatggg atataaagcc acgcacctgg 4920
acaaagtcac ctagggggtg aatatataaa aagaaaggga gttcaggaac tgaagctacg 4980
agtgttctaa tatttaaacg tcatacagag aagagaactc caaaaaagga aactcaaaca 5040
gcaggcaatg ggcaaaaga agaactgagt gagtttagga tctcagagac aaatgaagaa 5100
agtctttcat tgtggaaggg aataa 5125

<210> SEQ ID NO 22
<211> LENGTH: 1637
<212> TYPE: DNA
<213> ORGANISM: Homo sapiens

<400> SEQUENCE: 22
tttgtcttca actttttaaa tatccatcta ttttttagat tagatgccat ctgttgtatt 60
atcatatctg gttaaatctt attaaaattc ctggccaata tatcactctg ctgcggcaat 120
cttaccctgc tacctctcta ggcttttctg cagcattcaa taaagagcct gctattttaa 180
ctaattgctg aggcaggaca cagtgtgaga gtctaaaaca gaatcagcgc tatattgttt 240
ctacttttac ccatagagtg aacaactgtt catatcaaac ctggaatcat cccttcaagt 300
ctcctaaaca cagcacagtt tgagccaatg cagttaatcc accctccttc agtgctagtg 360
tcgaatggcg cttttgctgc agtattcacc ttgaaactaa gtaggcagga ttcattattt 420
gttgaagtca cctaactgcc agtttattct tatacgatca caaacaatca caacagaaga 480
caaatacagg catatatata actcacttac aagggaagca aatttgcagc cagagacaag 540
ggcaacgtaa cagccaagaa ctgcagtaaa tctctttgag ctaatagcca cctctaataa 600
tgctctccta caacacctcc aatcaaataa attgtattca gagtttaaat atcaaatcaa 660
cattcattcc ttgatggtta cagatgatgt ccgataagca aatttgaatt tatgatttat 720
ttactcctta agtgtctcaa agccaggatt actggaagac ttactatgct tattcaagca 780
tgctgacaga actgtaatct cagtaatttc tccctgcacc tctcagcatg actgacaggc 840
atctgccaag actgtagtac ataaactgct gaaacatgca aaaatattta cccccaaaag 900
atgtagtaaa agctcagctt cctccagctt ccataacccc tgaagtgtta atctggagga 960
acagttccat gagtttccac aggccagcag tgtgtctcct acacttgacc tagacagcct 1020
tacataacga agcaccagtg ctggggagct ctctgaatgt catcaccagc aagagcaaga 1080
agtattggca gcagcaggca gccaggcagg ctgggagttt gcatggaaat catgaagtct 1140
ttcttgtctt cctcttttga aatattttgg aaggcgagtt aagaatagct cagaaactgg 1200
tctcattctt tttgtgggaa gaatgaccag aagcataaaa gctaagtctt ccagcaagtg 1260
caagacacct cttttggtgt ttgcagtaaa cctaacaaga atgaattgct atcagtaaag 1320
tcctgtacca tgacacctaa aaggaaggaa atggtaaagc aaagtaataa ctcaaagaca 1380
gtcaccgagg gcttttgtcc acctttaact cattgtggtg agtagaggga aatatgtata 1440
tatgtaatga gattattatt gggggtgtga gttgttttgc aggatggtaa ctaaaggatt 1500
tgtaaagagt gtttatgttc cttaaagatc ttgtttgtga gcaaggtaat aggatatcaa 1560
attcagaacg tggtgggtta aactggttgt atttaatgta tttcaacttc tgaaaatctt 1620
atgcaactaa taagaaa 1637

<210> SEQ ID NO 23
<211> LENGTH: 637
<212> TYPE: DNA
<213> ORGANISM: Homo sapiens

<400> SEQUENCE: 23
tcccaaatgt gtgcaatgca agttatgctt ttaaaagcta gaaataataa aaccagtctt 60
ctattctgat tttgagtatg gtgatatagt attattaata aaagatgaca ttatattgtt 120
taattatata taaaattgtg gtttgatatg agttgttggc taatatgtat aattcctgag 180
gtaacagaaa tagagaagga accacacatc atttaaaaat aatcttaatg ttctgctctt 240
agctgggaaa cctatctgct aatgcatcac actaagtaga gtgaggaaat aagagaattt 300
agatctatga gggaacacag tgatctaatt ccaacccatt acttaactca taaggaaact 360
gaggtagaaa gaagttagat gatatgcctg acatagagga agaggtgagt gaaaaatggt 420
tttcctgaca ctaacttgtt attttgtcag ctatactgca atgaataatt gtcttttgat 480
actggagtaa aggcttgatg tacagtgatt tttttatatc atacaaatga cagaaaaaaa 540
aagtggagta gtactaaata tctgctttta gcagtagtct gattttggaa aaacaagttc 600
tgtactgatt ggaatgagaa actttcttca gttattt 637

<210> SEQ ID NO 24
<211> LENGTH: 587
<212> TYPE: DNA
<213> ORGANISM: Homo sapiens

<400> SEQUENCE: 24
tatcccagaa agaaggaaat ggtcagttta tctggagtta agcatttgtg tattatcatg 60
attaatcaca ggaacagttg ccaagctttc attataaaaa tattctccag gagaattcat 120
caagttccat tgcctattaa tttctgtcca tgcattttat ttggcatctt caatgacaga 180
ggacactttt aaaaaaaaga aatgaagaca aaagaaaaag ttcattagag aaataatgta 240
tgtgtgatat ttaaaaatta agccacatca tcatcctaag aaaactacga gactttagtt 300
ttagtataaa cttgcagtgt gttcttgaga tttctaaata taaggcttaa catttttttcc 360 ttaatacaca tcgatttggc atctcatatg tattatttat caggaaatta taaaacaaag 420
taaaatgatg ttttactaaa atgcacatca tttttagata tggatttta aaacttgatt 480 tataatacta cttttaccat gaaatactct tttgttgtat gaccttgagt acatttccca 540
tctgtgaatc tgtgtaatca tgtacaaaaa taaatgagac aaaacct 587

<210> SEQ ID NO 25
<211> LENGTH: 629
<212> TYPE: DNA
<213> ORGANISM: Homo sapiens

<400> SEQUENCE: 25
tcagcaagtc tgtcatcgac atcctgcaac tgtttgagcg ggcagagcaa gtgcgaaaag 60
attaaaaagt gcttttctca tcatttctgc tcatatgacc agcgctgcag tgctgcgcgc 120
cgggcgcacg cccgccgggc ctggcatggc gccaggggcc cggactctga gcgcagcggg 180
agcggctcag tccagccgcg ccgctgagca gcgccggccg ccggcaagaa ggcgcgcgga 240
cctgctacca ctcctgcacc gccaggccag gggtccgcgg gatcccaggg gctgcggcca 300
gggcacgagg gaaggggcca cctctgggat ttagggggca ctggcgtcac cagctgggtc 360
tggaaagtcc acctgccgtc aaggacacgc aggaggtgcg ccgtctcaga tctgggaacc 420
ttggcggatg tcctgccgcg tgggggaaga tcctgaacct tcagcggcca gcctgcacct 480
caggacctcc taggccctgc tccctttctc tctccactcc tacctcagcc tctgctctgg 540
tctgtcctgg atgcaaattt atgctgcaaa atctgagcgc tgaggtcctg aaacctgacc 600
cacccgacgc agggaggagg tggcaggga 629

<210> SEQ ID NO 26
<211> LENGTH: 237
<212> TYPE: DNA
<213> ORGANISM: Homo sapiens

<400> SEQUENCE: 26
tccctttctc tctccactcc tacctcagcc tctgctctgg tctgtcctgg atgcaaattt 60
atgctgcaaa atctgagcgc tgaggtcctg aaacctgacc cacccgacgc agggaggagg 120
tggcagggac agggacaggg acaggcagga gctgctgggg cccacttcgg gtgccccatc 180
ccacatctgg ccagggatgc atattctaaa acctgatttg atgttttact tttattt 237

<210> SEQ ID NO 27
<211> LENGTH: 594
<212> TYPE: DNA
<213> ORGANISM: Homo sapiens

<400> SEQUENCE: 27
cctgggctgc actaagtccc agtgtgacct tgggttgtga ccttctctgg gcttctgtct 60
ccttctgatg tgttgatgac gtcagtggtc ccatgtagtg ggacctgggg actgcaactt 120
aaggtattgg caggtaggca gggccttggg ctgtggtggc cctgggtggt ggggaccagg 180
gagagcagct gtccagctgc ccagtaactc aagttccctg acatcgctgt caacattgtc 240
tcctgcagct cagccctgga tggctgccct tcctggaaac cttaggatac ctctgctggc 300
tccagctgcc ccctccctgt gagtcagctc cttcaagcca cagcccgcca gatggcttcc 360
aaggcaccaa ggatgcagct cctgacctga tgcctctcag ctccaggact tcccaggacc 420
cctcagctgc cctggaccct gctgctactg ccgtcacctc tgcaccttgt ccccagctgg 480
gctgctgact cagatatgcc aggctcctat gctatcattt caactcccag gctcagctca 540
ctccaggagc ctagttggag aatggatttc cccagctgaa ggacgcttca gcta 594

<210> SEQ ID NO 28
<211> LENGTH: 638
<212> TYPE: DNA
<213> ORGANISM: Homo sapiens

<400> SEQUENCE: 28
gcacttcagt tccttttcat caaggaactg attaaagtgt ggtctattat ctctgtagtg 60
gggagtcccg aaagattcca cttcttcctc ttcttgccca atgagagggt caggaagctt 120
ccaccaccat cctgactgtg gccaccacat cctggtgtga agcaccacca gcttcctcca 180
caagaactct gaaggtcacc agccagcttg agtcctccga aggtgctgtg gctcaaccag 240
cagcctgtgt agcagagagc acaagacctg ggactcgaac tcagtcccac cttcaagagg 300
gatctccacc actttctgag cctcagtttt cacatctttg gttaggggca ggtgggaagt 360
tgccatattt accttgttgg gctctttgga aaaattaaat gaaatgttaa tgtatgttac 420
acaacgggct cataggaggg attcaaaagc tgctagttct ttttctcctt ttcctgaaaa 480
cggtattaaa gagtactgta gagacactgg agaattcctg cttcatatga gatgtccttg 540
gtctctcccg gggaatttga agacccagag actcgcagct ccccgtgagc ctccccgctg 600
acgccttacc tccccctctc caccatcccc tgccatcc 638

<210> SEQ ID NO 29
<211> LENGTH: 389
<212> TYPE: DNA
<213> ORGANISM: Homo sapiens

<400> SEQUENCE: 29
tgccttcccc tccccctgtc ggccgcccct cggtccctgg gggtggggtt tccctttgcg 60
ctcgccccct cccgccccca cccctcacgg gccctcccct cccccgcccg tccctatgta 120
tgtgtcacag cgcgccatgc ccgcccgccc gcccacctac ctccccgccg ctccagaggg 180
ggctcgcaga gctgaggacg cgcgcagcgc tgctcaaggt ctctctctct cagcaccctc 240
gccggccggc gtctgacgcg ggtgccaggg tctccgggca cctttcagtg tccattccct 300
cagccagcca ggactccgca acccagcagt tgccgctgcg gccacagccc gaggggacct 360
gcggacagga cgccggcagg aggaggggt 389

<210> SEQ ID NO 30
<211> LENGTH: 673
<212> TYPE: DNA
<213> ORGANISM: Homo sapiens

<400> SEQUENCE: 30
gccctgggaa aggggatcag gagcacatct tgggaacagg agccttcctc tcctgctgtc 60
aacggcctgg cctcgtggcc atgcttcgtg tcctgatggt agccgcactg ccgccctgat 120
aacttaaagg aagccccttc aatgggatga agggcccgtt tctgtgacag ctactttggg 180
agtggcagct ccccttcccc cagatccaac aggacacagc catccctgcg agggagtctg 240
ggcccctgga cgcagttgaa gaagggccac tgggaggccg gcagaacaag gggagggctg 300
gagaaggagc gggagtgcag gcgagaggag gaccagagag ggggaatttg tagagaaaac 360
ggtaaaacgg tttctttttt caaaagttga atccagggca agaacggaaa cggtggagtt 420
tacttttaaa aactcagagc ctccttataa gtggtggagt gtgtgtgtgt gtgtgtgtgt 480
gtgtgtgtgt gtgtgtgcat gctggcaggg cgggccctgc gggctggcca ggcctgtgag 540
aggtgacttc tctccctctc aatggcctta cagtgtatcc taaagaagct ttttgttaaa 600
ctcatgaata ggtggatttg gggtgtgtga tgctgggcat cacgatttgg atatttggtt 660
acctttgagg tta 673

<210> SEQ ID NO 31
<211> LENGTH: 595
<212> TYPE: DNA
<213> ORGANISM: Homo sapiens

<400> SEQUENCE: 31
ttcatttcag gctccccgtc cccttcctct gcctcaccta tgctgtcgcc ctgtcagcac 60
ctaattcagc ttcccatgga gaaaggcctc cctgttgaca gggccgtgct gggactcagg 120
gctgccaaag tcagtcttct cgcataaaag gctcagtgag tcctggagac acttggaagc 180
cagacagaat ggaatttctc cctattttct ttacagctga gaaaacacac acaaacacaa 240
gagcatattt attgcgatat ttctatccca aagtttgtct ttaaaaaaaa aaaagaaata 300
aaattagttt ctctgcccac tccaccccta tccccctacc cccactctcc tccccacctc 360
ttttcattcc ttcccatttc ctggtttagg ccagggagag aaatcaagcc gtccaagccc 420
cacagagcac tcctacaccc ccggacaatg tccagcttgt tcagagagtg agggaagaaa 480
cacagctccg aaaacataca cacaacctcc caatgaaggg tgttctgagg gaagaacagg 540
cgggccttgt gtctgaacac gaatccctaa ggctctggga agagaggagc cggaa 595

<210> SEQ ID NO 32
<211> LENGTH: 1031
<212> TYPE: DNA
<213> ORGANISM: Homo sapiens

<400> SEQUENCE: 32
ggtcttaaag taggaaaaca catggtgtga tttgggttgg tgaatagtcg acttgtagat 60
ctgcggactc gtcaacattg ctctgacatc agattttctg aagagcagtg tgggctcctt 120
ccccagggct ggccgagttt tgaggggaac tgcaggttct gatgtttcca actctgtatc 180
tctgccctcg tcatttccat ggacaagtta tttgtgctgg tgtgagatcc agaatcggtc 240
ctgctacgtg acaatgcctg gagcacggag ccaggaaccc aagctgcctc accagcgtgt 300
tagggttgtt actgtgcccg ttttagaaga tcacttggag gtgcaaaaat agagcagttt 360 tttttgttt ttttttttt gacatggagt ctcgctctgt cgcccaggct ggagtgcagt 420
ggcgcaatct cggctcactg caagctccgc ctccccggtt cacgccattc tcctgcctta 480
gcctcccgag tagctgggac tacaggagcc tgccaccatg cccggctaat ttttttgtat 540
tttttagtag agacggggtt tgaccatgtt agccaggatg gtctcgatct cctgacttca 600
tgatccgccc gcctcggcct cccaaagtgc tgggattaca ggcgtgagcc accacgcctg 660
gccaagagca gatttttta aaaaaattaa gtacctctat tcatttgcac cttcactacc 720
cagtgaggag atcaaaattt cctagagcaa atgcattcga tgccactcac agatttcgac 780
aggagagcac aatttcagga acgcctacat caaagcacta attggcactt ttacagtgtc 840
tttctccgca cgtgagcctt gctggtggaa ggagctgtca tagtaatgcg tattcctcca 900
tgcccagtga gtagggtgac ggtcaattca cagttcacta ggcacaaaag atgacggggc 960
tctcctctgc tcgggacagc aagaaggttg aggtgatacg gtttgtcggt gtccccaccc 1020
aaatctcatc t 1031

<210> SEQ ID NO 33
<211> LENGTH: 477
<212> TYPE: DNA
<213> ORGANISM: Homo sapiens

<400> SEQUENCE: 33
catgaaagtc actgttttac atactaattg cattttcccc aaaacatcaa gctaaataca 60
taactgatag catgtttaaa ggtcctatgt ttcacctcaa attatctcat atttcacatg 120
aggcaaaccc tgtcctgagg ccctgatgaa gatgggcagg cagatctgat atcagctgct 180
tttctttcct tgatggaacc tctggattgc gtgccctatc ctataatgtg aaaaaagggc 240
ttccagaaaa ggtggaggaa ttactttctg aaattctgaa aggctggatc caaaggtgca 300
gaaaggaaca ttatttccta ccatataaaa cccagtaggg cgtgtgatgc tgggacactg 360
tatgagtcca ttctcatact gccataaaga agtacctgag actgggtatt ttataaagga 420
aagaggtttg gttgactcac agttctgcag gcttaataga aagcataact gggaggc 477

<210> SEQ ID NO 34
<211> LENGTH: 566
<212> TYPE: DNA
<213> ORGANISM: Homo sapiens

<400> SEQUENCE: 34
aaaaatgaag aatttatatg ccaactccag gagaaatatt tcagtgaggt cctggcttgg 60
tgcaaggata tggaaccaga gccaagaatt ctatcagtta aaagcagctt agtttcctga 120
gcctggactg atgggggacg tggaagacaa agtgtcaggt ccatcagtgg aagattggcc 180
ttgagccact gtacacagaa tggagagccc actggcctaa aaggagagat tgtcaggcgt 240
gacgaagcag gaattttagc cgaagaatat tcacaaatta caggccaaga gggaagtggg 300
gacgttcgtc ttctcttcat agccttgctc gttgggggac cagctgtcct ttattgttaa 360
tagaaaaatc aatatagcaa gaggcgaatc tttgctgtga taacattggc tcctttcacc 420
aggcgtgtgg aattagatta ctgatagatg cacctctgtc gcctccccag gctccagata 480
gaatctatgg gctttgccaa taagcacggt aacagagtgt ggatcaggaa ccagcgggtg 540
gccaatggca gtggagaaaa tgtaat 566

<210> SEQ ID NO 35
<211> LENGTH: 472
<212> TYPE: DNA
<213> ORGANISM: Homo sapiens

<400> SEQUENCE: 35
atagaccata taattctcac atgtcaaggt tttaagccaa agccctcagg caccacttct 60
gattttcttg aaggatcaaa aataaaaggt tgcaaccctc acagccgtag gctcctgcag 120
caactctttg gtgcacctgt caccctgata cctgggagga ggctctgagt ccatgctgtg 180
ggaaggtgct ggccttcatg gatgggcctc ccctggtgtg tccactgtgg acctgagtgg 240
gtgtcccaga gccctggctc tcccttcttt tcctctagaa agggaatcgg catgttccca 300
atcatctctg agattatctt tattcttcaa ggagttgcag tggctcttgc caagtgccct 360
ggggtcttgg acatctgcct agtggccctg tagagacctc caccctccag acagctcaga 420
atttgctaaa gaaaatgtga attttggagt ccagggctag aaaatatgac at 472

<210> SEQ ID NO 36
<211> LENGTH: 489
<212> TYPE: DNA
<213> ORGANISM: Homo sapiens

<400> SEQUENCE: 36
aagaaaagtt ttattttgcc tctgtagtat tggggtttaa gtgatcacgg taattttcca 60
ttatcatttt gtgttttaaa taaatacaac aggctttatt gtgaaaatat ttgtctaata 120
ttgggcagta aatgtttaag tgattttggt ttaattacta ttacagtcat actattacag 180
tgcataaaat agaattcttc ttgagtttgt tcattagatg ggaagaggct gcatttttaa 240
aaaatatatg catgcctata atactacatt taaatatgtg cgtatataaa gagatgcttt 300
cttatttata tacatggtca ttatagagct ttgtgagaaa tagaattttc tctgtgcaat 360
ctgtactctg ggaggggtta tttgctgaca ctgtatgccc atttcctaac agaatgtctc 420
tagttaagta atcatatgat gaagacatcc cagctgggac tctatattta agccaagtta 480
ctatttcta 489

<210> SEQ ID NO 37
<211> LENGTH: 579
<212> TYPE: DNA
<213> ORGANISM: Homo sapiens

<400> SEQUENCE: 37
ctaaaaatgc ctcctcgcct ctgattttag ccgtggttgt tggagtaccg gttccagcag 60
gagctgtgat ttccattgag ctctcaaacc aaataaaatg caaatctccg aggatggctc 120
ctctccctgc ccccacagtt gtgctccgaa tagtgtctga gtttcatttt tacaaggggc 180
ctttaaaaac tcctgggccc cttgaaaact cccagccccc tttgtccaga tggggatgga 240
ggtggccagg ctgccccgtt gattgtgtgc cgaggagccc tccccgggaa ggctgtgatt 300
tatacgcgca ggcttgtcac ggggtgaaag gaagggccac tttttcattt tgatccaatg 360
ttaggtttga aagccaccca ctgctgtaaa ctcagctgga tccgcgggcc gtgattaaac 420
acattgcccg ctttgttgcc gagatggtgt ttcggaaggc gctgtgaatg cacttccctt 480
tgcggggctc acacagacaa gatgtgtgtt gcaaggatga ggcgcctgct cggcctccag 540
cccagggccg ggaagggaga aggtgctgtg cgtcgctgc 579

<210> SEQ ID NO 38
<211> LENGTH: 754
<212> TYPE: DNA
<213> ORGANISM: Homo sapiens

<400> SEQUENCE: 38
ttgaggcaag agcgagggtg gcatatccag ggtggccact gggtctggag tgtcagtagc 60
agggcagatt tagaaggtga ctttgcatac ctaggcaagg ccagctcatg cgggatgtcg 120
gagcccatgg gaagcacctt gcgtttgagg ctgcctgcgg tgggaagctt cagagtttca 180
agcggggctt tgctatgggt ttgttctgct ttcccgtttt ccccctttgga ggaggcttac 240 agagatagtg atgactttgc agctgttaat catcaggaag ctgtaatcac taagaatgtt 300
tgaaatcatc agttaaggat ttttagaagg aagtaaacca aagaaatact gcagtagcct 360
gccctaatta tttcctgggc ttaaagtaac caggtgcatt ggagagatta tttttcttct 420
tctgatttat gaaggtctca gggtccaaat tttgaaactg ctgatcgaat ttgttcttgg 480
atgttgtcat agaaatctga aactttccta cttgtctgag agtgaaattt ctttgattat 540
tcactcaagg gtttgatagg tttaaaaaaa ggccttcggg acatctcttg ttataaagtg 600
tcaactttag atatcaagag aatcatgata tatttattac tacaaaagag aaaataagca 660
actgaaaaac tcatgaactt gaagcatgaa gcaaacccct taagttctag gggtttcaag 720
atgtggatgc caacatgtga tgacatttaa aaga 754

<210> SEQ ID NO 39
<211> LENGTH: 378
<212> TYPE: DNA
<213> ORGANISM: Homo sapiens

<400> SEQUENCE: 39
ggcttttggt ttttacaaaa tattacaagt tgcctaaata gtccgtgttt aaggacatag 60
agccagagct ctttctggaa tgtcatacct cggcagggcc ttttgtgcat gttttaagct 120
gattctgaaa ttagggggtt aaaatggaag cgccgagcca tccctaaaga gagggaggcg 180
aatgtgccct tgttgctggt gaccccagaa caaggcctct gggctgagaa caggagagaa 240
tgttatttct ttgaaaagcc atcttgacaa tccaagtccg tttggctgca gcaccaaagg 300
cagctttgat ctgctcgcca gtgtccctgc cgggaaaagg attagggtcc ttccagagga 360
cagcagagcc aggctgcc 378

<210> SEQ ID NO 40
<211> LENGTH: 1490
<212> TYPE: DNA
<213> ORGANISM: Homo sapiens

<400> SEQUENCE: 40
gcccaggctg gagtgtggtg gcaaaatctc agataactga aacctctgct tcccaggctc 60
aagccatcct cccacctctg tctgcagagt agctgagact ataggcatgt gccacaatgc 120
tcagataatt acttaacatt ctagtagagt ctagtagaca tgggctatca ctatgttgcc 180
ctggctggtc tggaactcct gggctcaagt gattgttctg ccttggcttc ccaaagtgtt 240
gggattacgg ctgtaagccg ccatgcttgg cttcgcttta caattttttt ttttttttt 300
ttgagacaga gtcttactct gccacccagg ctggagtgta gtggctagat tttggctcac 360
tgcaaactct ggcccttggg ttaagagatt ctcctgcctc agcttcccaa gtagctggga 420
ttacaggcat ggacaaccat acctggctaa tattttgtat tagcagagac ggtatttcac 480
cgtgtcggcc gggctggtct cgaactcccg acctcatgat ccgcctacct cgggctccca 540
aagtgctggg attacaggca tgagccaccg tgcttggcca agaagacatt ttgttttctc 600
aaaaaagtgg agatctgagc ttcaaagatc cttggtaaca cttcccagtg ctatcagtgt 660
agtggtgcag tggctaataa ttcatggacc ctataggagg gatcttgcct gctctttaga 720
ggttgggaca cactcttctt ggtaccagaa gggcagaact atgcctctgt ggccacttat 780
tgcagaatgg aattggagta aactgagggc cctttcacac atgctagaga actgactttg 840
gccctaggag aagtgggggt tgcaggggat tggcctgaga aacttgcctt ttcactggat 900
tgtcctctag agtttttcac tggagatttg tcagaatgag cctccagtcc ccatccagac 960
tcctggagct ggcaggccag agcctgctga ggaaccagtt cttgaccatc ttcatcctgg 1020
acgagctgcc cagggaggtc ttccctctga tgttcatgga ggcctccagc atgagacatt 1080
ttgaggccct gaagctgatg gtgcaggcct ggcccttcct ccgcctccct ctgggatccc 1140
tgatgaagac acctcatctg gagaccttgc aagctgtgct gaagggactt gatacactgc 1200
tggcccagaa gcttcgcccc aggtgaggtg actcaggtgg cctggtggga agggtccagg 1260
catccaggga agggacagct ggctcaggag gagtggtggg gttggggagc tagggtggct 1320
cagaggcttc tgatggtgcc catgagagac cttgaccatt gcccagatcc tctggaaaag 1380
gactgctcac catacagggt ccactgagga aacaggaacc tgcttcctcc cagtggaagg 1440
taaaggttct agaagtgaga accaggcaga atccaagggg gagcgggatg 1490

<210> SEQ ID NO 41
<211> LENGTH: 1739
<212> TYPE: DNA
<213> ORGANISM: Homo sapiens

<400> SEQUENCE: 41
ttgggttcca atggaactac agagagcaat gactactggt cctgaatgtg ggtataaagt 60
tttaccctaa aagtaccttg tatttttttc caaggccaaa atataacaac tcatttgcac 120
cctggaaagg tatgtttatt taaaaaaaaa gattgcattt gcaaacagta gagaacactg 180
ctcttttttta tttaaaaaaa tctttaccat ggaaaaacaa taaagtttgc gtgtgtgttt 240
attggtctgg ggacttaaag aacaaagata ccttgtggat tgcagacaaa tgaaacccac 300
agaggtttgc tttgggtagg tttcaccata caggtgtttc aatagaccac tttgcaaata 360
ataaattact taacactcaa ggccgctaga ggccactaaa aaggagttta tggccaaggc 420
acagggctgg tggctggctc agtgagcggt ggcaggatat taatgagact cagagcctgg 480
acgtgctctg gatccagtta aatgtaatag agttggaaaa ccacctgccc ccagccactg 540
acggcaccta ggattcatgc ctgtaacttt gaccatctga gcctgtaggg acattgggga 600
ggagggggag ggtgagagga ggcagtggca acagcagcat ggatgttcca tgcaaaccct 660
tctctgtcac cagggaaagc agtctgagca catgaatttc ttagcctctc ttccaggatg 720
aagcctagtt tgaaccagca ctgccaggtt gaagtgttac tgcatcctgc agccagagcc 780
agggcatgtg gccacccccct tggtccctgc tgtggtaccc agagtcactt ggaacatgtg 840
tgaagccagg atgagggtgc atataccctc cagatgctga tatctaaata tttacaagtc 900
acaaatacag agaaactgtt tttttttgt tattgttgtt gttgttttga gaaggagtct 960
cgctctgtcg cccaggctgg agtgcagtag cgtgatctcg gctcaaagtt ctgcctcccg 1020
ggttcacgcc attctcctgc ctcagcctcc caagtagctg ggattatagg catgcaccac 1080
cacgcctagc aaattttgta tttttagtag agatggggtt tctccatgtt ggtcaggctg 1140
gtctcaactc ctgatctcag gtgatctgcc cacctcagcc tcccaaagtg ctgggattac 1200
aggtgtgagc caccgcaccc ggccaacaaa agtaccttct taatgacttc gaagactagg 1260
tttaaatggt aaattattaa attcttggaa atctgccaca gaatatggca ttgtggggac 1320
agctgagctg attgaaacct gctccctttc tcttcccact cccagctcca tcctgcacct 1380
taggggtcta tgcacacctg tgtggacatc ccaccctcac atccaacctc tattcacatt 1440
ccccaccacc atcctgtgtg gccactcagc ctgctctaaa gcagggatgc tgggaagatg 1500
cccacatcca agcttggaat cgtttttgcc agaaattggg ggccctaagt acccaaaaaa 1560
tgttctagaa ggggacatgt tctggatggc catggactcc ttgctccctg ggaagagca 1620 cagctggagg aggactggag caaggccccc taaagcactg gacccaagat aatgcccctc 1680
ttgcccaggt ccaagggctg tactagtggt acccgctgtc atcacagcat tcattactg 1739

<210> SEQ ID NO 42
<211> LENGTH: 736
<212> TYPE: DNA
<213> ORGANISM: Homo sapiens

<400> SEQUENCE: 42
cctcggaacc aaggttggct ctggcacctg tagggccacg ggcagctatg tcagcttcct 60
cggaaggacc gaggctggct ctggcatctc cccgaccaat cctggctcca ctgtgtaccc 120
ctgaagggca gaaaacagct actgcccacc gcagctccag cctggcccca acatctgtgg 180
gccagctggt gatgtctgcc tcagctggac caaagcctcc cccagcgacc acaggctcag 240
ttctggctcc gacgtccctg ggctggtgga tgcctgcctc agcagggcca agatctcccc 300
cagtcaccct ggggcccaat ctggccccaa cctccagaga ccagaagcag gagccacctg 360
cctccgtggg acccaagcca acactggcag cctctggcct gagcctggcc ctggcttctg 420
aggagcagcc cccagaactc ccctccaccc cttccccggt gcccagtcca gttctgtctc 480
caactcagga acaggccctg gctccagcat ccacggcatc aggcgcagcc tctgtgggac 540
agacatcagc tagaaagagg gatgccccag cccctagacc tctccctgct tctgaggggc 600
atctccagcc tccagctcag acatctggtc ctacaggctc cccaccctgc atccaaacct 660
ccccagaccc tcggctctcc ccctccttcc gagcccggcc tgaggccctc cacagcagcc 720
ctgaggatcc tgtttt 736

<210> SEQ ID NO 43
<211> LENGTH: 1288
<212> TYPE: DNA
<213> ORGANISM: Homo sapiens

<400> SEQUENCE: 43
agcctggcca acatggtgaa acgctgcctc tactaaaaat acaaaaatta gccaggcgtg 60
atggcggtac ctgtggtctc agctactggg gaggctgaga caggagaatc acttgaaccc 120
gggaggtgga ggttgcagtg agccgagatt gcaccactgc actccagcct gggtgacaga 180
gcgagactcc atctcagaaa aagaaaaaaa aaaaaaagag tctctgagtt tacagatgag 240
ggccctggca ttcagagagg ctgaggaact cacccagcct gtcaacggca gaaccagagc 300
caaatccagg atttgctagc ttcaaagcta tgttctcact cactccctaa ggaggctgtg 360
ggcagaagga accctgggct gggaggcagc acagggcttg gtatttatac tagacctgtt 420
ctgcctcagt ttcccagtct gtaaagtggc cctttgtctc aggcaatttg tgctaagacc 480
caagagcctt aagtgtgtgg gatactagag ggtctcccct gatgtggccc cctgcccctg 540
ccttgcctgg acagtttgcc ttcagggacg acatgccact ggtgcggctg gaggtggcag 600
atgagtgggt gcggcccgag caggcggtgg tgaggtaccg catggaaaca gtgttcgccc 660
gcagctcctg ggactggatc ggcttatacc gggtgagagg ggcagtggtg gtcagcgact 720
cagggaagaa aggggcctgg aggagcagct gaacagcatg gtggggtcac tggcttgtcc 780
agatcttgat gccacactgg gagactgctg ggatcagaca ttatagggtc acaacactga 840
ttccacaaca ctgatccccc aggtgggttt ccgccattgc aaggactatg tggcttatgt 900
ctgggccaaa catgaagatg tggatgggaa tacctaccag gtacttaaaa ggagtgggag 960
agtcagggca agtccttgtt gcctttggga cctcagaact caccttgggg gctctcaggt 1020
ggcctccctg acccccaact taggcttata cccctgggcc taccaggtaa cattcagtga 1080
ggaatcactg cccaagggcc atggagactt catcctgggc tactatagtc acaaccacag 1140
catcctcatc ggcatcactg aacccttcca ggtaagtagg ccagactgct gggctggggg 1200
tgcctaaaga cttttgtcaa atgccacagc ctctacattc tgctccttga gttcagacaa 1260
ataacctgac ctcccaagat ctgccaac 1288

<210> SEQ ID NO 44
<211> LENGTH: 1647
<212> TYPE: DNA
<213> ORGANISM: Homo sapiens

<400> SEQUENCE: 44
acatcttaaa cagtctttta atgttatgaa tttgattttt caagaaatac atgtcattta 60
ttttcaaaac gaaatgatag ctatactttc tagagtctat caatagtatt taaaataaga 120
tactcataac tttcaaatac tgcttttact agtcatcact cgtcattaaa tgtaactgta 180
tattcaagag ctttctaata atagccttta attaaacgaa ggactgttag agggtttctg 240
ttgccctttg aagttcttaa ttattacttg tatccagcat tttatggtac acttaaggtt 300
aaattaaatc atttaaatat accttgaaga gaaatatgaa gacttttgcc cattttaatt 360
aaatctctga atttcagtat ttgaaaataa taacatatgt tttgattttt ttttcatggc 420
cgaatggcaa aatgctcact atattaaaca acaaaaaaag aaatggtagc tttttatggg 480
actaatcgct aagcagatgc atgtaaatga gctattttct atgcatggct tccaaaagtg 540
ctaattaaat agttggtatt caaggctatg ctcgctcatt gtttagtgac acacaaatcc 600
agcgatgtgt gccagcagac attttaagtt gaatgttttc tcctctacgg tctttgtcat 660
gaaatggtgg caccatgatg agaacactag tgtaagcaaa acattgaaat atgctttaat 720
aatgttttaa ccatgtagtg acactagcct agttttctaa tgaattttta atttctgttt 780
tcttataagg gtgatatgag ttatcgctga tgcatattaa atcatataca tgagtcattt 840
tctctaaatt tgcataaaat ggctaaatgc taatgcacca aatggagctt actatatgtg 900
gtacagcaaa tattcccttg aagattttct gcaatcaatc tcctgtattt cattagcaac 960
cagataaggt gtggtctgca gaataaaaaa agaaaagtgt gtagctcatg aacttatgag 1020
gcttcagatg atttctacgt ggtgattaga gtggattctg caattagaat ttatgtaggt 1080
aaaacacaca tgtgcttcct ttaaaggcac agtgcaacaa aagttctgaa tacagccttg 1140
caattgttaa acaatgaaaa ggcaccattc aattattgtg attttttac atctataatt 1200 aaatgaagga aagccatact ttaaatttag tatcatttga ttggcataac ccttactgaa 1260
attttacaat ttccctacta tgtttataaa agaactttta aaaataacca tgtgtgaaat 1320
attttgtttg ctaactgttc ccattttcct tgtcaaataa tggtgaagaa ttttctggac 1380
taatgtttaa catttaaaaa tgttttttct atcatcaaat actcttactg aactgacatt 1440
aggatcatat gctttataaa aaattgcatt agggtaacag tattattggg caaaccagag 1500
atgtttactt gaaggataaa cttgctgctt actcactcca ctcatcaacc cttttctcgt 1560
ctcctacagt tccaccatct ggaatatttt ttaacccagt aaagaaaaaa ttggggaagg 1620
ggatggctat ttaaaaataa atgcttt 1647

<210> SEQ ID NO 45
<211> LENGTH: 315
<212> TYPE: DNA
<213> ORGANISM: Homo sapiens

<400> SEQUENCE: 45
tattatccta gtaaatcctt aaaaaacttt aagaggtggg tgattttata attcccattt 60
tacagatcct ggtactgggg ctttctggtc attaaaacac ctgcctaaaa ccactaatca 120
gtaaatggga ggctggcttt tgaacccagt tttggtcgtt gttcttaatc attattcttt 180
attgtttatg gacatgtttg tctaatagca taatatgtag aatcaaagaa atgatattaa 240
gtgtggaaat ggagtctcca aactctttat gcttgtttaa acgatcttct ctctcgagag 300
tgtatcttca tcctt 315

<210> SEQ ID NO 46
<211> LENGTH: 403
<212> TYPE: DNA
<213> ORGANISM: Homo sapiens

<400> SEQUENCE: 46
tttcccttac tcagctaaca aacatttacc aagtatctgc tgtgtgctaa cgcttaggtg 60
ttaaactggg catacaaact gaatgagaaa gagtttgcct ccacagagct gagcgtccta 120
gagagatgtg cccagatgtt gcaatcataa tgcaatgaga aatgtaatgt tggtacaggc 180
tactatgtaa gcacaggaaa gaggtgcata acttgtctgt tagagtcagg aaaggctttt 240
ctcaaatggc tgaactgaat tctgtgggat gacaaagagt gctcaatagc atgaagcaga 300
agaaggaaag gcatgctagg attgcatagg taagagtaag cggccgtgac attgccaagt 360
ggcggcacag tgtagcaatt aagagcacac actgaggccg ggt 403

<210> SEQ ID NO 47
<211> LENGTH: 1572
<212> TYPE: DNA
<213> ORGANISM: Homo sapiens

<400> SEQUENCE: 47
ataaaatatc aggtaaatat aatctctcat ctctcatctt ctctccatct ccctatgtcc 60
ctttccttct ctctctctct ctctctctca cacacacaca cacacacaca cacacacaca 120
cacacacaca cagagagaga gacacacatg ttcttcctct aaaaagaaaa accaataatc 180
ctctactgag acagttgtga atcaaaggtt tcttctgcag gagttacatc catctctgaa 240
tttcctagag agcagcaaag ggccttgtgt tttattcccc ttccacactt aatcactgga 300
ctgtgggccc agactgaatg agtagctcat tagaatcact gagttcactg aggggatgag 360
agattccttc ctggctgggt gctaagtgat actcccataa ggattttgtg gttacaaaac 420
gtgctggata tggaggtaac ctgtctggga gtcctgtcac tccaaggatc acttggaatg 480
ctctggaaaa acacatgacc tggctgaatg agttctgttg aattgtttag cctacacctt 540
catttcagca gcttatactg cattaatgag gttattgttc ctttgccgtc caattgttcc 600
caagctgatt ttttgcatat atgttttaca tccttaacaa gaatgcctgt ctcctgctgt 660
ttcagagtct cttccacagt gctgagcatg agtggagctt gctaaatcat tgctaaatga 720
agcaatgggc tgtaagcatg tcctgtggga tctgcatctt cagatcatcc tgaagtactc 780
aacaaccaca tcttcttcca ggaacagagc ccaacataaa ctggtagggt ttgctgtctt 840
agacagctaa gagaacgagg agtggagcta gtgaacaagc agtgaagggg gcagttcctt 900
aatgccatcc gaactgaatt tcaacagtct gacaagctag cgttttgggt aaatatccca 960
gtatacttgt cacagagtta agtaaaatgg acttccttca aaggaagtgc ttttaataca 1020
ataactgttt ttgttttttt aaccaatgga ttaaaaattt aacacattta ctaaatctgg 1080
catatttata tattgtatct aaacagatat tcaagctgca ttataatata atcataaaaa 1140
aactgatctc agtctgtctg ttaagccttt gtgagtcttt gtgccattgt tggagtagtg 1200
ctaattatca agcaaagaca tgataattac gcagagcttt tttgctaaaa gaaggaatct 1260
ttttcaacac ccacgcactg cacaatttcc tatgaccctg tagcactact ctggtatggc 1320
ccagaaattt gtatttctgt gtaaaggctg gaaattatat tatttctatc tctcccgata 1380
ccttttcttc ttgtgagtaa actgttttta gagggttaag gaagaggggt aatggtccaa 1440
atgggaaata taaaactaat gacccttcat gaaacatatt atgctcctca ttaaacttat 1500
tcagttaaat gtattccatt aaattaaaat aaataggatt taaaatttta cccaggagca 1560
gtaaacaatc tt 1572

<210> SEQ ID NO 48
<211> LENGTH: 219
<212> TYPE: DNA
<213> ORGANISM: Homo sapiens

<400> SEQUENCE: 48
tgctgaacca gtctccgctg catcgtctcc gctcgcgctc gggacctgca acagaaggga 60
atgggacccg agtgtcagtc tggactctcc atctccccgc actactccgc tccccctttt 120
tagcccgctc tcaaaaagcc tcttcaacat caagggcatc tcccaagttg aaaagaaaaa 180
aaatttctct ggagcctctc agcacttact tatttagca 219

<210> SEQ ID NO 49
<211> LENGTH: 668
<212> TYPE: DNA
<213> ORGANISM: Homo sapiens

<400> SEQUENCE: 49
caagctgatg ggatcctccc atgggaaaag tgggcctcac acccttcctc acccttccct 60
acttcctggg caatgttctg cttcccccaa actgaagcag gaggcccaga gaggaggcgg 120
tttcctggga ggaacccaaa ccaatgtgag atgagaaggt ctttaggaaa tgggggtctc 180
tgagaaccgg ttcttaaagg tcaagcactt gagcacctcg caaactcctg acaattgaaa 240
catatctgaa gagtcttctt cagatatgtc tctgtgtgtg tgtgtgtgtg tgtgtgtgtg 300
tgtgtgtgag agagagagag agagagagag agagagaata tgaatgtgca gtgtcccagt 360
cctgatctcc tggactggtg ccagccagcc agatgcctgc ccttggctgg ccaagttttt 420
ggctcctgaa agtaggcagc tctggacttg tacgaggcca cagagagagt tccaagcccc 480
acctggctca ggcgacaacc tctcaacctg aagtcaatct ccggtggcat cacagggccc 540
tcctggcagc agcccagttc cccacatgaa ccgaatggtc ctttcttaaa ttttgagccg 600
ggggctgcct aaaaggggct gcccccgcaa gcattttacc tccctaacac cattctctgc 660
ccgtgcca 668

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
caaagtggac agaggggagg 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
gtgctgttgg gagtggtgga 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
aatctaacat ggctgctata 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
caattgctca gagttatttt 20

```
<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

ataaaatttt attttcctaa                                                20


<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55

gaggaaatca gctacggggc                                                20


<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

tctgacagag caagtcttga                                                20


<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

tatcaaaatt gtatattcag                                                20


<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

aatgttttga tatttaggag                                                20


<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

ttgactctta aaatttaata                                                20


<210> SEQ ID NO 60
```

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
ttgtcacttt gttactctac 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
ttaaatctta aaattttcct 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
gatactgtat aattaattag 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
cttccttctg gttccttttt 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
attgatctcc aactttttaa 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
gttcatccaa gtaataagag 20

<210> SEQ ID NO 66
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66

atctcaagtg tatgtaacat                                              20


<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

gtctttttgt tttttttttt                                              20


<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

tattgcaaaa ggaaggaatg                                              20


<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

tcatggaaaa agaaaaaatc                                              20
```

INTERNEURON-SPECIFIC THERAPEUTICS FOR NORMALIZING NEURONAL CELL EXCITABILITY AND TREATING DRAVET SYNDROME

CROSS REFERENCE TO RELATED APPLICATIONS

This application is the U.S. national stage application, pursuant to 35 U.S.C. § 371, of PCT International Application No. PCT/US2020/015183, filed in English and designating the U.S. on Jan. 27, 2020, which claims priority to and benefit of U.S. Provisional Application No. 62/801,483, filed on Feb. 5, 2019, U.S. Provisional Application No. 62/823,281, filed on Mar. 25, 2019, and U.S. Provisional Application No. 62/916,477, filed on Oct. 17, 2019, the contents of each of which are incorporated by reference herein in their entireties.

STATEMENT REGARDING FEDERALLY SPONSORED RESEARCH

The invention was made with government support under grant number MH111529 awarded by the National Institutes of Health. The government has certain rights in the invention.

BACKGROUND

A delicate balance exists between excitation and inhibition that must be carefully maintained for proper functioning of brain circuits and the activities of the neuronal cells that function within these circuits. An alteration, defect, or disruption in the balance of excitation versus inhibition in the brain circuitry was shown to result in a number of neurological, neurogenetic, or neurodegenerative diseases and disorders. Moreover, the lack of proper cortical interneuron function was linked to neurodevelopment and neurological diseases and disorders.

Abnormal or aberrant interneuron function and activity may be a consequence of a deviation from the course of interneuron development (e.g., aberrant fate specification during embryonic development due to genetic mutation) or acute insult (e.g., stroke, concussion). Aberrant GABAergic neurotransmission and alterations in inhibitory cortical circuits may cause and induce the clinical features and symptoms, e.g., seizures and epilepsy, that afflict patients having serious neurological diseases and disorders, such as Dravet syndrome (DS), a pharmaco-resistant form of infantile epilepsy associated with cognitive impairment and premature death.

A dearth of therapeutic compositions and methods capable of modulating the activity of GABAergic interneurons, or other cortical neurons, with specificity and sensitivity severely impedes the ability of the medical community to alleviate the seizures in a wide variety of cases of epilepsy, particularly, in patients suffering from focal seizures and DS. Such compositions and methods are urgently needed to combat and treat the severe symptoms of these devastating conditions, as well as other neuropsychiatric diseases. The products, compositions and methods described herein are provided to address and meet these needs.

SUMMARY OF THE DISCLOSURE AND EMBODIMENTS

Featured herein are viral vectors, particularly, recombinant adeno-associated virus (rAAV) vectors, virus particles, and compositions and methods thereof. The rAAV vectors contain (are molecularly engineered to contain) at least one transgene (e.g., an effector gene such as the hM3Dq modified muscarinic receptor (Gq-DREADD), pharmacologically selective actuator molecule (PSAM), or a therapeutic gene such as SCN1A) and a specific regulatory polynucleotide sequence that restricts expression of the transgene to interneuron (IN) cells, particularly fast-spiking parvalbumin-expressing GABAergic interneurons (called PV-interneurons (PV INs) herein), or neuron cells of the brain cortex. In an embodiment, the specific regulatory polynucleotide sequence is derived from an enhancer sequence in the vicinity of the gene SCN1A and restricts expression of the transgene carried by the rAAV to fast-spiking parvalbumin-expressing GABAergic interneuron populations in brain. In an embodiment, the therapeutic gene is SCN1A. In a particular embodiment, the vector specifically transduces interneuron cells that are deficient or defective in the expression of the SCN1A gene that encodes the sodium chloride channel Nav1.1 in interneuron cells, in particular, cortical interneuron cells, and normalizes the excitability of the SCN1A-deficient or defective interneurons, thereby alleviating seizures and seizure symptoms in subjects suffering from Dravet syndrome (DS).

In an aspect, a suitable viral vector, e.g., a lentiviral vector or, in particular, a recombinant adeno-associated virus (rAAV) vector, is used to restrict expression of a transgene in GABA-ergic PV-expressing interneurons, or a pyramidal (PYR) neuron, or a vaso-intestinal peptide (VIP)-expressing cortical interneuron, in a mammal, and comprises an enhancer element polynucleotide (also called a regulatory element herein) as described herein. In an embodiment, the enhancer element is provided in cis. In an embodiment, the regulatory element is S5E1, S5E2, S5E3, S5E4, S5E5, S5E6, S5E7, S5E8, S5E9, or S5E10, particularly human E1-E10, as described herein. In an embodiment, the enhancer element is human E11-E35 as described herein. In an embodiment, the enhancer element is S5E1 (E1). In an embodiment, the enhancer element is S5E2 (E2). In an embodiment, the enhancer element is S5E3 (E3). In an embodiment, the enhancer element is S5E4 (E4). In an embodiment, the enhancer element is E5. In an embodiment, the enhancer element is E6. In an embodiment, the enhancer element is E11. In an embodiment, the enhancer element is E14. In an embodiment, the enhancer element is E22. In an embodiment, the enhancer element is E29.

In an aspect, the viral vector or rAAV vector comprising the enhancer drives the expression of a copy of SCN1A in a transduced PV-expressing interneuron cell for the treatment and therapy of DS. In other embodiments, the vector or rAAV vector comprising the enhancer drives the expression of effector genes such as Gq-DREADD receptor or such as a pharmacologically selective actuator molecule (PSAM), an orthogonal ligand-gated ion channel, (and its pharmacologically selective effector molecule (PSEMs)) for chemogenetic modulation of PV-interneuron activity for the treatment of all forms of epilepsy, including focal and pharmacologically intractable epilepsy and for the treatment of DS.

In an aspect, a viral vector comprising a transgene polynucleotide sequence and an enhancer polynucleotide sequence that specifically restricts expression of the transgene in parvalbumin (PV)-expressing interneuron cells of the brain is provided.

In an aspect, a viral vector comprising an enhancer polynucleotide sequence specifically associated with SCN1A gene expression and a transgene polynucleotide sequence, wherein the enhancer sequence restricts expression of the transgene in PV-expressing interneuron cells of the brain is provided.

In an aspect, a suitable viral vector, e.g., a lentiviral vector or, in particular, a recombinant adeno-associated virus (rAAV) vector, is used to restrict expression of a transgene in GABA-ergic, vaso-intestinal peptide-expressing cortical interneuron cells (VIP cINs) of the brain in a mammal, in which an enhancer element as described herein provided in cis. In an embodiment, the enhancer element is S5E6 as described herein.

In an aspect, a suitable viral vector, e.g., a lentiviral vector or, in particular, a recombinant adeno-associated virus (rAAV) vector, is used to restrict expression of a transgene in both GABA-ergic interneurons and glutamatergic pyramidal neurons in the brain in a mammal, in which an enhancer element as described herein provided in cis. In an embodiment, the pyramidal neurons are in cortical layer 5 of the brain in a mammal. In an embodiment, the enhancer element that restricts expression to pyramidal neurons is S5E5 as described herein.

In embodiments of the viral vector of the above-delineated aspects, the transgene is a reporter gene, a Designer receptor exclusively activated by designer drug (DREADD)-encoding gene, a pharmacologically selective actuator molecule (PSAM)-encoding gene, or a therapeutic gene, e.g., SCN1A. In an embodiment, the transgene is an SCN1A gene. In an embodiment, the transgene is a DREADD-encoding polynucleotide. In an embodiment, the DREADD-encoding polynucleotide is a Gq-DREADD-encoding gene that is activated by the chemogen clozapine-N4-oxide (CNO). In an embodiment, the transgene is a pharmacologically selective actuator molecule (PSAM)-encoding gene. In an embodiment, the expressed PSAM specifically interacts with a PSEM ligand. In an embodiment, the viral vector is recombinant adeno-associated virus (rAAV) vector.

In another aspect, a recombinant adeno-associated virus (rAAV) vector comprising an SCN1A transgene polynucleotide sequence, or a functional portion thereof, and an enhancer polynucleotide sequence that specifically restricts expression of the SCN1A transgene in interneuron cells of the brain is provided.

In embodiments of the viral vector or the rAAV vector of the above-delineated aspects, an Nav1.1 sodium channel encoded by the SCN1A transgene is functionally expressed in interneuron cells or neuron cells following transduction of the interneuron or neuron cells by the viral vector or rAAV vector. In embodiments of the viral vector or the rAAV vector of the above-delineated aspects, an Nav1.1 sodium channel encoded by the SCN1A transgene is functionally expressed in both GABA-ergic interneurons and glutamatergic pyramidal neurons following transduction of the interneuron or neuron cells by the viral vector or rAAV vector. In an embodiment, the interneuron cells are GABAergic interneuron cells. In an embodiment, the interneuron cells are GABAergic interneuron cells within the brain telencephalon. In an embodiment, the GABAergic interneuron cells express parvalbumin (PV). In an embodiment, the neuron cells are pyramidal neuron cells, e.g., glutamatergic pyramidal cells in the brain cortex. In an embodiment of any one of the above-delineated aspects, the enhancer polynucleotide sequence comprises the polynucleotide sequence of the mouse enhancer element E1, E2, E3, E4, E5, E6, E7, E8, E9, or E10 (SEQ ID NOs: 5-14, respectively), or an ortholog, such as a human ortholog, thereof. In an embodiment, the enhancer polynucleotide sequence comprises the polynucleotide sequence of human enhancer element E1, E2, E3, E4, E5, E6, E7, E8, E9, or E10 (SEQ ID NOs: 15-24, respectively). In an embodiment, the viral vector or rAAV vector comprises an enhancer polynucleotide sequence comprising a nucleotide sequence which contains one or more regions of about 100 bp or longer having at least 75% or greater sequence identity to a polynucleotide sequence of a human enhancer element E1, E2, E3, E4, E5, E6, E7, E8, E9, or E10 (SEQ ID NOs: 15-24, respectively). In another embodiment, the viral vector or rAAV vector comprises an enhancer polynucleotide sequence comprising a nucleotide sequence which contains one or more regions of about 100 bp or longer having at least 75% or greater sequence identity to a polynucleotide sequence of human enhancer element E2 (SEQ ID NO: 16). In another embodiment, the viral vector or rAAV vector comprises an enhancer polynucleotide sequence comprising a nucleotide sequence which contains one or more regions of about 100 bp or longer having at least 75% or greater sequence identity to a polynucleotide sequence of human enhancer element E5 (SEQ ID NO: 19). In another embodiment, the viral vector or rAAV vector comprises an enhancer polynucleotide sequence comprising a nucleotide sequence which contains one or more regions of about 100 bp or longer having at least 75% or greater sequence identity to a polynucleotide sequence of human enhancer element E6 (SEQ ID: 20). In an embodiment of the above-delineated aspects, the viral vector or rAAV vector comprises an enhancer polynucleotide sequence comprising the polynucleotide sequence of human enhancer element E2 (SEQ ID NO: 16). In other embodiments of the above-delineated aspects, the viral vector or rAAV vector comprises an enhancer polynucleotide sequence comprising the polynucleotide sequence of human enhancer element E5 (SEQ ID NO: 19) or an enhancer polynucleotide sequence comprising the polynucleotide sequence of human enhancer element E6 (SEQ ID NO: 20). In other embodiments of the above-delineated aspects, the viral vector or rAAV vector comprises any one (or one or more) of an enhancer polynucleotide sequence comprising the polynucleotide sequence of human enhancer element E11 (SEQ ID NO: 25) to E35 (SEQ ID NO: 49). In an embodiment, the capacity of the vector to package polynucleotide sequences of greater than about 4.7 kb comprises reassembly of multiple rAAV vectors by homologous recombination or by splicing mediated by acceptor sites. In an embodiment, the vector delivers the SCN1A gene to SCN1A-expressing GABAergic interneuron or glutamatergic pyramidal neuron cells in the brain, and wherein the SCN1A gene is functionally expressed, thereby restoring normal levels of SCN1A in the interneuron and neuron cells following administration of the vector to a subject. In an embodiment, the subject is a human patient. In an embodiment, the human patient is an infant suffering from Dravet syndrome (DS).

In another aspect, a viral particle or virus-like particle comprising the viral vector or rAAV vector of any of the above-delineated aspects is provided.

In another aspect, a cell comprising the viral vector or rAAV vector of any of the above-delineated aspects is provided. In an embodiment, the cell comprises the viral particle as delineated above.

In another aspect is provided a pharmaceutical composition comprising the viral vector or rAAV vector of any of the above-delineated aspects, and a pharmaceutically acceptable vehicle, carrier, or diluent.

In another aspect is provided a pharmaceutical composition comprising the viral particle of any of the above-delineated aspects, and a pharmaceutically acceptable vehicle, carrier, or diluent. In an embodiment of the above-delineated aspects, the pharmaceutical composition is in liquid dosage form.

In an aspect, a method of restoring normal levels of SCN1A expression in GABAergic interneuron cells in which SCN1A expression levels are deficient or defective is provided, in which the method comprises contacting the cells with an effective amount of the viral or rAAV vector of any of the above-delineated aspects, or a viral particle or a pharmaceutical composition thereof, to restore normal levels of SCN1A expression in the GABAergic interneuron cells.

In an aspect, a method of treating infantile epilepsy and/or seizures in an infant who has or is at risk of having epilepsy, seizures, or Dravet syndrome (DS) is provided, in which the method comprises administering to the infant a therapeutically effective amount of the viral or rAAV vector of any of the above-delineated aspects, the viral particle of any of the above-delineated aspects, or a pharmaceutical composition of any of the above-delineated aspects, to treat seizures, epilepsy, or DS in the subject.

In an aspect, a method of treating Dravet syndrome (DS) in a subject who has or is at risk of having DS is provided, in which the method comprises administering to the subject a therapeutically effective amount of the viral or rAAV vector of any of the above-delineated aspects, or a viral particle or a pharmaceutical composition thereof, to treat DS in the subject.

In an aspect, a method of inhibiting or preventing seizures and/or epilepsy in a subject having or at risk of having seizures and/or epilepsy is provided, the method comprising systemically administering to the subject a recombinant adeno-associated virus (rAAV) vector comprising an SCN1A transgene polynucleotide sequence, or a functional portion thereof, an enhancer polynucleotide sequence that specifically restricts expression of the SCN1A transgene in interneuron cells of the cerebral cortex of the subject, and a capsid that enhances transduction of the vector into interneuron cells.

In an embodiment of the methods in any of the above-delineated aspects, the infant or the subject is a human patient. In an embodiment of the methods in any of the above-delineated aspects, the enhancer polynucleotide sequence in the viral vector or rAAV vector is selected from human enhancer elements E1, E2, E3, E4, E5, E6, E7, E8, E9, or E10, or E11-E35 (SEQ ID NOs: 25-49, respectively). In an embodiment, the viral vector or rAAV vector comprises an enhancer polynucleotide sequence comprising a nucleotide sequence which contains one or more regions of about 100 bp or longer having at least 75% or greater sequence identity to a polynucleotide sequence of a human enhancer element E1, E2, E3, E4, E5, E6, E7, E8, E9, or E10 (SEQ ID NOs: 15-24, respectively) or E11-E35 (SEQ ID NOs: 25-49, respectively). In an embodiment, the enhancer polynucleotide sequence is the human E2 enhancer polynucleotide sequence or the enhancer polynucleotide sequence contains one or more regions of about 100 bp or longer having at least 75% or greater sequence identity to a polynucleotide sequence of a human enhancer element E1, E2, E3, E4, E5, E6, E7, E8, E9, or E10 (SEQ ID NOs: 15-24, respectively) or E11-E35 (SEQ ID NOs: 25-49, respectively). In an embodiment, the enhancer polynucleotide sequence is the human E5 enhancer polynucleotide sequence. In an embodiment, the enhancer polynucleotide sequence is the human E6 enhancer polynucleotide sequence. In a certain embodiment, the enhancer polynucleotide sequence contains one or more regions of about 100 bp or longer having at least 75% or greater sequence identity to a polynucleotide sequence of human enhancer element E2 (SEQ ID NO: 16). In other embodiments, the enhancer polynucleotide sequence contains one or more regions of about 100 bp or longer having at least 75% or greater sequence identity to a polynucleotide sequence of human enhancer element E5 (SEQ ID NO: 19) or to a polynucleotide sequence of human enhancer element E6 (SEQ ID NO: 20).

In an aspect, a method of delivering a transgene for restricted expression in an interneuronal cell or neuronal cell that expresses an SCN1A gene to inhibit or prevent seizures and/or epilepsy in a subject in need thereof is provided, in which the method comprises contacting the cell with a recombinant adeno-associated virus (rAAV) vector comprising an SCN1A transgene polynucleotide sequence, or a functional portion thereof, and an enhancer polynucleotide sequence that specifically restricts expression of the SCN1A transgene in interneuron or neuron cells of the cerebral cortex of the subject, thereby inhibiting or preventing seizures and/or epilepsy in the subject.

In an embodiment of the methods in any of the above-delineated aspects, the rAAV vector, viral particle, virus-like particle, or pharmaceutical composition is administered systemically. In an embodiment of the methods in any of the above-delineated aspects, the rAAV vector, viral particle, virus-like particle, or pharmaceutical composition is administered parenterally or intravenously. In an embodiment of the methods in any of the above-delineated aspects, the rAAV vector, viral particle, or pharmaceutical composition is administered intracerebrally. In an embodiment of the methods in any of the above-delineated aspects, the rAAV vector, viral particle, or pharmaceutical composition is administered as a prophylactic. In an embodiment of the methods in any of the above-delineated aspects, the method further comprises administering an adjunct anti-epileptic treatment to the infant or subject.

In another aspect, a viral vector comprising a transgene polynucleotide sequence and an enhancer polynucleotide sequence that specifically restricts expression of the transgene in vaso-intestinal peptide-expressing cortical interneuron cells (VIP cINs) of the brain is provided. In another aspect, a viral vector is provided, in which the vector comprises an enhancer polynucleotide sequence specifically associated with SCN1A gene expression and a transgene polynucleotide sequence, wherein the enhancer sequence restricts expression of the transgene in vaso-intestinal peptide-expressing cortical interneuron cells (VIP cINs) of the brain. In an embodiment, the enhancer polynucleotide sequence comprises a nucleotide sequence which contains one or more regions of about 100 bp or longer having at least 75% or greater sequence identity to a polynucleotide sequence of human enhancer element E6 (SEQ ID NO: 20). In a particular embodiment, the enhancer polynucleotide sequence is human enhancer element E6 (SEQ ID NO: 20). In an embodiment, the viral vector is recombinant adeno-associated virus (rAAV) vector. In an embodiment, the transgene is the SCN1A gene.

In another aspect, a viral vector comprising a transgene polynucleotide sequence and an enhancer polynucleotide sequence that specifically restricts expression of the transgene in pyramidal neurons of the brain is provided. In another aspect, a viral vector is provided, in which the vector comprises an enhancer polynucleotide sequence specifically associated with SCN1A gene expression and a transgene polynucleotide sequence, wherein the enhancer sequence restricts expression of the transgene in pyramidal neurons of the brain. In an embodiment, the enhancer polynucleotide sequence comprises a nucleotide sequence which contains one or more regions of about 100 bp or longer having at least 75% or greater sequence identity to a polynucleotide sequence of human enhancer element E5 (SEQ ID NO: 19). In a particular embodiment, the enhancer polynucleotide sequence is human enhancer element E5 (SEQ ID NO: 19). In another particular embodiment, the enhancer sequence restricts expression of the transgene in pyramidal neurons in cortical layer 5 of the brain. In an embodiment, the viral vector is recombinant adeno-associated virus (rAAV) vector. In an embodiment, the transgene is the SCN1A gene.

In an aspect, a viral vector that comprises an enhancer polynucleotide sequence selected from SEQ ID NOs: 15-24, or a functional portion thereof, is provided, wherein the vector specifically targets neuronal cells expressing SCN1A. In an embodiment, the neuronal cells are parvalbumin cortical interneurons (PV cINs), pyramidal (PYR) neurons, or vaso-intestinal peptide cortical interneurons (VIP cIN).

In an aspect, a viral vector that comprises an enhancer polynucleotide sequence selected from SEQ ID NOs: 25-27, or a functional portion thereof, is provided, wherein the vector specifically targets cells expressing Pvalb.

In an aspect, a viral vector that comprises an enhancer polynucleotide sequence selected from SEQ ID NOs: 28-31, or a functional portion thereof, is provided, wherein the vector specifically targets cells expressing Acan.

In an aspect, a viral vector that comprises an enhancer polynucleotide sequence selected from SEQ ID NOs: 32-39, or a functional portion thereof, is provided, wherein the vector specifically targets cells expressing Tmem132c.

In an aspect, a viral vector that comprises an enhancer polynucleotide sequence selected from SEQ ID NO: 40 or SEQ ID NO: 41, or a functional portion thereof, is provided, wherein the vector specifically targets cells expressing Lrrc38.

In an aspect, a viral vector that comprises an enhancer polynucleotide sequence selected from SEQ ID NO: 42 or SEQ ID NO: 43, or a functional portion thereof, is provided, wherein the vector specifically targets cells expressing Inpp5j.

In an aspect, a viral vector that comprises an enhancer polynucleotide sequence selected from SEQ ID NOs: 44-47, or a functional portion thereof, is provided, wherein the vector specifically targets cells expressing Mef2c.

In an aspect, a viral vector that comprises an enhancer polynucleotide sequence selected from SEQ ID NO: 48 or SEQ ID NO: 49, or a functional portion thereof, is provided, wherein the vector specifically targets cells expressing Pthlh.

In an aspect, a viral vector that comprises an enhancer polynucleotide sequence selected from SEQ ID NOS: 15-49, or a functional portion thereof, is provided, wherein the vector specifically targets cells PV-expressing cells.

In an embodiment of the viral vector of any of the above-delineated aspects, the target cells are PV-expressing neuronal cells. In an embodiment of the viral vector of any of the above-delineated aspects, the viral vector is a lentiviral vector or a recombinant adeno-associated virus (rAAV) vector.

In an aspect is provided a cell comprising the viral vector of any of the above-delineated aspects and embodiments.

In an aspect is provided a viral particle or virus-like particle comprising the viral vector of any of the above-delineated aspects and embodiments. In an aspect is provided a cell comprising the viral particle or virus-like particle comprising the viral vector of any of the above-delineated aspects and embodiments.

In an aspect is provided a pharmaceutical composition comprising the viral vector, or the viral particle or virus-like particle, of any of the above-delineated aspects and embodiments and a pharmaceutically acceptable vehicle, carrier, or diluent.

In another aspect, a method of restricting expression of a transgene in a neuronal cell of a subject is provided, in which the method comprises administering to the subject a delivery vector comprising at least one enhancer element polynucleotide comprising a sequence of SEQ ID NO: 15-49 and a transgene polynucleotide, wherein the transgene is specifically expressed in the neuronal cell. In an embodiment of the method, the transgene is SCN1A. In an embodiment, the neuronal cell is a cortical interneuron expressing parvalbumin (PV cIN). In an embodiment, the enhancer element polynucleotide comprises a sequence set forth in SEQ ID NOS: 15-18 or SEQ ID NOS: 21-24.

In another embodiment of the above method, the neuronal cell is a pyramidal (PYR) cell. In an embodiment, the enhancer element polynucleotide comprises the sequence set forth in SEQ ID NO: 19.

In another embodiment of the above method, the neuronal cell is a cortical interneuron expressing the vaso-intestinal peptide (VIP cIN). In an embodiment, the enhancer element polynucleotide comprises the sequence set forth in SEQ ID NO: 20.

In an embodiment of the above-delineated method and its embodiments, the delivery vector is a lentiviral vector or rAAV. In an embodiment of the method, the delivery vector is administered to the brain. In an embodiment of the method, the delivery vector is administered locally or systemically. In an embodiment, the subject is a mammal. In an embodiment, the subject is human.

In another aspect, a viral vector comprising a human enhancer polynucleotide sequence selected from SEQ ID NOS: 15-49 is provided. In an embodiment, the viral vector is a recombinant adeno-associated virus (rAAV) vector. In embodiments, a viral particle or virus-like particle comprises the above-delineated viral vector. In another embodiment, a cell comprises the above-delineated viral vector. In an embodiment, a cell comprises the above-delineated viral particle or the virus-like particle. In an embodiment, a pharmaceutical composition comprises the above-delineated viral vector, or the above-delineated viral particle or virus-like particle, and a pharmaceutically acceptable vehicle, carrier, or diluent.

DEFINITIONS

Unless defined otherwise, all technical and scientific terms used herein have the meaning commonly understood by a person skilled in the art to which the described aspects and embodiments belong. The following references provide one of skill with a general definition of many of the terms used in the described embodiments: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "administering" is meant giving, supplying, dispensing a composition, agent, therapeutic product, e.g., a virus vector (rAAV) harboring a transgene (e.g., an effector or a therapeutic gene), and the like to a subject, or applying or bringing the composition and the like into contact with the subject. Administering or administration may be accomplished by any of a number of routes, such as, for example, without limitation, parenteral or systemic, intravenous (IV), (injection), subcutaneous, intrathecal, intracranial, intramuscular, dermal, intradermal, inhalation, rectal, intravaginal, topical, oral, subcutaneous, intramuscular, or intraocular. In embodiments, administration is systemic, such as by inoculation, injection, or intravenous injection.

By "agent" is meant a peptide, polypeptide, nucleic acid molecule, or small molecule chemical compound, antibody, or a fragment thereof.

By "alteration" is meant a change (increase or decrease) in the expression levels or activity of a gene or polypeptide as detected by standard art known methods such as those described herein. As used herein, an alteration includes a 10% change in expression levels, a 25% change, a 40% change, or a 50% or greater change in expression levels."

By "ameliorate" and "amelioration" is meant decrease, suppress, attenuate, diminish, arrest, or stabilize the development or progression of a disease.

By "analog" or "derivative" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, polynucleotide binding activity. In another example, a polynucleotide analog retains the biological activity of a corresponding naturally-occurring polynucleotide while having certain modifications that enhance the analog's function relative to a naturally occurring polynucleotide. Such modifications could increase the polynucleotide's affinity for DNA, half-life, and/or nuclease resistance, an analog may include an unnatural nucleotide or amino acid.

As used herein, the term "at risk" as it applies to a neurological or neurogenetic disease, disorder, or pathology, such as seizures or epilepsy, refers to patients or individuals who have a family history or genetic risk factor genes for a neurological or neurogenetic disease, disorder, or pathology.

As used herein, the term "carrier" refers to a diluent, adjuvant, excipient, or vehicle with which a composition or pharmaceutical composition, e.g., comprising a polynucleotide, viral vector, or viral particle) can be administered. Pharmaceutical and pharmaceutically acceptable carriers include sterile liquids, such as water and oils, including those of petroleum, animal, vegetable or synthetic origin, such as peanut oil, soybean oil, mineral oil, sesame oil, and the like. Water or aqueous saline solutions and aqueous dextrose and glycerol solutions may be employed as carriers, particularly for injectable solutions. Carriers may also include solid dosage forms, including, but not limited to, one or more of a binder (for compressed pills), a glidant, an encapsulating agent, a flavorant, and a colorant. Suitable pharmaceutical carriers are described in "Remington's Pharmaceutical Sciences" by E. W. Martin.

As used herein, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited are not changed by the presence of more than that which is recited, but excludes prior art embodiments.

"DREADD" is an acronym for "designer receptor exclusively activated by a designer drug," which is a modified G protein coupled receptor (GPCR) that may be administered or specifically introduced into a subject, or cells thereof, e.g., PV-expressing interneurons, by use of a viral vector (which contains a polynucleotide sequence encoding the DREADD) or through genetic breeding. DREADDs are known as chemical genetic or "chemogenetic" molecules allow for a precise level of temporal control over the excitation and inhibition of neurons. Following expression of the DREADD, it may be activated by a specific ligand (or agonist), which may be administered by intravenous injection or orally. The DREADD and its ligand are designed to be orthogonal, i.e., they bind specifically to each other and do not cross-react. By way of nonlimiting example, five different classes of DREADDs are available for use: hM3Dq raises calcium levels in a cell, causing burst firing; hM4Di lowers cAMP and the activation of a particular potassium channel, causing neuronal silencing, and also inhibits presynaptic neurotransrnitter release; GsD enhances cAMP, causing modulation signaling; and Rq(R165L) enhances arrestin signaling, a specific pathway that has been linked to the mechanisms of psychoactive drugs; and K-opioid receptor DREADD or KORD, which reduces or inhibits excitation of neurons and also inhibits presynaptic neurotransmitter release. (See, e.g., Kelly Rae Chi, 2015, *The Scientist*; and S. M. Sternson and B. L. Roth, 2014, *Ann Rev Neuroscience,* 37:387-407).

Orthogonal ligand-gated ion channels, called pharmacologically selective actuator molecules (PSAMs) and pharmacologically selective effector molecules (PSEMs) are other types of chemogenetic molecules that are used as optogenetic agents and in optogenetic methods, in a manner similar to the use of DREADDs. Each PSAM is exclusively activated by a PSEM cognate synthetic agonist. By way of example, three specific PSAMIPSEM tools have been designed, each with different ion conductance properties for controlling neuronal excitability. (See, e.g., Shapiro, M. G. et al., 2012, *ACS Chem. Neurosci.,* 3(8):619-629). These include the cation-selective activator, $PSAM^{Q79G,Q139G}$-5HT3HC/$PSEM^{22S}$, the anion-selective silencer, $PSAM^{L141F,Y115F}$-GlyR/$PSEM^{89S}$, and a third $Ca^{2+}$-selective channel, $PSAM^{Q79G,L141S}$-nAChR V13'T/$PSEM^{9S}$. (See, Ibid., and Magnus, C. J. et al., 2011, Science, 333 (6047):1292-1296). Both DREADDS and PSAMs-PSEMs allow control over neuronal activity, in a temporal manner, from minutes to hours. (See, e.g., Kelly Rae Chi, 2015, *The Scientist*; and S. M. Sternson and B. L. Roth, 2014, *Ann Rev Neuroscience,* 37:387-407). By way of example, different PSAMs have been used with various ion channels and PSEMs to control neurons, e.g., E/I balance in neurons. Such PSAM-PSEM pairings include, without limitation, $PSAM^{L141F,Y115F}$-5HT3 HC, which is activated by the ligand $PSEM^{898}$, allowing cations to flow into the cell and boost excitability; $PSAM^{L141F,Y115F}$-GlyR, which is activated by the ligand $PSEM^{89S}$, silencing neurons; and $PSAM^{Q79G,L141S}$-nAChRk V13, which is activated by the ligand PSEM9S, enhancing calcium signaling. Because there are two different PSEM ligands, PSAMs-PSEMs can also be combined in the same animal (subject).

"Detect" refers to identifying the presence, absence or amount of a molecule, compound, or agent to be detected.

By "disease" is meant any condition or disorder that adversely affects, damages or interferes with the normal function of a cell, tissue, organ, or part of the body, such as the brain, including the cerebral cortex of the brain and brain tissues. In one embodiment, the disease is a seizure or epilepsy. In another embodiment, the disease is Dravet syndrome.

By "effective amount" is meant the amount of a required to ameliorate the symptoms of a disease relative to an untreated patient. The effective amount of active compound(s) used to practice the described methods for therapeutic treatment of a disease varies depending upon the manner of administration, the age, body weight, and general health of the subject. Ultimately, the attending physician, clinician, or veterinarian will decide the appropriate amount and dosage regimen. Such amount is referred to as an "effective" amount. In one embodiment, an effective amount is the amount of an rAAV vector comprising a specific enhancer sequence (e.g., an SCN1A-specific enhancer, such as E1-E10, as described herein) and one or more transgene sequences (e.g., SCN1A) inserted therein that is required to reduce, ameliorate, abate, inhibit, or stabilize a symptom of a neurological disease or disorder, such as seizures, epilepsy, Dravet syndrome (DS), or the severity thereof. In another embodiment, an effective amount is the amount of an rAAV vector comprising a specific enhancer sequence (e.g., an SCN1A-specific enhancer, e.g., E1-E10, as described herein) and one or more transgene sequences (e.g., SCN1A) inserted therein required to cause specific inhibitory activity of an interneuron cell, such as a GABAergic interneuron cell or a PV-expressing, GABAergic interneuron cell. In an embodiment, the enhancer is E2, as described herein, which restricts expression of a transgene, e.g., SCN1A or effectors like Gq-DREADD or PSAM for chemogenetic modulation of PV-interneuron activity, to PV-interneuron cells.

As used herein, the term "endogenous" describes a molecule (e.g., a polypeptide, peptide, nucleic acid, or cofactor) that is found naturally in a particular organism (e.g., a human) or in a particular location within an organism (e.g., an organ, a tissue, or a cell, such as a human cell).

As used herein, the term "exogenous" refers to a molecule (e.g., a polypeptide, peptide nucleic acid, or cofactor) that is not found naturally or endogenously in a particular organism (e.g., a human) or in a particular location within an organism (e.g., an organ, a tissue, or a cell, such as a human cell). Exogenous materials include those that are provided from an external source to an organism or to cultured matter extracted therefrom.

A "regulatory element," "regulatory sequence," "enhancer," "enhancer element" or "enhancer sequence" refers to a nucleic acid or polynucleotide sequence or a region of a nucleic acid or polynucleotide sequence, e.g., DNA or RNA, of about 50-2500 nucleotides, that contains one or more binding sites that are recognized and bound by one or more binding protein(s), e.g., transcription factor(s). In general, the binding proteins function as activators to increase the likelihood that transcription of a particular target gene will occur. Enhancers can activate transcription independent of their location, distance or orientation with respect to the promoters of genes. For example, enhancer sequences may be located upstream of a gene, downstream of a gene, within the coding region of a gene, or up to one million base pairs away from the gene. Typically, the binding of a DNA binding protein(s) or transcription factor(s) to an enhancer changes or alters the conformation of the DNA, thereby allowing interactions to occur between or among the transcription factor(s) bound to the DNA.

Enhancers have been described as clusters of DNA sequences capable of binding combinations of transcription factors that then interact with components of the mediator complex or TFIID to help recruit RNA polymerase II (RNAPII). To accomplish this, enhancer-bound transcription factors loop out the intervening sequences and contact the promoter region of a gene, thus allowing enhancers to act in a distance-independent fashion. In addition, activation of eukaryotic genes requires de-compaction of the chromatin fiber, which is carried out by enhancer-bound transcription factors that can recruit histone modifying enzymes or ATP-dependent chromatin remodeling complexes to alter chromatin structure and increase the accessibility of the DNA to other proteins. (For a review of enhancer function, see, e.g., Ong, C.-T. and Corces, V. G., 2011, *Nat. Rev. Genetics,* 12(4):283-293).

As described herein, ten enhancers in the vicinity of the SCN1A gene were screened for the ability to restrict expression of a transgene, namely, SCN1A, to PV-expressing interneuron cells (PV-cells), most of which express the SCN1A gene. The isolated enhancer sequences, called S5E1 (E1)-S5E10 (E10) herein, were discovered to have the ability to restrict expression of SCN1A to GABA-ergic interneurons. By way of example, the E2 enhancer (S5E2) was demonstrated to target and restrict expression of a transgene to PV-expressing interneurons, which express SCN1A. It will be appreciated that a large fraction of cells that express SCN1A are not PV-expressing interneurons. In an embodiment, the enhancers as described herein allow the restriction of expression of a transgene, e.g., SCN1A or another effector gene, e.g., Gq-DREADD or PSAM, in PV-interneurons, rather than in all SCN1A-expressing neurons. By way of further example, the isolated E5 enhancer (S5E5) was demonstrated to target and restrict expression of a transgene to glutamatergic pyramidal neurons in the brain. In embodiments, such an enhancer is E1, E2, E3, E4, E5, E6, E7, E8, E9, or E10, as described herein. In an embodiment, an enhancer element is isolated from is naturally occurring environment. Such an enhancer element is used in a vector, e.g., a viral vector, for delivery to a cell, tissue, or region of the body, such as the brain.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "functionally expressed" is meant that a gene or transgene contained in or inserted into the polynucleotide of an rAAV or rAAV vector as described herein is expressed in an infected or transduced cell and produces its encoded product, which is functional and/or active in the cell. In an embodiment, the cell is an interneuron cell. In an embodiment, the cell is a GABAergic interneuron cell. In an embodiment, the cell is a GABAergic interneuron cell that expresses parvalbumin (PV). In an embodiment, the cell is a neuron, in particular, a glutamatergic pyramidal interneuron cell. In an embodiment, the transgene is a detectable reporter gene, such as d-Tomato, ChR2, GFP, RFP, and the like. In an embodiment, the transgene is a Designer receptor exclusively activated by designer drugs (DREADD) or Gq-DREADD. In an embodiment, the transgene is PSAM. In an embodiment, the transgene is SCN1A which encodes the sodium channel Nav1.1.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The term "interneuron" refers to a neuron (nerve cell), or local circuit neuron in the central nervous system (CNS) that relays impulses between sensory neurons and motor neurons. In general, neurons are specialized cells that function primarily in the transmission of nerve impulses. Neurons have cellular processes, such as dendrites and axons. Dendrites, which are shorter processes in the cell body of a neuron, receive inputs from other neurons and conduct signals to the cell body. Axons are longer, single processes of the cell soma and relay signals toward the tip of the neuron (called the synaptic terminal). The three, main types of neurons include sensory neurons, interneurons (of the CNS), and motor neurons. In the human brain, there are about 100 billion interneurons, which receive impulses from the sensory neurons. Interneurons interpret the information received from other neurons and relay impulses to motor neurons for an appropriate response in a function called 'integration.'

The terms "isolated," "purified," or "biologically pure" refer to material that is free to varying degrees from components which normally accompany or are associated with it as found in its native state. "Isolate" denotes a degree of separation from original source or surroundings. "Purify" denotes a degree of separation that is higher than isolation. A "purified" or "biologically pure" protein or polynucleotide is sufficiently free of other materials such that any impurities do not materially affect the biological properties of the protein or polynucleotide, or cause other adverse consequences. That is, a polynucleotide (nucleic acid), polypeptide, or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid, protein, or peptide gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which flank the gene in the naturally-occurring genome of the organism from which a nucleic acid molecule, such as a nucleic acid molecule described herein, is derived. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide that has been separated from components that naturally accompany it. Typically, a polypeptide is isolated when it is at least 60%, by weight, free from the proteins and naturally-occurring organic molecules with which it is naturally associated. Preferably, the preparation is at least 75%, or at least 85%, or at least 90%, or at least 99%, by weight, a desired polypeptide. An isolated polypeptide may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression, level or activity that is associated with a disease or disorder. In one embodiment, a marker is an SCN1A polynucleotide or SCN1A polypeptide.

The term "mutation," as used herein, refers to a substitution of a nucleotide base or amino acid residue within a sequence, e.g., a nucleic acid or amino acid sequence, respectively, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* ($4^{th}$ ed., Cold Spring Harbor Laboratory Press, Cold Spring Harbor, N.Y. (2012)).

As used herein, "obtaining" as in "obtaining an agent" includes synthesizing, purchasing, or otherwise acquiring the agent.

By "polynucleotide" is meant a nucleic acid molecule, e.g., a double-stranded (ds) DNA polynucleotide, a single-stranded (ss) DNA polynucleotide, a dsRNA polynucleotide, or a ssRNA polynucleotide, that encodes one or more polypeptides. The term encompasses positive-sense (i.e., protein-coding) DNA polynucleotides, which are capable of being transcribed to form an RNA transcript, which can be subsequently translated to produce a polypeptide following one or more optional RNA processing events (e.g., intron excision by RNA splicing, or ligation of a 5' cap or a 3' polyadenyl tail). The term additionally encompasses positive-sense RNA polynucleotides, capable of being directly translated to produce a polypeptide following one or more optional RNA processing events. As used herein, a polynucleotide may be contained within a viral vector, such as a recombinant adeno-associated viral vector (rAAV).

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (2'—e.g., fluororibose, ribose, 2'-deoxyribose, arabinose, and hexose); and/or modified phosphate groups (e.g., phosphorothioates and 5'-N-phosphoramidite linkages).

As used herein, the term "pharmaceutically acceptable" refers to molecular entities, biological products and compositions that are physiologically tolerable and do not typically produce an allergic or other adverse reaction, such as gastric upset, dizziness and the like, when administered to a patient (e.g., a human patient).

As used herein, the terms "prevent," "preventing," "prevention," "prophylactic treatment" and the like refer to reducing the probability of developing a disorder or condition in a subject, who does not have, but who is at risk of, susceptible to, or predisposed to, developing a disorder or condition.

As used herein, the term "pseudotyped" refers to a viral vector that contains one or more foreign viral structural proteins, e.g., envelope glycoproteins. A pseudotyped virus may be one in which the envelope glycoproteins of an enveloped virus or the capsid proteins of a non-enveloped virus originate from a virus that differs from the source of the original virus genome and the genome replication apparatus. (D. A. Sanders, 2002, *Curr. Opin. Biotechnol.,* 13:437-442). The foreign viral envelope proteins of a pseudotyped virus can be utilized to alter host tropism or to increase or decrease the stability of the virus particles. Examples of pseudotyped viral vectors include a virus that contains one or more envelope glycoproteins that do not naturally occur on the exterior of the wild-type virus. Pseudotyped viral vectors can infect cells and express and produce proteins or molecules encoded by polynucleotides, e.g., reporter or effector proteins or molecules, contained within the viral vectors, e.g., the sodium channel Nav1.1 encoded by the SCN1A gene.

The term "recombinant" as used herein in the context of proteins or nucleic acids refers to proteins or nucleic acids that do not occur in nature (or in a naturally occurring protein or nucleic acid sequence), but are the product of human engineering, often or typically utilizing molecular biological or molecular genetic tools and techniques practiced by the skilled practitioner in the art. For example, in some embodiments, a recombinant protein or nucleic acid molecule comprises an amino acid or nucleotide sequence that comprises at least one, at least two, at least three, at least four, at least five, at least six, at least seven, or at least eight mutations as compared to any naturally occurring sequence.

By "reduces" is meant a negative alteration of at least 5%, 10%, 25%, 50%, 75%, or 100%.

By "reference" is meant a standard or control condition. A "reference sequence" is a defined sequence used as a basis for sequence comparison. A reference sequence may be a subset of or the entirety of a specified sequence, for example, a segment of a full-length cDNA or gene sequence, or the complete cDNA or gene sequence. For polypeptides, the length of the reference polypeptide sequence will generally be at least about 16 amino acids, at least about 20 amino acids, at least about 25 amino acids, or about 35 amino acids, about 50 amino acids, or about 100 amino acids. For nucleic acids, the length of the reference nucleic acid sequence will generally be at least about 50 nucleotides, at least about 60 nucleotides, at least about 75 nucleotides, or about 100 nucleotides, or about 300 nucleotides, or any integer thereabouts or therebetween.

By "specifically binds" is meant a nucleic acid molecule, polypeptide, or complex thereof (e.g., a binding protein such as a transcription factor and its cognate nucleic acid binding region), or a compound, or molecule that recognizes and binds a given polypeptide and/or nucleic acid molecule, but which does not substantially recognize and bind other molecules in a sample, for example, a biological sample.

By "subject" is meant a mammal, including, but not limited to, a human or non-human mammal, such as a non-human primate, e.g., a marmoset, or a non-human mammal, such as a bovine, equine, canine, ovine, or feline mammal, or a sheep, goat, llama, camel, or a rodent (rat, mouse), ferret, gerbil, hamster, or zebrafinch. A subject is typically a patient, such as a human patient, who receives treatment for a particular disease or condition as described herein (e.g., a neuropsychiatric, neurological, or neurogenetic disease, disorder, or pathology, such as seizures, epilepsy, or DS). Examples of subjects and patients include mammals, such as humans, receiving treatment for such diseases or conditions or who are at risk of having such diseases or conditions.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, inclusive of the first and last values.

As used herein, the term "therapeutically effective amount" refers to a quantity of a therapeutic agent that is sufficient to treat, abate, reduce, diagnose, prevent, and/or delay the onset of one or more symptoms of a disease, disorder, and/or condition upon administration to a patient in need of treatment. In some cases, a therapeutically effective amount may also refer to a quantity of a therapeutic agent that is administered prophylactically (e.g., in advance of the development of full-blown disease) to a subject who is at risk of developing a disease or the symptoms thereof, such as a neurological, neurodegenerative, or neurogenetic disease or disorder. In an embodiment, the disorder is Dravet syndrome (DS).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. "Treat" or "treatment" may refer to therapeutic treatment, in which the object is to prevent or slow down (lessen or reduce) an undesired physiological change or disorder. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder, as well as those prone to have the condition or disorder or those in whom the condition or disorder is to be prevented.

As used herein, the terms "prevent," "preventing," "prevention," "prophylactic treatment" and the like, refer to inhibiting or blocking a disease state, or the full development of a disease in a subject, or reducing the probability of developing a disease, disorder or condition in a subject, who does not have, but is at risk of developing, or is susceptible to developing, a disease, disorder, or condition.

As used herein, the term "vector" refers to a nucleic acid (e.g., a DNA vector, such as a plasmid), a RNA vector, virus or other suitable replicon (e.g., viral vector). A "vector" further refers to a nucleic acid (polynucleotide) molecule into which foreign nucleic acid can be inserted without disrupting the ability of the vector to be expressed in, replicate in, and/or integrate into a host cell. A variety of vectors have been developed for the delivery of polynucleotides encoding exogenous proteins into a prokaryotic or eukaryotic cell. A vector may contain a polynucleotide sequence that includes gene of interest (e.g., a transgene, such as a therapeutic gene, a reporter gene, or, more specifically, an SCN1A gene encoding an Nav1.1 sodium channel) as well as, for example, additional sequence elements capable of regulating transcription, translation, and/or the integration of these polynucleotide sequences into the genome of a cell. A vector may contain regulatory sequences, such as a promoter, e.g., a subgenomic promoter, region and an enhancer region, which direct gene transcription. A vector may contain polynucleotide sequences (enhancer sequences) that enhance the rate of translation of these genes or improve the stability or nuclear export of the mRNA that results from gene transcription. These sequence elements may include, e.g., 5' and 3' untranslated regions, an internal ribosomal entry site (IRES), and/or a polyadenylation signal site in order to direct efficient transcription of a gene carried on the expression vector. Vectors, such as viral vectors or the rAAV vectors described herein, may also be referred to as expression vectors.

"Transduction" refers to a process by which DNA or polynucleotide, e.g., one or more transgenes, contained in a virus or virus vector is introduced or transferred into a cell by the virus or virus vector, wherein the DNA or polynucleotide is expressed. In an embodiment, the DNA or polynucleotide transduced into a cell by a virus vector, such as an rAAV vector as described herein, is stably expressed in the cell. In some cases, a virus or virus vector is said to infect a cell.

As used herein, the term "vehicle" refers to a solvent, diluent, or carrier component of a pharmaceutical composition.

By "virus particle" (also called a virion) is meant a virus (infectious agent) that exists as an independent particle comprising the core viral genome or genetic material (RNA or DNA); a protein coat, called the capsid, which surrounds the genetic material and protects it; and, in some cases, an envelope of lipids surrounding the capsid. A virus particle may refer to the form of a virus before it infects a cell and becomes intracellular, or to the form of the virus that infects a cell.

By "virus-like particles (VLPs)" is meant virus particles made up of one of more viral structural proteins, but lacking the viral genome. Because VLPs lack a viral genome, they are non-infectious and yield safer and potentially more-economical vaccines and vaccine products. In addition, VLPs can often be produced by heterologous expression and can be easily purified. Most VLPs comprise at least a viral core protein that drives budding and release of particles from a host cell.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, preferably at least 70%, more preferably 80% or 85%, and most preferably 90%, 95% or even 99% identical at the amino acid level or nucleic acid to the sequence used for comparison, for example, over a specified comparison window. Optimal alignment may be conducted using the homology alignment algorithm of Needleman and Wunsch, 1970, *J. Mol. Biol.*, 48:443. An indication that two peptide or polypeptide sequences are substantially identical is that one peptide or polypeptide is immunologically reactive with specific antibodies raised against the second peptide or polypeptide, although such cross-reactivity is not required for two polypeptides to be deemed substantially identical. Thus, a peptide or polypeptide is substantially identical to a second peptide or polypeptide, for example, where the two differ only by a conservative substitution. Peptides or polypeptides that are "substantially similar" share sequences as noted above except that residue positions which are not identical may differ by conservative amino acid changes. Conservative substitutions typically include, but are not limited to, substitutions within the following groups: glycine and alanine; valine, isoleucine, and leucine; aspartic acid and glutamic acid; asparagine and glutamine; serine and threonine; lysine and arginine; and phenylalanine and tyrosine, and others as known to the skilled person in the art.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "substantially identical" is generally meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). In embodiments, such a sequence is at least 60%, at least 70%, at least 75%, at least 80%, at least 85%, at least 90%, at least 95%, or greater, or at least 99% identical at the amino acid level or nucleic acid to the sequence used for comparison.

Polynucleotides or viral nucleic acid molecules useful in the methods and compositions as described herein include any nucleic acid molecule that encodes a polypeptide, or a fragment thereof, or that encodes the components of viral vectors described herein. The polynucleotides or viral nucleic acid molecules may encode polypeptide products harbored by the viral vectors, such as recombinant adeno-associated virus (rAAV) and the like, as well as a peptide or fragment thereof. Such nucleic acid molecules need not be 100% identical with an endogenous sequence or a viral vector nucleic acid sequence, but will typically exhibit substantial identity. Polynucleotides having substantial identity to an endogenous sequence or to a viral vector sequence are typically capable of hybridizing with at least one strand of a double-stranded nucleic acid molecule or to a viral vector nucleic acid molecule. Nucleic acid molecules useful in the described methods include any nucleic acid molecule that encodes a polypeptide as described herein, or a fragment thereof. By "hybridize" is meant pairing or the nucleic acid molecules to form a double-stranded molecule between complementary polynucleotide sequences (e.g., a gene or nucleic acid sequence described herein), or portions thereof, under various conditions of stringency. (See, e.g., Wahl, G. M. and S. L. Berger (1987) *Methods Enzymol.* 152:399; Kimmel, A. R. (1987) *Methods Enzymol.* 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In another embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In an embodiment, wash steps will occur at 25° C. in 30 mM NaCl, 3 mM trisodium citrate, and 0.1% SDS. In another embodiment, wash steps will occur at 42 C in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations of these conditions will be readily apparent to those skilled in the art. Hybridization techniques are well known to those skilled in the art and are described, for example, in Benton and Davis (Science, 196:180, 1977); Grunstein and Hogness (*Proc. Natl. Acad. Sci., USA,* 72:3961, 1975); Ausubel et al. (*Current Protocols in Molecular Biology*, Wiley Interscience, New York, 2001); Berger and Kimmel (*Guide to Molecular Cloning Techniques,* 1987, Academic Press, New York); and Sambrook et al., *Molecular Cloning: A Laboratory Manual*, Cold Spring Harbor Laboratory Press, New York.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Nonlimiting examples of "moderately stringent hybridization conditions" include a hybridization in a buffer of 40% formamide, 1 M NaCl, 1% SDS at 37 C, and a wash in 1×SSC at 45 C. A positive hybridization is at least twice background. Those of ordinary skill will readily recognize that alternative hybridization and wash conditions can be utilized to provide conditions of similar stringency.

By "ortholog" is meant any polypeptide or nucleic acid molecule of an organism that is highly related to a reference protein or nucleic acid sequence from another organism. The degree of relatedness may be expressed as the probability that a reference protein would identify a sequence, for example, in a blast search. The probability that a reference sequence would identify a random sequence as an ortholog is extremely low, less than $e^{-1}$, $e^{-20}$, $e^{-30}$, $e^{-40}$, $e^{-50}$, $e^{-75}$, $e^{-100}$. The skilled artisan understands that an ortholog is likely to be functionally related to the reference protein or nucleic acid sequence. In other words, the ortholog and its reference molecule would be expected to fulfill similar, if not equivalent, functional roles in their respective organisms, e.g., mouse and human orthologs.

It is not required that an ortholog, when aligned with a reference sequence, have a particular degree of amino acid sequence identity to the reference sequence. A protein ortholog might share significant amino acid sequence identity over the entire length of the protein, for example, or, alternatively, might share significant amino acid sequence identity over only a single functionally important domain of the protein. Such functionally important domains may be defined by genetic mutations or by structure-function assays. Orthologs may be identified using methods practiced in the art. The functional role of an ortholog may be assayed using methods well known to the skilled artisan. For example, function might be assayed in vivo or in vitro using a biochemical, immunological, or enzymatic assay; or transformation rescue. Alternatively, bioassays may be carried out in tissue culture; function may also be assayed by gene inactivation (e.g., by RNAi, siRNA, or gene knockout), or gene over-expression, as well as by other methods.

Ranges as provided herein are understood to be shorthand for all of the values within the range. For example, a range of 1 to 50 is understood to include any number, combination of numbers, or sub-range from the group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, inclusive of the first and last values.

By SCN1A is meant a polypeptide or protein (the sodium channel Nav1.1) or fragment thereof having at least about or equal to 85%, or at least about or equal to 90%, 95%, 98%, 99%, or greater, amino acid sequence identity to the amino acid sequence of the canonical amino acid sequence of SCN1A, Human Isoform 1, OmniProt Identifier No. P35498-1 (Length 2,009 amino acids; Mass (Da): 228,972); RefSeq Nos. NP_001159435.1; NP_001189364.1; NP_001340877. The polypeptide (protein) sequence of human SCN1A is as follows:

```
                                                  (SEQ ID NO: 1)
        10         20         30         40         50
MEQTVLVPPG PDSFNFFTRE SLAAIERRIA EEKAKNPKPD KKDDDENGPK

        60         70         80         90        100
PNSDLEAGKN LPFIYGDIPP EMVSEPLEDL DPYYINKKTF IVLNKGKAIF

       110        120        130        140        150
RFSATSALYI LTPFNPLRKI AIKILVHSLF SMLIMCTILT NCVFMTMSNP

       160        170        180        190        200
PDWTKNVEYT FTGIYTFESL IKIIARGFCL EDFTFLRDPW NWLDFTVITF

       210        220        230        240        250
AYVTEFVDLG NVSALRTFRV LRALKTISVI PGLKTIVGAL IQSVKKLSDV

       260        270        280        290        300
MILTVFCLSV FALIGLQLFM GNLRNKCIQW PPTNASLEEH SIEKNITVNY

       310        320        330        340        350
NGTLINETVF EFDWKSYIQD SRYHYFLEGF LDALLCGNSS DAGQCPEGYM

       360        370        380        390        400
CVKAGRNPNY GYTSFDTFSW AFLSLFRLMT QDFWENLYQL TLRAAGKTYM

       410        420        430        440        450
IFFVLVIFLG SFYLINLILA VVAMAYEEQN QATLEEAEQK EAEFQQMIEQ

       460        470        480        490        500
LKKQQEAAQQ AATATASEHS REPSAAGRLS DSSSEASKLS SKSAKERRNR

       510        520        530        540        550
RKKRKQKEQS GGEEKDEDEF QKSESEDSIR RKGFRFSIEG NRLTYEKRYS

       560        570        580        590        600
SPHQSLLSIR GSLFSPRRNS RTSLFSFRGR AKDVGSENDF ADDEHSTFED

       610        620        630        640        650
NESRRDSLFV PRRHGERRNS NLSQTSRSSR MLAVFPANGK MHSTVDCNGV

       660        670        680        690        700
VSLVGGPSVP TSPVGQLLPE VIIDKPATDD NGTTTETEMR KRRSSSFHVS

       710        720        730        740        750
MDFLEDPSQR QRAMSIASIL TNTVEELEES RQKCPPCWYK FSNIFLIWDC

       760        770        780        790        800
SPYWLKVKHV VNLVVMDPFV DLAITICIVL NTLFMAMEHY PMTDHFNNVL

       810        820        830        840        850
TVGNLVFTGI FTAEMFLKII AMDPYYYFQE GWNIFDGFIV TLSLVELGLA

       860        870        880        890        900
NVEGLSVLRS FRLLRVFKLA KSWPTLNMLI KIIGNSVGAL GNLTLVLAII

       910        920        930        940        950
VFIFAVVGMQ LFGKSYKDCV CKIASDCQLP RWHMNDFFHS FLIVFRVLCG

       960        970        980        990       1000
EWIETMWDCM EVAGQAMCLT VFMMVMVIGN LVVLNLFLAL LLSSFSADNL

      1010       1020       1030       1040       1050
AATDDDNEMN NLQIAVDRMH KGVAYVKRKI YEFIQQSFIR KQKILDEIKP

      1060       1070       1080       1090       1100
LDDLNNKKDS CMSNHTAEIG KDLDYLKDVN GTTSGIGTGS SVEKYIIDES

      1110       1120       1130       1140       1150
DYMSFINNPS LTVTVPIAVG ESDFENLNTE DFSSESDLEE SKEKLNESSS

      1160       1170       1180       1190       1200
SSEGSTVDIG APVEEQPVVE PEETLEPEAC FTEGCVQRFK CCQINVEEGR
```

-continued

```
      1210       1220       1230       1240       1250
GKQWWNLRRT CFRIVEHNWF ETFIVFMILL SSGALAFEDI YIDQRKTIKT

      1260       1270       1280       1290       1300
MLEYADKVFT YIFILEMLLK WVAYGYQTYF TNAWCWLDFL IVDVSLVSLT

      1310       1320       1330       1340       1350
ANALGYSELG AIKSLRTLRA LRPLRALSRF EGMRVVVNAL LGAIPSIMNV

      1360       1370       1380       1390       1400
LLVCLIFWLI FSIMGVNLFA GKFYHCINTT TGDRFDIEDV NNHTDCLKLI

      1410       1420       1430       1440       1450
ERNETARWKN VKVNFDNVGF GYLSLLQVAT FKGWMDIMYA AVDSRNVELQ

      1460       1470       1480       1490       1500
PKYEESLYMY LYFVIFIIFG SFFTLNLFIG VIIDNFNQQK KKFGGQDIFM

      1510       1520       1530       1540       1550
TEEQKKYYNA MKKLGSKKPQ KPIPRPGNKF QGMVFDFVTR QVFDISIMIL

      1560       1570       1580       1590       1600
ICLNMVTMMV ETDDQSEYVT TILSRINLVF IVLFTGECVL KLISLRHYYF

      1610       1620       1630       1640       1650
TIGWNIFDFV VVILSIVGMF LAELIEKYFV SPTLFRVIRL ARIGRILRLI

      1660       1670       1680       1690       1700
KGAKGIRTLL FALMMSLPAL FNIGLLLFLV MFIYAIFGMS NFAYVKREVG

      1710       1720       1730       1740       1750
IDDMFNFETF GNSMICLFQI TTSAGWDGLL APILNSKPPD CDPNKVNPGS

      1760       1770       1780       1790       1800
SVKGDCGNPS VGIFFFVSYI IISFLVVVNM YIAVILENFS VATEESAEPL

      1810       1820       1830       1840       1850
SEDDFEMFYE VWEKFDPDAT QFMEFEKLSQ FAAALEPPLN LPQPNKLQLI

      1860       1870       1880       1890       1900
AMDLPMVSGD RIHCLDILFA FTKRVLGESG EMDALRIQME ERFMASNPSK

      1910       1920       1930       1940       1950
VSYQPITTTL KRKQEEVSAV IIQRAYRRHL LKRTVKQASF TYNKNKIKGG

      1960       1970       1980       1990       2000
ANLLIKEDMI IDRINENSIT EKTDLTMSTA ACPPSYDRVT KPIVEKHEQE

GKDEKAKGK.
```

The Nav1.1 sodium channel is encoded by a human SCN1A polynucleotide sequence or fragment thereof having at least about or equal to 85%, or at least about or equal to 90%, 95%, 98%, 99%, or greater, sequence identity to the SCN1A polynucleotide sequence under Accession No. NCBI CCDS 54413.1 (RefSeq Nos. NM_001165963.2; NM_001202435.2; NM_001353948.1) as set forth below. (Genome information from Genome Reference Consortium GRCh38.p12. GenBank assembly accession: GCA_000001405.27 (latest); RefSeq assembly accession: GCF_000001405.38 (latest))

```
SCN1A Nucleotide Sequence (6030 nt):
                                                        (SEQ ID NO: 2)
atggagcaaacagtgcttgtaccaccaggacctgacagcttcaacttcttcaccagagaatctcttgcg

gctattgaaagacgcattgcagaagaaaaggcaaagaatcccaaaccagacaaaaaagatgacgacgaa

aatggcccaaagccaaatagtgacttggaagctggaaagaaccttccatttatttatggagacattcct

ccagagatggtgtcagagcccctggaggacctggacccctactatatcaataagaaaacttttatagta

ttgaataaagggaaggccatcttccggttcagtgccacctctgccctgtacattttaactcccttcaat

cctcttaggaaaatagctattaagattttggtacattcattattcagcatgctaattatgtgcactatt

ttgacaaactgtgtgtttatgacaatgagtaaccctcctgattggacaaagaatgtagaatacaccttc

acaggaatatatacttttgaatcacttataaaaattattgcaaggggattctgtttagaagattttact

ttccttcgggatccatggaactggctcgatttcactgtcattacatttgcgtacgtcacagagtttgtg
```

-continued gacctgggcaatgtctcggcattgagaacattcagagttctccgagcattgaagacgatttcagtcatt ccaggcctgaaaaccattgtgggagccctgatccagtctgtgaagaagctctcagatgtaatgatcctg actgtgttctgtctgagcgtatttgctctaattgggctgcagctgttcatgggcaacctgaggaataaa tgtatacaatggcctcccaccaatgcttccttggaggaacatagtatagaaaagaatataactgtgaat tataatggtacacttataaatgaaactgtctttgagtttgactggaagtcatatattcaagattcaaga tatcattatttcctggagggtttttagatgcactactatgtggaaatagctctgatgcaggccaatgt ccagagggatatatgtgtgtgaaagctggtagaaatcccaattatggctacacaagctttgataccttc agttgggctttttttgtccttgtttcgactaatgactcaggacttctgggaaaatctttatcaactgaca ttacgtgctgctgggaaaacgtacatgatatttttttgtattggtcattttcttgggctcattctaccta ataaatttgatcctggctgtggtggccatggcctacgaggaacagaatcaggccaccttggaagaagca gaacagaaagaggccgaatttcagcagatgattgaacagcttaaaaagcaacaggaggcagctcagcag gcagcaacggcaactgcctcagaacattccagagagcccagtgcagcaggcaggctctcagacagctca tctgaagcctctaagttgagttccaagagtgctaaggaaagaagaaatcggaggaagaaaagaaaacag aaagagcagtctggtggggaagagaaagatgaggatgaattccaaaaatctgaatctgaggacagcatc aggaggaaaggttttcgcttctccattgaagggaaccgattgacatatgaaaagaggtactcctcccca caccagtctttgttgagcatccgtggctccctattttcaccaaggcgaaatagcagaacaagccttttc agctttagagggcgagcaaaggatgtgggatctgagaacgacttcgcagatgatgagcacagcaccttt gaggataacgagagccgtagagattccttgtttgtgccccgacgacacggagagagacgcaacagcaac ctgagtcagaccagtaggtcatcccggatgctggcagtgtttccagcgaatgggaagatgcacagcact gtggattgcaatggtgtggtttccttggttggtggaccttcagttcctacatcgcctgttggacagctt ctgccagaggtgataatagataagccagctactgatgacaatggaacaaccactgaaactgaaatgaga aagagaaggtcaagttctttccacgtttccatggactttctagaagatccttcccaaaggcaacgagca atgagtatagccagcattctaacaaatacagtagaagaacttgaagaatccaggcagaaatgcccaccc tgttggtataaattttccaacatattcttaatctgggactgttctccatattggttaaaagtgaaacat gttgtcaacctggttgtgatggacccatttgttgacctggccatcaccatctgtattgtcttaaatact cttttcatggccatggagcactatccaatgacggaccatttcaataatgtgcttacagtaggaaacttg gttttcactgggatctttacagcagaaatgtttctgaaaattattgccatggatccttactattatttc caagaaggctggaatatctttgacggttttattgtgacgcttagcctggtagaacttggactcgccaat gtggaaggattatctgttctccgttcatttcgattgctgcgagttttcaagttggcaaaatcttggcca acgttaaatatgctaataaagatcatcggcaattccgtgggggctctgggaaatttaaccctcgtcttg gccatcatcgtcttcatttttgccgtggtcggcatgcagctctttggtaaaagctacaaagattgtgtc tgcaagatcgccagtgattgtcaactcccacgctggcacatgaatgacttcttccactccttcctgatt gtgttccgcgtgctgtgtggggagtggatagagaccatgtgggactgtatggaggttgctggtcaagcc atgtgccttactgtcttcatgatggtcatggtgattggaaacctagtggtcctgaatctctttctggcc ttgcttctgagctcatttagtgcagacaaccttgcagccactgatgatgataatgaaatgaataatctc caaattgctgtggataggatgcacaaaggagtagcttatgtgaaaagaaaaatatatgaatttattcaa cagtccttcattaggaaacaaaagattttagatgaaattaaaccacttgatgatctaaacaacaagaaa gacagttgtatgtccaatcatacagcagaaattgggaaagatcttgactatcttaaagatgtaaatgga actacaagtggtataggaactggcagcagtgttgaaaaatacattattgatgaaagtgattacatgtca ttcataaacaaccccagtcttactgtgactgtaccaattgctgtaggagaatctgactttgaaaattta -continued

```
aacacggaagactttagtagtgaatcggatctggaagaaagcaaagagaaactgaatgaaagcagtagc
tcatcagaaggtagcactgtggacatcggcgcacctgtagaagaacagcccgtagtggaacctgaagaa
actcttgaaccagaagcttgtttcactgaaggctgtgtacaaagattcaagtgttgtcaaatcaatgtg
gaagaaggcagaggaaaacaatggtggaacctgagaaggacgtgtttccgaatagttgaacataactgg
tttgagaccttcattgttttcatgattctccttagtagtggtgctctggcatttgaagatatatatatt
gatcagcgaaagacgattaagacgatgttggaatatgctgacaaggttttcacttacattttcattctg
gaaatgcttctaaaatgggtggcatatggctatcaaacatatttcaccaatgcctggtgttggctggac
ttcttaattgttgatgtttcattggtcagtttaacagcaaatgccttgggttactcagaacttggagcc
atcaaatctctcaggacactaagagctctgagacctctaagagccttatctcgatttgaagggatgagg
gtggttgtgaatgcccttttaggagcaattccatccatcatgaatgtgcttctggtttgtcttatattc
tggctaattttcagcatcatgggcgtaaatttgtttgctggcaaattctaccactgtattaacaccaca
actggtgacaggtttgacatcgaagacgtgaataatcatactgattgcctaaaactaatagaaagaaat
gagactgctcgatggaaaaatgtgaaagtaaactttgataatgtaggatttgggtatctctctttgctt
caagttgccacattcaaaggatggatggatataatgtatgcagcagttgattccagaaatgtggaactc
cagcctaagtatgaagaaagtctgtacatgtatctttactttgttattttcatcatctttgggtccttc
ttcaccttgaacctgtttattggtgtcatcatagataatttcaaccagcagaaaaagaagtttggaggt
caagacatctttatgacagaagaacagaagaaatactataatgcaatgaaaaaattaggatcgaaaaaa
ccgcaaaagcctatacctcgaccaggaaacaaatttcaaggaatggtctttgacttcgtaaccagacaa
gtttttgacataagcatcatgattctcatctgtcttaacatggtcacaatgatggtggaaacagatgac
cagagtgaatatgtgactaccattttgtcacgcatcaatctggtgttcattgtgctatttactggagag
tgtgtactgaaactcatctctctacgccattattatttaccattggatggaatatttttgattttgtg
gttgtcattctctccattgtaggtatgtttcttgccgagctgatagaaaagtatttcgtgtcccctacc
ctgttccgagtgatccgtcttgctaggattggccgaatcctacgtctgatcaaaggagcaaaggggatc
cgcacgctgctctttgctttgatgatgtcccttcctgcgttgtttaacatcggcctcctactcttccta
gtcatgttcatctacgccatctttgggatgtccaactttgcctatgttaagagggaagttgggatcgat
gacatgttcaactttgagacctttggcaacagcatgatctgcctattccaaattacaacctctgctggc
tgggatggattgctagcacccattctcaacagtaagccacccgactgtgaccctaataaagttaaccct
ggaagctcagttaagggagactgtgggaacccatctgttggaatttctttttttgtcagttacatcatc
atatccttcctggttgtggtgaacatgtacatcgcggtcatcctggagaacttcagtgttgctactgaa
gaaagtgcagagcctctgagtgaggatgactttgagatgttctatgaggtttgggagaagtttgatccc
gatgcaactcagttcatggaatttgaaaaattatctcagtttgcagctgcgcttgaaccgcctctcaat
ctgccacaaccaaacaaactccagctcattgccatggatttgcccatggtgagtggtgaccggatccac
tgtcttgatatcttatttgcttttacaaagcgggttctaggagagagtggagagatggatgctctacga
atacagatggaagagcgattcatggcttccaatccttccaaggtctcctatcagccaatcactactact
ttaaaacgaaaacaagaggaagtatctgctgtcattattcagcgtgcttacagacgccaccttttaaag
cgaactgtaaaacaagcttcctttacgtacaataaaaacaaaatcaaaggtggggctaatcttcttata
aaagaagacatgataattgacagaataaatgaaaactctattacagaaaaaactgatctgaccatgtcc
actgcagcttgtccaccttcctatgaccgggtgacaaagccaattgtggaaaaacatgagcaagaaggc
aaagatgaaaaagccaaagggaaataa.
```

The sodium channel Nav1.1 encoded by the SCN1A gene is expressed in multiple distinct neuronal populations in the cortex. These include 3 non-overlapping neuronal populations: fast-spiking cortical interneurons expressing parvalbumin (PV cINs), dis-inhibitory cortical interneurons expressing the vaso-intestinal peptide (VIP cINs) and layer 5 pyramidal neurons.

The amino acid sequence of the unmodified human muscarinic acetylcholine receptor M3 is provided under NCBI Reference Sequence NP_000731.1 as set forth below. Also encompassed herein is a polypeptide or protein or functional fragment thereof having at least about or equal to 85%, or at least about or equal to 90%, 95%, 98%, 99%, or greater, amino acid sequence identity to the following amino acid sequence:

```
                                                      (SEQ ID NO: 3)
  1 MTLHNNSTTS PLFPNISSSW IHSPSDAGLP PGTVTHFGSY NVSRAAGNFS SPDGTTDDPL

 61 GGHTVWQVVF IAFLTGILAL VTIIGNILVI VSFKVNKQLK TVNNYFLLSL ACADLIIGVI

121 SMNLFTTYII MNRWALGNLA CDLWLAIDYV ASNASVMNLL VISFDRYFSI TRPLTYRAKR

181 TTKRAGVMIG LAWVISFVLW APAILFWQYF VGKRTVPPGE CFIQFLSEPT ITFGTAIAAF

241 YMPVTIMTIL YWRIYKETEK RTKELAGLQA SGTEAETENF VHPTGSSRSC SSYELQQQSM

301 KRSNRRKYGR CHFWFTTKSW KPSSEQMDQD HSSSDSWNNN DAAASLENSA SSDEEDIGSE

361 TRAIYSIVLK LPGHSTILNS TKLPSSDNLQ VPEEELGMVD LERKADKLQA QKSVDDGGSF

421 PKSFSKLPIQ LESAVDTAKT SDVNSSVGKS TATLPLSFKE ATLAKRFALK TRSQITKRKR

481 MSLVKEKKAA QTLSAILLAF IITWTPYNIM VLVNTFCDSC IPKTFWNLGY WLCYINSTVN

541 PVCYALCNKT FRTTFKMLLL CQCDKKKRRK QQYQQRQSVI FHKRAPEQAL.
```

The amino acid sequence of the human Gq-DREADD (hM3Dq) excitatory receptor is derived from the amino-acid sequence of the unmodified human muscarinic acetylcholine receptor M3 set forth above. In the Gq-DREADD (hM3Dq) receptor amino acid sequence (590 aa), the tyrosine in position 149 is replaced by a cysteine, and the arginine in position 239 is replaced by a glycine (US Publication No. 2018/0078658), as shown below:

```
                                                              (SEQ ID NO: 4)
Met Thr Leu His Asn Asn Ser Thr Thr Ser Pro Leu Phe Pro Asn Ile Ser Ser Ser Trp

Ile His Ser Pro Ser Asp Ala Gly Leu Pro Pro Gly Thr Val Thr His Phe Gly Ser Tyr

Asn Val Ser Arg Ala Ala Gly Asn Phe Ser Ser Pro Asp Gly Thr Thr Asp Asp Pro Leu

Gly Gly His Thr Val Trp Gln Val Val Phe Ile Ala Phe Leu Thr Gly Ile Leu Ala Leu

Val Thr Ile Ile Gly Asn Ile Leu Val Ile Val Ser Phe Lys Val Asn Lys Gln Leu Lys Thr

Val Asn Asn Tyr Phe Leu Leu Ser Leu Ala Cys Ala Asp Leu Ile Ile Gly Val Ile Ser

Met Asn Leu Phe Thr Thr Tyr Ile Ile Met Asn Arg Trp Ala Leu Gly Asn Leu Ala Cys

Asp Leu Trp Leu Ala Ile Asp Cys Val Ala Ser Asn Ala Ser Val Met Asn Leu Leu Val

Ile Ser Phe Asp Arg Tyr Phe Ser Ile Thr Arg Pro Leu Thr Tyr Arg Ala Lys Arg Thr

Thr Lys Arg Ala Gly Val Met Ile Gly Leu Ala Trp Val Ile Ser Phe Val Leu Trp Ala

Pro Ala Ile Leu Phe Trp Gln Tyr Phe Val Gly Lys Arg Thr Val Pro Pro Gly Glu Cys

Phe Ile Gln Phe Leu Ser Glu Pro Thr Ile Thr Phe Gly Thr Ala Ile Ala Gly Phe Tyr

Met Pro Val Thr Ile Met Thr Ile Leu Tyr Trp Arg Ile Tyr Lys Glu Thr Glu Lys Arg

Thr Lys Glu Leu Ala Gly Leu Gln Ala Ser Gly Thr Glu Ala Glu Thr Glu Asn Phe Val

His Pro Thr Gly Ser Ser Arg Ser Cys Ser Ser Tyr Glu Leu Gln Gln Gln Ser Met Lys

Arg Ser Asn Arg Arg Lys Tyr Gly Arg Cys His Phe Trp Phe Thr Thr Lys Ser Trp Lys
```

-continued

Pro Ser Ser Glu Gln Met Asp Gln Asp His Ser Ser Ser Asp Ser Trp Asn Asn Asn Asp

Ala Ala Ala Ser Leu Glu Asn Ser Ala Ser Ser Asp Glu Glu Asp Ile Gly Ser Glu Thr

Arg Ala Ile Tyr Ser Ile Val Leu Lys Leu Pro Gly His Ser Thr Ile Leu Asn Ser Thr Lys

Leu Pro Ser Ser Asp Asn Leu Gln Val Pro Glu Glu Glu Leu Gly Met Val Asp Leu

Glu Arg Lys Ala Asp Lys Leu Gln Ala Gln Lys Ser Val Asp Asp Gly Gly Ser Phe Pro

Lys Ser Phe Ser Lys Leu Pro Ile Gln Leu Glu Ser Ala Val Asp Thr Ala Lys Thr Ser

Asp Val Asn Ser Ser Val Gly Lys Ser Thr Ala Thr Leu Pro Leu Ser Phe Lys Glu Ala

Thr Leu Ala Lys Arg Phe Ala Leu Lys Thr Arg Ser Gln Ile Thr Lys Arg Lys Arg Met

Ser Leu Val Lys Glu Lys Lys Ala Ala Gln Thr Leu Ser Ala Ile Leu Leu Ala Phe Ile

Ile Thr Trp Thr Pro Tyr Asn Ile Met Val Leu Val Asn Thr Phe Cys Asp Ser Cys Ile

Pro Lys Thr Phe Trp Asn Leu Gly Tyr Trp Leu Cys Tyr Ile Asn Ser Thr Val Asn Pro

Val Cys Tyr Ala Leu Cys Asn Lys Thr Phe Arg Thr Thr Phe Lys Met Leu Leu Leu

Cys Gln Cys Asp Lys Lys Lys Arg Arg Lys Gln Gln Tyr Gln Gln Arg Gln Ser Val Ile

Phe His Lys Arg Ala Pro Glu Gln Ala Leu.

Unless specifically stated or obvious from context, as used herein, the term "or" is understood to be inclusive. Unless specifically stated or obvious from context, as used herein, the terms "a", "an", and "the" are understood to be singular or plural.

As used herein, the term "about" or "approximately" means within an acceptable error range for the type of value described and the method used to measure the value. For example, these terms can signify within 20%, more preferably within 10%, and most preferably still within 5% of a given value or range. More specifically, "about" can be understood as within 20%, 10%, 9%, 8%, 7%, 6%, 5%, 4%, 3%, 2%, 1%, 0.5%, 0.1%, 0.05%, or 0.01% of the stated value or range. Alternatively, especially in biological systems, the term "about" means within one log unit (i.e., one order of magnitude), preferably within a factor of two of a given value. Unless specifically stated or obvious from context, as used herein, the term "about" is understood as within a range of normal tolerance in the art, for example within 2 standard deviations of the mean. Unless otherwise clear from context, all numerical values provided herein are modified by the term about.

The recitation of a listing of chemical groups or component groups in any definition of a variable herein includes definitions of that variable as any single group or combination of listed groups. The recitation of an embodiment for a variable or aspect herein includes that embodiment as any single embodiment or in combination with any other embodiments or portions thereof as described in the disclosure.

Any compositions or methods provided herein can be combined with one or more of any of the other compositions and methods provided herein.

BRIEF DESCRIPTION OF THE DRAWINGS

FIGS. 1A-1, 1A-2, 1A-3, 1B-1, 1B-2, 1C and 1D present tabular data and information related to the discovery and identification of specific enhancer (regulatory) sequences, called "E1-E35" herein. Shown are enhancers specific for SCN1A-restricted gene expression, such as E1-E10, in GABAergic interneurons, such as PV-expressing interneurons, as well as enhancers that target other genes presented in the tables. FIG. 1A-1 presents tabular data depicting gene, target (e.g., neuronal cell type), specificity, position (e.g., intergenic or intronic), chromosome location and genome sequence start and stop site characteristics of thirty-five (35) enhancer elements, called E1-E35, in the mouse genome. Similarly, FIGS. 1A-2 and 1A-3 present tabular data depicting the gene, target (e.g., neuronal cell type), specificity, position (e.g., intergenic or intronic), chromosome location and genome sequence start and stop site characteristics of these thirty-five (35) E1-E35 enhancer elements in the human genome. By way of example, enhancer (regulatory) elements E1-E10 (also called S5E1-S5E10 herein) were identified in the vicinity of the human SCN1A gene, in the mouse genome (FIG. 1A-1) and in the human genome (FIGS. 1A-2 and 1A-3). In FIGS. 1A-1 to 1A-3, the polynucleotide sequences of the mouse and human enhancer elements described herein have the start and stop sites in the mouse and human genomes as set forth in the tables (as well as in the tables of FIGS. 15A-1, 15A-2, 16A-1 and 16A-2); the mouse and human enhancer sequences are provided via the web-accessible genome information listed in the tables of FIGS. 1A-1 to 1A-3. FIGS. 1B-1 and 1B-2 present images showing E1-E10 enhancer element-restricted reporter gene expression in PV-expressing interneurons in cortical layers of brain. The images show the results of immunohistochemical (IHC) staining analysis for dTomato in brain sections following systemic in vivo injection of the pAAV-S5-E2-dTomato vector into an animal (mouse), allowing for detection of specific cells transduced by the vector. FIGS. 1C and 1D show graphs depicting the quantification of the degree of the specificity (FIG. 1C) and sensitivity (FIG. 1D) of expression of a reporter gene in PV-expressing interneurons in the cortex. The expression of the reporter gene is controlled by the E1-E10 enhancer elements contained in rAAV vectors. The specificity was quantified as the proportion of cells expressing the viral reporter dTomato co-expressing the PV-interneuron marker PV assessed by immunohistochemistry on brain sections following systemic in vivo injection of the pAAV-S5-E2-dTomato vector into an animal (mouse). The sensitivity was quantified as the proportion of cells expressing the PV-interneuron marker PV that co-expressed in the viral reporter dTomato as assessed by immunohistochemistry on brain sections following systemic in vivo injection of the pAAV-S5-E2-dTomato vector into an animal (mouse). Bar graphs represent mean+/−standard error of the mean (s.e.m.).

FIG. 2A presents an image showing the results of immunohistochemical (IHC) staining analysis for the dTomato reporter in brain sections (sagittal sections in the top portion of the figure; coronal sections in the lower portions of the figure) following systemic in vivo injection of the pAAV-S5-E2-dTomato vector into an animal (mouse), allowing for detection of specific cells transduced by the vector. FIG. 2B presents images showing the results of immunohistochemical (IHC) staining analysis for the dTomato reporter expressed in brain sections following systemic in vivo injection of the pAAV-S5-E2-dTomato vector, or into an animal (mouse), allowing for detection of specific cells expressing PV. Reporter gene expression from the pAAV-S5-E2-dTomato vector is visualized in brain sections (in red in the left panel of FIG. 2B). Reporter gene expression from the pAAV-S5-E2-Gq-DREADD-dTomato is visualized in green for Gq-DREADD and red for dTomato in the right panel of FIG. 2B). Detection of specific PV-expressing cells transduced by the vector is visualized (in the left panel of FIG. 2B, and in the right panel of FIG. 2B).

FIG. 3A provides a schematic representation of the scATAC-seq pipeline. Interneurons were collected from the visual cortex of adult Dlx6a$^{Cre}$::Sun1-eGFP mice. FIG. 3B shows a plot of the 3500 nuclei in UMAP space. The clusters obtained from the SnapATAC pipeline were lumped into the four cardinal classes of interneurons. FIG. 3C presents a Venn diagram showing the numbers of unique and shared peaks across the four interneuron populations, PV, SST, VIP and ID2. FIG. 3D shows a schematic representation of the enhancer selection method at the SCN1A locus, as described in the Methods herein (Example 8). FIGS. 3E and 3F illustrate results obtained following the systemic injection of adult mice with the indicated rAAV-E[x]-dTomato vector containing an enhancer element as described and the analysis 3 weeks post-injection. Immunohistochemical (IHC) evaluation for the reporter and indicated markers in the S1 cortex was used to assess the strength of expression of the reporter (FIG. 3E, upper panel) and the specificity of expression of the viral reporter for the indicated markers (all other panels). Representative fluorescent images of the indicated viral reporter in the somatosensory cortex (FIG. 3F, left panels). Dashed lines represent the limits of anatomical structures. Scale bars represent 100 μm. On the graphs, the dots represent individual measurements and the lines represent average+/−s.e.m.

FIG. 4C shows a slice recoding of the intrinsic properties of virally labeled neurons. FIG. 4D (right panel) presents a graph illustrating the specificity of expression shown as the proportion of cells expressing the reporter that co-express the PV relative to the strength of expression of the reporter. FIG. 4E presents images resulting from experiments in which mice were injected locally with rAAV-E2-dTomato expressing the reporter dTomato under the control of the E2 regulatory element and analyzed at the indicated developmental stages for the reporter and the indicated markers. Scale bars represent 250 μm (FIG. 4A) and 50 μm (FIGS. 4B, 4D, 4E). In the graphs, the dots represent individual measurements, and the lines represent average+/−s.e.m.

FIG. 5B—P14 injection with rAAV-E2-GCaMP6f, FIGS. 5D and 5E—Adult injection with rAAV-E2-CIV1-eYFP), or systemically (FIG. 5C—Adult injection with rAAV-E2-PSAM4-5HT3-LC-GFP). FIG. 5A presents representative images of the co-localization between the SYP-dTomato reporter and the synaptic marker Syt2 one-week post-injection and corresponding quantification. FIG. 5B shows results of Ca2+ imaging upon whisker stimulation performed 2-3 weeks post-injection. In the right panel, the success rate was calculated as the proportions of ΔF/F peaks above threshold in response to whisker stimulation. FIG. 5C shows the results of current clamp recording performed on brain sections 4 weeks after injection. The traces show a representative cellular response at the indicated currents at both baseline and after bath application of varenicline. FIG. 5D shows the results of current clamp recording performed on brain sections 1 week after injection. Cells expressing the viral reporter were exposed to 2 seconds of constant laser stimulation (550 nm) while the voltage was recorded over 3 seconds. Neighboring pyramidal cells that did not express the viral reporter were also recorded from during laser stimulation. FIG. 5E illustrates in vivo single-unit analysis of neuronal activity and shows Raster plots of virally infected neurons upon laser stimulation and corresponding population quantification data. The left panels show fast-spiking cells and the right panels show regular spiking excitatory cells. Notably, due to the mosaic nature of local viral injection, individual cell responses were bimodal. This likely reflects whether or not particular cells were infected. Scale bars represent 5 μm. The middle bars at the top of the "Trial" versus "Time" graphs represent laser stimulation. In the graphs, dots represent individual measurements and the lines represent average+/−s.e.m.

FIG. 6A: Animals from indicated species were locally (rat and macaque) or systemically (marmoset) injected with rAAV-E2-C1V1-eYFP (macaque) or rAAV-E2-dTomato (rat and marmoset) and analyzed 2-8 weeks post-injection. The specificity of expression is shown as the proportion of virally labeled cells co-expressing PV. FIG. 6B: Human brain tissue obtained from surgical resection was exposed to either rAAV-E2-dTomato (i-iii) or rAAV-E2-C1V1-eYFP (iv) and maintained in culture for 7-14 days. The upper right panel shows the proportion of fast-spiking neurons among the virally-labeled cells assessed by electrophysiological recordings of intrinsic properties. (iv) Electrophysiology current clamp recording of virally labeled cells upon laser stimulation. Scale bars represent 25 μm. The bar at the top of the "Direct photoactivation (PV)" trace represents laser stimulation and the arrowheads point at neurons co-expressing PV and the viral reporter. On the graphs, dots represent individual measurements and the lines represent average+/−s.e.m.

FIG. 8A relates to slice recording of the intrinsic properties of virally labeled neurons. The left panel shows a representative cell expressing the viral reporter. The triangular trace in the middle, top represents the recording pipet. The quantifications show the indicated parameters. The darker gray dots in the "Identity" graph represent cells with stereotypical fast-spiking (FS) properties. FIG. 8B shows representative slice recording traces of positive and negative fast-spiking cells (FS and nFS, respectively. Scale bars represent 20 μm. On the graphs, dots represent individual measurements and the lines represent average+/−s.e.m. FIGS. 8C and 8D show results following systemic injection of adult mice with rAAV-E2-dTomato and analysis 3 weeks post-injection. FIG. 8C: Coronal and sagittal sections were analyzed with IHC for the viral reporter and PV and the specificity to PV was reported across brain regions. FIG. 8D: The native viral expression was analyzed from the indicated organs. Scale bars represent 100 μm (FIG. 8C) and 250 μm (FIG. 8D). On the graphs, dots represent individual measurements and the lines represent average+/−s.e.m.

(FIG. 9A: P14 injection with rAAV-E2-GCaMP6f) and locally (FIG. 9B: rAAV-E2-C1V1-eYFP; FIG. 9C: rAAV-E2-GqDREADD) in the somatosensory cortex. FIG. 9A: Mice were analyzed 1-week post-injection. The left panel shows widefield images of two representative peaks shown by the pound sign in the middle panels. The right panel shows a fluorescent image taken after GCaMP recordings. FIG. 9B: Slice electrophysiology current clamp recording were performed 1-week post-injection. Cells expressing the viral reporter were targeted with either 10 Hz or 40 Hz laser stimulation (550 nm) while the voltage was recorded over 3 seconds. FIG. 9C: Slice electrophysiology current clamp recordings were performed 1-week post-injection. The voltage was recorded before and after bath application of CNO. Scale bars represent 500 μm. The "+CNO" bars represent laser stimulation. On the graphs, dots represent individual measurements.

FIG. 10A: Representative image of the dendrites of virally labeled cells filled with Biocytin during the recording session. FIG. 10B: Slice recording of the intrinsic properties of virally labeled neurons. The quantifications show the indicated parameters. The darker, rightmost dots in the "Identity" graph represent cells with stereotypical fast-spiking (FS) properties. Scale bar represent 100 μm. In the graphs, the dots represent individual measurements and the lines represent average+/−s.e.m.

FIG. 11 provides a table showing quantifications of cells expressing markers/reporters. As described in Example 7, quantifications were performed using a minimum of two independent biological replicates, and the specific numbers of cells and conditions are indicated for each individual quantification in the table.

FIG. 13A: Adult mice were injected systemically with the indicated rAAV vector containing an enhancer element polynucleotide sequence and a detectable reporter or marker (e.g., GFP) polynucleotide, i.e., rAAV-E[x]-eGFP, and analyzed 3 weeks post-injection. Immunohistochemistry (IHC) for the reporter and indicated markers in the S1 cortex was used to assess the density of neuronal cell-bodies expressing the viral reporter (left panels) and the specificity of expression of the viral reporter for the indicated markers (right panels). For the E29 virus, no cell bodies are observed in the thalamus, with the exception of the thalamic reticular nucleus (TRN). FIG. 13B: An adult macaque was injected in V1 with rAAV-E22-eGFP and analyzed 8 weeks post-injection with IHC for the reporter and indicated markers. Scale bars represent 100 μm (a), 50 μm (b, left) and 10 μm (b, right). On the graphs, dots represent individual measurements and the lines represent average+/−s.e.m.

FIGS. 15A-1 and 15A-2 present a table containing the specifications for all tested enhancers, including their associated gene, target population, specificity for target population, location, presence of ATAC peaks, and conservation with the human sequence.

FIGS. 16A-1 and 16A-2 present a table that compiles various parameters related to each of the tested enhancers, including enhancer name (E1-E35), gene, target, % specificity, murine chromosome location (Mouse_mm10_Chr), enhancer sequence start site in murine genome (Mouse_mm10_Start), enhancer sequence stop site in murine genome (Mouse_mm10_Stop), size (base pairs (bp)), human chromosome location (Human_hg38_Chr), enhancer sequence start site in human genome (Human_hg38_Start), enhancer sequence stop site in human genome (Human_hg38_Stop), and Percentage of conservation between the mouse and human enhancer sequences. In the tables presented in FIGS. 15A-1 and 15A-2, and FIGS. 16-A1 and 16-A2, as well as in FIGS. 1A1 to 1A3, the total number of base pairs (bp) shown for the polynucleotide sequence of each of the listed enhancers E1-E35 reflects that the numerical value of the first base pair (bp) counted in the sequence is valued at zero (0), as would be appreciated by one skilled in the art. Notwithstanding, the total number of bp comprising the polynucleotide sequence of each enhancer (E1-E35) is obtainable simply by counting the number of total bp in the sequence, based on the tabularized data presented in the figures described herein.

DETAILED DESCRIPTION OF THE EMBODIMENTS

Figures 1, 1B:
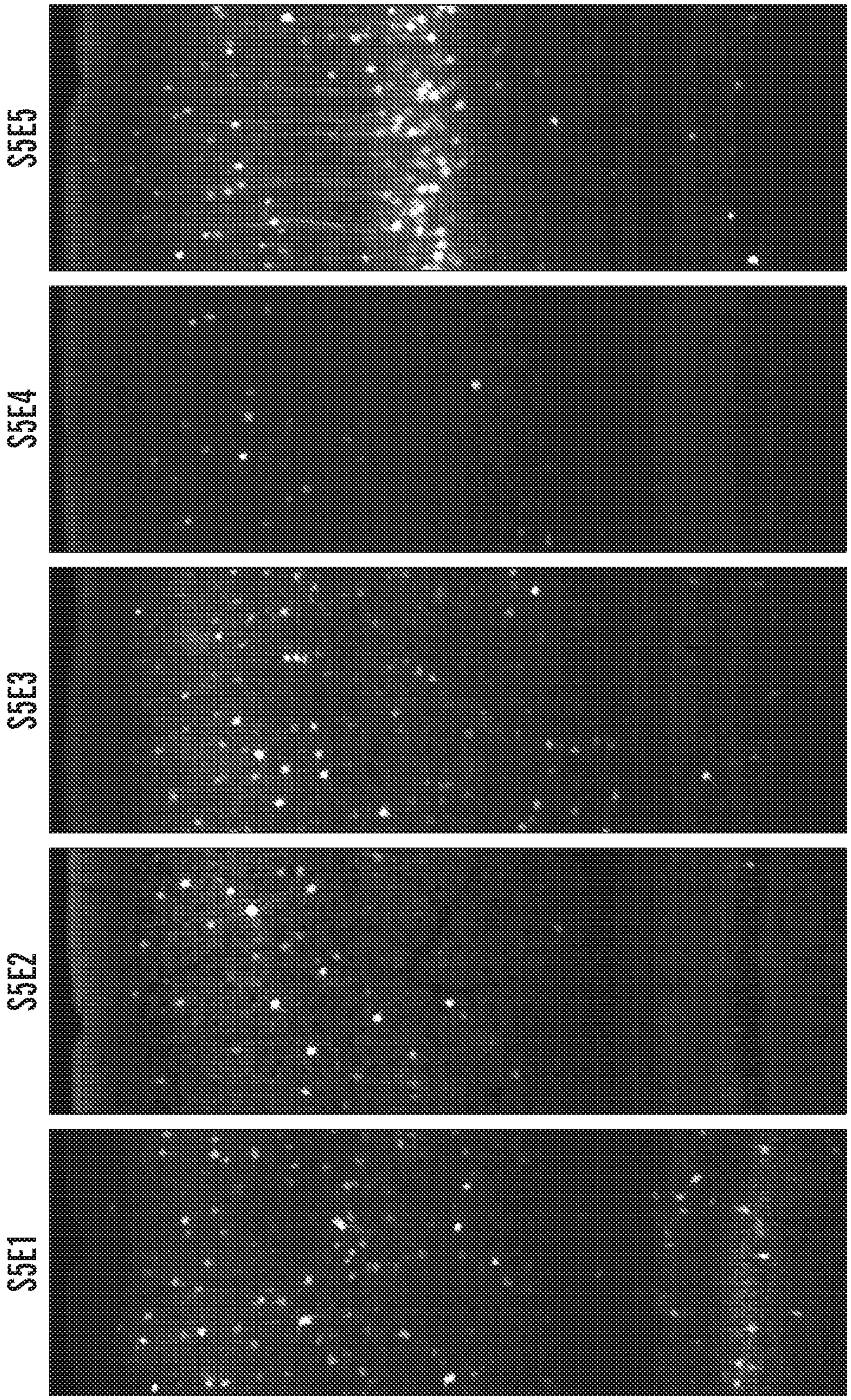

The embodiments featured and described herein relate to strategies, methods and products developed to identify multiple new enhancers, (E1-E35), for use with viral vectors, such as recombinant adeno-associated virus (rAAV) vectors, for example, to target functionally distinct neuronal subtypes, particularly, within the cerebral cortex. Investigation of the regulatory landscape of the disease gene SCN1A led to the identification of enhancers that target the breadth of its expression, including, by way of nonlimiting example, two enhancers that are selective for parvalbumin (PV) and vasoactive intestinal peptide (VIP) cortical interneurons. The functional utility of these regulatory elements was demonstrated, and it was found that the PV-specific enhancers allowed for the selective targeting and manipulation of these neurons across species, from mice to humans. Moreover, the selection method as described herein is generalizable to other genes and characterized certain PV-specific enhancers, such as, for example, E11, E14, E22 and E29, which have a high degree of specificity for distinct regions of the brain. Recombinant viral vectors, e.g., rAAV vectors, harboring the enhancer sequences provide viral tools for use in cell-type specific circuit manipulation and in therapeutic interventions to treat and ameliorate neuropathological or neuropsychiatric diseases, conditions and pathologies.

Specific viral-based therapeutic products, compositions, methods and approaches for treating or ameliorating neurological, neurodevelopmental, neurogenetic, or neuropsychiatric diseases, disorders, and pathologies are described herein. As described, virus vectors and vehicles for gene delivery are designed and produced to contain a specific enhancer sequence (enhancer) and a polynucleotide sequence of a gene of interest, such as an effector gene (e.g., a transgene or reporter gene), which is specifically and functionally expressed in specific interneuron or neuron cell populations following transduction of the interneuron or neuron cells by the virus vector or vehicle. In an embodiment, a virus vector or vehicle is provided which comprises the polynucleotide of a specific enhancer sequence (enhancer), which is specifically and functionally expressed in specific interneuron or neuron cell populations following transduction of the interneuron or neuron cells by the virus vector or vehicle. In an embodiment, the enhancer harbored by the virus is capable of restricting the expression of the transgene to certain interneuron cells or neuronal cells. In embodiments, expression of the transgene is restricted to expression in cells that are deficient for that gene. In an embodiment, the expression of the transgene is specifically modulated in the interneuron cell or other neuronal cell. In other embodiments, the transgene is an effector gene or a therapeutic gene. In embodiments, the enhancer element restricts expression of a gene to one or more neuronal cell types, including a parvalbumin (PV)-expressing cortical interneuron cell (PV-cIN cell), which is a fast-spiking cortical interneuron; a dis-inhibitory cortical interneuron cell expressing vaso-intestinal peptide (VIP), (VIP cIN cell); and a pyramidal (PYR) neuron, in particular, a pyramidal neuron of cortical layer 5 of the brain.

In an embodiment, the virus vector contains a specific enhancer sequence and a transgene (effector gene) associated with a neurological, neurodevelopmental or neurogenetic disease, disorder, or condition, and the enhancer is capable of restricting the expression of the transgene to an interneuron cell population that has loss-of-function for the gene, is deficient for the gene, or that expresses a mutant, variant, or defective form of the gene associated with the neurological or neurogenetic disease, disorder, and pathology. In a particular embodiment, the enhancer sequence inserted in the virus vector polynucleotide is identified as one having specificity for regulating the expression of the SCN1A gene, which encodes the Nav1.1 sodium channel, and restricting expression to SCN1A-expressing cells, in particular, GABAergic interneuron cells. Loss of function of the SCN1A gene is the most prevalent cause of the debilitating disease Dravet syndrome (DS), which is a pharmacoresistant form of infantile epilepsy associated with cognitive impairment and premature death. In certain embodiments, the specific expression of the transgene (effector gene) in interneurons may be determined by the detection of markers that are specific for interneuron cells, e.g., without limitation, GABA GAD67, or PV interneuron cell markers. In an embodiment, the virus vector or vehicle is an adeno-associated virus (AAV) or a recombinant AAV (rAAV). The terms "AAV" and "rAAV" are used interchangeably herein.

The term "transgene" is used herein to refer to a gene (or genes) of interest (an effector gene) contained in the rAAV vector or vehicle as described herein and is specifically expressed and functional in a certain cell types or populations as described herein, especially by virtue of the enhancer sequence also contained in the rAAV vector, which restricts the expression of the gene to a defined population of cells, e.g., PV-expressing or SCN1A-expressing interneurons or subtypes thereof. In some cases, the gene of interest (effector gene) is a normal form of a gene that is expressed in the cell type transduced by rAAV and whose encoded product functions to provide a normal or normally-functioning product in the cell, such as a cell in which there is a loss of function of the same gene as the transgene. In some cases, the transgene or effector gene may be a reporter gene, e.g., green fluorescent protein (GFP) or red fluorescent protein (RFP) that provides a detectable signal following transduction of a cell by the rAAV vector. In some cases, the transgene or effector gene may be both a reporter and a gene that encodes a product whose expression and activity provide for normal cell function. The latter type of gene may be considered to be a therapeutic gene. In a particular embodiment, the rAAV contains an SCN1A-specific enhancer sequence and an SCN1A transgene.

The rAAV vectors and methods described herein are based, at least in part, on the discovery and demonstration that a specific enhancer can restrict the expression of a transgene carried by the virus vector, such as a gene associated with a neurological disease, disorder, or pathology, or a reporter gene, to interneuron cells ("interneurons") in the brain where the gene is expressed and the encoded gene (transgene) product is functional. In an embodiment, such an expressed, functional gene offsets, replaces, or substitutes for, the abnormal, aberrant, or lack of function of a gene encoding a product involved in the normal functioning of an interneuron cell.

In an embodiment, a suitable viral vector, e.g., a lentiviral vector or, in particular, a recombinant adeno-associated virus (rAAV) vector, is used to restrict expression of a transgene in GABA-ergic PV-expressing interneurons a mammal, in which an enhancer element as described herein provided in cis. In embodiments, the enhancer element is one of S5E1 (E1), S5E2 (E2), S5E3 (E3), S5E4 (E4), S5E6 (E6), S5E7 (E7), S5E8 (E8), S5E9 (E9), S5E10 (E10). In embodiments, the enhancer element is E2, which is capable of restricting the expression of a viral reporter to parvalbumin (PV)-expressing cortical interneurons (PV cINs), E6, which is selective for VIP interneurons; or E5, which labels interneuron populations across all cortical layers, yet is especially selective for pyramidal neurons in layer 5 of the brain cortex, in particular, glutamatergic pyramidal neurons, as described herein. In a particular embodiment, the enhancer element is E2. In another particular embodiment, the enhancer element is E5. In yet another particular embodiment, the enhancer element is E6.

In an embodiment, the viral vector or rAAV vector comprising the enhancer drives the expression of a copy of SCN1A in a transduced PV-expressing interneuron cell for the treatment and therapy of seizures, all forms of epilepsy, or DS. In other embodiments, the vector or rAAV vector comprising the enhancer drives the expression of effectors like Gq-DREADD or PSAM for chemogenetic modulation of PV-interneuron activity for the treatment of all forms of seizures, epilepsy, including focal and pharmacologically intractable epilepsy, and also for the treatment of DS and the symptoms thereof.

In general, a viral vector or rAAV vector comprises a polynucleotide comprising an enhancer sequence selected from S5E1-S5E10 as described herein, and a transgene sequence, such as, a polynucleotide sequence encoding an SCN1A gene, a polynucleotide sequence encoding hM3Dq modified muscarinic receptor (Gq-DREADD) receptor, or a polynucleotide sequence encoding PSAM. In an embodiment, the polynucleotide comprises an enhancer sequence selected from E2, E5, or E6 as described herein. In certain embodiments, methods are provided for therapeutic and prophylactic treatments for seizures and epilepsy, and more specifically, Dravet syndrome, in an individual (e.g., a human patient) in need thereof.

In an embodiment, a method is provided in which an individual or subject in need, e.g., a patient afflicted with seizures, epilepsy, or DS, is administered a viral vector, such as a recombinant adeno-associated virus (rAAV) vector. comprising an enhancer sequence as described herein, such as E2, E5, or E6, and a transgene polynucleotide sequence encoding, for example, an SCN1A-encoding polynucleotide sequence, a hM3Dq modified muscarinic receptor (Gq-DREADD)-encoding polynucleotide sequence, or a PSAM-encoding polynucleotide sequence, such that SCN1A, Gq-DREADD, or PSAM, respectively, is expressed in interneurons of the individual or subject, especially in PV-expressing interneurons. Thus, a method is provided for converting interneurons, especially, PV-expressing interneurons, in an individual or subject in need, that do not express SCN1A, Gq-DREADD, or PSAM to interneurons that do express SCN1A, Gq-DREADD, or PSAM, respectively. As such, the expression of the genes and encoded proteins is linked to the presence of the enhancer element (E1-E10) as described herein that is also provided as a component of the rAAV vector genome. In an embodiment, the enhancer element is E2, E5, or E6. In an embodiment, an individual or subject in need, e.g., a patient afflicted with seizures, epilepsy, or DS, is administered a viral vector, such as a recombinant adeno-associated virus (rAAV) vector. comprising an enhancer sequence as described herein, such as E2, and a transgene polynucleotide sequence encoding SCN1A.

In an embodiment, a prophylactic or therapeutic treatment method is provided for prophylaxis and/or therapy for seizures, epilepsy, or DS, which comprises introducing into an individual or subject in need a viral vector or an rAAV vector which comprises an enhancer sequence (E1-E10) as described herein, and a sequence encoding an SCN1A-encoding polynucleotide sequence such that the severity of the seizures, epilepsy, or DS symptoms experienced by the individual or subject is reduced, or the seizures, epilepsy, or DS symptoms are treated or prevented. In an embodiment, the enhancer element is E2, E5, or E6. In an embodiment, the individual or subject in need is experiencing a seizure (e.g., an epileptic seizure) or a symptom of DS at the time of administering the vector. Following administration of the vector to the individual or subject, the severity of the seizures, epilepsy, or DS symptoms is reduced, or the seizures, epilepsy, or DS symptoms are treated or prevented.

In an embodiment, a prophylactic or therapeutic treatment method is provided for prophylaxis and/or therapy for seizures, epilepsy, or DS, which comprises introducing into an individual a viral vector or an rAAV vector which comprises an enhancer sequence (E1-E10) as described herein, and a sequence encoding an hM3Dq modified muscarinic receptor (Gq-DREADD)-encoding polynucleotide sequence, and subsequently administering to the individual an effective amount of an agonist of the Gq-DREADD such that the severity of the seizures, epilepsy, or DS symptoms is reduced, or the seizures, epilepsy, or DS symptoms are treated or prevented. In an embodiment, the enhancer element is E2, E5, or E6. In an embodiment, the individual or subject in need is experiencing a seizure (e.g., and epileptic seizure) at the time of administering the agonist of the Gq-DREADD receptor. Following administration of the agonist, the severity of the seizure is reduced. In embodiments, Gq-DREADD receptor agonist is clozapine-N4-oxide (CNO) or another suitable Gq-DREADD receptor agonist as known and used in the art.

In embodiments of the therapeutic and prophylactic methods described herein, the individual or subject is experiencing, or is at risk for developing, a partial seizure or a generalized seizure. In other embodiments the individual or subject has, is suspected of having, or has been diagnosed with epilepsy of any form, including, without limitation, pharmaco-resistant epilepsy. In accordance with the described methods, seizures, epilepsy, or DS symptoms are inhibited, blocked, reduced, abated, or prevented.

In an embodiment, a composition comprising a viral vector or rAAV vector is administered to a subject in need thereof. In an embodiment, the administration of a composition comprising a vector (or the vector itself) comprising an enhancer element, e.g., E1-E10, as described herein and a polynucleotide encoding SCN1A facilitates conversion of interneurons or PV-expressing interneurons of an individual or subject that do not express SCN1A into SCN1A-expressing interneurons or PV-expressing interneurons in the brain. In another embodiment, the administration of a composition comprising a vector (or the vector itself) comprising an enhancer element, e.g., E1-E10, as described herein and a polynucleotide encoding Gq-DREADD receptor facilitates conversion of interneurons or PV-expressing interneurons of an individual or subject that do not express Gq-DREADD receptor into Gq-DREADD receptor-expressing interneurons or PV-expressing interneurons in the brain, thereby resulting in interneurons or PV-expressing interneurons that are responsive to a Gq-DREADD agonist. In another embodiment, the administration of a composition comprising a vector (or the vector itself) comprising an enhancer element, e.g., E1-E10, as described herein and a polynucleotide encoding a PSAM facilitates conversion of interneurons or PV-expressing interneurons of an individual or subject that do not express PSAM into PSAM-expressing interneurons or PV-expressing interneurons in the brain. In an embodiment, the vectors, compositions and methods as described herein are used in the prophylactic or therapeutic treatment of partial and/or generalized seizures. In an embodiment, the enhancer element is E2, E5, or E6.

In an embodiment, the vectors, compositions and methods as described herein are used in the prophylactic or therapeutic treatment of various forms of epilepsy, including, without limitation, pharmaco-resistant epilepsy and/or may constitute a replacement of a pharmacological treatment. In embodiments, the vectors, compositions and methods as described herein are used in the prophylactic or therapeutic treatment of one or more seizure disorders, which include, but are not limited to, epilepsy, including, localization-related epilepsies, generalized epilepsies, epilepsies with both generalized and/or local seizures, and the like, seizures associated with Lennox-Gastaut syndrome, seizures as a complication of a disease or condition (such as seizures associated with encephalopathy, phenylketonuria, juvenile Gaucher's disease, Unvericht-Lundborg's progressive myoclonic epilepsy, stroke, head trauma, stress, hormonal changes, drug use or withdrawal, alcohol use or withdrawal, sleep deprivation, fever, infection, brain cancer, and the like, or chemically-induced seizure disorders.

In embodiments, the vectors or rAAV vectors, compositions and methods as described herein are used in the prophylactic or therapeutic treatment of an individual or subject in need, e.g., one who has experienced, and/or is at risk of experiencing a seizure, and thus may be diagnosed with or be suspected of having any seizure disorder. In an embodiment, administration of a viral vector or rAAV vector comprising an enhancer element as described herein and a transgene may occur at a time prior to the onset of the seizure, e.g., epileptic seizure, or DS symptom, for example, days, weeks, months, or years prior to administration. By way of example, those in the art have demonstrated that rAAV driven expression can last for at least six years in a non-human primate model (Rivera, V. M. et al., 2005, *Blood*, 105:1424-1430).

In an embodiment, the rAAV vector, which comprises an SCN1A-specific enhancer sequence, also comprises capsid proteins that enhance the targeting ability of the virus vector and allow the vector to specifically transduce interneuron cells, such as GABAergic interneuron cells, and/or specific subpopulations of GABAergic interneuron cells, particularly in the cerebral cortex of the brain. rAAV vectors that transduce GABAergic interneurons and rAAV vectors that comprise capsid proteins which increase the likelihood that the virus will specifically transduce GABAergic interneurons, in particular, the subpopulation of GABAergic interneurons that also express parvalbumin (PV), called PV-expressing interneurons, (also called PV-expressing cortical interneurons) are highly suitable for use in the compositions and methods described herein. In another embodiment, the rAAV vector containing an SCN1A-specific enhancer sequence, e.g., E5, also comprises capsid proteins that enhance the targeting ability of the virus vector and allow the vector to specifically transduce pyramidal neurons, e.g., glutamatergic pyramidal neuron cells of the brain cortex.

In an embodiment, the transgene (effector gene) inserted into the virus vector is one whose function (or loss of function) has been found to be causally associated with a neurological disease characterized by the deleterious symptoms of seizures or epilepsy, such as infantile febrile epilepsy, or Dravet syndrome (DS). The enhancer sequence in the vector restricts expression of the transgene to interneurons or subtypes thereof, or neurons, such as pyramidal neurons, and specifically modulates, e.g., increases or enhances, the expression of a normal, functional version of this gene in an interneuron cell. In an embodiment, the interneuron cell is a GABAergic interneuron cell. In an embodiment, the interneuron GABAergic cell is a PV-expressing interneuron cell. In an embodiment, the neuron cell is a pyramidal neuron cell. In an embodiment, the pyramidal neuron cell is a glutamatergic pyramidal neuron.

In a particular embodiment, the AAV vectors, vector-based compositions, and delivery and treatment methods provided herein are useful for treating a patient who is afflicted with Dravet syndrome (DS), and the serious symptoms thereof, such as epilepsy and accompanying seizures. In an embodiment, the patient is a human patient, in particular, an infant or young child afflicted with DS. As described further infra, Dravet syndrome (DS) is a form of infantile epilepsy that is associated with many serious symptoms, including cognitive impairment and life-threatening seizures. The loss of function of the sodium channel Nav1.1 encoded by the SCN1A gene is the most prevalent cause for DS. Previous studies using mouse models of DS suggest that it is the loss of SCN1A gene function in GABAergic interneurons that is the primary defect underlying the seizures that represent the most deleterious symptom in this syndrome. There is currently no reliable treatment to eliminate or reduce seizures in DS patients. Therefore, the viral products, compositions and methods as described herein provide a much needed and highly beneficial treatment for patients afflicted with DS.

Accordingly, in a particular embodiment, the transgene or effector gene contained in the AAV vector or vehicle is SCN1A and the enhancer is a nucleic acid sequence (e.g., a cis-acting control element in the AAV vector) that restricts the expression of the SCN1A gene to SCN1A-expressing interneurons and is specific for modulating the expression of the SCN1A gene in interneuron cells, e.g., GABAergic interneurons, or PV-expressing, GABAergic interneurons. In another particular embodiment, the transgene or effector gene contained in the AAV vector or vehicle is SCN1A and the enhancer is a nucleic acid sequence (e.g., a cis-acting control element in the AAV vector) that restricts the expression of the SCN1A gene to SCN1A-expressing pyramidal neurons and is specific for modulating the expression of the SCN1A gene in pyramidal neuron cells, e.g., glutamatergic pyramidal neurons, in the brain cortex, e.g., cortical layer 5 of the brain.

Methods utilizing an AAV vector, which is designed and molecularly engineered to harbor a specific enhancer that restricts that expression of a normal SCN1A effector gene encoding the Nav1.1 sodium channel to interneuron cells, involve administering a therapeutically effective amount of the viral vector, a viral particle, or a pharmaceutical composition comprising the viral vector or particle to a subject (e.g., a human infant having DS), in particular, to transduce interneuron cells in the subject with the vector harboring an SCN1A-specific enhancer sequence and an SCN1A gene, express the gene in the interneuron cells and provide a functional response, e.g., the provision of a functional Nav1.1 sodium channel or an increase in function of the sodium channel, in interneuron cells of the subject following administration. The functional expression of SCN1A in the transduced interneuronal cells normalizes the excitability of SCN1A-deficient interneuron cell populations, such as GABAergic interneurons and PV-expressing, GABAergic interneurons. Such a result restores the delicate E/I balance in regions of the brain.

To successfully and specifically express genes contained in AAV as a form of therapy for DS, an approach was developed in which the regulatory landscape of the SCN1A gene was explored to identify enhancer polynucleotide sequences capable of restricting expression specifically to the neuronal cell population that is deficient for this effector gene. (FIGS. 3A-3D). In an embodiment, the enhancer sequence is a cis-acting element that modulates, e.g., increases, enhances, augments, or otherwise improves, expression of the SCN1A gene, particularly in an interneuron cell, such as a GABAergic interneuron cell or a PV-expressing GABAergic interneuron cell, particularly in interneurons in which there is a loss of function of the SCN1A gene. In an embodiment, the enhancer sequence is a cis-acting element that modulates, e.g., increases, enhances, augments, or otherwise improves, expression of the SCN1A gene, particularly in a pyramidal neuron, such as a glutamatergic pyramidal neuron cell. The terms "enhancer" and "enhancer element" are used interchangeably herein. In some cases herein, the term "enhancer element" is referred to as a "regulatory element."

In an embodiment, the enhancer polynucleotide sequence that specifically regulates the expression of the SCN1A gene in an interneuron cell is about 25-50, 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1050, 1100, 1150, 1200, 1250, 1300, 1350, 1400, 1450, 1500, 1550, 1600, 1650, 1700, 1650, 1800, 1850, 1900, 1950, 2000, 2050, or 2500 nucleotides (base pairs (bp)), or longer, e.g., greater than 2500 nucleotides (bp) in length, including all larger and smaller values in between these aforementioned bp lengths. In some embodiments, PV-specific enhancer sequence suitable for use is 261 bp, 521 bp, 547 bp, 606 bp, 618 bp, 663 bp, 832 bp, 1280 bp, 1644 bp, or 2430 bp. In other embodiments, PV-specific enhancer sequence suitable for use is 267 bp, 586 bp, 636 bp, 665 bp, 844 bp, 849 bp, 894 bp, 1636 bp, 1766 bp, or 5124 bp. The enhancer sequence having specificity for modulating (e.g., enhancing) expression of the SCN1A gene in an interneuron cell may be derived from an intronic or intergenic sequence of genomic polynucleotide, e.g., DNA or RNA. (FIGS. 1A-1 to 1A-3).

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following mouse polynucleotide (DNA) sequence (E1), also called "S5E1," located on chromosome 2, at start/stop positions 66256056/66257335, shown in FIG. 1A-1, or a human ortholog thereof.

(SEQ ID NO: 5)

```
caaagtggacagaggggaggggaggggatgcgaggggaggggaggggaat
gatcgcgaaaggcttccaaaccttgtccttgtttttcaccatttctgaaa
tatatgctgagtgcaactatgggaagaccattttcataatctataatact
cctccttttaaaggactttcgttaaccgcttgcaaaggtgagtgccgggt
agaggacattagctcgctaagtccctagaaatcacacttggagactaagc
aggctttcccaggagaagtccaaagccaacataagcaggaggctgggggc
tggccgttaaccgcaaggcagtggttgagccctcgggatcatcccggcgg
ggggcgcagcatctccgccaaggccgcaggctctcaccatcagctgcccg
agccaccctgtacctcgcagtccactcgccctgcccacgccccgcgccgc
ccgctcaccttcagcccctgggagtccatggccgccggctacccggaggg
tgcccaccgctgcccgccgcagggttaggggttcagacccacttcccggg
ccctcaaaccctaagggacgcggcgtgcagcacgaggggcgtggcccgat
```

-continued

```
ctccattggttgtcggcgtgagggggcggagcttagttgtaggactagga
aggagggggccaccggagcaggcgaggagggaaccccgagggaggaccgc
gagggcgactggggctggaatccgctgagcattgagtgctgccgagttgt
ggggctagaggagggaggtccagcctggaaacggcgcgaggaggagggat
tgggtggagcaagagatatgagattaaagaataaagatgatgaagcagca
aataggagggagagccatgccgcttttcatccctgcaaacaaaggccgac
tccattttctcagcatttttgtggaagccgatttgcgcaatgcggctta
gtacttgaccagggaaaatgatttacctgacacgtgtagtaatcgtgtct
gggccacaaggtggcgcagaaaaatcacagttcggcaaaaaccttgaagc
ctggcttgggcttgttctaaatcttttcaggcgctgctgtaattttgcta
ttcgagtgcttattaaactgctccgccagatttccacccccaaagtctta
tttaaaaatatgtggttacctcttttagatttctatttcttaagtgtttg
ctgtagtttggatctaaactgtccctcaaagacacacgtgctgaatgttc
cccagcccgtgtgctgttgggagtggtgga.
```

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following mouse polynucleotide (DNA) sequence (E2), also called "S5E2," located on chromosome 2, at start/stop positions 66364036/66364653, shown in FIG. 1A-1, or a human ortholog thereof.

(SEQ ID NO: 6)

```
aatctaacatggctgctatagcttactgactagaagttaagtgcacactt
cctaaaagaaggctttgacacaagccacttcagttccctcctcattttct
tgtccccattcctctctctgtagaattctgagatttcaattcagttttat
acagaaaccacattactgtaagccctacaaagttatggcaatatagctat
atggagtcaagtaatgtaggttatttttttcccaatggtgctggtgaagg
tggcaattatgtagctatacttagcagactgaggaaattctgctagagtc
agcatttgtctcttcattgctatgaaacagtaatggaaaaataaacaaaa
acaaaaggcaaacactatgcataattccctcagatcatattaacatgtga
tgttggagtaaattgttataaccccattttggaaatacttaccttaatta
actatgatttccttaaaataatgcagtatttacaatctatatgaaagcac
tatatgggacacatggtatgatggaacagtgcacccaagagacaccaaga
acattcctgtctgtggcagtcttttctctatacagaggcatttagtctca
attgctcagagttatttt.
```

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following mouse polynucleotide (DNA) sequence (E3), also called "S5E3," located on chromosome 2, at start/stop positions 66383190/66384021, shown in FIG. 1A-1, or a human ortholog thereof.

(SEQ ID NO: 7)
```
ataaaattttattttcctaaaatttacatttaaaagccatccaacttacc
aaagtgatttcaaaccacaattacattttatctcaactaccagcatttta
tttagccaggatctacatgagacacatatcatgatgtgctatgtacatct
tgttatacagtgttatattgataacaaatgtcatcaatataacattgaat
taatcttccataatttatggggaaaaaaggagcagccttactgaagggca
aagttatacaacagctttacagaagctgcatgcgagtgcagtaccgggac
acgggcacggacggcggcactataaccattttccgtggtggtaatcttgc
tttcatctgacacagaaaagagaccgccgttttgaaaactcacagaacta
gcctcacggttttgtgagtccattgagcgctggctgcgaagaacggtgtt
taactcgagaaatcattgaacaagttttagaaaataaagatgcttatgac
aatttcaaacttgaaggtctccaaagaaggactgagatattggtgagagg
agtaaagagaatcctggtgcatttatttcatgcttccttctgttcgaaga
tcattttgaggtttataaaaggtggggtgatccaaaaatctccaggctga
gagtcctggctgaggctgtgaactgggctgcagagaaagggccacgcctc
cctcctctgctcgcattactcagcagcttttctgcatgtggctggctgca
gacaatctaaacccttccgctgtcgctccccccttatactgttctgccaa
aaggaaggcagagaggaaatcagctacggggc.
```

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following mouse polynucleotide (DNA) sequence (E4), also called "S5E4," located on chromosome 2, at start/stop positions 66387764/66388024, shown in FIG. 1A-1, or a human ortholog thereof.

(SEQ ID NO: 8)
```
tctgacagagcaagtcttgacctgcttaacattatgttatgctagtcatt
ttaaaatgagtctttatttcccatagaaggtcagtttttttacattatta
tataatcttttgacagaataacaaataacattctgaatgtctcatttcta
aatacaaaacatcttagtataaaattatgcattgttttaaatgcttggaa
gtaggtccacatgtagaaaacaaagtacgtatgataaaaaatatcaaaat
tgtatattcag.
```

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following mouse polynucleotide (DNA) sequence (E5), also called "S5E5," located on chromosome 2, at start/stop positions 66392447/66393109, shown in FIG. 1A-1, or a human ortholog thereof.

(SEQ ID NO: 9)
```
aatgttttgatatttaggagaaaattgcaaaacaaaatgatgacagtgtt
tgaaagtgtttgatcagtgccaagcatcactttatgtacttggcaaacat
gacttgaggccttaagctgtgatttgcaaatgtagattggaatcaagatc
tttatagatgaggaagcaaaaatcagaagacaaaataacattatcaactt
gatctcatgtgcagccagggctgaactgcaaatgctgatttgccccagtc
tgggctcctcaaatcgttccttggaatcctattagttggaactttatctc
tgctcgtggcagggtgcctgggaccatgtttataaatatctgctgaatga
agaataagtgagtcaatcgaaccagaactcactttggttagttaatttca
ttcgtggtatttatggagagcagaagaaagaattccagagacacgatttg
tcaaaactctctaaagaaaatgatgacactatatattgatgaaaatgaat
gttcttgttcttgctttatttgattttcttgtcccccactccccatctg
ctagggtctcattacagcatagttcttgaatatcccaggttgacctgaag
ttacaatatattcttgatttagatggcagacattgggaatattttgactc
ttaaaatttaata.
```

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following mouse polynucleotide (DNA) sequence (E6), also called "S5E6," located on chromosome 2, at start/stop positions 66401767/66402372, shown in FIG. 1A-1, or a human ortholog thereof.

(SEQ ID NO: 10)
```
ttgtcactttgttactctacagtgttgcctggagttcgatacttcattac
tctatagtggggtgaagaagttcaccttcttattttcatttccttccctc
aatgatttcttcagagctagctcttaccagctagaaattcttcaaacgac
actcgtgccttccttcacacaggttgaactatttgtctctaatgccctaa
agtactggtgttcaatcttccaggcacttccaatgatctgaaatctgacc
tgcttaggtcagctggctctgagattatggtattctagtcctcaaaccaa
cctgttggctcgttggttttgtaccaaacacactgacttacatagctcaa
aataccactggccttttaaaaatggcatatcacattccaggggaggatca
aaactgctggctggtgatatttgtcaagtctctcaaagttgcactttcca
ggattttcaattcactgaattcttagacagacatgtttatgtgaaagaat
tctttatatatttttctcctctttgagtgggcaaatgaaaatcttgacc
tctgggttccttattttatttgactctctgtagtatttaaatcttaaaat
tttcct.
```

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following mouse polynucleotide (DNA) sequence (E7), also called "S5E7," located on chromosome 2, at start/stop positions 66407834/66410263, shown in FIG. 1A-1, or a human ortholog thereof.

(SEQ ID NO: 11)

```
gatactgtataattaattaggcctccaatcatgccttcccagcctccacg
gatggagaaaccctctccgccatgccttaaagaggaattgctgtaataaa
tgagtctcctgatagcaaatttctcagcaaggggaatcgcgtaaatgga
gacatagtattgacagcaaagtccaatgtgttatttttaccagaacgaac
tctccggttcaagcctttgaaagagacatttgaaaaccaaaaacaaacaa
tgtaatggagcgaggaaaaaagccacagaagtgagtggcagggagtttaa
aagagcagatgccactgccaggtctatgggacataaccagccacttgtgc
tgggtcttggcagtttataatgctacctcatcttctccgcgaaattgttt
tcccgtaaatctctgtggccatccattcctgtctacacattatgttccta
aaatagacaccatctaaaaatcacttcaaggagctttgtggaggaaggcc
taaattgcaacactcctccagcgaagatagatgcagtgtttgatggcatt
accagtcggtagccaggaaggggagtttgtgaggagtttttccaccacag
ttaatctgtttctggaaggaaagggaagtgtcagacttcccgaggaggca
aacgtgtgtggaagctctcatttgcatcaccccccggcctgtcaggtattg
cagcaaaagggagaggtgagctaccctggctctccttgggcaggagggac
agaatcaggaagcatcaacctcagcatggaattttcctattcctgtttgg
catcctcctcttgggatgatttacagcgcgggttggagaaacacgctctg
ccactccactagcgcaccagatagacagtgcagacctgcagatccatacc
cgaggagaagccacatttcctacgtgtgatagcaacagcgtttggcaatt
tgcgactttgctactgcagcttagaaaatatttagtcacatgcacatctg
aacagaaagacacccaggcttgactcagtcatttccgtcagacacacgaa
agaaaaagcgtctctgctcacaagcttatttggactgctttgttgaaagg
aggggcggcagacactttgtagatgtggcaagagggctttatatccagac
ctcaaacaggtaggagagaaggaagccaggagaggtaaggaaggggcgtg
gaaaagcctcacagccacctcgaagaaaacagtttttttgccctgttcag
aaagcaagaggttccacagtggttttgtgtcaatggagcacatctgcagt
atcattgccgttggtgacctctgtctaattaaaagtaagtcagtccttcc
cacccggcattgtctgaaacccgggactctttatcactttgctaaagttc
atttgcaagtgtagttaaggaagagtcagggggaaacagcatctgtccc
ttctggtcctggggaggaggcactcctttccaagagtcaagcctctgccc
aaagaagctgcctcccctgcaatgctaggatccaggagcagccccgctgc
cttcttgcttcctctgtgaggtctaattttgcatcatctttaggagcga
tatgacctctattcacagccatcgaatccagttccaaagcaccaatgaca
gagggggcttcaagacaagaccttgcctaggaggatgcaggcaagcaaag
gcaagagctggcccgatgccaagttattttaggccaaagaatctcatcct
tctatcaaaatgctgaactgcaaaacgaacctgatttcagttcatggaag
gttgagaggaggaggaggggaggggaggaggaggaagagaggaggaggg
gaggaggagggaggaggaggaggggaggaggaggggggacagttggtccga
attcacatgcaaaaatagacttcctgttctgccccaactcttatttccgt
gggctcttctccccaaggatttaccaggtaagaattcaccaccaaagaag
atcacaatgagataatcagatggcttacctgataaaaaggaaaattatcc
atctgcagtgaggagcaacatctccccacgacgagtccgcaccttccgtt
gcaacgattcagattccttcttgcaaaaggtgaccaagtgcttcacaagg
gctgcagcctcatagggg cagaacacacgtacacaaacacacgcacacac
acacacacatgcaccagagacctctgcagtatcctctcggcttcatcctc
gcctcactctatggtacctaatacaaatcagcaaatagcttgttttaaaa
aaaaaagaaagaaaaaaaagcggagacagcacctaacgttacagtgccat
ctagtggctacatcgtaaataggttctcacagcctggatttctgtgttct
ttctcaaccgcttccttctggttcctttt.
```

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following mouse polynucleotide (DNA) sequence (E8), also called "S5E8," located on chromosome 2, at start/stop positions 66439814/66441457, shown in FIG. 1A-1, or a human ortholog thereof.

(SEQ ID NO: 12)

```
attgatctccaactttttaaatccctctgtcattttaaatgaggtgcact
cggttgtgtcatcatctcggttttaattgtgtgaaaatttcctgccaatc
tcacaccgctgcggcaacctcaccttgctacttgccctgcaagttctgca
gtgtgccgttctgagtatgccgttttaactagttcttgcagcaggacaca
aagcgagatagtctgatagaaccagttctcctctggttttacctttactc
ttagatgagttaagggtcacatcaaaccagggctcagcccgccagatctc
ctaagcacagcccctcctgacccaatgcagttaacccaacctcattcagc
gctagtatcaaatgacactggagctgctgcagtatgcatcccgagactaa
gtaggcaggatttattatcagcagaagtcccctaactaccaggttattca
agctccgttcttgtcacaaacaggcgcggcggaagacacagtgcagcaga
ctcagagctcatttacaagacaagcgaattctcagttagagacaagggca
gcgcggcagcgaactgcagtaaatcttttcacgctcacagcaacatctaa
caatgctctcctgcaacgcctcagatcaaacgaatcctacttggtttaaa
catcaaatcaacaccataaaaaaggcttcattagcaaagttcaatttagg
atgtttttaatcgtgtcttaattctagaaccagtgcgagactttccatgc
ttattcaagcatgctgacagaattggaacctcttagaattgcctacctgc
acctatcagcctggctgacaggagcccgccaaaggattaaaaaaaaacaa
aacccaaaacataaaatcatgcaaaaaaatatttacccccgaaagatgta
tgtagttaaagctcagcttcctgcagcctcgatagcccctgaagtgttaa
tctgaagaaacagttccatgagtttccacaggccggtagtgagtctccta
cacttgacctagacagacttacataatgaagcatcagtgctggggagctt
```

-continued gcacgatgtcatcaccagcaagagtaagaagtattggcagcagcaagcag gcgggcaggctgagatcttgcatggaaatcatgaaccaggtcttgctttt cgtttttgaaacgttttggaaggagagttatgaatagcccagaaataggt ctcattttgtgggtaggaagaatgaccagaagcatgaaagctaaatctcc tggcaagtgcaggggacctctcttggagtgtgcagtaaacccgaggggac gacttctcctgctgtcaactcctgaaccatcacatctggagtgaaggaag gggctggtgaagccttgtaataaatgcaaaggatgctgctgagagctttg gtctgcctttaactcattgtggtgagtagaggggatgtggcagtatgcaa tgagagttggttgtgtaggttgctttgcagagtaataaccaaaaaaaaaa aaatctgtgaagtgctcaatactttagacacattttaataaacaagatga tagtaaaattactcttctccatcaaattgagactgtgctgggttaaactg ttttaatgcattttaactcctgatgttcatccaagtaataagag.

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following mouse polynucleotide (DNA) sequence (E9), also called "S5E9," located on chromosome 2, at start/stop positions 66441748/66442268, shown in FIG. 1A-1, or a human ortholog thereof.

(SEQ ID NO: 13)

atctcaagtgtatgtaacatgagctacagtcttaaaacctacaaacagta catccagtctcctaccatgattctgagtgtgatgatttcatatgagcaca agatgacatcatactatttagttatatgtaaaatcatggtcttacatggg ttgtggacaaaaccatctagttttggaggtgacagaaatagagaggacgc catgcactacttaaaaataatcgcagccttcttttcttagctagggagtt tgctgctatgagccacattaagaccagggtgaggagatgagacgatacag gggcatgaaagaacacggtgatctactttctcctgttaattaacgagtaa ggaaatagacattaaaagaagttaaatgtgtctgagccaacgtaggtgag gtttcccccaaattcacctggtagttttgctactgcagtatagtaaatac ttgttttcatttgtttttttttttttgtttttttttgtttttttgtttttt tgtctttttgtttttttttt.

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following mouse polynucleotide (DNA) sequence (E10), also called "S5E10," located on chromosome 2, at start/stop positions 66450594/66451140, shown in FIG. 1A-1, or a human ortholog thereof.

(SEQ ID NO: 14)

tattgcaaaaggaaggaatgagacagtttatgcagagctaagggtttgtg cgttattatgattaatcacaaggacagctgccaagcttccatcatgacaa -continued tattctctgggagaattcatcaggttctactgtctattaatttctgttga tgtatcttatctggcatcttcaatgacagaggacacttgttagttttttt ttttaagtgaaggttaaaagacaaagttcattaaagaaatgatttatata tgacatttaagaactagcaatgtcattgcttcaagaaaattatgagaatt tagtcttggtaggagtttacaccatgtccttgaagtgtctaattatgtga cttgatagttttacttagtacatatcgattaggctgtatctattatttat caagaaattatggaaggaggcaatgtggcataggcatacacattctgatt ttaaaataatcctgcttttaccattaactccttctcagataattctgaat acatatcttgtctatgaatctgtgtaatcatggaaaagaaaaaatc.

In an aspect, the human sequences (human ortholog sequences) for the ten above-described murine enhancer sequences were determined based on alignment of the mouse sequence to the human genomic sequence of SCN1A, including 100 kb both upstream and downstream. Accordingly, human ortholog sequences that are highly conserved between mouse and human sequences were identified.

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E1 or S5E1 herein, located in the human genome sequence at human_hg38 start 165953030/human_hg38 stop 165954796 (FIGS. 1A-2 and 1A-3):

(SEQ ID NO: 15)

tctaatggacatacagtaacccttcataaatatttgctgaacgagtgatt cagtgaacaaatgaatagagaagaccaacatccgaaaagttattttattt tcaagcctcatgtctttaactgttttatatcagcctttcttaagttgacc gtcattaatatttgctgaatgaatgagtcagtgataaacagagaagacca tcaccctaaaataacgacccctccacttttaagtcttacgtctttaatgg gtttcatataatctttctgcgctctttttactgtccagtgtgggagctga cactagtttgccttaagtccttaaaaatcgcacccggaggcgcagtgtca taggtaacccaagctttcctagtaaacatgatacaaaagtaaacacaacc aacagcatggggaccagcaattcagaaacaccgagcgggcgggctgccca gacctgggcttccccagcagggcccgcggagaccggccgtgagcagaggc tgcaggcccaccccgcaacccgagcagccggggcaccgcagggaaacagc ggcctagcgaagccacccgagctccctccgcgcccccgggccaaaaggcc gcaaaggaactccgcccgcccgcccgctcacccgctcacccgctcacccg ctcaccttcaattcctgcgagtccatggctgccccgaggccgggccgcgg ggctctggggattgtctcgccgcagcctaaaggaagacgcagaattcagc tcccctagcctcccggagcgctctagcgccccgggccccagcgggagggg cggggtcgcgccgcgattggctgtcggagggagaggcgggcctgtgtggc ggggatcgtgctgtaatggagcaggggcggcggggacccggaggtgaggg ctgcgagggccgcccgggagggtccgggctgggaaaagggcctccgccgg -continued agagtgcagctggaaaaggaggtcacactgggaaacggctgtctgaggac
agtgggtgggcgggccgaggaaatggaattcaggaataaaggaaacggag
tatgaagaaggggaagtctgtttcctgtcactggttgtaaaggaagacac
cattttctgcacgtttgtctggaggcggattcccgcagtgcggctctcag
caaggctctgccggcgcgggaaaaagcggtcaactttcacgtgggcaagt
tgttttacggccacaaggtggcgcagaaaaaaaaaatcacacgttcttaa
cagaaatacggtgcgcttgggcccgtctttgcaggcgttgctgcaatctt
tgttagaatgtgtgttcaattagccctttttaccagccccgataataag
agggacaaataaattaaacttccagaaaattagtgtcttgttttcaatga
tactactgattttaaactgagaataaaatgaatcccaatgcaaattttta
tgtttgcaccccattaggcaactcaatcagtcacacatagatttcttaag
tccaggaaattaaatggaaatataatagactaagattttctatttctgct
taaataaatatttaaaatagtgcataaggtctgagatttaagtgatcttt
gcagaatctttcacgtggattccaaattttgatcctagtgttaattatct
tactttagttgacatgatacgtagttgccttttccagattttaagtttct
taaggagtttataaacattgactttttccccatgccaataggttatgtaa
ggacagtctt.

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E2 or S5E2 herein, located in the human genome sequence at human_hg38 start 166084035/human_hg38 stop 166084884 (FIGS. 1A-2 and 1A-3):

(SEQ ID NO: 16)
agtgtgggcctcccagggctgtttagctagcaatgagagaggcactgcct
atatccaagttgtatatggcaggttttgcacaaagtggattactcgaaga
gaaagcctaatggccagtctattcatcttcccctttctcgatgttcatct
tttctctcccagctctcctttattctcaatttcttttttttttttttt
tgctcagcctccatctcacttccgttgctgtcctctccccaccccttccc
actctggactgtgcctctcctttgtagacacttcaagtccattctatttc
attcaaaaaccatggtctagaagtaacttaatgtaaacccacaaagatgg
agacagaatgaatgccattcttcttgctgctctctcagacaatgcaggtc
atttttgcctatggtgctggtaaagccaggagttatgtagctataagtag
cagccagaggaaatagtgcctgagtcagcaattgtctttttattgctgtg
gggcaataatgggagaaaaaatcaggcttggtacaattccctttgaagga
aaaagatgccaacactagcattttaacacaaaatgctggttgggggttgg
gaggaaggatgcttacattccttctttggaaatatctactttgataacca
ttttggtaaaataatgcagtgttttcagtgtgcaaatcctttcaggactc
atggttgtatggcagacgcacctgacagcaataatttaagggtaccctga
gaatgactctgtggtctaaaaagaatgtgtgtttggaagtctgaggtaag
aaatctggctggaagtggccaacctggaaatttgctccttattattaag
g.

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E3 or S5E3 herein, located in the human genome sequence at human_hg38 start 166090876/human_hg38 stop 166091720 (FIGS. 1A-2 and 1A-3):

(SEQ ID NO: 17)
atagtgcaaagtttaaatttcattttcctaagatttgttttaaaataaca
cgatttacccaagtgatttcaaaccacaattacattctgtttaaattact
aatattttattgcatcacaatctgcatgaaacagatgtcaggatataatg
aactaacctgcattgtatttttatttttgtctcctgtggcataacgattt
cataggaaagagaactacacagctgactgactgatggggaaagttacaca
atggatagctttgcagcaacatactaatgcggtagggagatgctgcagag
aggctagaaataaaatcatttctttccggagcagcactgcttgctgtcgg
ctgagacaaaaaagagatttcctttttttcctttctttttttttgaaaact
cacataacattaattctgttaagcactggatacacggaaaggtgtttacc
ttagaaaatcatttagcaatttttagaaactagacatatagcaattttaa
atctttttaactatctaatgaccaaagcagagggtcctcacaagagggat
ttagatgctactgaattgaataaagaaaatatggatacatttattgtatg
ccttattcagtttgaggttcattttgagtttagaaatagggatataaaaa
catcaggggttaaatagcatgggtaaaggacatgaaccaagctgcagaga
agaggctgactgcctgctatatttgcaggcattactcagcactttttctta
aaccgatacatcttgctggctgcataagcaagacaagacccttttcccta
tggctcaggaaggcagagaagtcaacttcagccttgaaaaaggca.

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E4 or S5E4 herein, located in the human genome sequence at human_hg38 start 166094366/human_hg38 stop 166094633 (FIGS. 1A-2 and 1A-3):

(SEQ ID NO: 18)
tgccagacagaacaagttttagtgtagttgatagtaagttgtgcccagaa
tattaaattgagtcaaatttattttccacataaagtcacagttttatatg
tcattatataatctcttggcagaaataaggaataacattctgaatgttgc
actccaaaattcaaagaatcttagtataaaaatatctagcattttagatg -continued tttcaaagtagggccaaatgcagaaaataagttggatatgataaaaatac cagaaagttctattcagt.

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E5 or S5E5 herein, located in the human genome sequence at human_hg38 start 166103693/human_hg38 stop 166104587 (FIGS. 1A-2 and 1A-3):

(SEQ ID NO: 19)

catgtaaaattaatatgatcttttagtcacttagaaaaaataccataaag aacactaatagtgtttaaaagcatctacccagtgccaagaactgcattat gtattggtgaacataactttagactttaccatacaacgtgaaaatatata ttattatcactattttacagatgaagcaataaaagtcagaaaaaatgtag ctaattaaagtgatactgtgtatagctagagcagtgtatagctagagctg atttgtctgactctagccctagtttctttccattatatcaatttcctgga aatgtatctctgttcatggcatagtgcctgacactatgcttattaatatc ttttgaataaaagaaccactgagtgatttgaaataaaactaaatttagtt agttaattttattggtggtatatagagatagtaggaaaaataattgaaaa gagacataaacagatttgccaatactttctaagaaaaattatggaactag agtttagtcaaaatgaatgctttcattgttagaattcaactttaatcttt gcagaatacaaacaaagacccattttctagaagaagtaacagggaagaga gagtaagaaagagataatgatgaacattgtctaatgttacagcataatct agtaaggtaagaacagaagagagttcattgacttaccaacatagttgtcc ctaatcacctctgtgaacctagagtgctacgatataataatgattgtggt ggtttaaaaagtaaatggggctgggcatggtggctcacatctgtaatccc atcactttggaaggctgaggcaggtgtattgcttgagctcacaagctcga caccagcctgggcaacatggcaaaaccccgtctctacaaaaaata.

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E6 or S5E6 herein, located in the human genome sequence at human_hg38 start 166118214/human_hg38 stop 166118879 (FIGS. 1A-2 and 1A-3):

(SEQ ID NO: 20)

tccacttttgctattccacagagatttcaggaagaaaaatcacactcct attttctttttctttgcttactgatttctatttagtttcttttttttttt tttttttttttttttgagaaagcgtctcactctcttgcgcaggctgga gtgcagtggctagattcttcttgagtatgctcaaacttccttttggaat gtcttccaaaggcactcttgccttcatttgtacaagttgattgaccettt aaaggccttaaatattattgtgcgacctcacagactcctcaaatcacctg aaacctgaaatgctgaggcccaggtggcactgaaatgatggtattctaga cctgacaccggactgttttctccttggttttgtcccaacacactgacata catagcccaaaatactactggcctttttaagtggcatatcacattccagg gtaatatcaaaactgctgcctggtagcatttgtgaagtctcaaagtaact ctttccaggattttcaaatccactgaatttcttagattgaaatatgtatg tgacagaattctcttagctttctttcctctatgaatatgtaattggaaac tctgagatccggtttctcatctttattggatttttttctttaatcttaaaa ttatgaatatttgctt.

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E7 or S5E7 herein, located in the human genome sequence at human_hg38 start 165892760/human_hg38 stop 165897884 (FIGS. 1A-2 and 1A-3):

(SEQ ID NO: 21)

tggcaaaaacgcaaaacgttgatggataacggtgatgacttacacaacaatgcgaatgcatttaatgcc actgaacagtacacttaaaaatggttaagatgatgaattttgtgttatatatgtttcaccacaatacaa aatattctttaaaaaagacttttggaaatactgtatctacttaattacaggatgtcaaactaatacagg ctgatagtatcatttgtccccttgacacacaatcttgggtccagagattttgttcaccacacctttag catcactaaaaagggcacaataagaatatggtttcagaaaaagacaattcaaatattggtcttgtcctt tagctatgtgaattcaatcaaattactcaaattctttgagtccaatatacttattttcttaaaatagga ttataatattgactgtaggagtgctacagaaataaaggcatgaaaaatatttataaattacaaatgtta ttaataatatttatacttccaaaaatgttgacaagaaatagagtaactaccccataataaagccacagc atctggaagctatattggattaagcaagaactaaaggttaaaatttcggattaaatttttttgcatga tactgctagtattatcaacattgggaaggcaatttcttgaatatttcttatatactattgaaatgtatt -continued cattattagttcaagttataattaccagtgacagattaaattacattcacttgtctttggttaaccatg
acatttgacagaaggcaaatttctgcacttaagaaatgtattaaaaactaaaatgtatattaccttcta
aaaaacttagctggtccatctttattgatgaatagtaggaagatatcaaaatagttatagggtgatgag
atgtggcaagcatgcagtgctatggtatggtattacaaagcacaggattcttaactttgcctggaggag
ttgggaaatttcacataggagttgacctttgagcagcctcaaggataggaggaagatcttactagacgg
acaaaggcattccaagtagcagaaggcatgcgccaagagggaagcagagaacagtgtggggagtgttgg
taactttgatattattaaagcggaggaagaaggataagaaatataaatggccaaataatttgcggccat
attattattaaaataatgctatgattttagactttatcctgaagcactaacttaaattttaagcaaagg
gtaggttttgatttttagaactgatatgctagtcctatgatgacctggagcagccagaacctagaagct
ggaagatgagttgggaatctgcactagttcagatgagaggtgataagggtcttcattagagcagtgggt
taggatacgacagactggatgtgttagctagctatcaagcaaacagagctgaggagacatgttaaccaa
ttagtatgaaggaaggggaaagctcaaggcgatctggagattctgagagagaaaggggcaatctgtcg
tgagagcagtaattagatctagaagaggaatttttcaactacttaaattaggtcaaatttgtatggtac
atttctgaaataagctaaaatagagccttaatctaaagtacaagatgagttactgaggataaccaataa
tgtacacataaaatgaacggagatgcatgttttagagtaattccaacaaaatagatctgtggataagta
tgtaaggtactagtaagaataaagcatacaacacaagattaaaaactcttaagattaaaaatatcacat
agacaataaaaatttacttaaaattttgtggttgtttttgagaccaagtctcactctgtcaccgaggct
ggagtgcagtggtgtgatcttggctcacggcaacctccacctcccaggttcaagcgattctcctgctgt
gtttttaattgacttggtgttttacagtcattcactgatccattcaaccaataaacatctatgttgcca
catccatgtgtgtggcattttgtctgatattgggaatatggtgtgatccctgaactcgaggagtctaca
gtgtaataaagaacacaaatatgcacataaatatttttagtaaaatactataagtaataaagacgtatg
gacaaagtaaccgaggattagggttaccaactcatcccagtttgcctgtgactttctgttagcatggga
agtcctgcatccaggaaaccctttgctccgaggcaaatctaggatggttggtcatgctacccagcacc
acataagacatttttttaatgtaggtggtggtagtgggatgcagatttactttttttattttcccccaaga
gggatatattttagattatgtgtttggaaagagaaaagggataaggaagctaaagttcattttaggcaa
aaggaaaaaacccaagcaaagacttggaagcatggttgtatgtcatttggtgttgctggagtacaagat
ccttatattgcatttataaaaaattgcttttatatttgtttacaaacagtccaaagcagccagtctact
aagccaatttttttgggaaaaaggctgctgccaagcaacagaaacttacgtgaaacaaaacccacaaga
cacatgaagacttcttcaaatcttagaaaactataatgtgtgagattcttcaaatcttagaaaactata
atacttttaatgacttaaaatattcacagtggaagaagtctgtttttttaaagaaataaagttagatcat
tgtctcaaagggaaagactgtgaaatgggaacagcttgagatagaatgaatatattatgtatattactt
ttaaatggtagtttagagaagaggaataagagaaaacagtgtggaacacaaggtagaaatggcagggaa
aaaaacgatacaggcctgaagaaaataaaagtaggtttgggcaatgtgggtggcaagatgagcccatat
tttggacccagagtgagtggaagaggtgagatggtcaagtagttcacagcattcttttaaataacatct
gagtatactctggaatagacagggcaaaaaacaaatgaaattgcctgtggtagtccccatattaaataa
atttaatttatttaattaaaaaactcaaagagtaaaaataataaagagaaagtgttgatattactgtaa
aaaacagaccatattttctcctttcaatttttgtgctcgctggggatattttatttttaaatacaaact
gatgttctctaaattcaaacatctttttattaaaagcgttactagaggtagcctgcagagcatatctag
ttctttgagttgccctgcttgaaggattgccacctctgtgtctctgaggctctgagcacagatgcctag
ggcatcagcctgagatgaaggtggtggggtttagaagaactgaaacacagctctaggacttcctctgcc -continued

```
atttcaaactctttttagtaacacaggtagtaacatacagtcatgtattagtcaaacagttcccacctc

tttctttttctctttcctctcctccctccatccctgcttccctttcttccttttctccctcactcttct

ttccatctagtatttgttgagtactaactaggccagatattcttctaaattctggaaacacagcagtga

aggacaacgtttctggtcacttgatgcttccattctatgatttgtagtttttttgcttttgtttcacaag

ggctacacaaaacccaaaaatcctaaagccaaaccccaaaaactcaactgaacagaaaacaggataaag

ggacagagagcaagaagtggtgctacttgatgtaggccagtgagggaggggcattctaaggaagaagca

gcaccagagcaaaggcacaaaagaaaatgaggcagcagccagatagacctgtgggagcagcatattccg

ggaagtagaaacagcaaacaaaaaggctcaaggctgtaattggcttgggcttttgcctacctagtttct

gttgtccctttcttctttactatcagaattctgattttattctacagggtattagattcagctaaaaga

taacatttcccaccttcttttgcagccacggaggtgatactactaagggtttttttgtttgtttgtttg

ttttgtttttaataaaacgatgatttgctggttgggaagcccttttgcccagctctgcacccaccttcc

ccacctgggccctggaacatcaatgcccagcactgcggtggtcatcttgaaccatgaggtgatgctcag

gcaagtcagggtaacaacgtagaacaaaaagagagaaggctctggtttcctgatgatactgtggaaccg

ccacaccagtccctacacagtgtacttttcatttcttttacagagagaaaactaaaaaccgtgattttt

agcctagaattttcaggggtatctctgccattttcaatgaaagtatttctaaattcttcataggctagg

gatggaaacacagatgagttatgacgacgctgcaataatctatgtggaagatggcaatgccttagacca

gggtggcactaacagaggtggtaaaaagtgatggcattctaggtatactttgaatgtagcactaacaag

gatttgctgatagactggaggtgatatatgagagaaagatgagacaaaggttaactgtgaggtctgggc

cggcacaacagtgagcagtgatgccagtcactgaggtgagaggtgggggtggagcaaacttagaggcga

gggaaagttcaggtgttctattttggacatgttaagcttgagttactcctagacatctgagtgggaatg

caaagaggcagaggtgtacatgagtaagggctgcagataaatgtttaggacacatctgcacatacatgg

gatataaagccacgcacctggacaaagtcacctagggggtgaatatataaaaagaaagggagttcagga

actgaagctacgagtgttctaatatttaaacgtcatacagagaagagaactccaaaaaaggaaactcaa

acagcaggcaatggggcaaaagaagaactgagtgagtttaggatctcagagacaaatgaagaaagtctt

tcattgtggaagggaataa.
```

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E8 or S5E8 herein, located in the human genome sequence at human_hg38 start 166148156/human_hg38 stop 166149792 (FIGS. 1A-2 and 1A-3):

```
                                                  (SEQ ID NO: 22)
tttgtcttcaactttttaaatatccatctatttttttagattagatgccat

ctgttgtattatcatatctggttaaatcttattaaaattcctggccaata

tatcactctgctgcggcaatcttaccctgctacctctctaggcttttctg

cagcattcaataaagagcctgctattttaactaattgctgaggcaggaca

cagtgtgagagtctaaaacagaatcagcgctatattgtttctacttttac

ccatagagtgaacaactgttcatatcaaacctggaatcatcccttcaagt

ctcctaaacacagcacagtttgagccaatgcagttaatccaccctccttc
```

-continued

```
agtgctagtgtcgaatggcgcttttgctgcagtattcaccttgaaactaa

gtaggcaggattcattatttgttgaagtcacctaactgccagtttattct

tatacgatcacaaacaatcacaacagaagacaaatacaggcatatatata

actcacttacaagggaagcaaatttgcagccagagacaagggcaacgtaa

cagccaagaactgcagtaaatctctttgagctaatagccacctctaataa

tgctctcctacaacacctccaatcaaataaattgtattcagagtttaaat

atcaaatcaacattcattccttgatggttacagatgatgtccgataagca

aatttgaatttatgatttatttactccttaagtgtctcaaagccaggatt

actggaagacttactatgcttattcaagcatgctgacagaactgtaatct

cagtaatttctccctgcacctctcagcatgactgacaggcatctgccaag

actgtagtacataaactgctgaaacatgcaaaaatatttacccccaaaag

atgtagtaaaagctcagcttcctccagcttccataacccctgaagtgtta

atctggaggaacagttccatgagtttccacaggccagcagtgtgtctcct

acacttgacctagacagccttacataacgaagcaccagtgctggggagct
```

-continued

```
ctctgaatgtcatcaccagcaagagcaagaagtattggcagcagcaggca
gccaggcaggctgggagtttgcatggaaatcatgaagtctttcttgtctt
cctcttttgaaatattttggaaggcgagttaagaatagctcagaaactgg
tctcattctttttgtgggaagaatgaccagaagcataaaagctaagtctt
ccagcaagtgcaagacacctcttttggtgtttgcagtaaacctaacaaga
atgaattgctatcagtaaagtcctgtaccatgacacctaaaaggaaggaa
atggtaaagcaaagtaataactcaaagacagtcaccgagggcttttgtcc
acctttaactcattgtggtgagtagagggaaatatgtatatatgtaatga
gattattattgggggtgtgagttgttttgcaggatggtaactaaaggatt
tgtaaagagtgtttatgttccttaaagatcttgtttgtgagcaaggtaat
aggatatcaaattcagaacgtggtgggttaaactggttgtatttaatgta
tttcaacttctgaaaatcttatgcaactaataagaaa.
```

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E9 or S5E9 herein, located in the human genome sequence at human_hg38 start 166150066/human_hg38 stop 166150702 (FIGS. 1A-2 and 1A-3):

```
                                          (SEQ ID NO: 23)
tcccaaatgtgtgcaatgcaagttatgcttttaaaagctagaaataataa
aaccagtcttctattctgattttgagtatggtgatatagtattattaata
aaagatgacattatattgtttaattatatataaaattgtggtttgatatg
agttgttggctaatatgtataattcctgaggtaacagaaatagagaagga
accacacatcatttaaaaataatcttaatgttctgctcttagctgggaaa
cctatctgctaatgcatcacactaagtagagtgaggaaataagagaattt
agatctatgagggaacacagtgatctaattccaacccattacttaactca
taaggaaactgaggtagaaagaagttagatgatatgcctgacatagagga
agaggtgagtgaaaaatggttttcctgacactaacttgttattttgtcag
ctatactgcaatgaataattgtcttttgatactggagtaaaggcttgatg
tacagtgatttttttatatcatacaaatgacagaaaaaaaaagtggagta
gtactaaatatctgcttttagcagtagtctgattttggaaaaacaagttc
tgtactgattggaatgagaaactttcttcagttattt.
```

In an embodiment, an SCN1A-specific enhancer sequence comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E10 or S5E10 herein, located in the human genome sequence at human_hg38 start 166160023/human_hg38 stop 166160609 (FIGS. 1A-2 and 1A-3):

```
                                          (SEQ ID NO: 24)
tatcccagaaagaaggaaatggtcagtttatctggagttaagcatttgtg
tattatcatgattaatcacaggaacagttgccaagctttcattataaaaa
tattctccaggagaattcatcaagttccattgcctattaatttctgtcca
tgcattttatttggcatcttcaatgacagaggacacttttaaaaaaaaga
aatgaagacaaaagaaaaagttcattagagaaataatgtatgtgtgatat
ttaaaaattaagccacatcatcatcctaagaaaactacgagactttagtt
ttagtataaacttgcagtgtgttcttgagatttctaaatataaggcttaa
catttttccttaatacacatcgatttggcatctcatatgtattatttat
caggaaattataaaacaaagtaaaatgatgttttactaaaatgcacatca
tttttagatatgggattttaaaacttgatttataatactacttttaccat
gaaatactcttttgttgtatgaccttgagtacatttcccatctgtgaatc
tgtgtaatcatgtacaaaaataaatgagacaaaacct.
```

In an embodiment, an SCN1A-specific enhancer sequence comprises a nucleotide sequence which contains one or more regions of about 100 bp or longer having at least 75% or greater sequence identity to a human polynucleotide (DNA) sequence of the above-described E1 (S5E1) to E10 (S5E10) enhancer element sequences (e.g., SEQ ID NOs: 15-24). In another embodiment, an SCN1A-specific enhancer sequence comprises a nucleotide sequence which contains one or more regions of about 100 bp or longer having at least 75% or greater sequence identity to a human polynucleotide (DNA) sequence of the above-described E2 (S5E2) enhancer element sequence (e.g., SEQ ID NO: 16).

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E11 herein, located in the human genome sequence at human_hg38 start 36816984/human_hg38 stop 36817612 (FIGS. 1A-2 and 1A-3):

```
                                          (SEQ ID NO: 25)
tcagcaagtctgtcatcgacatcctgcaactgtttgagcgggcagagcaa
gtgcgaaaagattaaaaagtgcttttctcatcatttctgctcatatgacc
agcgctgcagtgctgcgcgccgggcgcacgcccgccgggcctggcatggc
gccaggggcccggactctgagcgcagcgggagcggctcagtccagccgcg
ccgctgagcagcgccggccgccggcaagaaggcgcgcggacctgctacca
ctcctgcaccgccaggccaggggtccgcgggatcccaggggctgcggcca
gggcacgagggaaggggccacctctgggatttagggggcactggcgtcac
cagctgggtctggaaagtccacctgccgtcaaggacacgcaggaggtgcg
ccgtctcagatctgggaaccttggcggatgtcctgccgcgtgggggaaga
tcctgaaccttcagcggccagcctgcacctcaggacctcctaggccctgc
```

-continued

```
tccctttctctctccactcctacctcagcctctgctctggtctgtcctgg
atgcaaatttatgctgcaaaatctgagcgctgaggtcctgaaacctgacc
cacccgacgcagggaggaggtggcaggga
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E12 herein, located in the human genome sequence at human_hg38 start 36817484/human_hg38 stop 36817720 (FIGS. 1A-2 and 1A-3):

(SEQ ID NO: 26)

```
Tccctttctctctccactcctacctcagcctctgctctggtctgtcctgg
atgcaaatttatgctgcaaaatctgagcgctgaggtcctgaaacctgacc
cacccgacgcagggaggaggtggcagggacagggacagggacaggcagga
gctgctggggcccacttcgggtgccccatcccacatctggccagggatgc
atattctaaaacctgatttgatgttttacttttattt
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E13 herein, located in the human genome sequence at human_hg38 start 36818134/human_hg38 stop 36818727 (FIGS. 1A-2 and 1A-3):

(SEQ ID NO: 27)

```
Cctgggctgcactaagtcccagtgtgaccttgggttgtgaccttctctgg
gcttctgtctccttctgatgtgttgatgacgtcagtggtcccatgtagtg
ggacctggggactgcaacttaaggtattggcaggtaggcagggccttggg
ctgtggtggccctgggtggtggggaccagggagagcagctgtccagctgc
ccagtaactcaagttccctgacatcgctgtcaacattgtctcctgcagct
cagccctggatggctgcccttcctggaaaccttaggatacctctgctggc
tccagctgccccctccctgtgagtcagctccttcaagccacagcccgcca
gatggcttccaaggcaccaaggatgcagctcctgacctgatgcctctcag
ctccaggacttcccaggacccctcagctgccctggaccctgctgctactg
ccgtcacctctgcaccttgtccccagctgggctgctgactcagatatgcc
aggctcctatgctatcatttcaactcccaggctcagctcactccaggagc
ctagttggagaatggatttccccagctgaaggacgcttcagcta
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E14 herein, located in the human genome sequence at human_hg38 start 88802240/human_hg38 stop 88802877 (FIGS. 1A-2 and 1A-3):

(SEQ ID NO: 28)

```
gcacttcagttccttttcatcaaggaactgattaaagtgtggtctattat
ctctgtagtggggagtcccgaaagattccacttcttcctcttcttgccca
atgagagggtcaggaagcttccaccaccatcctgactgtggccaccacat
cctggtgtgaagcaccaccagcttcctccacaagaactctgaaggtcacc
agccagcttgagtcctccgaaggtgctgtggctcaaccagcagcctgtgt
agcagagagcacaagacctgggactcgaactcagtcccaccttcaagagg
gatctccaccactttctgagcctcagttttcacatctttggttaggggca
ggtgggaagttgccatatttaccttgttgggctctttggaaaaattaaat
gaaatgttaatgtatgttacacaacgggctcataggagggattcaaaagc
tgctagttctttttctccttttcctgaaaacggtattaaagagtactgta
gagacactggagaattcctgcttcatatgagatgtccttggtctctcccg
gggaatttgaagacccagagactcgcagctccccgtgagcctccccgctg
acgccttacctcccccctctccaccatcccctgccatcc
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E15 herein, located in the human genome sequence at human_hg38 start 88803290/human_hg38 stop 88803678 (FIGS. 1A-2 and 1A-3):

(SEQ ID NO: 29)

```
tgccttcccctccccctgtcggccgcccctcggtccctgggggtggggtt
tccctttgcgctcgcccccctcccgcccccacccctcacgggccctcccct
cccccgcccgtccctatgtatgtgtcacagcgcgccatgcccgcccgccc
gcccacctacctccccgccgctccagagggggctcgcagagctgaggacg
cgcgcagcgctgctcaaggtctctctctctcagcaccctcgccggccggc
gtctgacgcgggtgccagggtctccgggcacctttcagtgtccattccct
cagccagccaggactccgcaacccagcagttgccgctgcggccacagccc
gaggggacctgcggacaggacgccggcaggaggaggggt
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E16 herein, located in the human genome sequence at human_hg38 start 88807290/human_hg38 stop 88807962 (FIGS. 1A-2 and 1A-3):

(SEQ ID NO: 30)

gccctgggaaaggggatcaggagcacatcttgggaacaggagccttcctc tcctgctgtcaacggcctggcctcgtggccatgcttcgtgtcctgatggt agccgcactgccgccctgataacttaaaggaagccccttcaatgggatga agggcccgtttctgtgacagctactttgggagtggcagctccccttcccc cagatccaacaggacacagccatccctgcgagggagtctgggcccctgga cgcagttgaagaagggccactgggaggccggcagaacaaggggagggctg gagaaggagcgggagtgcaggcgagaggaggaccagagaggggggaatttg tagagaaaacggtaaaacggtttctttttttcaaaagttgaatccagggca agaacggaaacggtggagtttacttttaaaaactcagagcctccttataa gtggtggagtgtgtgtgtgtgtgtgtgtgtgtgtgtgtgtgtgtgtgcat gctggcagggcgggccctgcgggctggccaggcctgtgagaggtgacttc tctccctctcaatggccttacagtgtatcctaaagaagcttttgttaaa ctcatgaataggtggatttggggtgtgtgatgctgggcatcacgatttgg atatttggttacctttgaggtta In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E17 herein, located in the human genome sequence at human_hg38 start 88833390/human_hg38 stop 88833984 (FIGS. 1A-2 and 1A-3):

(SEQ ID NO: 31)

Ttcatttcaggctccccgtccccttcctctgcctcacctatgctgtcgcc ctgtcagcacctaattcagcttcccatggagaaaggcctccctgttgaca gggccgtgctgggactcagggctgccaaagtcagtcttctcgcataaaag gctcagtgagtcctggagacacttggaagccagacagaatggaatttctc cctattttctttacagctgagaaaacacacacaaacacaagagcatattt attgcgatatttctatcccaaagtttgtctttaaaaaaaaaaaagaaata aaattagtttctctgcccactccacccctatcccccctacccccactctcc tccccacctcttttcattccttcccatttcctggtttaggccagggagag aaatcaagccgtccaagccccacagagcactcctacacccccggacaatg tccagcttgttcagagagtgagggaagaaacacagctccgaaaacataca cacaacctcccaatgaagggtgttctgagggaagaacaggcgggccttgt gtctgaacacgaatccctaaggctctgggaagagaggagccggaa In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E18 herein, located in the human genome sequence at human_hg38 start 128377753/human_hg38 stop 128378783 (FIGS. 1A-2 and 1A-3):

(SEQ ID NO: 32)

ggtcttaaagtaggaaaacacatggtgtgatttgggttggtgaatagtcg acttgtagatctgcggactcgtcaacattgctctgacatcagattttctg aagagcagtgtgggctccttccccagggctggccgagttttgaggggaac tgcaggttctgatgtttccaactctgtatctctgccctcgtcatttccat ggacaagttatttgtgctggtgtgagatccagaatcggtcctgctacgtg acaatgcctggagcacggagccaggaacccaagctgcctcaccagcgtgt tagggttgttactgtgcccgttttagaagatcacttggaggtgcaaaaat agagcagtttttttttgtttttttttttttgacatggagtctcgctctgt cgcccaggctggagtgcagtggcgcaatctcggctcactgcaagctccgc ctccccggttcacgccattctcctgccttagcctcccgagtagctgggac tacaggagcctgccaccatgcccggctaatttttttgtatttttttagtag agacggggtttgaccatgttagccaggatggtctcgatctcctgacttca tgatccgcccgcctcggcctcccaaagtgctgggattacaggcgtgagcc accacgcctggccaagagcagatttttttaaaaaaattaagtacctctat tcatttgcaccttcactacccagtgaggagatcaaaatttcctagagcaa atgcattcgatgccactcacagatttcgacaggagagcacaatttcagga acgcctacatcaaagcactaattggcacttttacagtgtctttctccgca cgtgagccttgctggtggaaggagctgtcatagtaatgcgtattcctcca tgcccagtgagtagggtgacggtcaattcacagttcactaggcacaaaag atgacggggctctcctctgctcgggacagcaagaaggttgaggtgatacg gtttgtcggtgtccccacccaaatctcatct In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E19 herein, located in the human genome sequence at human_hg38 start 128289803/human_hg38 stop 128290279 (FIGS. 1A-2 and 1A-3):

(SEQ ID NO: 33)

catgaaagtcactgttttacatactaattgcattttccccaaaacatcaa gctaaatacataactgatagcatgtttaaaggtcctatgtttcacctcaa attatctcatatttcacatgaggcaaaccctgtcctgaggccctgatgaa gatgggcaggcagatctgatatcagctgcttttctttccttgatggaacc tctggattgcgtgccctatcctataatgtgaaaaaagggcttccagaaaa ggtggaggaattactttctgaaattctgaaaggctggatccaaaggtgca gaaaggaacattatttcctaccatataaaacccagtagggcgtgtgatgc tgggacactgtatgagtccattctcatactgccataaagaagtacctgag actgggtattttataaaggaaagaggtttggttgactcacagttctgcag gcttaatagaaagcataactgggaggc In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E20 herein, located in the human genome sequence at human_hg38 start 128323153/human_hg38 stop 128323718 (FIGS. 1A-2 and 1A-3):

(SEQ ID NO: 34)

```
aaaaatgaagaatttatatgccaactccaggagaaatatttcagtgaggt

cctggcttggtgcaaggatatggaaccagagccaagaattctatcagtta

aaagcagcttagtttcctgagcctggactgatgggggacgtggaagacaa

agtgtcaggtccatcagtggaagattggccttgagccactgtacacagaa

tggagagcccactggcctaaaggagagattgtcaggcgtgacgaagcag

gaattttagccgaagaatattcacaaattacaggccaagagggaagtggg

gacgttcgtcttctcttcatagccttgctcgttgggggaccagctgtcct

ttattgttaatagaaaaatcaatatagcaagaggcgaatctttgctgtga

taacattggctcctttcaccaggcgtgtggaattagattactgatagatg

cacctctgtcgcctccccaggctccagatagaatctatgggctttgccaa

taagcacggtaacagagtgtggatcaggaaccagcgggtggccaatggca

gtggagaaaatgtaat
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E21 herein, located in the human genome sequence at human_hg38 start 128332503/human_hg38 stop 128332974 (FIGS. 1A-2 and 1A-3):

(SEQ ID NO: 35)

```
atagaccatataattctcacatgtcaaggttttaag

ccaaagccctcaggcaccacttctgattttcttga

aggatcaaaaataaaaggttgcaaccctcacagcc

gtaggctcctgcagcaactctttggtgcacctgtc

accctgatacctgggaggaggctctgagtccatgc

tgtgggaaggtgctggccttcatggatgggcctcc

cctggtgtgtccactgtggacctgagtgggtgtcc

cagagccctggctctcccttcttttcctctagaaa

gggaatcggcatgttcccaatcatctctgagatta

tctttattcttcaaggagttgcagtggctcttgcc

aagtgccctggggtcttggacatctgcctagtggc

cctgtagagacctccaccctccagacagctcagaa

tttgctaaagaaaatgtgaattttggagtccaggg

ctagaaaatatgacat
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E22 herein, located in the human genome sequence at human_hg38 start 128336003/human_hg38 stop 128336491 (FIGS. 1A-2 and 1A-3):

(SEQ ID NO: 36)

```
aagaaaagttttattttgcctctgtagtattgggg

tttaagtgatcacggtaattttccattatcatttt

gtgttttaaataaatacaacaggctttattgtgaa

aatatttgtctaatattgggcagtaaatgtttaag

tgattttggtttaattactattacagtcatactat

tacagtgcataaaatagaattcttcttgagtttgt

tcattagatgggaagaggctgcatttttaaaaaat

atatgcatgcctataatactacatttaaatatgtg

cgtatataaagagatgctttcttatttatatacat

ggtcattatagagctttgtgagaaatagaattttc

tctgtgcaatctgtactctgggaggggttatttgc

tgacactgtatgcccatttcctaacagaatgtctc

tagttaagtaatcatatgatgaagacatcccagct

gggactctatatttaagccaagttactatttcta
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E23 herein, located in the human genome sequence at human_hg38 start 128365603/human_hg38 stop 1283366181 (FIGS. 1A-2 and 1A-3):

(SEQ ID NO: 37)

```
ctaaaaatgcctcctcgcctctgattttagccgtg

gttgttggagtaccggttccagcaggagctgtgat

ttccattgagctctcaaaccaaataaaatgcaaat

ctccgaggatggctcctctccctgcccccacagtt

gtgctccgaatagtgtctgagtttcatttttacaa

ggggcctttaaaaactcctgggccccttgaaaact

cccagccccctttgtccagatggggatggaggtgg

ccaggctgccccgttgattgtgtgccgaggagccc

tccccgggaaggctgtgatttatacgcgcaggctt

gtcacggggtgaaaggaagggccactttttcattt

tgatccaatgttaggtttgaaagccacccactgct
```

-continued

```
gtaaactcagctggatccgcgggccgtgattaaac
acattgcccgctttgttgccgagatggtgtttcgg
aaggcgctgtgaatgcacttccctttgcggggctc
acacagacaagatgtgtgttgcaaggatgaggcgc
ctgctcggcctccagcccagggccgggaagggaga
aggtgctgtgcgtcgctgc
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E24 herein, located in the human genome sequence at human_hg38 start 128375853/human_hg38 stop 128376606 (FIGS. 1A-2 and 1A-3):

```
                                         (SEQ ID NO: 38)
Ttgaggcaagagcgagggtggcatatccagggtgg
ccactgggtctggagtgtcagtagcagggcagatt
tagaaggtgactttgcatacctaggcaaggccagc
tcatgcgggatgtcggagcccatgggaagcacctt
gcgtttgaggctgcctgcggtgggaagcttcagag
tttcaagcggggctttgctatgggtttgttctgct
ttcccgttttcccctttggaggaggcttacagaga
tagtgatgactttgcagctgttaatcatcaggaag
ctgtaatcactaagaatgtttgaaatcatcagtta
aggatttttagaaggaagtaaaccaaagaaatact
gcagtagcctgccctaattatttcctgggcttaaa
gtaaccaggtgcattggagagattatttttcttct
tctgatttatgaaggtctcagggtccaaattttga
aactgctgatcgaatttgttcttggatgttgtcat
agaaatctgaaactttcctacttgtctgagagtga
aatttctttgattattcactcaagggtttgatagg
tttaaaaaaaggccttcgggacatctcttgttata
aagtgtcaactttagatatcaagagaatcatgata
tatttattactacaaaagagaaaataagcaactga
aaaactcatgaacttgaagcatgaagcaaacccct
taagttctaggggtttcaagatgtggatgccaaca
tgtgatgacatttaaaaga
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E25 herein, located in the human genome sequence at human_hg38 start 128408553/human_hg38 stop 128408930 (FIGS. 1A-2 and 1A-3):

```
                                         (SEQ ID NO: 39)
ggcttttggtttttacaaaatattacaagttgcct
aaatagtccgtgtttaaggacatagagccagagct
ctttctggaatgtcatacctcggcagggccttttg
tgcatgttttaagctgattctgaaattagggggtt
aaaatggaagcgccgagccatccctaaagagaggg
aggcgaatgtgcccttgttgctggtgaccccagaa
caaggcctctgggctgagaacaggagagaatgtta
tttctttgaaaagccatcttgacaatccaagtccg
tttggctgcagcaccaaaggcagctttgatctgct
cgccagtgtccctgccgggaaaaggattagggtcc
ttccagaggacagcagagccaggctgcc
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E26 herein, located in the human genome sequence at human_hg38 start 13388723/human_hg38 stop 13390212 (FIGS. 1A-2 and 1A-3):

```
                                         (SEQ ID NO: 40)
gcccaggctggagtgtggtggcaaaatctcagata
actgaaacctctgcttcccaggctcaagccatcct
cccacctctgtctgcagagtagctgagactatagg
catgtgccacaatgctcagataattacttaacatt
ctagtagagtctagtagacatgggctatcactatg
ttgccctggctggtctggaactcctgggctcaagt
gattgttctgccttggcttcccaaagtgttgggat
tacggctgtaagccgccatgcttggcttcgcttta
caattttttttttttttttttgagacagagtctt
actctgccacccaggctggagtgtagtggctagat
tttggctcactgcaaactctggcccttgggttaag
agattctcctgcctcagcttcccaagtagctggga
ttacaggcatggacaaccatacctggctaatattt
tgtattagcagagacggtatttcaccgtgtcggcc
gggctggtctcgaactcccgacctcatgatccgcc
tacctcgggctcccaaagtgctgggattacaggca
tgagccaccgtgcttggccaagaagacattttgtt
ttctcaaaaaagtggagatctgagcttcaaagatc
```

-continued cttggtaacacttcccagtgctatcagtgtagtgg tgcagtggctaataattcatggaccctataggagg gatcttgcctgctctttagaggttgggacacactc ttcttggtaccagaagggcagaactatgcctctgt ggccacttattgcagaatggaattggagtaaactg agggccctttcacacatgctagagaactgactttg gccctaggagaagtgggggttgcaggggattggcc tgagaaacttgccttttcactggattgtcctctag agtttttcactggagatttgtcagaatgagcctcc agtccccatccagactcctggagctggcaggccag agcctgctgaggaaccagttcttgaccatcttcat cctggacgagctgcccagggaggtcttccctctga tgttcatggaggcctccagcatgagacattttgag gccctgaagctgatggtgcaggcctggcccttcct ccgcctccctctgggatccctgatgaagacacctc atctggagaccttgcaagctgtgctgaagggactt gatacactgctggcccagaagcttcgccccaggtg aggtgactcaggtggcctggtgggaagggtccagg catccagggaagggacagctggctcaggaggagtg gtggggttggggagctagggtggctcagaggcttc tgatggtgcccatgagagaccttgaccattgccca gatcctctggaaaaggactgctcaccatacagggt ccactgaggaaacaggaacctgcttcctcccagtg gaaggtaaaggttctagaagtgagaaccaggcaga atccaaggggggagcgggatg In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E27 herein, located in the human genome sequence at human_hg38 start 13469123/human_hg38 stop 13470861 (FIGS. 1A-2 and 1A-3):

(SEQ ID NO: 41)

ttgggttccaatggaactacagagagcaatgacta ctggtcctgaatgtgggtataaagttttaccctaa aagtaccttgtattttttttccaaggccaaaatata acaactcatttgcaccctggaaaggtatgtttatt taaaaaaaaagattgcatttgcaaacagtagagaa cactgctctttttttatttaaaaaaatctttaccat ggaaaaacaataaagtttgcgtgtgtgtttattgg -continued tctggggacttaaagaacaaagataccttgtggat tgcagacaaatgaaacccacagaggtttgctttgg gtaggtttcaccatacaggtgtttcaatagaccac tttgcaaataataaattacttaacactcaaggccg ctagaggccactaaaaaggagtttatggccaaggc acagggctggtggctggctcagtgagcggtggcag gatattaatgagactcagagcctggacgtgctctg gatccagttaaatgtaatagagttggaaaaccacc tgcccccagccactgacggcacctaggattcatgc ctgtaactttgaccatctgagcctgtagggacatt ggggaggaggggggagggtgagaggaggcagtggca acagcagcatggatgttccatgcaaacccttctct gtcaccagggaaagcagtctgagcacatgaatttc ttagcctctcttccaggatgaagcctagtttgaac cagcactgccaggttgaagtgttactgcatcctgc agccagagccagggcatgtggccaccccccttggtc cctgctgtggtacccagagtcacttggaacatgtg tgaagccaggatgagggtgcatataccctccagat gctgatatctaaatatttacaagtcacaaatacag agaaactgttttttttttgttattgttgttgttgt tttgagaaggagtctcgctctgtcgcccaggctgg agtgcagtagcgtgatctcggctcaaagttctgcc tcccgggttcacgccattctcctgcctcagcctcc caagtagctgggattataggcatgcaccaccacgc ctagcaaattttgtatttttagtagagatggggtt tctccatgttggtcaggctggtctcaactcctgat ctcaggtgatctgcccacctcagcctcccaaagtg ctgggattacaggtgtgagccaccgcacccggcca acaaaagtaccttcttaatgacttcgaagactagg tttaaatggtaaattattaaattcttggaaatctg ccacagaatatggcattgtggggacagctgagctg attgaaacctgctccctttctcttcccactcccag ctccatcctgcaccttaggggtctatgcacacctg tgtggacatcccaccctcacatccaacctctattc acattccccaccaccatcctgtgtggccactcagc ctgctctaaagcagggatgctgggaagatgcccac atccaagcttggaatcgtttttgccagaaattggg ggccctaagtacccaaaaaatgttctagaaggga catgttctggatggccatggactccttgctccctg gggaagagcacagctggaggaggactggagcaagg -continued cccccctaaagcactggacccaagataatgcccctc ttgcccaggtccaagggctgtactagtggtacccg ctgtcatcacagcattcattactg In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E28 herein, located in the human genome sequence at human_hg38 start 31124894/human_hg38 stop 31125629 (FIGS. 1A-2 and 1A-3):

(SEQ ID NO: 42)

cctcggaaccaaggttggctctggcacctgtaggg ccacgggcagctatgtcagcttcctcggaaggac cgaggctggctctggcatctccccgaccaatcctg gctccactgtgtacccctgaagggcagaaaacag ctactgcccaccgcagctccagcctggccccaaca tctgtgggccagctggtgatgtctgcctcagctg gaccaaagcctcccccagcgaccacaggctcagtt ctggctccgacgtccctggggctggtgatgcctg cctcagcagggccaagatctcccccagtcaccctg gggcccaatctggccccaacctccagagaccaga agcaggagccacctgcctccgtgggacccaagcca acactggcagcctctggcctgagcctggccctgg cttctgaggagcagcccccagaactcccctccacc ccttccccggtgcccagtccagttctgtctccaa ctcaggaacaggccctggctccagcatccacggca tcaggcgcagcctctgtgggacagacatcagcta gaaagagggatgccccagcccctagacctctccct gcttctgaggggcatctccagcctccagctcaga catctggtcctacaggctccccaccctgcatccaa acctccccagaccctcggctctccccctccttcc gagcccggcc tgaggccctccacagcagccctga ggatcctgtttt In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E29 herein, located in the human genome sequence at human_hg38 start 31132544/human_hg38 stop 31133831 (FIGS. 1A-2 and 1A-3):

(SEQ ID NO: 43)

agcctggccaacatggtgaaacgctgcctctacta aaaatacaaaaattagccaggcgtgatggcggta cctgtggtctcagctactggggaggctgagacagg agaatcacttgaacccgggaggtggaggttgcag tgagccgagattgcaccactgcactccagcctggg tgacagagcgagactccatctcagaaaaagaaaa aaaaaaaaaagagtctctgagtttacagatgaggg ccctggcattcagagaggctgaggaactcaccca gcctgtcaacggcagaaccagagccaaatccagga tttgctagcttcaaagctatgttctcactcactc cctaaggaggctgtgggcagaaggaaccctgggct gggaggcagcacagggcttggtatttatactaga cctgttctgcctcagtttcccagtctgtaaagtgg ccctttgtctcaggcaatttgtgctaagacccaa gagccttaagtgtgtgggatactagagggtctccc ctgatgtggccccctgcccctgccttgcctggac agtttgccttcagggacgacatgccactggtgcgg ctggaggtggcagatgagtgggtgcggcccgagc aggcggtggtgaggtaccgcatggaaacagtgttc gcccgcagctcctgggactggatcggcttatacc gggtgagaggggcagtggtggtcagcgactcaggg aagaaaggggcctggaggagcagctgaacagcat ggtggggtcactggcttgtccagatcttgatgcca cactgggagactgctgggatcagacattataggg tcacaacactgattccacaacactgatcccccagg tgggtttccgccattgcaaggactatgtggctta tgtctgggccaaacatgaagatgtggatgggaata cctaccaggtacttaaaaggagtgggagagtcag ggcaagtccttgttgcctttgggacctcagaactc accttgggggctctcaggtggcctccctgacccc caacttaggcttataccccctgggcctaccaggtaa cattcagtgaggaatcactgcccaagggccatgg agacttcatcctgggctactatagtcacaaccaca gcatcctcatcggcatcactgaacccttccaggt aagtaggccagactgctgggctgggggtgcctaaa gacttttgtcaaatgccacagcctctacattctg ctccttgagttcagacaaataacctgacctcccaa gatctgccaac In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E30 herein, located in the human genome sequence at human_hg38 start 88655733/human_hg38 stop 88657379 (FIGS. 1A-2 and 1A-3):

(SEQ ID NO: 44)

```
acatcttaaacagtcttttaatgttatgaatttga
tttttcaagaaatacatgtcatttattttcaaaa
cgaaatgatagctatactttctagagtctatcaat
agtatttaaaataagatactcataactttcaaat
actgcttttactagtcatcactcgtcattaaatgt
aactgtatattcaagagctttctaataatagcct
ttaattaaacgaaggactgttagagggtttctgtt
gccctttgaagttcttaattattacttgtatcca
gcattttatggtacacttaaggttaaattaaatca
tttaaatataccttgaagagaaatatgaagactt
ttgcccattttaattaaatctctgaatttcagtat
ttgaaaataataacatatgttttgattttttttt
catggccgaatggcaaaatgctcactatattaaac
aacaaaaaaagaaatggtagcttttatgggact
aatcgctaagcagatgcatgtaaatgagctatttt
ctatgcatggcttccaaaagtgctaattaaatag
ttggtattcaaggctatgctcgctcattgtttagt
gacacacaaatccagcgatgtgtgccagcagaca
ttttaagttgaatgttttctcctctacggtctttg
tcatgaaatggtggcaccatgatgagaacactag
tgtaagcaaaacattgaaatatgctttaataatgt
tttaaccatgtagtgacactagcctagttttcta
atgaatttttaatttctgttttcttataagggtga
tatgagttatcgctgatgcatattaaatcatata
catgagtcattttctctaaatttgcataaaatggc
taaatgctaatgcaccaaatggagcttactatat
gtggtacagcaaatattcccttgaagattttctgc
aatcaatctcctgtatttcattagcaaccagata
aggtgtggtctgcagaataaaaaaagaaaagtgtg
tagctcatgaacttatgaggcttcagatgatttc
tacgtggtgattagagtggattctgcaattagaat
ttatgtaggtaaaacacacatgtgcttcctttaa
aggcacagtgcaacaaaagttctgaatacagcctt
gcaattgttaaacaatgaaaaggcaccattcaat
tattgtgatttttttacatctataattaaatgaag
```

-continued

```
gaaagccatactttaaatttagtatcatttgatt
ggcataacccttactgaaattttacaatttcccta
ctatgtttataaaagaacttttaaaaataaccat
gtgtgaaatattttgtttgctaactgttcccattt
tccttgtcaaataatggtgaagaattttctggac
taatgtttaacatttaaaaatgttttttctatcat
caaatactcttactgaactgacattaggatcata
tgctttataaaaaaattgcattagggtaacagtatt
attgggcaaaccagagatgtttacttgaaggata
aacttgctgcttactcactccactcatcaacccctt
ttctcgtctcctacagttccaccatctggaatat
tttttaacccagt aaagaaaaaaattggggaaggg
gatggctatttaaaaataaatgcttt
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E31 herein, located in the human genome sequence at human_hg38 start 88872683/human_hg38 stop 88872997 (FIGS. 1A-2 and 1A-3):

(SEQ ID NO: 45)

```
tattatcctagtaaatccttaaaaaactttaagag
gtgggtgattttataattcccattttacagatcc
tggtactggggctttctggtcattaaaacacctgc
ctaaaaccactaatcagtaaatgggaggctggct
tttgaacccagttttggtcgttgttcttaatcatt
attctttattgtttatggacatgtttgtctaata
gcataatatgtagaatcaaagaaatgatattaagt
gtggaaatggagtctccaaactctttatgcttgt
ttaaacgatcttctctctcgagagtgtatcttcat
cctt
```

In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E32 herein, located in the human genome sequence at human_hg38 start 88745133/human_hg38 stop 88745535 (FIGS. 1A-2 and 1A-3):

(SEQ ID NO: 46)

```
tttcccttactcagctaacaaacatttaccaagta
tctgctgtgtgctaacgcttaggtgttaaactgg
```

-continued gcatacaaactgaatgagaaagagtttgcctccac
agagctgagcgtcctagagagatgtgcccagatg
ttgcaatcataatgcaatgagaaatgtaatgttgg
tacaggctactatgtaagcacaggaaagaggtgc
ataacttgtctgttagagtcaggaaaggcttttct
caaatggctgaactgaattctgtgggatgacaaa
gagtgctcaatagcatgaagcagaagaaggaaagg
catgctaggattgcataggtaagagtaagcggcc
gtgacattgccaagtggcggcacagtgtagcaatt
aagagcacacactgaggccgggt In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E33 herein, located in the human genome sequence at human_hg38 start 88799783/human_hg38 stop 88801354 (FIGS. 1A-2 and 1A-3):

(SEQ ID NO: 47)
ataaaatatcaggtaaatataatctctcatctctc
atcttctctccatctccctatgtccctttccttc
tctctctctctctctctcacacacacacacaca
cacacacacacacacacacacacacagagaga
gagacacacatgttcttcctctaaaaagaaaaacc
aataatcctctactgagacagttgtgaatcaaag
gtttcttctgcaggagttacatccatctctgaatt
tcctagagagcagcaaagggccttgtgttttatt
ccccttccacacttaatcactggactgtgggccca
gactgaatgagtagctcattagaatcactgagtt
cactgaggggatgagagattccttcctggctgggt
gctaagtgatactcccataaggattttgtggtta
caaaacgtgctggatatggaggtaacctgtctggg
agtcctgtcactccaaggatcacttggaatgctc
tggaaaaacacatgacctggctgaatgagttctgt
tgaattgtttagcctacaccttcatttcagcagc
ttatactgcattaatgaggttattgttcctttgcc
gtccaattgttcccaagctgatttttttgcatata
tgttttacatccttaacaagaatgcctgtctcctg
ctgtttcagagtctcttccacagtgctgagcatg
agtggagcttgctaaatcattgctaaatgaagcaa
tgggctgtaagcatgtcctgtgggatctgcatct -continued tcagatcatcctgaagtactcaacaaccacatctt
cttccaggaacagagcccaacataaactggtagg
gtttgctgtcttagacagctaagagaacgaggagt
ggagctagtgaacaagcagtgaagggggcagttc
cttaatgccatccgaactgaatttcaacagtctga
caagctagcgttttgggtaaatatcccagtatac
ttgtcacagagttaagtaaaatggacttccttcaa
aggaagtgcttttaatacaataactgtttttgtt
tttttaaccaatggattaaaaatttaacacattta
ctaaatctggcatatttatatattgtatctaaac
agatattcaagctgcattataatataatcataaaa
aaactgatctcagtctgtctgttaagcctttgtg
agtctttgtgccattgttggagtagtgctaattat
caagcaaagacatgataattacgcagagcttttt
tgctaaaagaaggaatctttttcaacacccacgca
ctgcacaatttcctatgaccctgtagcactactc
tggtatggcccagaaatttgtatttctgtgtaaag
gctggaaattatattatttctatctctcccgata
ccttttcttcttgtgagtaaactgtttttagaggg
ttaaggaagaggggtaatggtccaaatgggaaat
ataaaactaatgacccttcatgaaacatattatgc
tcctcattaaacttattcagttaaatgtattcca
ttaaattaaaataaataggatttaaaattttaccc
aggagcagtaaacaatctt In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E34 herein, located in the human genome sequence at human_hg38 start 27969472/human_hg38 stop 27969690 (FIGS. 1A-2 and 1A-3):

(SEQ ID NO: 48)
tgctgaaccagtctccgctgcatcgtctccgctcg
cgctcgggacctgcaacagaagggaatgggacccg
agtgtcagtctggactctccatctccccgcactac
tccgctcccccttttttagcccgctctcaaaaagcc
tcttcaacatcaagggcatctcccaagttgaaaag
aaaaaaaatttctctggagcctctcagcacttac
ttatttagca In another embodiment, an enhancer sequence as described herein comprises a nucleotide sequence which contains one or more regions of 50-500 bp or longer, 50-250 bp or longer, 100-200 bp or longer, or 100 bp or longer, having at least 70% or greater, at least 75% or greater, at least 80% or greater, at least 85% or greater, at least 90% or greater, or at least 95% or greater sequence identity to the following human polynucleotide (DNA) sequence, called E35 herein, located in the human genome sequence at human_hg38 start 27973822/human_hg38 stop 27974489 (FIGS. 1A-2 and 1A-3):

(SEQ ID NO: 49)

```
Caagctgatgggatcctcccatgggaaaagtgggc
ctcacacccttcctcacccttccctacttcctgg
gcaatgttctgcttcccccaaactgaagcaggagg
cccagagaggaggcggtttcctgggaggaaccca
aaccaatgtgagatgagaaggtctttaggaaatgg
gggtctctgagaaccggttcttaaaggtcaagca
cttgagcacctcgcaaactcctgacaattgaaaca
tatctgaagagtcttcttcagatatgtctctgtg
tgtgtgtgtgtgtgtgtgtgtgtgtgtgtgtgaga
gagagagagagagagagagagagagaatatgaat
gtgcagtgtcccagtcctgatctcctggactggtg
ccagccagccagatgcctgcccttggctggccaa
gtttttggctcctgaaagtaggcagctctggactt
gtacgaggccacagagagagttccaagccccacc
tggctcaggcgacaacctctcaacctgaagtcaat
ctccggtggcatcacagggccctcctggcagcag
cccagttccccacatgaaccgaatggtcctttctt
aaattttgagccgggggctgcctaaaaggggctg
cccccgcaagcattttacctccctaacaccattct
ctgcccgtgcca
```

In an embodiment, an enhancer sequence as described herein comprises a nucleotide sequence which contains one or more regions of about 100 bp or longer having at least 75% or greater sequence identity to a human polynucleotide (DNA) sequence of the above-described E11 to E35 enhancer element sequences (e.g., SEQ ID NOs: 25-49). In another embodiment, an enhancer sequence comprises a nucleotide sequence which contains one or more regions of about 100 bp or longer having at least 75% or greater sequence identity to a human polynucleotide (DNA) sequence of the above-described E1 (SEQ ID NO: 15), E2 (SEQ ID NO: 16), E5 (SEQ ID NO: 19), E6 (SEQ ID NO: 20), E11 (SEQ ID NO: 25), E14 (SEQ ID NO: 28), E22 (SEQ ID NO: 36), or E29 (SEQ ID NO: 43) enhancer element sequences, for example.

Genetic Epilepsy with Febrile Seizures Plus (GEFS+) and Dravet Syndrome

Genetic epilepsy with febrile seizures plus (GEFS+) is a rare condition that constitutes a spectrum of seizure disorders of varying severity. GEFS+ is usually diagnosed in families whose members have a combination of febrile seizures, which are triggered by a high fever and recurrent seizures (epilepsy) of other types, including seizures that are not related to fevers (afebrile seizures). The additional seizure types, called generalized seizures, usually involve both sides of the brain; however, seizures that involve only one side of the brain (partial seizures) occur in some affected individuals. The most common types of seizures in individuals with GEFS+ include myoclonic seizures that cause involuntary muscle twitches; atonic seizures that involve sudden episodes of weak muscle tone; and absence seizures that cause loss of consciousness for short periods that appear as staring spells. While GEFS+ is usually diagnosed in families, it can occur in individuals with no history of the condition in their family.

The most common and mildest feature of the GEFS+ spectrum is simple febrile seizures, which begin in infancy and typically stop by the age of five. When the febrile seizures continue after age five, or when other types of seizures develop, the condition is called febrile seizures plus (FS+), which typically cease in early adolescence.

Dravet syndrome (DS), also known as severe myoclonic epilepsy of infancy (SMEI) or early infantile epileptic encephalopathy-6 (EIEE6), is a condition frequently considered to be part of the GEFS+ spectrum and is the most severe disorder in this group of disorders. The term Dravet syndrome is preferably used, because not all affected individuals exhibit myoclonic epilepsy. Affected infants typically have prolonged seizures that last several minutes (status epilepticus) and are triggered by fever. Other types of seizures, including afebrile seizures, begin in early childhood. These seizure types can include myoclonic or absence seizures. In Dravet syndrome, these seizures are difficult to control with medication, and they can worsen over time. A decline in brain function is also common in Dravet syndrome. Children affected with Dravet syndrome usually develop normally in the first year of life, but then development stalls; some affected children lose previously acquired skills and suffer developmental regression. Many children afflicted with Dravet syndrome have difficulty coordinating movements (ataxia) and have intellectual disabilities.

Causes of GEFS+

Mutations in several genes, including some that have not been identified, can cause GEFS+. The most commonly associated gene is SCN1a. More than 80% of Dravet syndrome cases and about 10% of other GEFS+ cases are caused by changes in this gene. Mutations in other genes have been found in only a small number of affected individuals or families. The SCN1A gene and other genes associated with GEFS+ encode subunits of ion channels that transport positively charged ions into cells. The transport of these ions helps generate and transmit electrical signals between neurons (nerve cells). Mutations in the SCN1A gene have a variety of effects on sodium channels. Many genetic mutations that cause or are associated with Dravet syndrome reduce the number of functional channels in each cell. Mutations that cause the milder GEFS+ disorders likely alter the channel's structure. All of these genetic changes affect the ability of the channels to transport sodium ions into neurons. Some deleterious mutations are thought to reduce channel activity while others may increase it. Changes in GABAergic receptor subunit genes impair the channel's function, causing uncontrolled signaling between neurons, which likely leads to seizures. Without wishing or intending to be bound by theory, some studies have reported that certain SCN1A gene mutations cause constant stimulation of signaling between neurons. Such overstimulation of certain neurons in the brain triggers the abnormal brain activity associated with seizures.

While it is not known if all SCN1A gene mutations have the same effect, genome-wide association studies have demonstrated that loss of function of the voltage-gated sodium channel Nav1.1 encoded by the SCN1A gene is the most prevalent cause for Dravet syndrome. Previous studies using mouse models of Dravet syndrome suggest that it is the loss of SCN1A gene function in GABAergic interneurons that is the primary defect underlying the seizures that represent the most deleterious symptom of this syndrome.

In animal studies, it was found that SCN1A−/− mice developed severe ataxia and seizures and died on postnatal day 15. SCN1A+/− mice had spontaneous seizures and sporadic deaths beginning after postnatal day 21, with a notable dependence on genetic background. Loss of SCN1A did not change voltage-dependent activation or inactivation of sodium channels in hippocampal neurons. However, the sodium current density was substantially reduced in inhibitory interneurons of SCN1A−/− and +/− mice. (Yu, F. H. et al., 2006, *Nat Neurosci,* 9(9):1142-1149; Yu et al., 2007, Nat Neurosci, 10(1):134). The studies suggested that reduced sodium currents in GABAergic inhibitory interneurons resulting from heterozygous SCN1A mutations may cause the hyperexcitability that leads to epilepsy in patients with SMEI.

GABAergic Cortical Interneurons

GABAergic interneurons, which release the neurotransmitter gamma-aminobutyric acid (GABA) are inhibitory neurons of the central nervous system and are essential for regulating and maintaining neural circuitry and activity. (Kelsom, C. and Lu, W., 2013, *Cell Biosci.,* 3:19). GABAergic interneurons of the mammalian cerebral cortex comprise several different cortical interneuron subtypes that may be categorized and classified by their expressed protein markers.

Interneurons play a key role in the wiring and neural circuitry of the developing nervous system of both invertebrate and vertebrate organisms. In general, an interneuron is a specialized type of neuron (nerve cell) whose primary role is to form a connection between other types of neurons. Interneurons, which are neither motor neurons nor sensory neurons, differ from projection neurons in that projection neurons send their signals to more distant locations, such as the brain or the spinal cord. Critically, interneurons function to modulate neural circuitry and circuit activity. A large majority of interneurons of the central nervous system are of the inhibitory type. In contrast to excitatory neurons, inhibitory cortical interneurons typically release the neurotransmitters gamma-aminobutyric acid (GABA) and glycine. Cortical interneurons are localized in the cerebral cortex, which is defined as a sheet of outer neural tissue that functions to cover the cerebrum and cerebellum structures in the brain. (Id.)

GABAergic interneurons include numerous interneuron subtypes that may be categorized by the surface markers they express. Four major cortical interneuron subtypes are parvalbumin (PV)-expressing interneurons, somatostatin (SST)-expressing interneurons (which constitute a heterogeneous population), and ionotropic serotonin receptor 5HT3a (5HT3aR)-expressing interneurons. These three subtypes together account for approximately 100% of the neocortical GABAergic interneuron population in mice. Although these interneurons home to their respective layers of the cerebral cortex, they are generated in various subpallial locations and they subsequently migrate to the cerebral cortex.

Cortical circuit function is maintained by the balance between excitatory inputs and inhibitory inputs. A disruption of the balance of neural circuits is likely to contribute to the emergence of neurological, neurodevelopmental, or neuropsychiatric disorders such as, without limitation, epilepsy, autism spectrum disorders, and intellectual disabilities.

The Role of GABAergic Cortical Interneurons

GABAergic neurons play an inhibitory role and synaptically release the neurotransmitter GABA to regulate the firing rate of target neurons. Neurotransmitter release typically acts through postsynaptic $GABA_A$ ionotropic receptors in order to trigger a neuronal signaling pathway. Interneuron role/function is typically categorized into three components: (1) afferent input, (2) intrinsic properties of the interneuron, and (3) targets of the interneuron. In general, interneurons receive input from various sources, including pyramidal cells, as well as cells from other cortical and subcortical regions. (Kelsom, C. and Lu, W., 2013, *Cell Biosci.,* 3:19). With regard to output, cortical interneurons engage in feed-forward and feedback inhibition. Regardless of the mode of output, the cortical interneuron network is further complicated by the fact that a single cortical interneuron is capable of making multiple connections with its excitatory neuronal target(s).

Cortical Interneuron Subtypes

It is estimated that there are over 20 different subtypes of GABAergic interneurons in the cerebral cortex. The subtypes are also distinguished from each other based upon the calcium-binding proteins they express, which serve as markers. Based on studies performed in both mouse and rat brain tissue, the calcium-binding protein, parvalbumin (PV), and the neuropeptide somatostatin (SST), are key markers found to define the most predominant interneuron subtypes within the cerebral cortex. Of particular note, the PV-expressing interneuron population is independent from the SST-expressing population, in that expression of these markers does not overlap. In addition to PV- and SST-positive GABAergic interneurons, which together comprise approximately 70% of the total GABAergic cortical interneuron population, another subgroup of interneurons that express 5HT3aR were found to comprise approximately 30% of all interneurons. These three interneuron subpopulations account for nearly or equal to 100% of all GABAergic cortical interneurons, yet each of these populations, especially the 5HT3aR-expressing population, is heterogeneous and expresses other proteins or neuropeptides that contribute to their characterization. (Kelsom, C. and Lu, W., 2013, *Cell Biosci.,* 3:19).

Parvalbumin (PV)-Expressing Interneurons

PV-expressing interneuron represent approximately 40% of the GABAergic cortical interneuron population. This population of interneurons possesses a fast-spiking pattern, and fire sustained high-frequency trains of brief action potentials. These interneurons also possess the lowest input resistance and the fastest membrane time constant of all interneurons.

Two types of PV-interneurons comprise the PV interneuron group: basket cells and chandelier cells. Basket cells are interneurons that make synapses at the soma and proximal dendrite of target neurons, and usually have multipolar morphology. Several studies have shown that fast-spiking basket neurons are the dominant inhibitory system in the neocortex, where they mediate the fast inhibition of target neurons, among many other functions. Such fast-spiking basket neurons likely play a large role in regulating the delicate balance between excitatory and inhibitory inputs in the cerebral cortex. Unlike basket neurons, the chandelier cell subgroup of PV-expressing interneurons targets the axon initial segment of pyramidal neurons. Both basket cells and chandelier cells are fast-spiking, but they differ in electrophysiological properties. In contrast to other interneurons, chandelier cells may be excitatory rather than inhibitory due to their depolarizing effects on membrane potential. (Kelsom, C. and Lu, W., 2013, *Cell Biosci.,* 3:19).

Another group of PV-expressing cells that is independent from chandelier and basket neurons in the neocortex, e.g., mouse neurocortex, are called multipolar bursting cells, which differ from chandelier and basket cells in both electrophysiology and connectivity. Multipolar bursting neurons possess synapses with pyramidal cells (or other multipolar bursting cells) that demonstrate a paired-pulse facilitation; in contrast, chandelier and basket cells are usually strongly depressing. (Kelsom, C. and Lu, W., 2013, *Cell Biosci.,* 3:19).

Somatostatin (SST)-Expressing Interneurons

SST-expressing interneurons constitute the second-largest interneuron group in the mouse neocortex and represent approximately 30% of the total cortical interneuron population. SST GABAergic interneurons represent a heterogeneous population of cortical interneurons. SST-positive interneurons are called Martinotti cells and possess ascending axons that arborize layer I of the cerebral cortex and establish synapses onto the dendritic tufts of pyramidal neurons. Martinotti cells are also found throughout cortical layers II-VI, but are most abundant in layer V. In contrast to PV-positive interneurons, excitatory inputs onto Martinotti cells are strongly facilitating. Additional subpopulations of SST-expressing cortical interneurons show differences in firing properties, expression of molecular markers and connectivity of different neurons within this population. (Kelsom, C. and Lu, W., 2013, *Cell Biosci.,* 3:19).

5HT3aR-Expressing Interneurons

The third population of GABAergic cortical interneurons is designated as the 5HT3aR interneuron group, which accounts for approximately 30% of the GABAergic cortical interneuron population. Based on mouse studies, this population of GABAergic interneurons in the cortex express the 5HTa3 receptor, but do not express either PV or SST.

5HT3aR interneurons represent a heterogeneous population. Within the 5HT3aR interneuron group are several subsets of interneurons that also express other protein or neuropeptide markers, including vasoactive intestinal peptide (VIP). VIP-expressing interneurons are localized in cortical layers II and III. The VIP-expressing interneurons do not express PV or SST, but do express the 5HTa3 receptor, accounting for approximately 40% of the 5HT3aR population. VIP interneurons generally make synapses onto dendrites; some have been observed to target other interneurons. Compared with other cortical interneurons, VIP interneurons possess a very high input resistance and are among the most excitable of interneurons.

60% of cortical interneurons in the 5HT3aR-expressing population do not express VIP. Of this VIP-negative 5HT3aR group, nearly 80% express the interneuron marker reelin. In this latter category of cortical interneurons, the neurogliaform cell population, called spiderweb cells, express neuropeptide Y (NPY), and exhibit multiple dendrites radiating from a round soma. Neurogliaform interneurons can form synaptic connections with each other as well as with other interneuron types, in contrast to other types of interneurons that can only make synapses onto homologous neurons. Thus, neurogliaform cells play an important role in regulating neural circuitry and function by activating slow $GABA_A$ and $GABA_B$ receptors in order to provoke long-lasting inhibitory postsynaptic potentials onto pyramidal neurons and other interneurons.

Pyramidal Neurons

Pyramidal neurons, also known as pyramidal cells, are neurons with a pyramidal shaped cell body (soma), which ranges from 20-120 μm in diameter, and two distinct dendritic trees. The basal dendrites emerge from the base and the apical dendrites from the apex of the pyramidal cell body. Like most neurons, pyramidal neurons have multiple dendrites and a single axon, but both dendrites and axons branch extensively. The dendrites of pyramidal neurons are usually regarded as input structures, receiving synaptic contacts from other neurons, while the axon serves as its output to other neurons. Pyramidal neuron dendrites can also release retrograde signaling molecules (e.g. endocannabinoids), so communication is somewhat bidirectional. The extensive branching of the dendrites and the axon allows a single neuron to communicate with thousands of other neurons in a network. (Spruston, N., 2009, *Scholarpedia,* 4(5):6130).

Pyramidal neurons are found in forebrain structures, such as the cerebral cortex, hippocampus, and amygdala, but not in the olfactory bulbs, striatum, midbrain, hindbrain, or spinal cord of mammals, as well as birds, fish and reptiles. Pyramidal neurons are the most populous members of the excitatory family of neurons, e.g., neurons that release the neurotransmitter glutamate, in the brain areas that they inhabit, such as brain cortical structures. Their abundance suggests that they play critical roles in the functioning of the nervous system, as well as in cognitive processing. Pyramidal neurons comprise about two-thirds of all neurons in the mammalian cerebral cortex, where they function to transform synaptic inputs into a patterned output of action potentials. Pyramidal neurons receive synaptic inputs from tens of thousands of excitatory synapses and several thousand inhibitory synapses. Most of the excitatory inputs use glutamate as the neurotransmitter, e.g., glutamatergic pyramidal neurons, while inhibitory inputs use GABA.

While the nature of a stimulus can determine the type of output generated by a pyramidal neuron (e.g., single spike vs. burst), the intrinsic neuronal excitability is another important determinant of how the neuron responds to an input. Typically, neurons are classified according to how they respond to current injection, which may vary from one type of pyramidal neuron to the next. Most pyramidal neurons respond to continuous depolarizing current injection with a train of spikes that exhibits spike-frequency adaptation (accommodation). Many pyramidal neurons respond with one or more bursts of action potentials. The nature of this response is largely determined by the types of voltage-gated ion channels expressed in the neuron, but the structure of the dendritic tree is also important (Mainen, Z. F. et al., 1996, *Nature,* 382:363-366; Spruston, N., 2008, *Nature Reviews Neuroscience,* 9:206-221; Spruston, 2009, *Scholarpedia,* 4(5):6130).

Adeno-Associated Virus (AAV)

AAV is a small (25 nm), nonenveloped virus that contains a linear single-stranded DNA genome packaged into the viral capsid. It belongs to the family Parvoviridae and is of the genus Dependovirus, because productive infection by AAV occurs only in the presence of either an adenovirus or herpesvirus helper virus. In the absence of helper virus, AAV (serotype 2) can establish latency after transduction into a cell by specific but rare integration into chromosome 19q13.4. Accordingly, AAV is the only mammalian DNA virus known to be capable of site-specific integration. (Daya, S. and Berns, K. I., 2008, *Clin. Microbiol. Rev.,* 21(4):583-593).

There are two stages to the AAV life cycle after successful infection: a lytic stage and a lysogenic stage. In the presence of adenovirus or herpesvirus helper virus, the lytic stage persists. During this period, AAV undergoes productive infection characterized by genome replication, viral gene expression, and virion production. The adenoviral genes that provide helper functions for AAV gene expression include E1a, E1b, E2a, E4, and VA RNA. While adenovirus and herpesvirus provide different sets of genes for helper function, they both regulate cellular gene expression and provide a permissive intracellular milieu for a productive AAV infection. Herpesvirus aids in AAV gene expression by providing viral DNA polymerase and helicase as well as the early functions necessary for HSV transcription.

In the absence of adenovirus or herpesvirus, AAV replication is limited; viral gene expression is repressed; and the AAV genome can establish latency by integrating into a 4-kb region on chromosome 19 (q13.4), called AAVS1. The AAVS1 locus is near several muscle-specific genes, TNNT1 and TNNI3. The AAVS1 region itself is an upstream part of the gene MBS85 whose product has been shown to be involved in actin organization. Tissue culture experiments suggest that the AAVS1 locus is a safe integration site.

Recombinant AAV (rAAV) as a Vector for Gene Delivery and Therapeutic Treatment

AAVs are well suited for use as vectors and vehicles for gene transfer to the nervous system, as they enable gene expression and knockdown, gene editing, circuit modulation, in vivo imaging, disease model development, and the assessment of therapeutic candidates for the treatment of neurological diseases. AAVs provide safe, long-term expression in the nervous system. Most of the foregoing applications rely on local AAV injections into the adult brain to bypass the blood-brain barrier (BBB) and to temporally and spatially restrict transgene expression.

AAV vectors have been highly successful in fulfilling all of the features desired for a delivery vehicle, such as the ability to attach to and enter the target cell, successful transfer to the nucleus, the ability to be expressed in the nucleus for a sustained period of time, and a general lack of pathogenicity and toxicity. Recombinant AAV (rAAV) is advantageous as a delivery vector, particularly for delivery to interneurons in brain tissue, as it is focally injectable; it exhibits stable expression over time; and it is both non-pathogenic and non-integrative into the genome of the cell into which it is transduced. Twelve human serotypes of AAV (AAV serotype 1 (AAV-1) to AAV-12) and more than 100 serotypes from nonhuman primates have been reported to date. (Daya, S. and Berns, K. I., 2008, *Clin. Microbiol. Rev.,* 21(4):583-593). In addition, rAAV has been approved by the FDA for use as a vector in at least 38 protocols for several different human clinical trials. AAV's lack of pathogenicity, persistence and its many available serotypes have increased the potential of the virus as a delivery vehicle for a gene therapy application in accordance with the described compositions and methods.

Recombinant AAV (rAAV) vectors have been constructed that do not encode the replication (Rep) proteins and that lack the cis-active, 38 base pair integration efficiency element (IEE), which is required for frequent site-specific integration. The inverted terminal repeats (ITRs) are retained because they are the cis signals required for packaging. Thus, current recombinant AAV (rAAV) vectors persist primarily as extrachromosomal elements.

Recombinant AAV (rAAV) vectors for gene therapy have been based mostly on the AAV-2 serotype. AAV-2-based rAAV vectors can transduce muscle, liver, brain, retina, and lungs, requiring several weeks for optimal expression. The efficiency of rAAV transduction is dependent on the efficiency at each step of AAV infection, i.e., virus binding, entry, trafficking, nuclear entry, uncoating, and second-strand synthesis.

Several novel AAV vector technologies have been developed to either increase the genome capacity for AAV or enhance gene expression. Trans-splicing AAV vectors have been used to increase the capacity of the vector for harboring heterologous polynucleotides by taking advantage of AAV's ability to form head-to-tail concatemers via recombination in the ITRs. In this approach, the transgene cassette is split between two rAAV vectors containing adequately placed splice donor and acceptor sites. Transcription from recombined AAV molecules, followed by the correct splicing of the mRNA transcript, results in a functional gene product. While somewhat less efficient than rAAV vectors, trans-splicing AAV vectors permit delivery of therapeutic genes up to 9 kb in size and have been successfully used for gene expression in the retina, lung and muscle.

Polynucleotides encoding rAAVs as described herein comprise an SCN1A enhancer polynucleotide sequence. Because of its nature as an enhancer, the orientation of the enhancer polynucleotide sequence, i.e., 5'-3' or 3'-5', is not material to its function. Accordingly, the enhancer sequences (e.g., the E1-E10, e.g., E2, a PV-specific enhancer sequence, or E5 or E6, as described herein) may be used in a reverse orientation and may be used as reverse-complementary sequences. A "PV-specific enhancer" refers to the enhancer sequences described herein that target and restrict expression of a transgene in PV-expressing cortical interneurons (PV-cINs) as described herein.

Moreover, the enhancer need not be specifically spaced relative to other sequences, such as the SCNJA coding sequence. In addition, the rAAV polynucleotides may include additional elements, for example, a sequence encoding a reporter or a detectable marker, such as a fluorescent protein, or an element such as a Woodchuck Hepatitis Virus Posttrascriptional Regulatory Element (WPRE), which may increase RNA stability and protein yield. An rAAV polynucleotide may also comprise a promoter to drive transcription of one or more polynucleotides (genes) which are inserted between inverted terminal repeats (ITRs). A polyadenylation signal, such as bovine growth hormone polyadenylation signal and/or SV40 polyomavirus simian virus 40 polyadenylation signal, may be included as elements in the rAAV polynucleotide. The rAAV polynucleotide can comprise a minimal promoter, e.g., a human beta-globin minimal promoter (phog) and a chimeric intron sequence (Hermeming et al., 2004, *J Virol Methods,* 122(1):73-77). Without wishing to be bound by theory, ITRs may aid in concatamer formation in the nucleus after the single-stranded, AAV vector DNA is converted into double stranded (ds) DNA by host cell DNA polymerase complexes. Thus, the administration of the described rAAVs may form episomal concatemers in the nucleus of interneuron cells into which they are transduced. In non-dividing cells, such as adult interneurons, concatemers may remain intact in these cells for the lifetime of the interneurons. Advantageously, integration of rAAV polynucleotides into host chromosomes is likely to be negligible or absent and will not alter or affect the expression or regulation of any other human gene.

Recombinant AAV vectors can be made using standard and practiced techniques in the art and employing commercially available reagents. It will be appreciated by the skilled practitioner that rAAV vectors that been used in several clinical trials that have yielded promising results. By way of example, rAAV based therapy received marketing approval by the European Union in 2012, as reported by Kotterman, M. A. et al., 2014, *Nat. Rev. Genet.,* 15:445-451. In some embodiments, plasmid vectors may encode all or some of the well-known replication (rep), capsid (cap) and adeno-helper components. The rep component comprises four overlapping genes encoding Rep proteins required for the AAV life cycle (e.g., Rep78, Rep68, Rep52 and Rep40). The cap component comprises overlapping nucleotide sequences of capsid proteins VP1, VP2 and VP3, which interact together to form a capsid of an icosahedral symmetry. A second plasmid that encodes helper components and provides helper function for the AAV vector may also be co-transfected into cells. The helper components comprise the adenoviral genes E2A, E4orf6, and VA RNAs for viral replication.

In an embodiment, a method of making rAAVs for the products, compositions, and uses described herein involves culturing cells that comprise an rAAV polynucleotide expression vector as described; culturing the cells to allow for expression of the polynucleotides to produce the rAAVs within the cell, and separating or isolating the rAAVs from cells in the cell culture and/or from the cell culture medium. Such methods are known and practiced by those having skill in the art. The rAAVs can be purified from the cells and cell culture medium to any desired degree of purity using conventional techniques.

In an embodiment, the rAAV vector contains an SCN1A-restricted enhancer polynucleotide sequence and a chemogenetic DREADD ('Designer receptor exclusively activated by designer drug')-encoding sequence, e.g., a Gq-DREADD receptor (Hu, J. et al., 2016, *J Biol Chem,* 291:7809-7820), or a. The amino acid sequence of the Gq-DREADD receptor has been reported by Armbruster et al. (2007, *Proc Natl Acad Sci USA,* 104:5163-5168). The amino acid sequence of the Gq-DREADD receptor is a derivative of the amino-acid sequence of the human muscarinic acetylcholine receptor, M3, in which the tyrosine in position 149 is replaced by a cysteine, and the arginine in position 239 is replaced by a glycine. The unmodified human sequence is provided under NCBI accession no. NP 000731.1. In an embodiment, the polynucleotide sequence that encodes the Gq-DREADD receptor in the rAAV vector can be modified, for example, by including optimized codons for expression of the Gq-DREADD receptor in human interneurons.

In an embodiment, the rAAV vector contains an SCN1A-restricted enhancer polynucleotide sequence and a chemogenetic PSAM-encoding sequence.

Recombinant AAV vectors, which have a genome of small size (about 5 kb), can be engineered to package and contain larger genomes (transgenes), e.g., those that are greater than 4.7 kb. By way of example, two approaches developed to package larger amounts of genetic material (genes, polynucleotides, nucleic acid) include split AAV vectors and fragment AAV (fAAV) genome reassembly (Hirsch, M. L. et al., 2010, *Mol Ther* 18(1):6-8; Hirsch, M. L. et al., 2016, *Methods Mol Biol,* 1382:21-39). Split rAAV vector applications were developed to take advantage of the fact that rAAV genomes naturally concatemerize in the cell post-transduction and are substrates for enhanced homologous recombination (HR) (Hirsch, M. L. et al., 2016, *Methods Mol Biol,* 1382:21-39). This approach comprises "splitting" a large transgene into two separate vectors and upon co-transduction, intracellular large gene reconstruction via vector genome concatemerization occurs via HR or nonhomologous end joining (NHEJ). In general, three strategies exist within the split rAAV approaches: overlapping, trans-splicing, and hybrid trans-splicing.

Fragment AAV (fAAV) as an approach for AAV-mediated large gene delivery was developed based on reports that attempted encapsidation of transgenic cassettes exceeding the packaging capacity of the AAV capsid resulted in the packaging of heterogeneous single-strand genome fragments (<5 kb) of both polarities. After transduction by multiple fAAV particles, the genome fragments can undergo opposite strand annealing, followed by host-mediated DNA synthesis to reconstruct the intended oversized genome within the cell. (Hirsch, M. L. et al., 2016, *Methods Mol Biol,* 1382:21-39).

An advantage and benefit of the vectors, compositions and methods described herein is the identification and use of sufficiently small enhancer elements (cis-acting elements) that are capable of specifically restricting gene expression to a defined population of cells, e.g., interneuron cells. In an embodiment, the enhancer element is at least one of the E1-E10 enhancer sequences as described herein, which are SCN1A-specific and restrict gene expression, e.g., the SCN1A gene, to interneuron cells such as GABAergic interneurons and PV-expressing GABAergic interneurons, or pyramidal neurons, such as glutamatergic pyramidal neurons. The genes (transgenes) delivered by the rAAV vectors described herein are active and functional in the specific cells in which they are expressed, i.e., the products that they encode are produced, and are functionally expressed by the cells. By way of specific example, an rAAV vector as described herein which is engineered to contain an enhancer sequence that specifically restricts expression of a transgene, e.g., a reporter gene or SCN1A, to a GABAergic interneuron cell or a GABAergic, PV-expressing, cortical interneuron cell, transduces these specific cell types, and the encoded reporter protein, or Nav1.1 sodium channel in the case of SCN1A, is functionally expressed in the specific cell type. By way of another specific example, an rAAV vector as described herein is engineered to contain an enhancer sequence that specifically restricts expression of a transgene, e.g., a reporter gene or SCN1A, to pyramidal cell, such as a glutamatergic pyramidal cell in the brain cortex.

As another advantage, the described SCN1A-specific enhancer control elements E1-E10 are of a size/length (kb), e.g., less than approximately 2 kb, to allow for their insertion in a rAAV vector along with other effector element polynucleotide sequences, e.g., reporter polynucleotides, DREADDs, transgenes. By way of example, given the obligate minimal size of reporter elements (e.g., Enhanced green fluorescent protein (EGFP), orange fluorescent protein (dTomato)), alone or in combination with effector or reporter elements, (e.g. Channelrhodopsin (ChR2), DREADDs), which average about 700 bp to 2 kb, respectively, a maximum of ~2 kb in packaging capacity remains for the insertion of a cis-acting DNA control element such as an enhancer sequence into an rAAV vector. The SCN1A-restrictive enhancer sequences identified and described herein are capable of restricting expression to a defined population of cells, e.g., interneurons or GABAergic interneurons, or pyramidal neuron cells, and are sufficiently small elements to allow for additional nucleic acid sequences, reporter elements and transgenes, to also be cloned into the AAV vector.

Cell-Specific AAV Capsids

The rational design of AAV vectors that display selective tissue/organ targeting has broadened the applications of AAV as vector/vehicle for gene therapy. Both direct and indirect targeting approaches have been used to enhance AAV vector cell targeting specificity and retargeting. By way of example, in direct targeting, AAV vector targeting to certain cell types is mediated by small peptides or ligands that have been directly inserted into the viral capsid sequence. This approach has been successfully employed to target endothelial cells. Direct targeting requires detailed knowledge of the capsid structure such that peptides or ligands are positioned at sites that are exposed to the capsid surface; the insertion does not significantly affect capsid structure and assembly; and the native tropism is ablated to maximize targeting to a specific cell type. In indirect targeting, AAV vector targeting is mediated by an associating molecule that interacts with both the viral surface and the specific cell surface receptor. Such associating molecules for AAV vectors may include bispecific antibodies and biotin. The advantages of indirect targeting are that different adaptors can be coupled to the capsid without resulting in significant changes in the capsid structure, and the native tropism can be easily ablated. A disadvantage of using adaptors for targeting involves a potential for decreased stability of the capsid-adaptor complex in vivo.

In addition, AAV vectors may be produced that comprise capsids that allow for the increased transduction of cells and gene transfer to the central nervous system and the brain via the vasculature. (Chan, K. Y. et al., 2017, *Nat. Neurosci.,* 20(8):1172-1179). Such vectors facilitate robust transduction of neuronal cells, including interneurons. When used with enhancers and cell-type specific promoters, such AAVs provide targeted gene expression in neuronal cells of the nervous system.

For applications that do not require high expression levels per cell, the amount of virus used, i.e., the viral dose, could be lowered. Lowering the viral load used for systemic gene delivery can reduce cost and production burden and minimize a potential risk for adverse reactions to viral components.

Delivery of Recombinant Adeno-Associated Viral Vectors and Treatment Approaches

In general, the delivery of an effector gene to treat a neurological disease at the genetic level, e.g., by modifying or correcting gene expression, such as by gene therapy, may be achieved using appropriate and effective vectors, such as viral or virus vectors, e.g., AAV or rAAV. The use of a rAAV vector provides efficient delivery of therapeutic genes to a cell where the genes are expressed. While other methods and approaches for delivering genes to cells involve, for example, the use of purified DNA under hydrodynamic pressure, a shotgun approach using DNA adhering to gold particles, or lipid-DNA complexes, such methods and approaches frequently do not provide efficient gene delivery and result in gene expression that is lower than that required for therapeutic efficacy. Moreover, such methods are not applicable to human use. Viruses, on the other hand, represent natural vectors for the delivery and expression of exogenous genes in host cells in vivo.

An advantage associated with the use of rAAV as a viral vector is that rAAV transgene expression typically persists for years or for a life time, as has been demonstrated in animal models. This stands in contrast to non-rAAV viral vectors, which often lead to an initial burst of transgene expression that commonly disappears after a relatively short time, e.g., weeks.

To achieve enhanced therapy or treatment, the dose of rAAV vector that is required for a therapeutic response may be reduced, e.g., by using certain rAAV serotypes. Alternatively, the surface of the rAAV vector capsid may be altered to include specific ligands for attachment to target tissues and cells as described above. Another approach takes into consideration the trafficking of the virus particle from the endocytoplasmic vesicle to the nucleus. (Zhao, W. et al., 2007, *Gene Ther.,* 14:545-550; Daya, S. and Berns, K I., 2008, *Clin. Microbiol. Rev.,* 21(4):583-593). Typically, the virus particle-to-infectivity ratio of rAAV vector preparations ranges from 10:1 to 100:1. The high ratios reflect incomplete or empty vector particles, as well as trafficking from the endocytoplasmic vesicle to the nucleus. During trafficking, the vector particle may become ubiquitinated and directed to a proteasome for degradation, rather than to the nucleus where the transgene may be expressed. It was found that ubiquitination and direction to the proteasome require phosphorylation of tyrosine residues on the surface of the rAAV vector capsid. When the seven tyrosine residues on the surface of the AAV-2 capsid were replaced phenylalanine residues, the multiplicity of infection (MOI) required for the detection of transgene expression was greatly reduced both in cell culture and in several mouse models of transduction of cells in the liver and eye. Consequently, the ability to increase transgene expression to therapeutic levels in the treatment of diseases may be enhanced.

One or more treatment approaches to gain control over seizures are embraced by the therapeutic products, compositions and methods described herein involving state-of-the-art gene therapy or pharmaco-genetic approaches. Such approaches may likely lead to the development of a clinically relevant therapies to alleviate the seizure symptoms of DS.

For direct delivery to the brain, rAAV vectors may be administered by open neurosurgical procedure or by focal injection in order to bypass the blood-brain barrier, to temporally and spatially restrict transgene expression, and to target specific areas of the brain, e.g., interneuron cells and brain tissue comprising these cells.

Systemic rAAV delivery (by intravenous injection) provides a non-invasive alternative for broad gene delivery to the nervous system; however, the high viral load required and relatively low transduction efficiency have limited wide adoption of this method. Several groups have developed rAAV capsids that enhance gene transfer to the CNS and certain tissues and cell populations after intravenous delivery. By way of example, AAV-AS capsid18 utilizes a polyalanine N-terminal extension to the AAV9.4719 VP2 capsid protein to provide higher neuronal transduction, particularly in the striatum. The AAV-BR1 capsid20, based on AAV2, may be useful for more efficient and selective transduction of brain endothelial cells. Another AAV capsid, AAV-PHP.B, comprises a capsid that transduces the majority of neurons and astrocytes across many regions of the adult mouse brain and spinal cord after intravenous injection. In an embodiment, rAAV comprises a capsid which specifically transduced interneurons, including PV interneurons, in the cerebral cortex (brain).

Other modes of rAAV vector administration may include lipid-mediated vector delivery, hydrodynamic delivery, and a gene gun. In a particular embodiment, the rAAV vectors comprise a capsid that increases the likelihood of directly infecting or transducing interneuron cells, such as GABAergic interneuron cells and GABAergic, PV-expressing interneuron cells, or pyramidal cells, e.g., glutamatergic pyramidal cells, and brain tissue comprising these cells.

The virus vectors and compositions thereof as described herein may be used in the treatment of neurological, neurodevelopmental and neurodegenerative diseases and disorders, particularly, for the treatment of DS, which includes epilepsy and its attendant, often severe, seizure symptoms. A characteristic that distinguishes categories of seizures is whether the seizure activity is partial (e.g., focal) or generalized. In an embodiment, virus vectors and compositions thereof as described herein are used to treat partial and/or generalized seizures. Partial seizures are typically considered to be those in which the seizure activity is restricted to discrete areas of the cerebral cortex. As will be appreciated by the skilled practitioner, a seizure is characterized as a simple-partial seizure if consciousness is fully preserved during the course of the seizure. If consciousness is impaired, then the seizure is characterized as a complex-partial seizure. Complex-partial seizures also include those that initiate as partial seizures and subsequently extend through the cortex; as such, these types of seizures are considered to be partial seizures with secondary generalization.

Generalized seizures encompass distant regions of the brain simultaneously in a bilaterally symmetric manner and can include sudden, brief lapses of consciousness, such as in the case of absence or petit mal seizures, without loss of postural control. Atypical absence seizures usually include a longer period of lapse of consciousness and more gradual onset and termination. Generalized tonic-clonic or grand mal seizures, considered as the main type of generalized seizures, typically have an abrupt onset without warning. The initial phase of the seizure usually involves tonic contraction of muscles, impaired respiration, a marked enhancement of sympathetic tone leading to increased heart rate, blood pressure and pupil size. After approximately 10-20 seconds, the tonic phase of the seizure typically evolves into a clonic phase, which is produced by periods of muscle relaxation superimposed on the tonic muscle contraction. The periods of relaxation progressively increase until the end of the ictal phase, which usually lasts no more than one minute. The postictal phase is characterized by unresponsiveness, muscular flaccidity, and excessive salivation that can cause stridorous breathing and partial airway obstruction.

Atonic seizures are characterized by sudden loss of postural muscle tone lasting approximately 1-2 seconds. While consciousness is briefly impaired, there is usually no postictal confusion. Myoclonic seizures are characterized by a sudden and brief muscle contraction that may involve one part of the body or the entire body. Without limitation, the rAAV products, compositions and methods of use thereof as described herein embrace the prophylactic and/or therapeutic treatment of the above-described seizures, including the seizures afflicting those with DS. In an embodiment, the rAAV products, compositions and methods of use thereof as described herein are used for the prophylactic and/or therapeutic treatment of epilepsy associated with a loss of function or impairment of function of the sodium channel Nav1.1 encoded by the SCN1A gene. In a particular embodiment, the rAAV products, compositions and methods of use thereof as described herein are used for the prophylactic and/or therapeutic treatment of Dravet syndrome (DS). In another embodiment, the rAAV products, compositions and methods of use thereof as described herein are used for the prophylactic and/or therapeutic treatment of pharmaco-resistant epilepsy, which refers to an epileptic condition that is uncontrolled, despite use of two or more drugs that are suitable for treating this type of epilepsy and that have been administered at maximum tolerated doses (MTDs). In embodiments, a pharmacoresistant epilepsy embraces a condition in which seizures have failed to be eliminated by previous anti-epileptic drug treatments or treatment combinations.

Pharmacogenetic Approaches

Pharmacogenetic approaches are contemplated for use with the virus vectors, rAAV vectors, compositions thereof, and methods described herein. Such approaches deliver either Gq-DREADD receptor or PSAM into PV-interneurons specifically using a viral vector, such as a rAAV vector comprising an enhancer element (e.g., E1-E10) as described herein and a polynucleotide encoding a Gq-DREADD receptor or PSAM. The targeted PV-neurons, either in a specific region upon focal injection or throughout the cortex upon systemic injection, as dictated by the type of pathology being treated, stably express the receptor (Gq-DREADD or PSAM). Thereafter, an individual (patient) is administered the drug that activates the receptor (e.g. CNO or PSEM, respectively). This approach results in a controlled alteration of the excitability of the PV-interneurons expressing the receptor and allows for a dose-dependent and time-dependent modulation of the excitation/inhibition (E/I) balance in neurons (interneurons and PV-expressing interneurons), resulting in a normalization of brain activity.

Pharmaceutical COMPOSITIONS

Provided also are pharmaceutical compositions or formulations for treating subjects who are afflicted with, or who are at risk of developing, a neurological or neurogenetic disease, disorder, or pathology such as DS. In an embodiment, the pharmaceutical composition includes an AAV vector or virus particle, such as one containing an SCN1A-specific enhancer sequence, as described herein (as active agent) and a pharmaceutically acceptable carrier, excipient, or diluent. When formulated in a pharmaceutical composition, an rAAV vector as therapeutic compound or product can be admixed with a pharmaceutically acceptable carrier, diluent, or excipient.

The therapeutic agent(s) may be contained in any appropriate amount in any suitable carrier substance, and is/are generally present in an amount of 1-95% by weight of the total weight of the composition. The composition may be provided in a dosage form that is suitable for a parenteral (e.g., subcutaneous, intravenous, intramuscular, or intraperitoneal) administration route, such that the agent, such as a viral vector described herein, is systemically delivered. In an embodiment, systemic injection of an rAAV vector as described herein allows for the characterization of specificity of expression across brain regions, particularly when a reporter product is also encoded by the vector. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions may be formulated to release the active agent substantially immediately upon administration or at any predetermined time or time after administration. The latter types of compositions are generally known as controlled release formulations, which include (i) formulations that create a substantially constant concentration of the agent within the body over an extended period of time; (ii) formulations that after a predetermined lag time create a substantially constant concentration of the drug within the body over an extended period of time; (iii) formulations that sustain action during a predetermined time period by maintaining a relatively constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with a target site or location, e.g., in a region of a tissue or organ; (v) formulations that allow for convenient dosing, such that doses are administered, for example, once every one, two, or several weeks; and (vi) formulations that target a specific tissue or cell type using carriers, chemical derivatives, or specifically designed vectors (e.g., comprising a certain capsid composition) to deliver the therapeutic agent, e.g., to interneurons or PV-expressing GABAergic interneurons, or pyramidal neurons, e.g., glutamatergic pyramidal neurons. For some applications, controlled release formulations obviate the need for frequent dosing during the day to sustain the plasma level of the administered agent at a therapeutic level.

Methods by which to obtain controlled release in which the rate of release outweighs the rate of metabolism of the agent in question are not meant to be limiting. By way of example, controlled release is obtained by appropriate selection of various formulation parameters and ingredients, including, e.g., various types of controlled release compositions and coatings. Thus, the therapeutic agent is formulated with appropriate excipients into a pharmaceutical composition that, upon administration, releases the agent in a controlled manner. Examples include single or multiple unit tablet or capsule compositions, oil solutions, suspensions, emulsions, microcapsules, microspheres, molecular complexes, nanoparticles, patches, and liposomes.

The administration of a composition comprising a combination of agents for the treatment of a neurological disease or disorder such as DS may be by any suitable means that results in a concentration of the therapeutic that, combined with other components, is effective in ameliorating, abating, reducing, decreasing, or stabilizing seizures in a subject. The composition may be administered systemically, for example, formulated in a pharmaceutically-acceptable buffer such as physiological saline. In an embodiment, systemic injection of an rAAV vector as described herein allows for the characterization of specificity of expression across brain regions, particularly when a reporter product is also encoded by the vector.

Routes of administration include, for example, intracranial, parenteral, subcutaneous (s.c.), intravenous (i.v.), intraperitoneal (i.p.), intramuscular (i.m.), or intradermal administration, e.g., by injection, that optimally provide continuous, sustained levels of the agent in the patient. The amount of the therapeutic agent to be administered varies depending upon the manner of administration, the age, physical condition and body weight of the patient, and with the clinical symptoms of the neurological disease or disorder, such as DS. Generally, amounts will be in the range of those used for other viral vector-based agents employed in the treatment of neurological diseases and disorders, particularly in the brain, although in certain instances lower amounts are needed if the agent exhibits increased specificity. A composition is administered at a dosage that shows a therapeutic effect, such as, for example, ameliorating, abating, reducing, decreasing, or stabilizing seizures in a patient, as determined by methods known to one skilled in the art.

The pharmaceutical composition may be administered parenterally by injection, infusion or implantation (subcutaneous, intravenous, intramuscular, intraperitoneal, intracranial, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation, and can be found, for example, in Remington: The Science and Practice of Pharmacy, supra. In particular embodiments, administration is systemic and parenteral, such as by injection or intravenous delivery.

Compositions for parenteral delivery and administration may be provided in unit dosage forms (e.g., in single-dose ampules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent (e.g., viral vector or particle comprising enhancer sequences and polynucleotides encoding an effector gene and associated regulatory sequences, as described herein), the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

In some embodiments, the composition comprising the active therapeutic(s) (i.e., viral vector or particle described herein) is formulated for intravenous delivery. As noted above, the pharmaceutical compositions according to the described embodiments may be in the form suitable for sterile injection. To prepare such a composition, the suitable therapeutic(s) are dissolved or suspended in a parenterally acceptable liquid vehicle. Acceptable vehicles and solvents that may be employed include water, water adjusted to a suitable pH by addition of an appropriate amount of hydrochloric acid, sodium hydroxide or a suitable buffer, 1,3-butanediol, Ringer's solution, isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Methods of Administration and Delivery

Administration of a viral vector or pharmaceutical composition as described herein to a subject, e.g., a patient or infant patient having DS. In embodiments, the viral vector, viral particle, or pharmaceutical composition may be delivered to a cell (a target cell such as an interneuron or a brain layer comprising interneurons) in any manner such that the viral vector, particle or composition is functional and active to express the sequences contained in the vector or virus particle. Illustratively, rAAV comprising an SCN1A-specific enhancer and an effector gene (e.g. SCN1A) polynucleotide sequence may be delivered to interneuron cells or tissue comprising interneuron cells to provide for targeted expression of SCN1A in the interneurons. Thus, viral vectors or viral particles are delivered to a cell by contacting the cell with a composition comprising the viral vectors, or viral particles and by heterologous expression of the polynucleotides harbored by the viral vector or viral particles in the cell. The polynucleotides harbored by the rAAV vector must be delivered to the cells of a subject in a form in which they can be taken up so that therapeutically effective levels of the encoded products can be produced.

Transducing rAAV vectors are used for the delivery and expression of genes encoding desired proteins, polypeptides, or peptides to cells, especially because of their high efficiency of infection and stable integration and expression (see, e.g., Cayouette et al., *Human Gene Therapy,* 8:423-430, 1997; Kido et al., *Current Eye Research,* 15:833-844, 1996; Bloomer et al., *Journal of Virology,* 71:6641-6649, 1997; Naldini et al., *Science,* 272:263-267, 1996; and Miyoshi et al., *Proc. Natl. Acad. Sci. U.S.A.,* 94:10319, 1997). By way of example, rAAV is engineered to contain a polynucleotide encoding an SCN1A-specific enhancer nucleic acid sequence as described herein that preferentially directs gene expression in specific interneuron cell types and is used to direct and restrict the expression of a gene, e.g., SCN1A, in GABAergic interneuron target cells or in pyramidal target cells, such as glutamatergic pyramidal cells. In an embodiment, expression of the gene can be driven from any suitable promoter, such as a promoter specific for the target cells. In an embodiment, the rAAV vector is administered systemically. In an embodiment, systemic injection of an rAAV vector as described herein allows for the characterization of specificity of expression across brain regions, particularly, for example, when a reporter product is also encoded by the vector.

Gene transfer can also be achieved using in vitro transfection methods. Such methods include the use of calcium phosphate, DEAE dextran, electroporation, and protoplast fusion. Liposomes can also be potentially beneficial for delivery of DNA into a cell.

Treatment Methods and Protocols

Provided are methods of administering a therapeutic agent to a subject in need, such as a subject having, undergoing, having experienced, and/or at risk of experiencing a neurological disease or disorder, more particularly, a seizure, epilepsy, or DS, and who also may be diagnosed with, or be suspected of having, or having symptoms of, a seizure disorder, or who is identified as being in need of such treatment, in which an effective amount of a viral vector or viral particle as described herein, or a composition described herein, is administered to the subject to produce a therapeutic effect. According to the described methods, a therapeutic effect includes, without limitation, that amount of rAAV that is introduced into a sufficient number of interneurons so as to inhibit, reduce, or ameliorate one or more symptoms of the neurological disease or disorder, e.g., a seizure or epilepsy, or to prevent one or more symptoms subsequent to the administration of the rAAV vector product or composition to the subject. The amount of rAAV that is administered may be determined by the skilled practitioner in the art, such as a medical or clinical practitioner, and, as appreciated by one skilled in the art, is based on factors such as the size of the epileptic focus, the titer of the virus preparation and from data acquired in non-human primates (e.g., Colle, M.-A. et al., 2010, *Hum. Mol. Genet.,* 19:147-158). By way of example, from $10^{10}$ to $10^{12}$ rAAV particles may be used to transduce rAAV vectors or particles thereof to a therapeutically relevant number of interneurons. Identifying a subject in need of such treatment can be in the judgment of a subject or a health care professional and can be subjective (e.g. opinion) or objective (e.g. measurable by a test or diagnostic method).

The therapeutic methods (which include prophylactic treatment) in general comprise administration of a therapeutically effective amount of the agents described herein, such as an rAAV vector, a viral particle, or composition containing the aforementioned agents, to a subject (e.g., animal, human) in need thereof, including a mammal, particularly a human. Such treatment will be suitably administered to subjects, particularly humans or infant humans, suffering from, having, susceptible to, or at risk for a neurological disease or disorder, such as seizures and/or epilepsy, or DS. Determination of those subjects "at risk" can be made by any objective or subjective determination by a diagnostic test or opinion of a subject or health care provider (e.g., genetic test, enzyme or protein marker or biomarker, family history, and the like).

Viral vectors and pharmaceutical compositions as described can be used therapeutically to treat patients suffering from neurological or neurodegenerative diseases or disorders, e.g., seizures, epilepsy, or DS, or prophylactically to provide advanced treatment or protection to patients at risk for certain neurological or neurodegenerative diseases or disorders, such as a prophylactic vaccination to reduce, diminish, abate, or ward off a seizure, epilepsy, one or more symptoms of DS, or the severity thereof. A prophylactically effective amount of the rAAV vectors as described herein are not intended to be limiting herein, and may range between about $10^2$ TU (transducing units) per kilogram body weight of the recipient and about $10^{20}$ TU kilogram body weight of the recipient, or any TUs in between those values. Mouse models of seizures and DS can be used to optimize dosages and regimens.

The therapeutic vectors as described herein may be administered to a subject in need thereof in an effective amount to normalize the excitability of SCN1A-deficient interneurons and alleviate seizures and seizure symptoms of Dravet syndrome (DS). The vectors and methods described herein may be of therapeutic value for an individual, e.g., a human infant, child or adult, who experiences or is at risk for experiencing one or more seizures and/or DS. In an embodiment, an rAAV or a composition comprising an rAAVs as described herein is administered to an individual whose interneurons do not express or exhibit loss of function or expression, at the time of administration, of the SCN1A gene encoding the Nav1.1 sodium channel, which is dependent on an SCN1A-specific enhancer, such as E1-E10 described herein, for expression. In an embodiment, the expression of SCN1a in interneuron cells transduced by the described rAAV vectors containing an SCN1A-restricting enhancer sequence normalizes the excitability of interneurons deficient in, or having abnormal expression of, SCN1A. In an embodiment, a composition comprising an rAAV vector as described herein is administered to an individual whose interneurons no longer express the SCN1A gene. In an embodiment, a composition comprising an rAAV vector as described herein is administered to an individual who is at least one month old. In embodiments, the individual is at least 1, 2, 3, 4, 5, 6, 7, 8, 9, 10, 11, 12, 13, 14, 15, 16, 17 or 18 years of age.

Subjects, e.g., mammalian subjects, and human patients to whom the rAAV vectors as described herein are administered may also benefit from adjunct or additional treatments or therapeutic compounds or drugs, such as anti-seizure modalities, including but not necessarily limited to, use with other anti-epileptic therapeutic agents, and/or surgical techniques. as are well known to those having skill in the art. By way of example, anti-epileptic drugs (AEDs) that may be used in conjunction with the therapeutic products and compositions described herein include, without limitation, Acetazolamide, Brivaracetam, Carbamazepine, Clobazam, Clonazepam; Eslicarbazepine acetate, Ethosuximide, Gabapentin, Lacosamide, Lamotrigine, Levetiracetam, Oxcarbazepine, Perampanel, Phenobarbital, Phenytoin, Pregabalin, Primidone, Rufinamide, Sodium valproate, Stiripentol, Tiagabine, Topiramate, Valproic acid, (available as Convulex, Epilim Chrono, Epilim Chronosphere), Vigabatrin and Zonisamide.

Kits

Also provided are kits for preventing or treating a neurological or neuropsychiatric disease, condition, or pathology, e.g., seizures and/or epilepsy, as well as the symptoms of Dravet syndrome (DS), in a subject in need thereof. In one embodiment, the kit provides a therapeutic or prophylactic composition containing an effective amount of a rAAV vector or viral particle as described herein, which comprises an enhancer polynucleotide sequence specific for the SCN1A gene that restricts the expression of an SCN1A gene, e.g., contained in the virus vector, to interneuron cells, including GABAergic interneuron cells in the brain (i.e., in the telecephalon), or to pyramidal cells, such as glutamatergic pyramidal cells in the brain cortex, or to VIP cells. In an embodiment, the SCN1A-specific enhancer is an E1, E2, E3, E4, E5, E6, E7, E8, E9, or E10 human enhancer sequence as described herein. In an embodiment, the SCN1A-specific enhancer is an E2 human enhancer polynucleotide sequence. In an embodiment, the SCN1A-specific enhancer is an E5 human enhancer polynucleotide sequence. In an embodiment, the SCN1A-specific enhancer is an E6 human enhancer polynucleotide sequence.

In another embodiment, the kit provides a therapeutic or prophylactic composition containing an effective amount of a rAAV vector or viral particle as described herein, which comprises an E11-E35 enhancer polynucleotide sequence, in particular a human E11-E35 sequence, specific for a gene expressed in a neuron or interneuron cell, especially a PV-expressing neuron.

In some embodiments, the kit comprises a sterile container which contains the therapeutic or prophylactic composition; such containers can be boxes, ampoules, bottles, vials, tubes, bags, pouches, blister-packs, or other suitable container forms known in the art. The containers can be made of plastic, glass, laminated paper, metal foil, or other materials suitable for holding medicaments.

A composition comprising an rAAV vector comprising at least an SCN1A-specific enhancer polynucleotide sequence as described herein is provided together with instructions for administering the composition to a subject having or at risk of developing a seizure, epilepsy, or DS. In an embodiment, the rAAV vector comprises an SCN1A transgene for expression in interneuron cells including GABAergic interneurons and PV-expressing interneurons, or in pyramidal cells, such as glutamatergic pyramidal cells. The instructions will generally include information about the use of the composition for the treatment or prevention of the seizure, epilepsy, or DS. In other embodiments, the instructions include at least one of the following: description of the therapeutic agent (rAAV comprising SCN1A-specific enhancer polynucleotide sequence, etc.); dosage schedule and administration for treatment or prevention of ischemia or symptoms thereof, precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Further Embodiments and Advantages Thereof

Figure 3A:
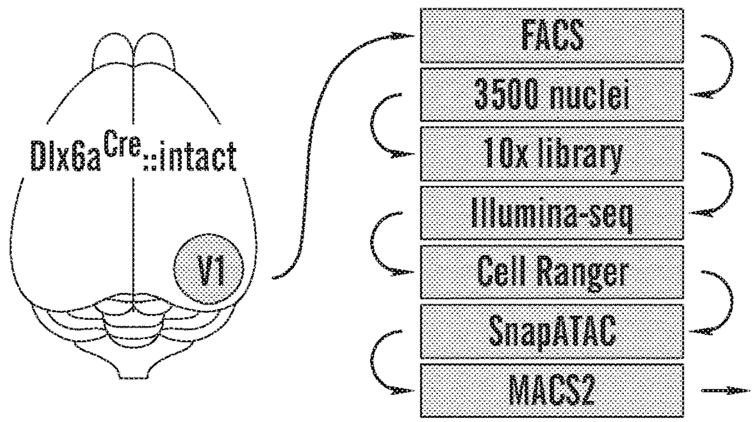
FIGS. 3A-3F show schematics, plots, graphs and confocal microscope images related to the identification of SCN1A enhancers.
Figure 3B:
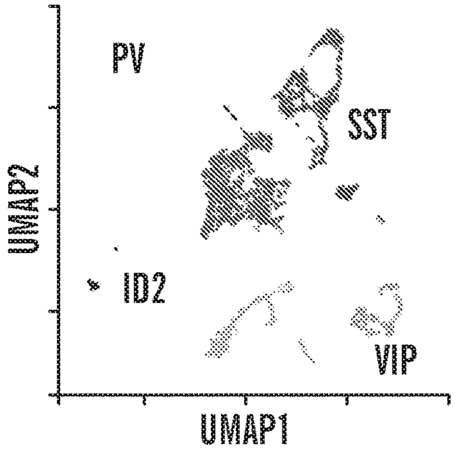
Figure 3C:
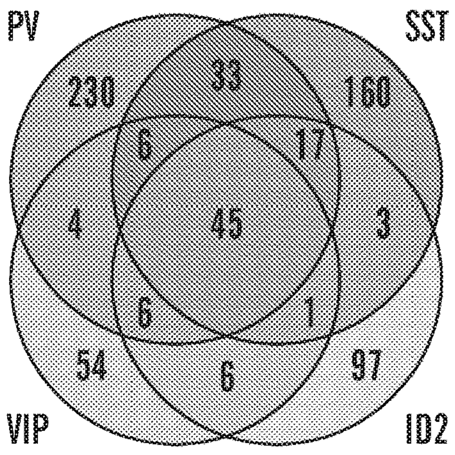
Figure 3D:
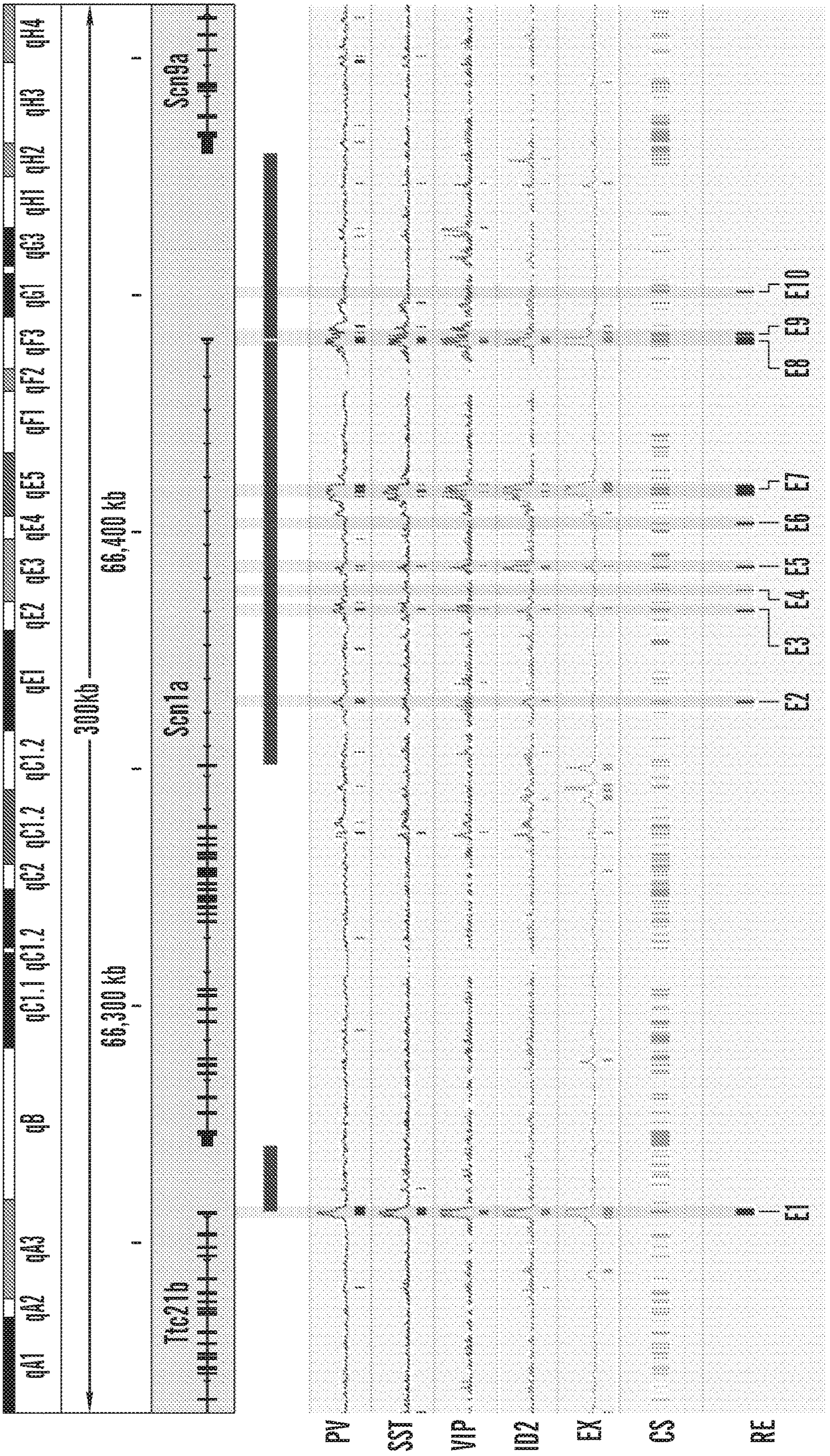

Understanding and developing methods of treating neurological disorders stems from the complexity of the neuronal types involved. The products and methods of the embodiments described herein were developed to deconvolve the cellular actions of a disease gene, or a disease-associated gene. As such, the SCN1A locus was systematically dissected, thereby resulting in the identification of 10 different enhancer elements (enhancers E1-E10), in particular, human enhancer elements and the sequences thereof, that were found to be distributed across the intronic and intergenic region of the SCN1A gene (FIG. 3D). By creating AAVs whose expression was dependent on each of these enhancers, at least three enhancers that recapitulated the global pattern of SCN1A gene expression were identified, e.g., E2 (for PV-specific expression), E6 (for VIP-specific expression) and E5 (for expression related to pyramidal layer 5. The other seven elements (e.g., E1, E3, E4, E7, E8, E9 and E10) were all highly specific for GAD1, labeled an assortment of interneuron subpopulations and may recruit distinct combinations of subtypes. In a particular embodiment, the E2 enhancer element was identified as being selective for a certain cIN subtype, namely, the PV-expressing fast spiking cells. As loss of expression of SCN1A is especially associated with PV cIN disfunction, the E2 enhancer proved to be particularly adept at selectively targeting this cell population, not only in rodents but also within various primates, including humans. In addition, the E2 enhancer was determined to be useful for investigating aspects of PV cIN function, including, without limitation, connectivity, monitoring excitability, and manipulating PV cIN activity with optogenetics. The demonstration of the utility of the E2 enhancer in a range of species highlights the breadth of basic and clinical applications that are provided by this approach. Other uses provided by the E2 enhancer include, by way of example, broader exploration of circuits (e.g. creating starter cells for monosynaptic tracing using recombinant-virus, such as rabies), cell type-specific gene loss of function (e.g CRISPR) and targeted drug screening. In addition, use of the E2 enhancer provides an agent for investigating species specific differences in the numbers, distribution or physiological properties of PV cINs. Generalized to other cell types, the approach is advantageous for investigating a range of species, most notably, both primates and humans.

As described herein, the strategy of systematically examining enhancers at a specific disease locus, such as the SCN1A gene locus, successfully identified key regulatory elements for each of the cell types that expresses this gene, thus, highlighting the benefits of the approach. It both clarifies the regulatory landscape controlling the expression of the SCN1A gene, as well as providing a tool kit for the manipulation of the distinct subpopulations of cells that express it.

Many of the SNPs associated with the SCN1A locus map to intron 1. In particular embodiments and as described herein, the three enhancers that were identified as having high specificity for SCN1A-expressing populations, namely, E2, E5 and E6, were located within this region. Without wishing to be limited by theory, the identified SNPs may represent mutations in these enhancers that affect the expression of SCN1A. It has been reported that GTEx data show multiple eQTLs within these enhancers that are associated with alterations in SCN1A expression in humans (Auget, F. et al., 2017, *Nature,* 550:204-213). E2 is especially noted, as conditional removal of SCN1A from forebrain interneurons has been shown to recapitulate the seizure phenotype in mice. As SCN1A expression is largely restricted to the PV-expressing subpopulation of interneurons, mutations in the E2 enhancer may be a direct cause of Dravet syndrome.

One of the great impediments to examining the early dynamics of circuit maturation has been the inaccessibility to specific cell types without the use of transgenic animals. Young PV cINs have been particularly problematic to target even with complex genetic strategies. In view of the abundance of PV-cINs (they represent 40% of all inhibitory cINs), as well as their implication in neurodevelopmental disorders, accessing these cells prior to the onset of PV expression is a priority in the field. The specificity of the E2 enhancer at these developmental stages and the use of viral injection provide agents and tools to understand the normal development of neuronal cell types such as PV cINs and their role in neurological or neuropsychiatric diseases. In an embodiment, the E2 enhancer provides an agent for studying the normal development of PV-cINs and their role in disease. In addition, the E2 enhancer, as well as other enhancer elements provided herein, may serve to target specific cells and are advantageous for the treatment of diseases, e.g., neuronal diseases, including Dravet syndrome.

In other embodiments, the enhancers identified and described herein provide access to particular cell populations with distinct clinical relevance. By way of example, these enhancers be used to alleviate the debilitating aspects of Dravet syndrome, e.g., either through gene therapy or via modulation of neuronal activity, e.g., via optogenetic or chemogenetic approaches. (See, e.g., Walker, M. C. et al., 2019, Neuropharmacology, 107751. doi: 10.1016/j.neuropharm.2019.107751. Review. PMID: 31494141). As described and demonstrated herein, local and systemic injections can be used for effective viral delivery to the brain, thus providing delivery and administration methods for clinical interventions. By way of example, local injections (e.g., of recombinant virus carrying an enhancer element and target polynucleotide) may be employed to alleviate focal epilepsy, prefrontal cortex dysfunction or hippocampal memory disorders. Systemic administration or delivery of virus may be employed in contexts where global interventions are necessary, for example, to correct generalized seizures or for psychiatric and neurodegenerative disorders. As provided by the embodiments described and exemplified herein, the rigorous identification of regulatory elements allows for accessing specific cell types. Such elements are advantageous for use in both experimental and therapeutic procedures and methods.

The practice of the described embodiments employs, unless otherwise indicated, conventional techniques of molecular biology (including recombinant techniques), microbiology, cell biology, biochemistry and immunology, which are well within the purview of the skilled artisan. Such techniques are explained fully in the literature, such as, “Molecular Cloning: A Laboratory Manual”, second edition (Sambrook, 1989); “Oligonucleotide Synthesis” (Gait, 1984); “Animal Cell Culture” (Freshney, 1987); “Methods in Enzymology” “Handbook of Experimental Immunology” (Weir, 1996); “Gene Transfer Vectors for Mammalian Cells” (Miller and Calos, 1987); “Current Protocols in Molecular Biology” (Ausubel, 1987); “PCR: The Polymerase Chain Reaction”, (Mullis, 1994); “Current Protocols in Immunology” (Coligan, 1991). These techniques are applicable to the production of the polynucleotides, viral vectors and viral particles and, as such, may be considered in making and practicing the embodiments described herein. Particularly useful techniques for particular embodiments will be discussed in the sections that follow.

The following examples are put forth so as to provide those of ordinary skill in the art with a complete disclosure and description of how to make and use the products, compositions and therapeutic methods as described herein, and are not intended to limit the scope of what is described and exemplified herein.

EXAMPLES

Example 1—Identification of Cis-Regulatory Sequences (PV-Interneuron-Specific Enhancer Sequences) that Restrict Expression of Reporter and Effector Genes to PV-Expressing Cortical Interneuron Cell Populations SCN1A, the gene that encodes the Nav1.1 sodium channel, is expressed in multiple distinct neuronal populations in the cortex. These include three, non-overlapping neuronal populations: fast-spiking cortical interneurons expressing parvalbumin (PV cINs), dis-inhibitory cortical interneurons expressing the vaso-intestinal peptide (VIP cINs) and layer 5 pyramidal neurons. In a particular embodiment, SCN1A is expressed in PV-expressing cortical interneurons. SCN1A is of particular interest, as its loss of function is associated with Dravet syndrome, an early-onset and intractable form of epileptic encephalopathy characterized by the early onset of seizures. More specifically, haploinsufficiency or pathogenic variants of SCN1A cause Dravet Syndrome.

An integrative method to systematically identify candidate enhancers within the SCN1A locus was developed and devised as a genetic strategy to target the distinct cortical populations expressing this gene. Regulatory sequences were selected based on the following three criteria. First, because it has been posited that the proximity of the enhancer to the transcriptional start site (TSS) of a gene scales directly to the level of expression, the intergenic and intronic regions of SCN1A closest to its TSS were examined to identify enhancers capable of driving functional levels of transgenes. Second, because the location of active enhancers within a given cell type correlates with chromatin accessibility, interneurons from the visual cortex were collected using Dlx6a$^{cre}$; Sun1-eGFP transgenic mice to assess the chromatin landscape of the cellular populations expressing SCN1A. The location of active enhancers within a given cell type correlates with chromatin accessibility and DNA hypomethylation.

After the nuclei were isolated, single-cell ATAC-seq profiling (see, e.g., Buenrostro, J. D. et al., *Nature,* 523:486-90 (2015) and Cusanovich, D. A. et al., Science, 348: 910-4 (2015)) was performed using the SnapATAC analysis pipeline (described in the Methods infra) to identify differentially accessible chromatin regions in each of the four major classes of cortical interneurons, including PV cINs, VIP cINs and pyramidal neurons, which express the highest levels of SCN1A. (FIGS. 3A-3C and FIG. 12). Third, because regulatory elements are subject to positive selection pressure, sequences showing the highest conservation across mammalian species, including humans, were identified. Thus, to determine and isolate enhancers with therapeutic potential, ten selectively accessible intronic and intergenic regions near the TSS of SCN1A that are highly conserved through evolution were evaluated, e.g., E1-E10 as described herein. (FIG. 3D and FIGS. 15A-1, 15A-2, 16A-1 and 16A-2).

Figure 3E:
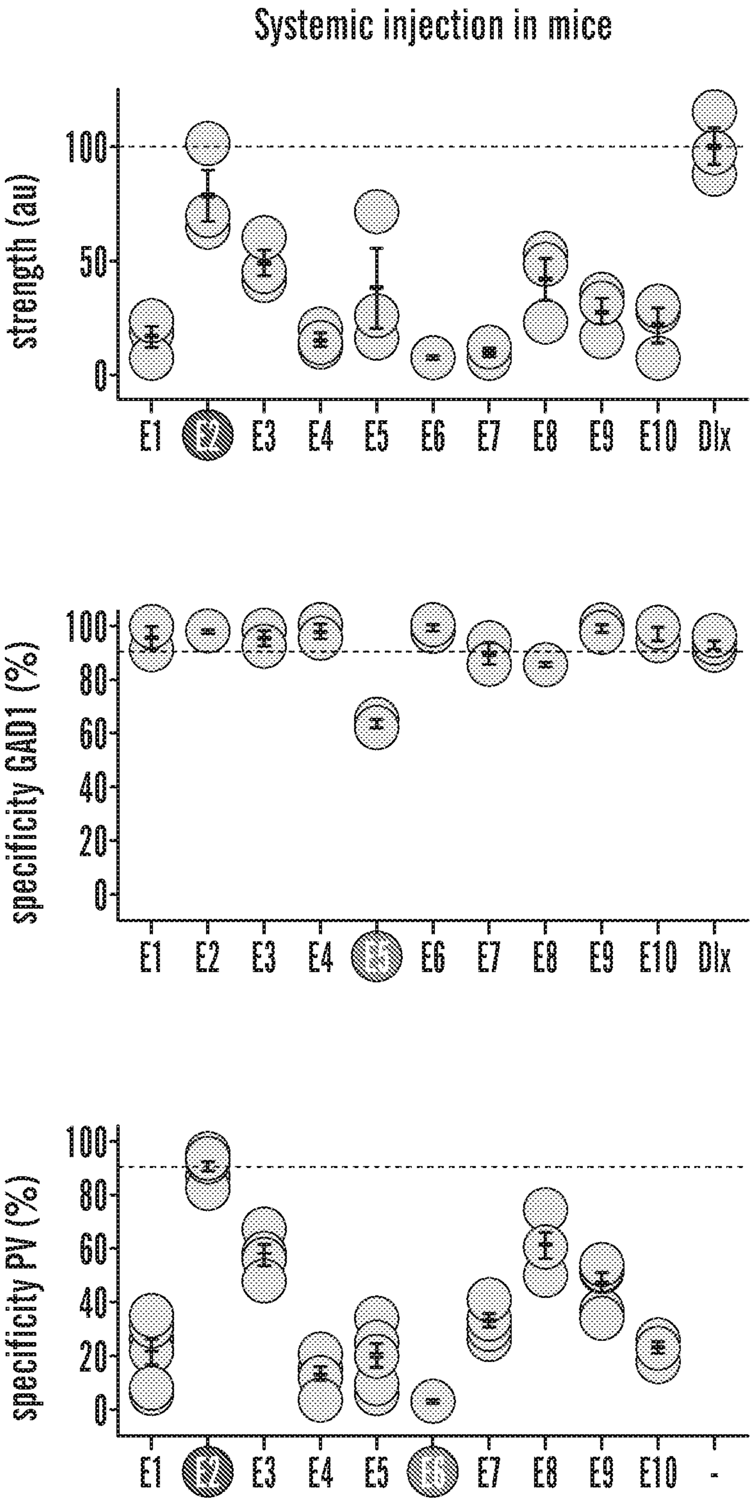
Figure 3F:
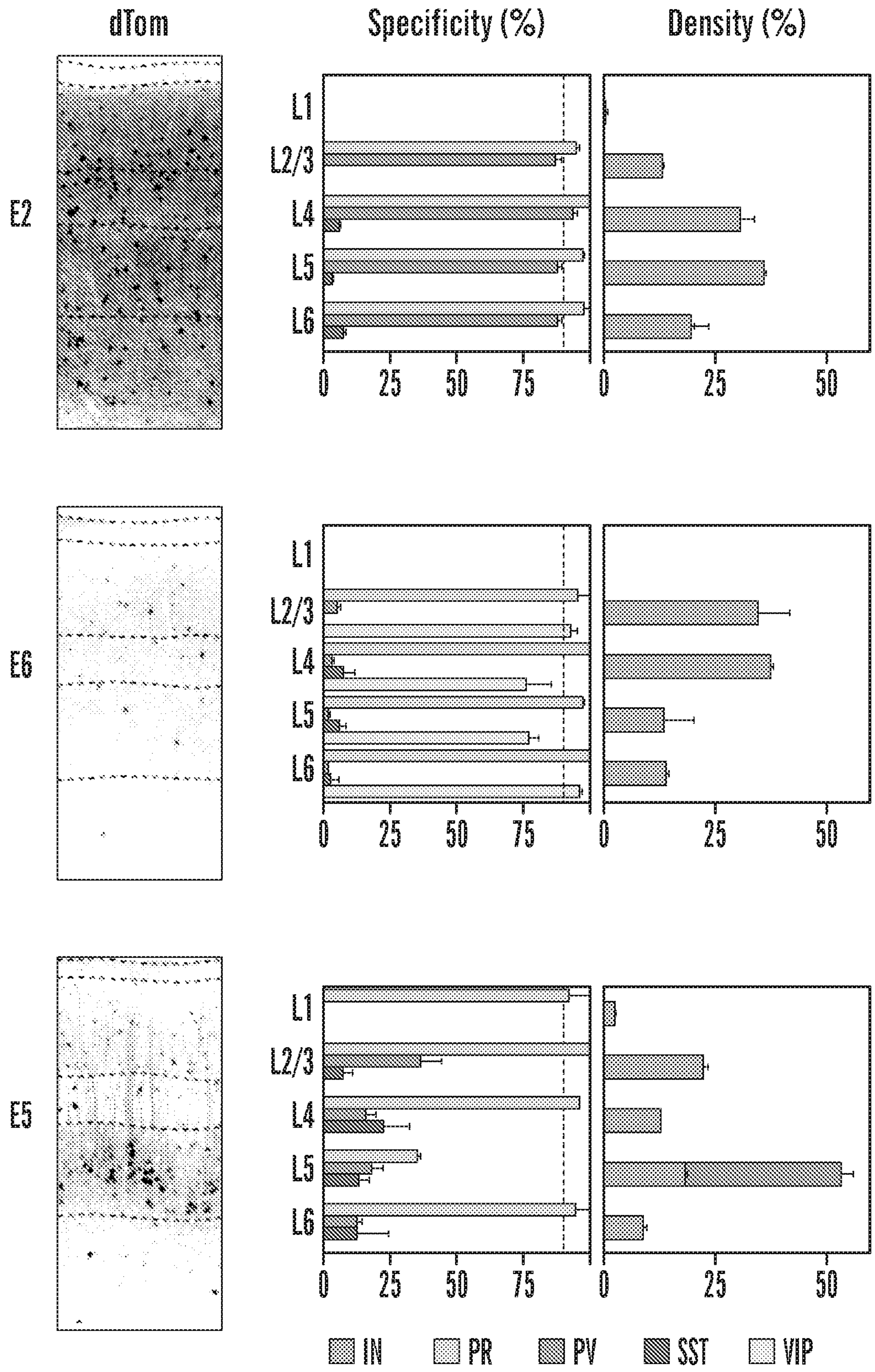
Figure 7:
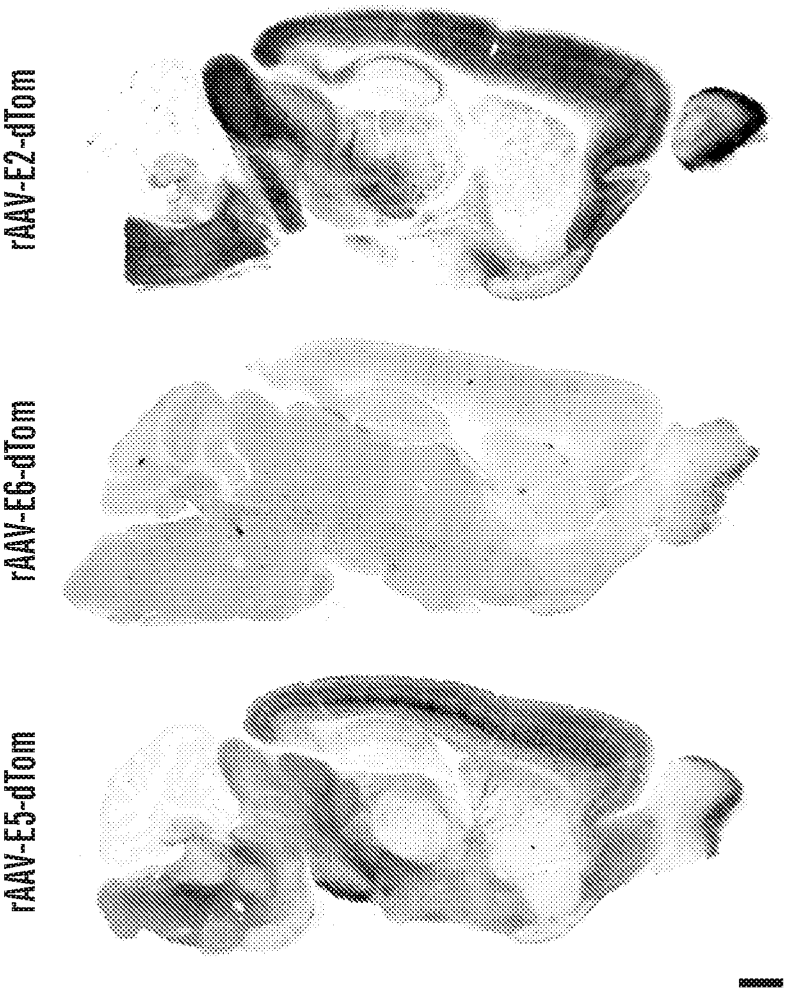
FIG. 7 depicts fluorescent images of sagittal sections from adult mice that were injected systemically with the indicated rAAV-E[x]-dTom viral reporter vector and analyzed 3 weeks post-injection with IHC for the viral reporter. Scale bar represents 500 μm.

To examine the ability of the candidate enhancers to target the neuronal populations that express SCN1A, each enhancer sequence was inserted into an rAAV-backbone containing a minimal promoter upstream of a red fluorescent reporter (rAAV-E[x]-dTomato). From these constructs, rAAVs were then produced with the PHPeB capsid (Chan, K. Y. et al., *Nat. Neurosci.,* 20:1172-1179 (2017)) and were systemically injected into adult mice. After 3 weeks, all viruses showed strong and sparse expression within the cortex, as well as across multiple brain regions. Except for E5, the vast majority of virally-labelled cells expressed the pan-interneuron marker Gad1. However, the degree of co-localization for PV within cortical neurons varied and ranged from over 90% for E2 to below 5% for E6, with all remaining enhancers displaying intermediate levels of PV specificity (FIG. 3E and FIG. 7). Thereafter, the identity and layer distribution of the neuronal populations captured by the E2, E5 and E6 enhancers were further examined. Consistent with their layer distribution, co-localization analysis with various markers revealed that the E2 regulatory element restricted the expression of the viral reporter to PV cINs, while E6 was selective for VIP interneurons. By contrast, the E5 regulatory element, while sparsely labeling interneurons across all layers, had a notable enrichment for pyramidal neurons in layer 5 (FIG. 3F). Thus, a significant fraction of the cortical expression profile of SCN1A was mirrored by the collective expression of three enhancers. These regulatory elements therefore account for largely non-overlapping expression in populations of interneurons and neurons with distinct functions and developmental origins. The viral tools developed as described herein provide a means for dissecting neuronal subtypes and can be advantageously used to study their normal function, as well as abnormalities in diseased cortex.

Figure 2A:
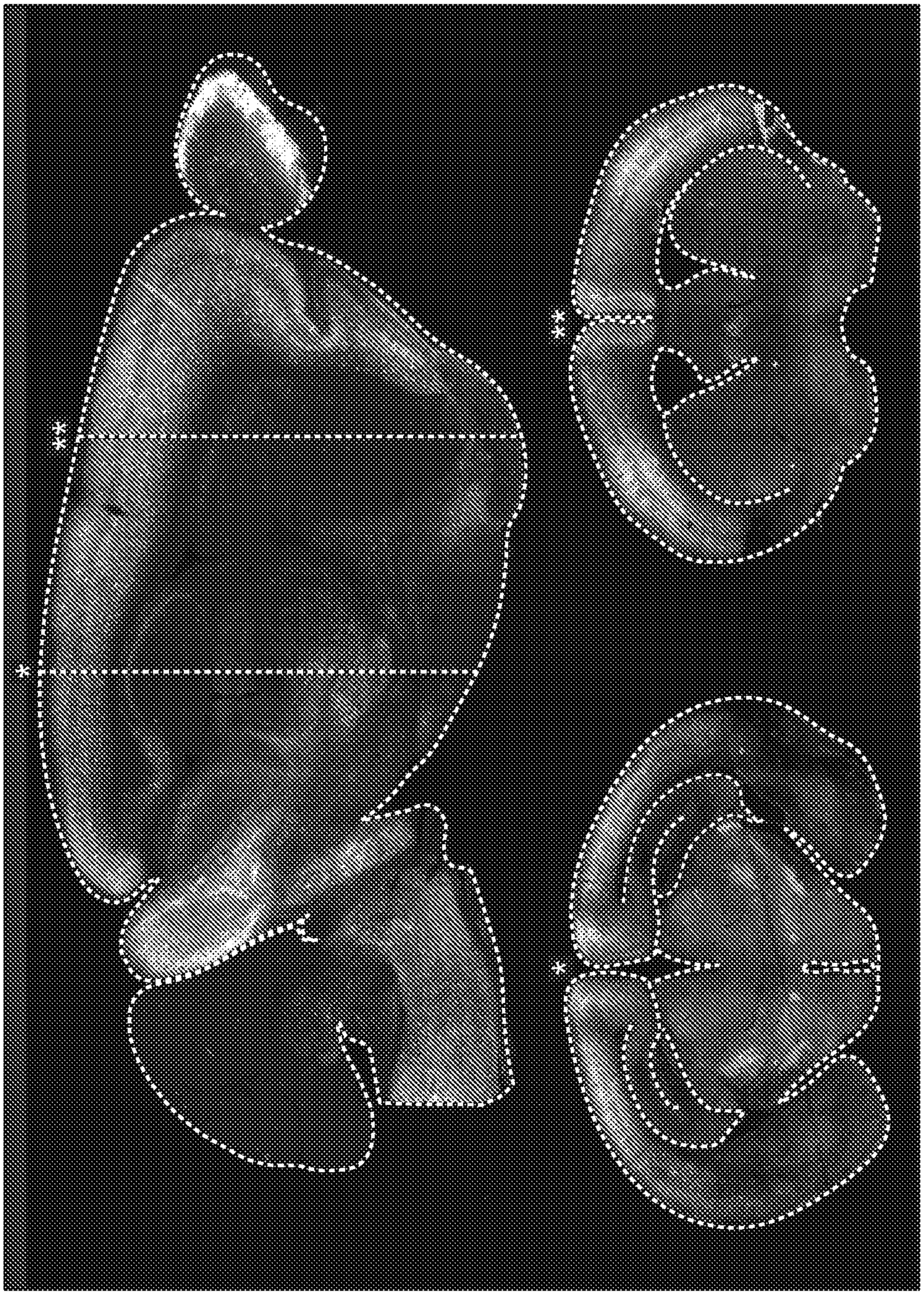
FIGS. 2A and 2B present images showing localization of reporter gene expression, using rAAV vectors containing the E2 enhancer element sequence and reporter transgene (e.g., d-Tomato) or an effector gene (e.g. Gq-DREADD) across brain structures including the cortex.
Figure 2B:
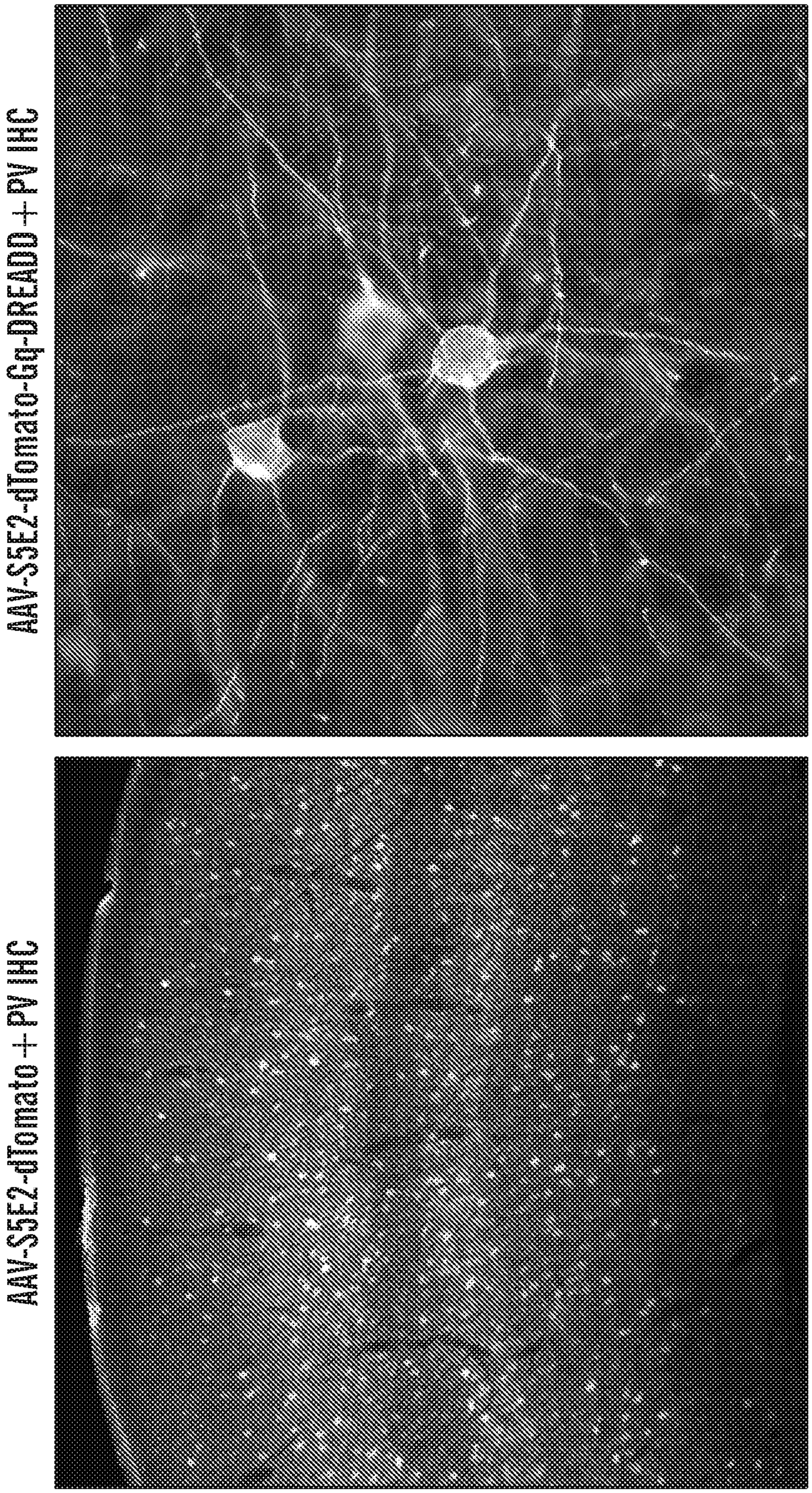

In a particular aspect, the S5E2 (E2) enhancer element sequence was incorporated into a recombinant AAV (rAAV) vector, which comprised a minimal basal promoter and a reporter transgene (e.g., d-Tomato) or an effector gene (e.g. Gq-DREADD), to generate the rAAV vector called pAAV-S5-E2-dTomato. The ability of the E2 enhancer to restrict expression of the reporter gene (transgene) to PV-expressing interneurons in brain was assessed by injecting the E2 enhancer-containing rAAV vector systemically into animals (mice) and analyzing the co-localization between the expressed reporter across brain structures including the cortex. An image showing the results of immunohistochemical (IHC) staining analysis for the dTomato reporter in brain sections is shown in FIG. 2A (sagittal sections in the top portion of the figure; coronal sections in the lower portions of the figure) following systemic in vivo injection of the pAAV-S5-E2-dTomato vector into an animal (mouse), allowing for detection of specific cells transduced by the vector. Images showing the results of immunohistochemical (IHC) staining analysis for the dTomato reporter expressed in brain sections following systemic in vivo injection of the pAAV-S5-E2-dTomato vector, or into an animal (mouse), allowing for detection of specific cells expressing PV are shown in FIG. 2B. Reporter gene expression from the pAAV-S5-E2-dTomato vector is visualized in brain sections (FIG. 2B, left panel, red). Reporter gene expression from the pAAV-S5-E2-Gq-DREADD-dTomato is visualized for Gq-DREADD (green) and for dTomato (red) (FIG. 2B, right panel). Detection of specific PV-expressing cells transduced by the vector is also visualized (FIG. 2B, left panel, green; FIG. 2B, right panel, blue).

Identification of Candidate Enhancers

Using the above enhancer sequence selection approach, ten candidate enhancer sequences proximal to the SCN1A gene transcriptional start site were discovered in the mouse genome. These enhancer sequences, called S5E1 (E1), S5E2 (E2), S5E3 (E3), S5E4 (E4), S5E5 (E5), S5E6 (E6), S5E7 (E7), S5E8 (E8), S5E9 (E9) and S5E10 (E10) herein, were identified in the vicinity of the SCN1A gene (FIG. 1A-1). The human polynucleotide sequences corresponding to the E1-E10 enhancer sequences (SEQ ID NOs: 15-24) are also provided and described herein, as well as additional human enhancer polynucleotide sequences E11-E35 (SEQ ID NOs: 25-49) as described herein. (FIGS. 1A-2 and 1A-3).

The human (human ortholog) sequences for the E1-E10 enhancers were determined based on alignment of the mouse sequences to the human genomic sequence of SCN1A, including 100 kb both upstream and downstream, leading to the identification of human ortholog sequences that are highly conserved between the two species (FIGS. 1A-1 to 1A-3, 16A-1, 16A-2). As will be appreciated by the skilled practitioner, enhancer regulatory elements comprise a series of transcription binding sites that are relatively well conserved across species, but are interspersed with spacer sequences that are not contiguously conserved across species. Accordingly, in an embodiment, a SCN1A enhancer element can constitute a nucleotide sequence containing any regions of more than 100 bp that have at least 75% or greater sequence identity with a human polynucleotide (DNA) enhancer sequence as described herein, namely, E1-E10. In an embodiment, a SCN1A enhancer element constitutes a nucleotide sequence containing any regions of more than 100 bp that has at least 75% or greater sequence identity with the human E2 (S5E2) polynucleotide (DNA) enhancer sequence. For such enhancer sequences, the size of the nucleic acid sequence is not limiting, so long as the sequence contains any regions of more than 100 bp that have at least 75% or greater sequence identity with a human polynucleotide (DNA) E1-E10 or E11-E35 enhancer sequence as described herein. The data related to each of the identified enhancer sequences (35 enhancer sequences) described herein is provided in the tables shown in FIGS. 1A-1 to 1A-3, 15A-1, 15A-2, 16A-1 and 16A-2.

Figures 1, 1B, 2:
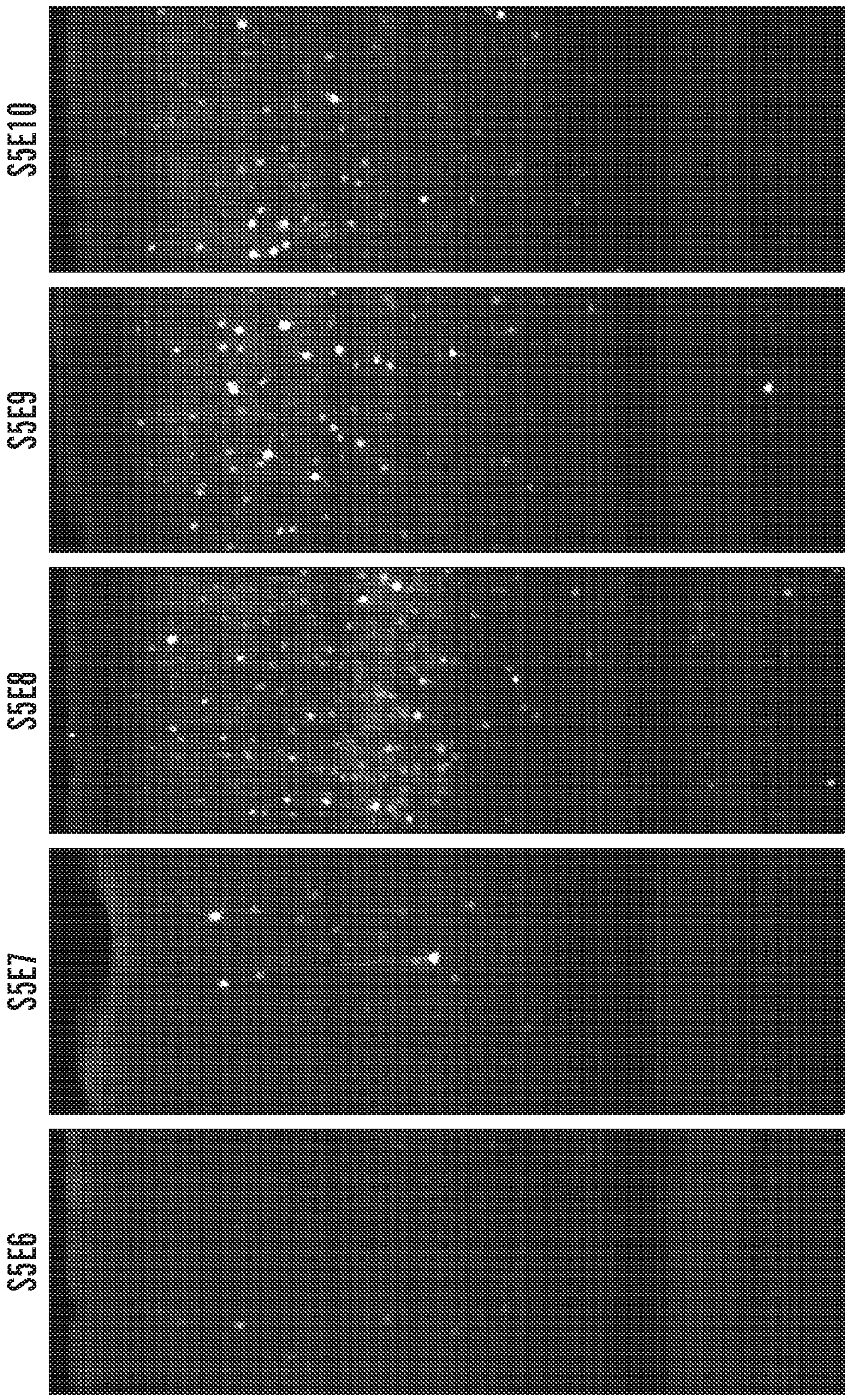
Figure 1C:
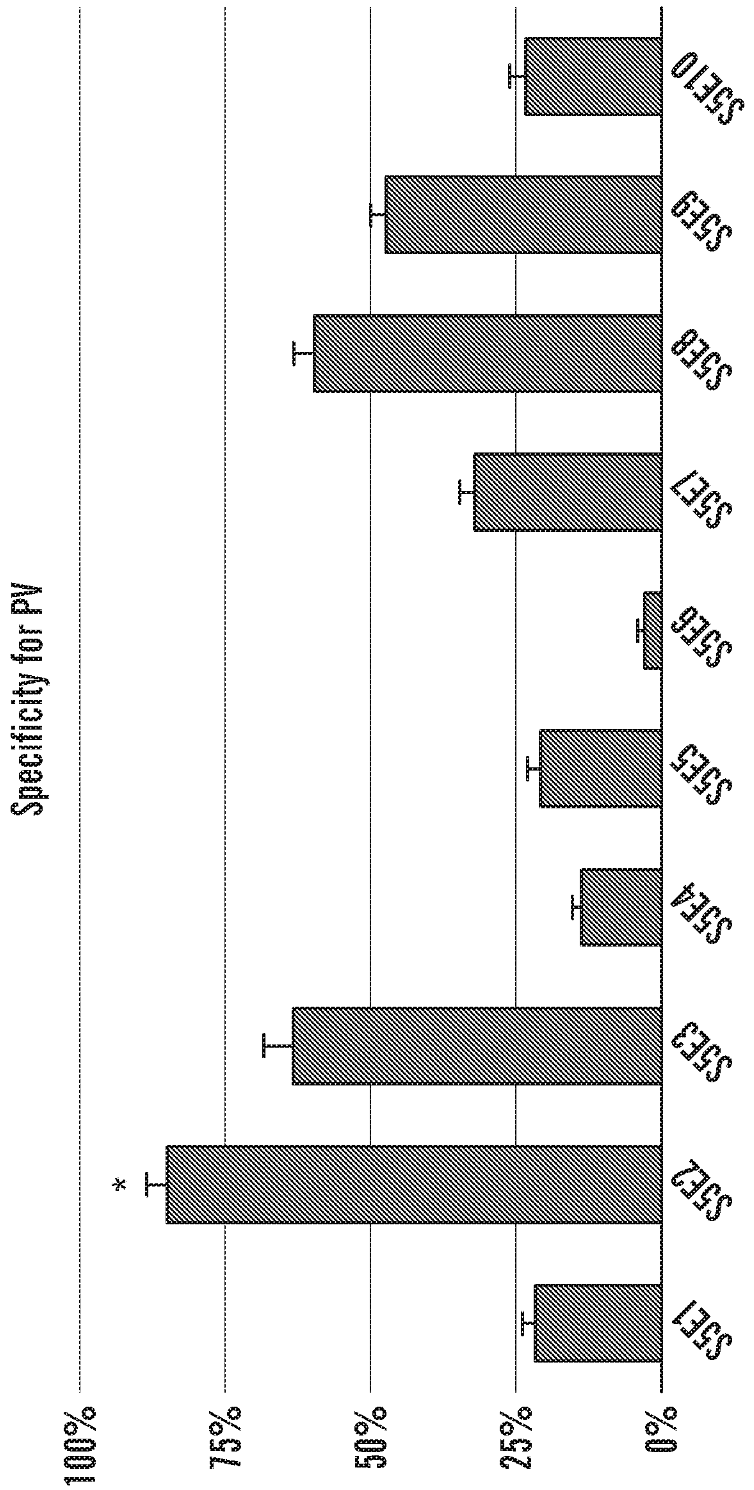
Figure 1D:
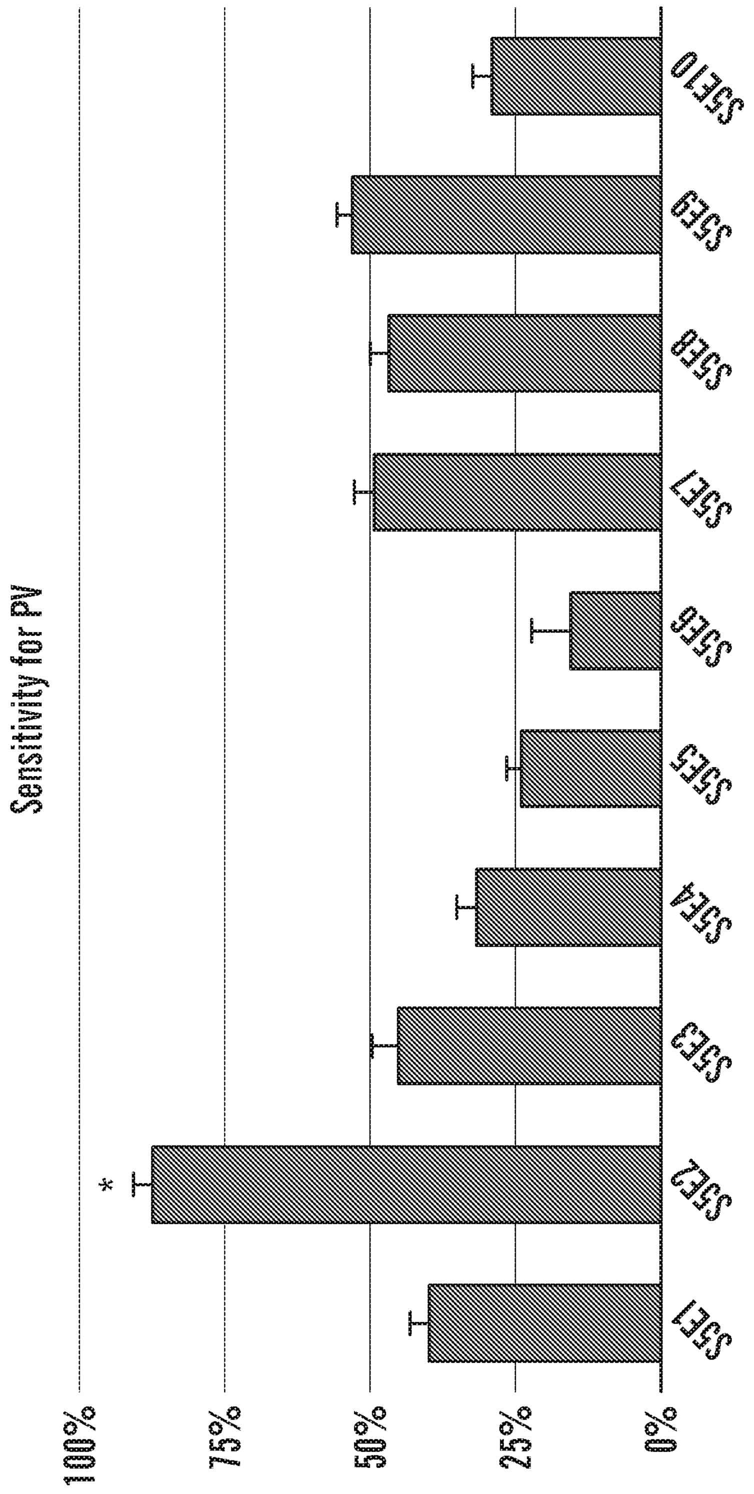

E1-E10 enhancer element-restricted reporter gene expression in PV-expressing interneurons in cortical layers of the mouse brain is shown in FIGS. 1B-1 and 1B-2, which present immunohistochemical (IHC) staining analysis for dTomato in brain sections following systemic in vivo injection of the pAAV-S5-E2-dTomato vector into an animal (mouse). Quantification of the degree of the specificity (FIG. 1C) and sensitivity (FIG. 1D) of expression of the reporter gene in PV-expressing interneurons in the cortex is demonstrated graphically. The expression of the reporter gene is controlled by the E1-E10 enhancer elements contained in rAAV vectors. The specificity was quantified as the proportion of cells expressing the viral reporter dTomato co-expressing the PV-interneuron marker PV assessed by immunohistochemistry on brain sections following systemic in vivo injection of the pAAV-S5-E2-dTomato vector into an animal (mouse). The sensitivity was quantified as the proportion of cells expressing the PV-interneuron marker PV that co-expressed in the viral reporter dTomato as assessed by immunohistochemistry on brain sections following systemic in vivo injection of the pAAV-S5-E2-dTomato vector into an animal (mouse). Bar graphs represent mean+/−standard error of the mean.

Example 2—Viral Targeting of PV Cortical Interneurons (PV cIns) in Mice

The 90% specificity of the E2 regulatory element for PV cINs provides a means for targeting fast-spiking neurons (e.g., basket and chandelier cells), which collectively constitute 40% of all cortical (GABAergic) interneurons. These neurons exert a strong level of inhibition over local networks, and their dysfunction has been directly implicated in neurological and neuropsychiatric disorders including Dravet syndrome, focal epilepsy, Autism Spectrum Disorder (ASD) and schizophrenia. As such, gaining control over their activity is of particular interest for both fundamental research and clinical applications. Thus, the E2 regulatory element was investigated and characterized in order to develop an agent having broad utility, e.g., as a viral tool or a therapeutic agent.

Figure 4A:
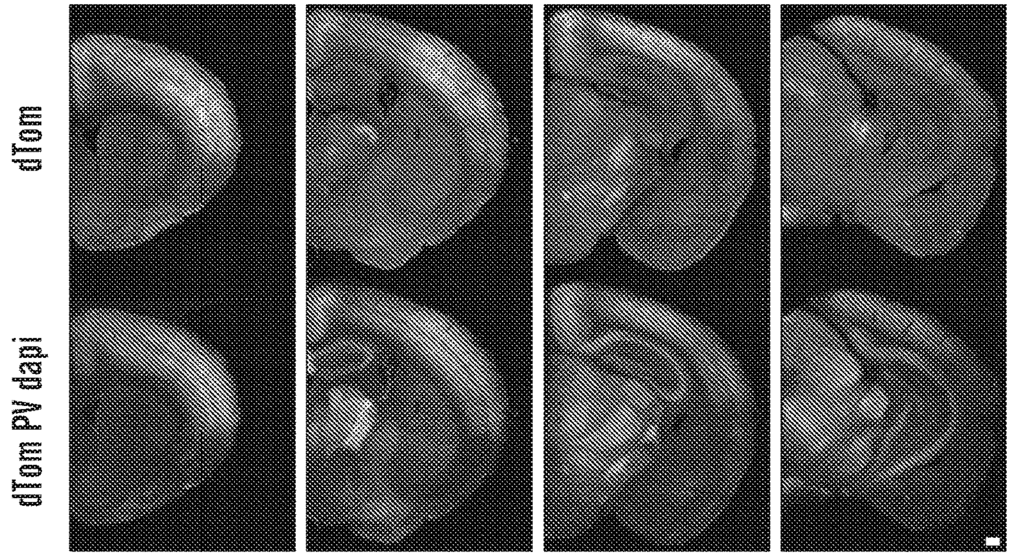
FIGS. 4A-4E presents images, graphs and recording traces related to viral targeting of PV cortical interneurons (PV cINs) in mice. Adult mice were injected systemically (FIGS. 4A-4B images) or locally (FIG. 4D) with rAAV-E2-dTomato expressing the reporter dTomato under the control of the E2 regulatory element and analyzed 3 weeks post-injection by immunohistochemistry (IHC) or ISH for both the reporter and the PV marker.
Figure 4B:
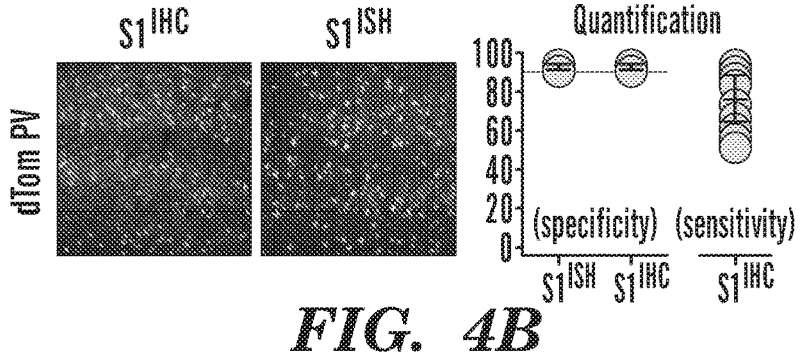
Figure 4C:
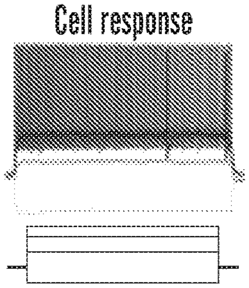
Figure 8A:
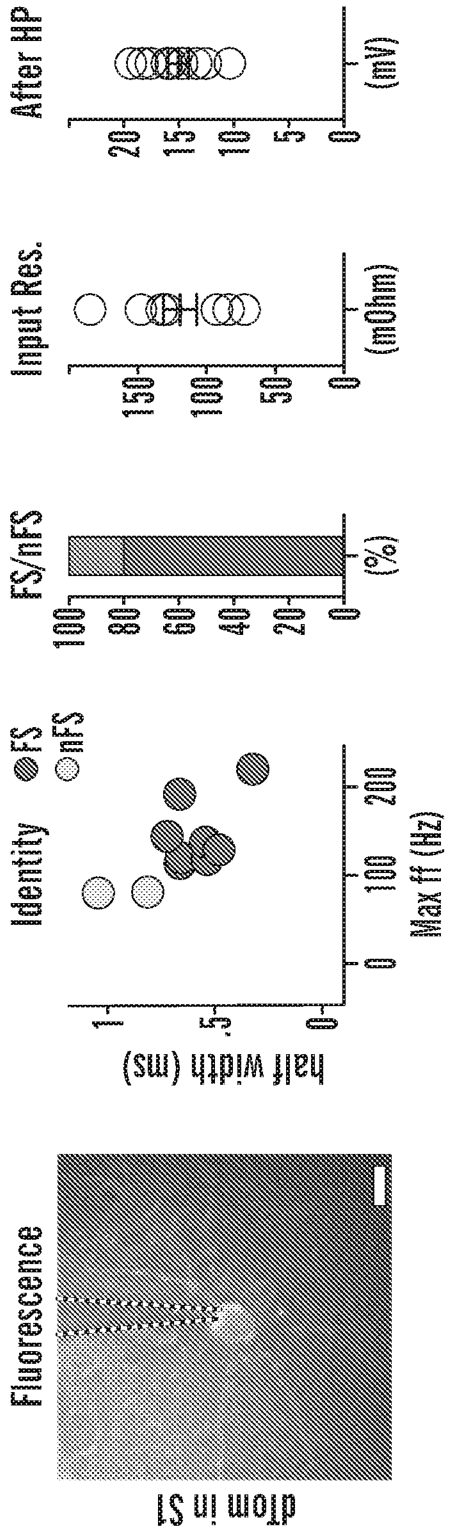
FIGS. 8A-8D present images and graphs of results following systemic injection of adult mice with rAAV-E2-dTomato.
Figure 8B:
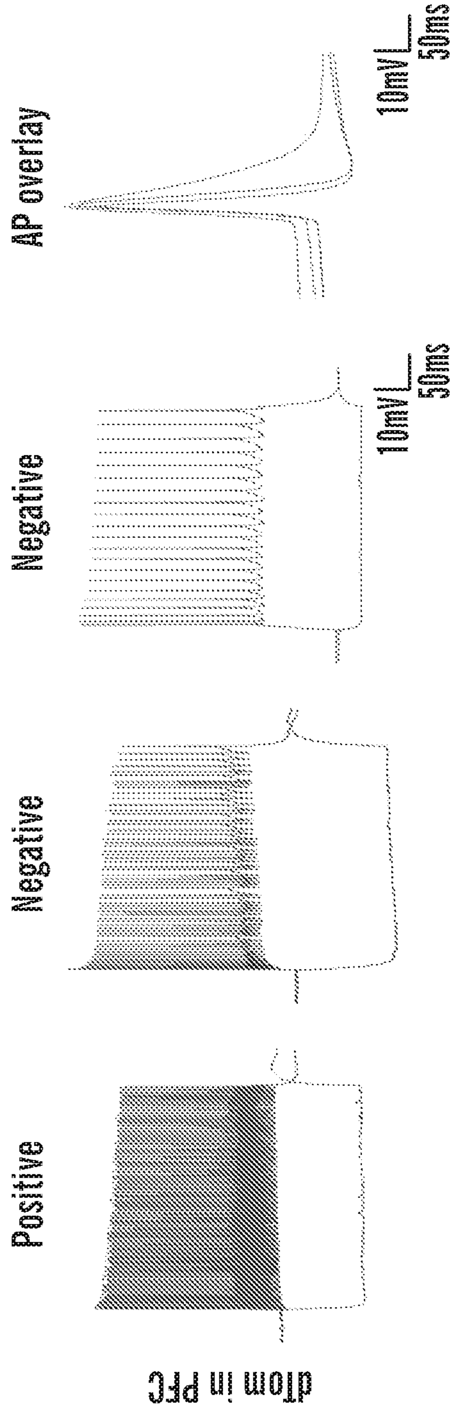

Adult mice systemically-injected with rAAV-E2-dTomato showed detectable expression of the viral reporter after one week and reached a high and stable level of expression after 3 weeks. Immunohistochemistry and in situ hybridization were performed and consistently showed that ~90% of virally labeled cells were PV INs in the cortex (i.e., PV-expressing cortical interneurons). Conversely, on average, 75% of PV cINs expressed the viral reporter, with a maximum sensitivity reaching 93% (FIGS. 4A and 4B). This is indicative of the capability of E2 to target all PV cINs without bias for layers or subtypes. Consistent with the specificity for PV cINs, slice recordings from mice showed that the neurons expressing the viral reporter exhibited electrophysiological properties characteristic of fast-spiking PV cINs both within the primary somatosensory cortex (S1) and the pre-frontal cortex (PFC), (FIG. 4C and FIGS. 8A and 8B).

Figure 8C:
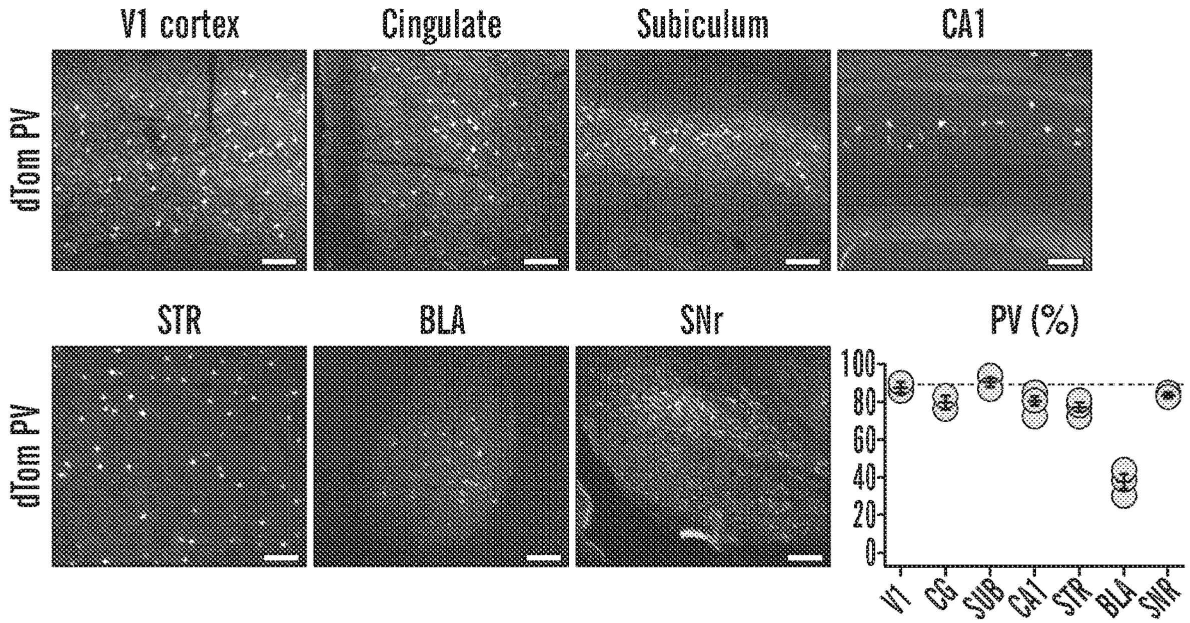
Figure 8D:
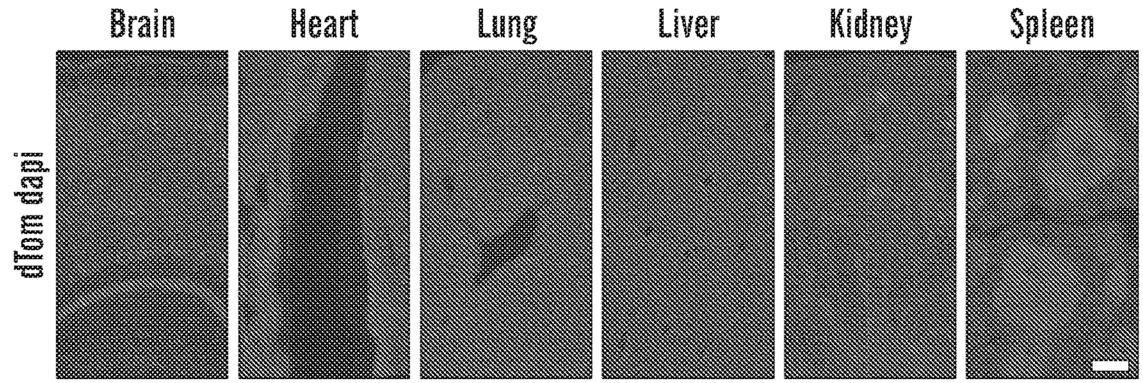

Although the viral reporter was predominantly confined to the brain cortex, some positive cells were observed in other brain regions closely corresponding to areas of SCN1A expression. E2 maintained high specificity for PV-expressing neurons within the primary visual cortex (V1) and cingulate cortex, subiculum, hippocampal CA1, substantia nigra pars reticulata (FIG. 8C). Of note, virtually no viral reporter expression was observed outside of the brain, with the exception of a few cells observed in the liver (which is expected upon systemic delivery of any AAVs) and in the lungs (where SCN1A is expressed at a low level (FIG. 8D). These results show that, despite systemic delivery, the vector containing E2 can be used to selectively target PV-expressing neurons in various brain regions, with insignificant off-target expression outside of the central nervous system.

Figure 4D:
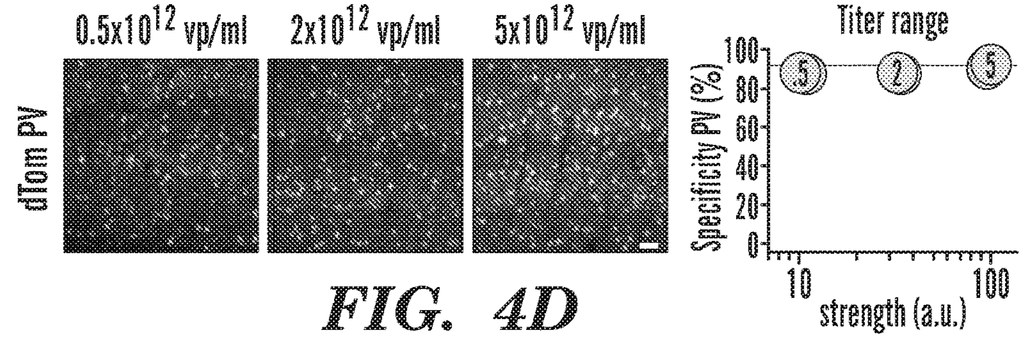

Many experimental paradigms and clinical applications may require local rather than systemic injection. To be useful in these contexts, viral expression must retain a high level of specificity for PV cINs. Stereotactically guided injections typically lead to a higher number of viral particles per cell compared to systemic delivery, which may result in off-target expression. To test whether increasing the viral load altered the specificity, the same volume of rAAV-E2-dTomato was locally injected at various titers into the cortex of adult mice and reporter expression was assessed within PV cINs after one week (FIG. 4D). The results showed that while higher titers had increased levels of reporter expression, no significant alteration of specificity was observed.

Despite the prevalence of PV-expressing interneurons in the mature cortex, targeting these PV cINs at early postnatal stages has been hampered by the relatively late expression of parvalbumin (approximately 15 days after birth, i.e., P15) and the lack of other early markers for this population. The involvement of PV cINs in developmental disorders highlights the need to target and manipulate this cell population during cortical circuit assembly. Complex genetic strategies offer only a partial solution to achieving this in mice (i.e., Lhx6-Cre, Sst-Flp and Cre and Flp-dependent reporter); however, these strategies do not offer the means to easily manipulate these neurons prior to the second postnatal week.

Figure 4E:
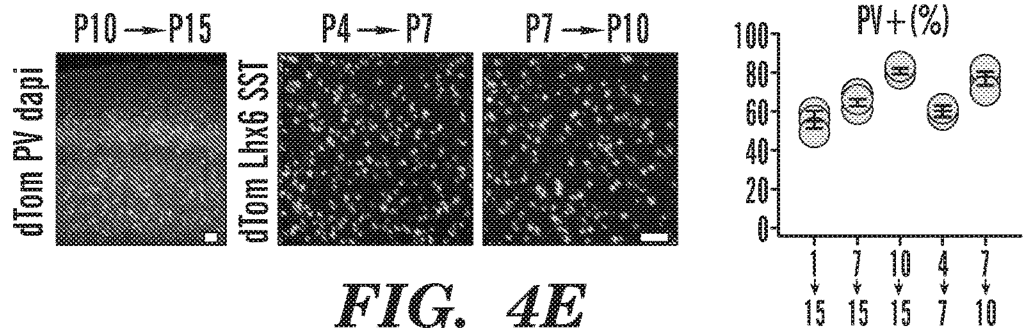

To test whether the E2 enhancer targeted fast-spiking cINs before the onset of expression of parvalbumin, its activity was examined at various postnatal stages. To this end, the analysis was tiled across the early postnatal period, through a series of stereotactically-guided injections of rAAV-E2-dTomato (FIG. 4E). The selectivity of the reporter was assessed upon the onset of parvalbumin expression at P15. This assessment revealed that greater than 50% selectivity was obtained for PV cINs upon injection at P1, increasing to 67% by P7 injection, and to over 80% after P10 injection. This approach was further used to label PV cINs prior to P15. To identify fast spiking cINs in this context, Lhx6-Cre/Intact transgenic mice, in which GFP is expressed in medial ganglionic eminence (MGE)-derived interneurons (both PV cINs and SST cINs), were used. By co-staining for SST, the PV cINs could be distinguished as GFP-positive/SST-negative. 72% and 78% specificity was obtained for PV with a P4-P7 or a P7-P10 time course, respectively. Thus, this approach provides a means to study such neurons during circuit maturation using a single viral injection.

Example 3—Viral Monitoring and Manipulation of PV Cortical Interneurons in Mice

Figure 5A:
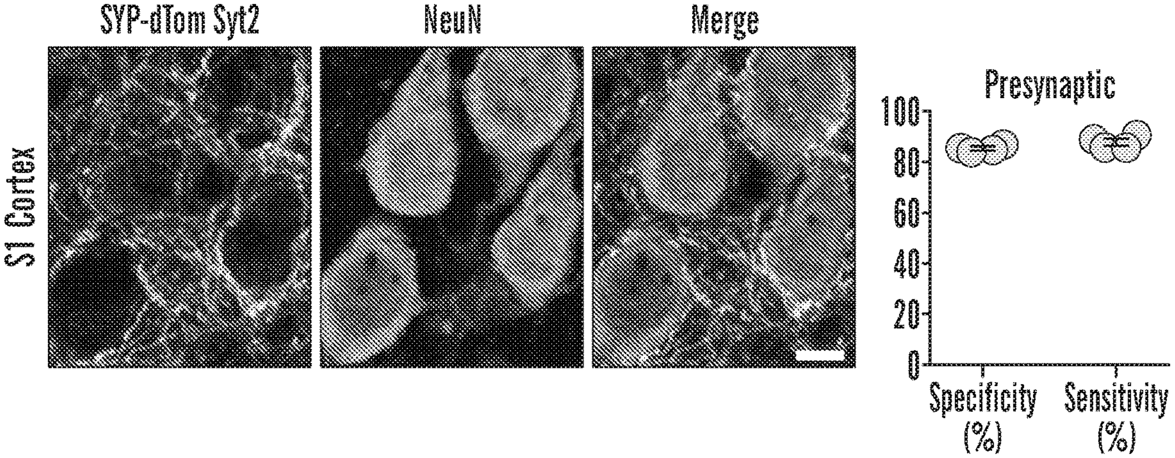
FIGS. 5A-5E present images, current clamp recording traces and graphs related to viral monitoring and manipulation of PV cortical interneurons (PC cINs) in mice. Mice were injected locally in the somatosensory (S1) cortex with rAAVs (FIG. 5A—P10 injection with rAAV-E2-SYP-dTomato.
Figure 5B:
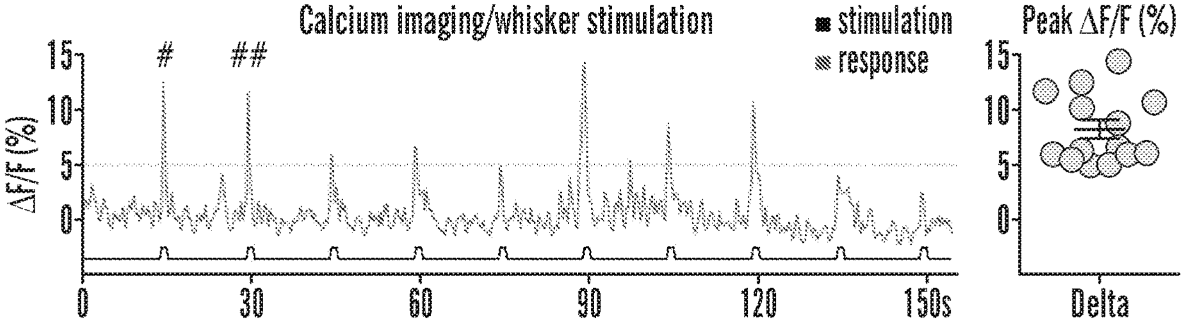
Figure 9A:
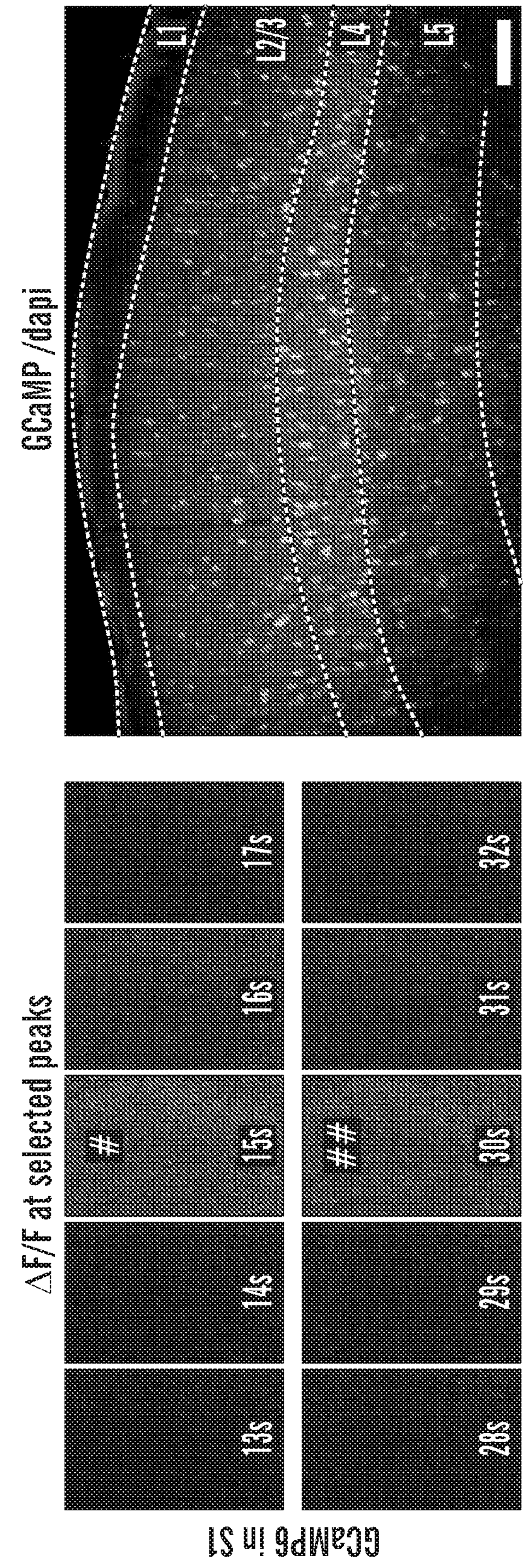
FIGS. 9A-9C present images, recording trace data and graphs. Mice were injected systemically

Having demonstrated the fidelity of E2 expression for PV cINs with differing modes of injection and across developmental stages as described in Example 2, the utility of this vector was assessed for studying connectivity (using a presynaptic reporter) and activity (using imaging, coupled with a genetically encoded calcium-reporter). When E2 was used to drive a synaptophysin-tdTomato fusion gene (see, e.g., Madisen, L. et al., 2012, *Nat Neurosci,* 15(5):793-802), reporter expression was restricted pre-synaptically to PV cINs, with terminals peri-somatically located onto pyramidal neurons (FIG. 5A). When this vector was used to drive GCaMP6f expression (Chen, T. W. et al., *Nature,* 499: 295-300 (2013)), it was demonstrated that PV cINs were recruited upon whisker stimulation (FIG. 5B and FIG. 9A). Together these results demonstrated that E2 provides an effective means to monitor various aspects of PV cIN biology.

Figure 5C:
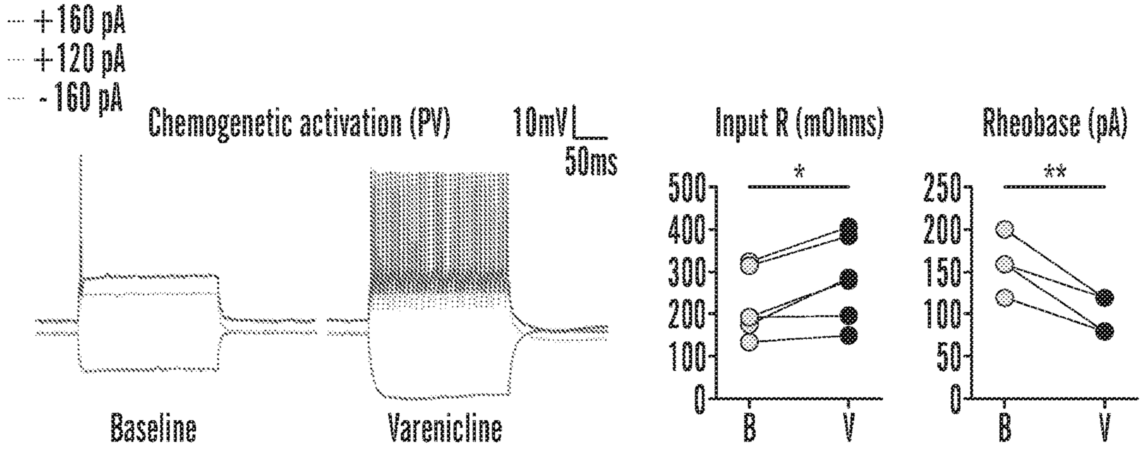
Figure 5D:
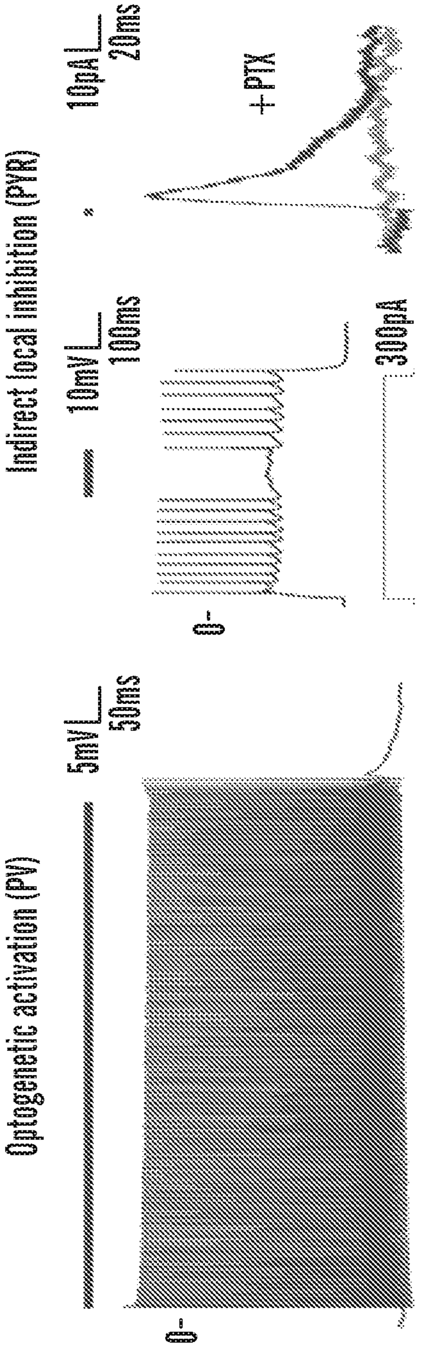
Figure 5E:
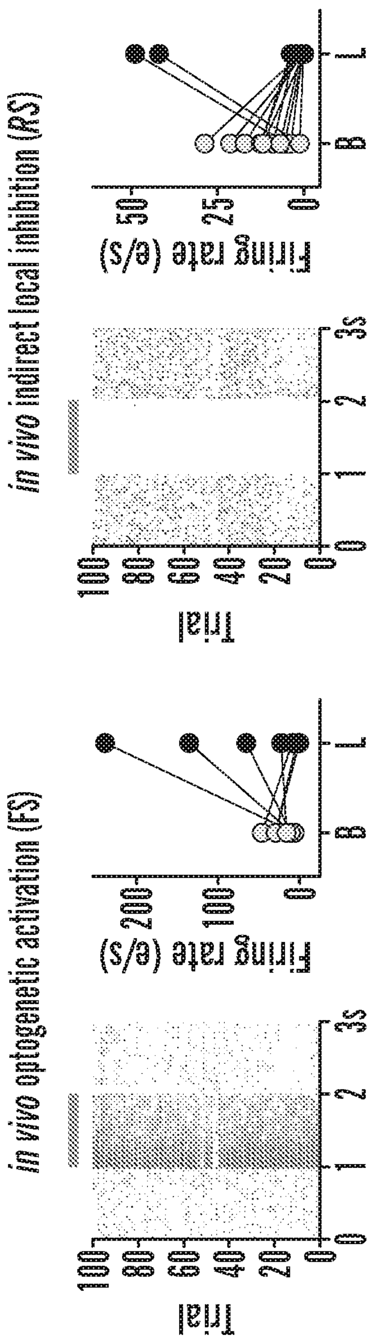
Figure 9B:
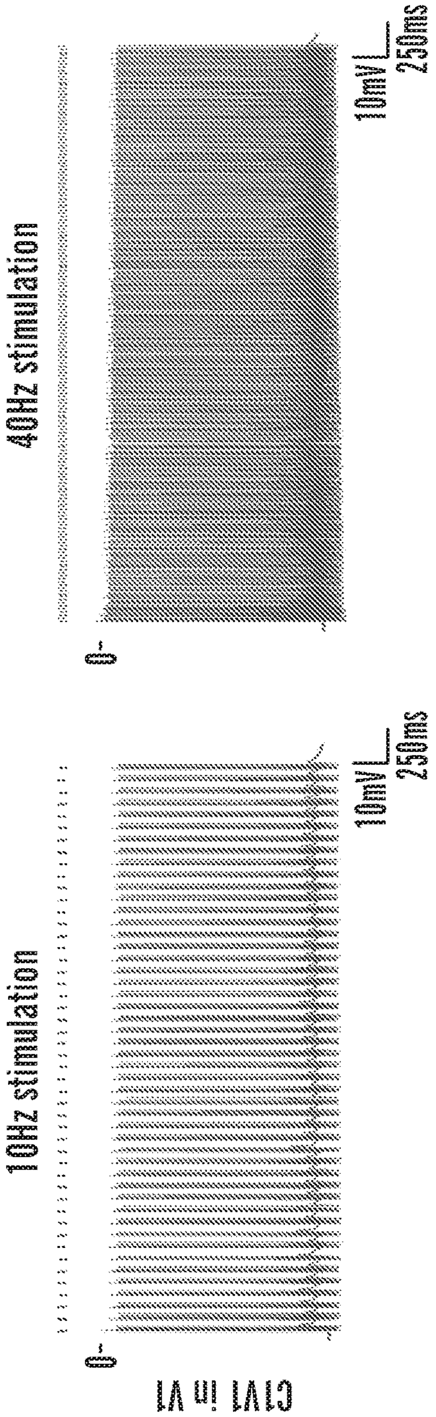
Figure 9C:
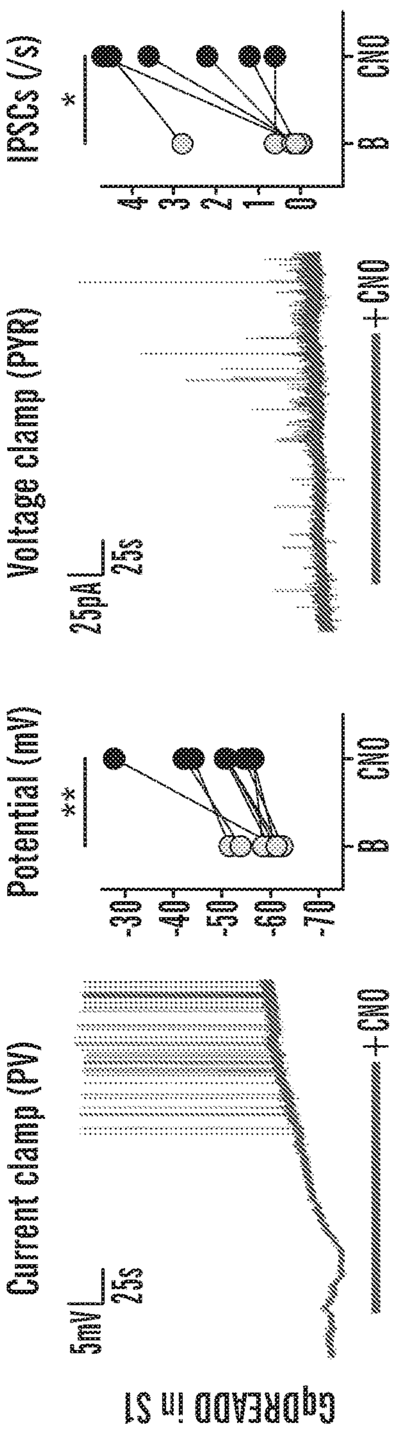

Further studies were conducted to examine whether E2 was sufficient to elicit functional changes in activity using chemo- or optogenetic approaches. E2 was used to direct the expression of the chemogenetic receptor PSAM4-5HT3-LC (Magnus, C. J. et al., 2019, *Science,* 364(6436) in adult animals. It was observed that PV cINs in brain sections collected from these animals, when exposed to the actuator varenicline, could be induced to fire when current clamped below threshold (FIG. 5C). Similar results were obtained using the chemogenetic receptor Gq-DREADD (Armbruster, B. N. et al., *PNAS USA,* 104:5163-5168 (2007), (FIG. 9C). Finally, both constant and high frequency laser stimulation of PV cINs expressing the red-shifted opsin C1V1 in brain slices resulted in firing time-locked to the stimulus (FIGS. 5D and 5E and FIGS. 9A and 9B). Demonstrating that engagement of these neurons resulted in concomitant local inhibition, pyramidal neuron activity in the vicinity of virally labeled PV cINs was consistently interrupted by laser stimulation. Notably, this effect was abolished by treatment with picrotoxin (FIG. 5D and FIG. 9B). Having demonstrated the efficacy of the method ex vivo, the ability to alter excitatory networks in vivo by opto-genetically stimulating PV cINs was examined. Three weeks following local injection of AAV-E2-C1V1 into the primary visual cortex of adult animals, single unit recordings within the infected region were performed both at baseline and upon laser stimulation. The identity of recorded neurons was distinguished based upon their spike width and maximal firing frequency. Reliably, inhibitory interneuron firing rates were increased by laser stimulation, while excitatory neuronal firing was silenced (FIG. 5E). Together, these results demonstrated that E2 can functionally engage PV cINs and elicit network inhibition using chemo- or optogenetics approaches both ex vivo and in vivo.

Figure 6A:
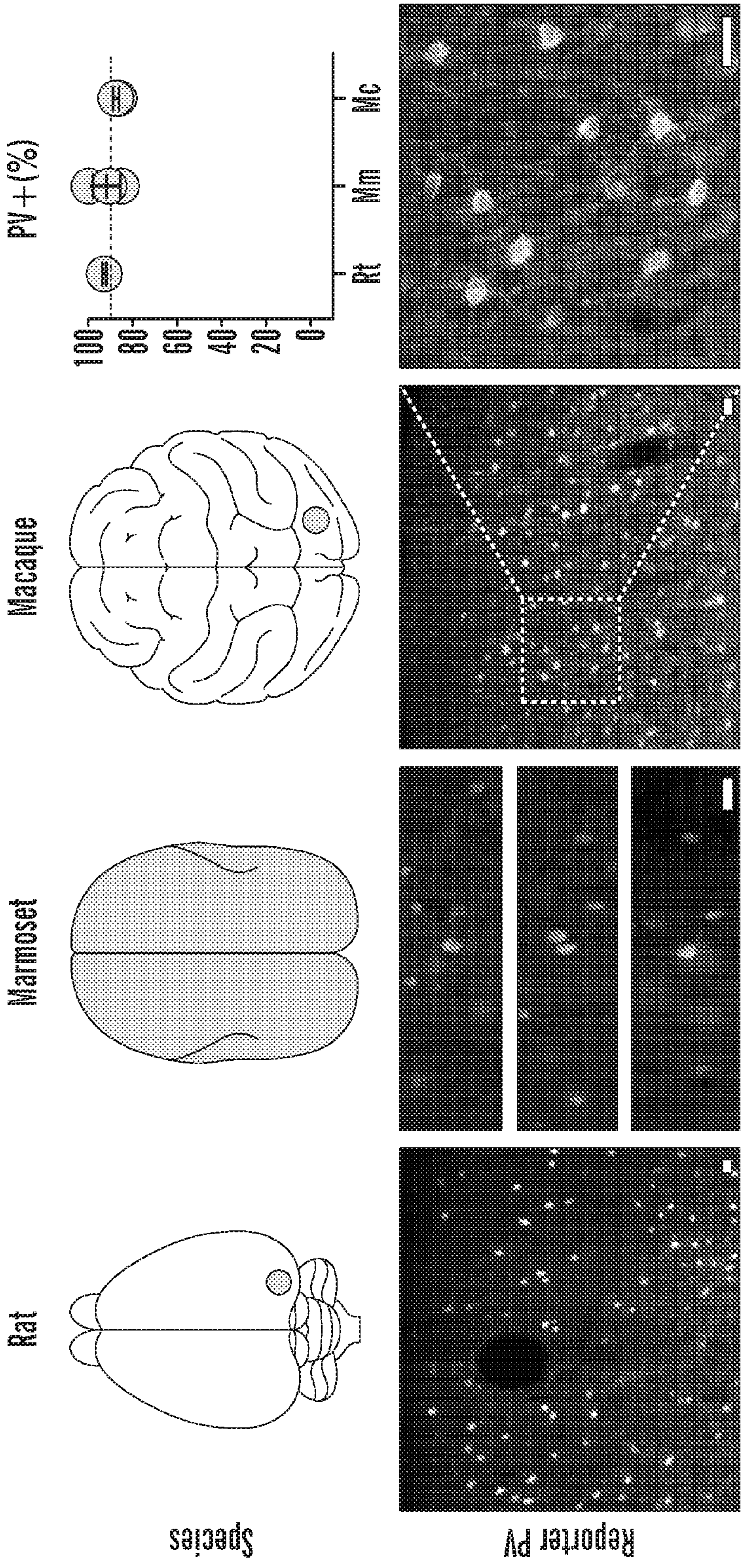
FIGS. 6A and 6B present drawings, graphs, images and recording traces related to viral targeting and manipulation PV cortical interneurons (PV cINs) in primates, including humans.
Figure 6B:
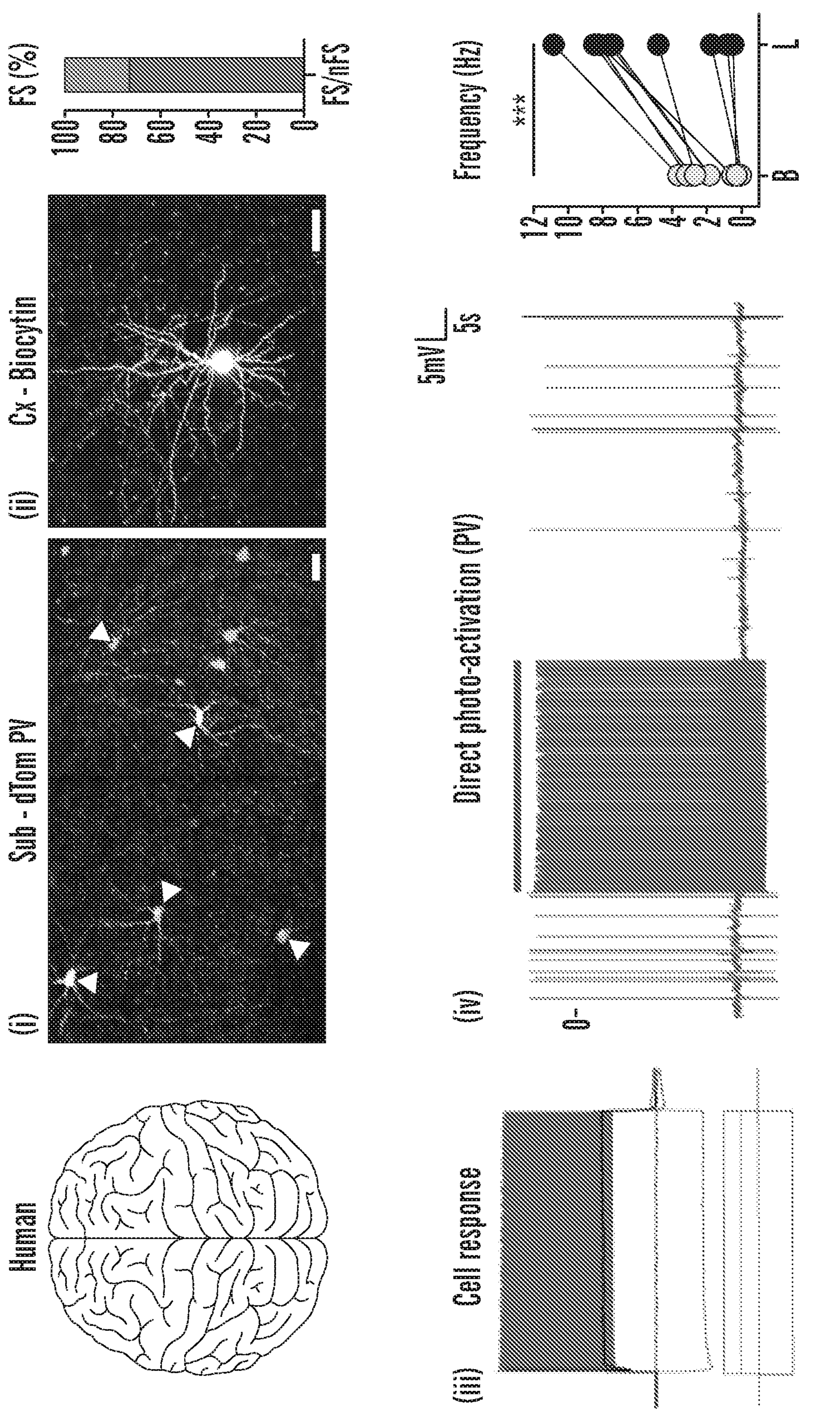
Figure 10A:
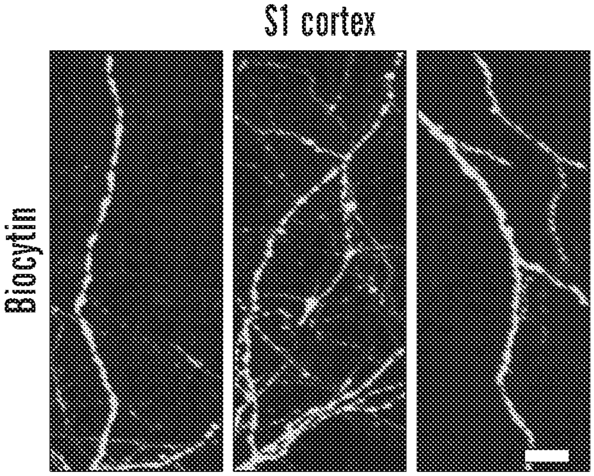
FIGS. 10A and 10B present stained images and data plots related to studies in which human brain tissue obtained from surgical resection was exposed to either AAV-E2-dTomato and maintained in culture for 7-14 days.
Figure 10B:
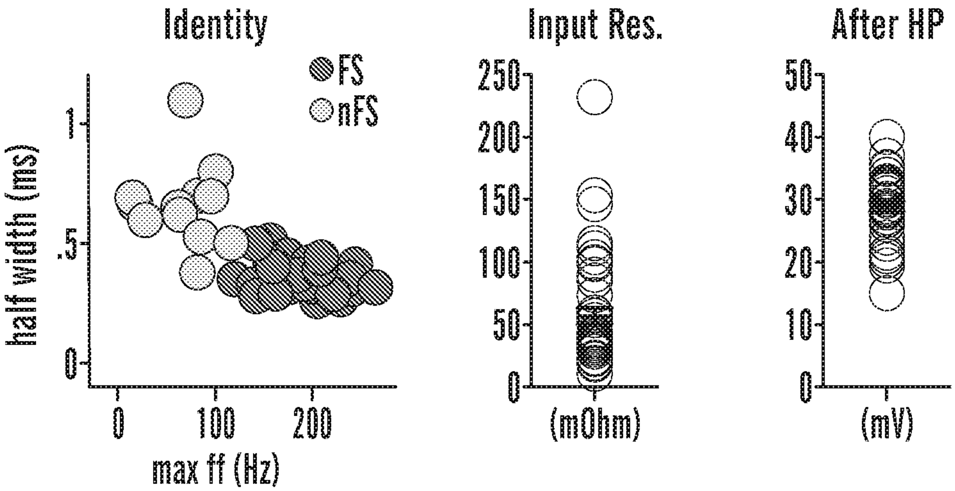
Figure 12:
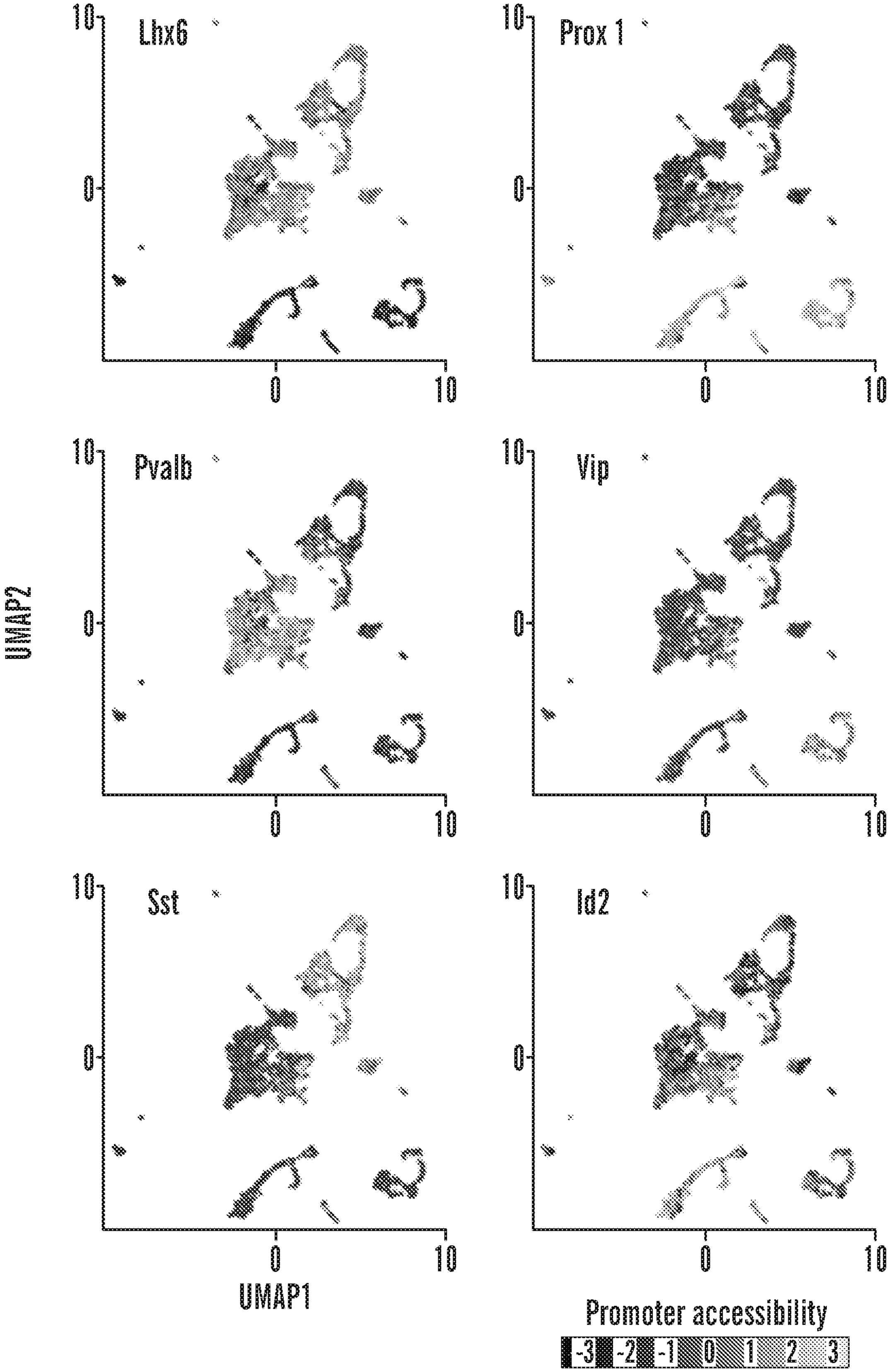
FIG. 12 presents UMAP plots of 3500 neuronal nuclei collected from 4 Dlx6a$^{Cre}$::Sun1-GFP mice reflecting promoter accessibility of the indicated canonical interneuron markers.

Example 4—Viral Monitoring and Manipulation of PV Cortical Interneurons in Primates, Including Humans The sequence of the E2 enhancer is highly conserved across mammalian species, including humans, thus suggesting a conserved role in gene regulation. Studies were conducted to establish whether the E2 regulatory element could be used to target PV cINs across mammalian species. Using systemic injections (in marmoset) or focal injections (in rat and macaque) of virus vector harboring E2 (E2 virus), it was demonstrated that PV cINs were targeted with approximately 90% specificity (FIG. 6A). It has been reported that human brain tissue obtained during surgical resection can be cultured for prolonged periods (Eugene, E. et al., 2014, *J. Neurosci Methods,* 235:234-244). Taking advantage of the resilience of human brain to remain healthy ex vivo, freshly resected subiculum or medial temporal cortex were exposed to E2 virus. Over the two-week culture period, the progressive appearance of fluorescently labeled cells was observed. In regions where PV staining reflected the expected distribution of these cells, virally labeled cells were PV-positive (FIG. 6B (i); see methods for details). In addition, the majority of cells within both the cortex and the subiculum showed the characteristic hallmarks of PV INs as indicated by multiple criteria, including morphology, maximal firing rate when evoked through direct depolarization, or optogenetic light stimulation (FIG. 6B (ii-iv) and FIGS. 10A and 10B).

Figure 14:
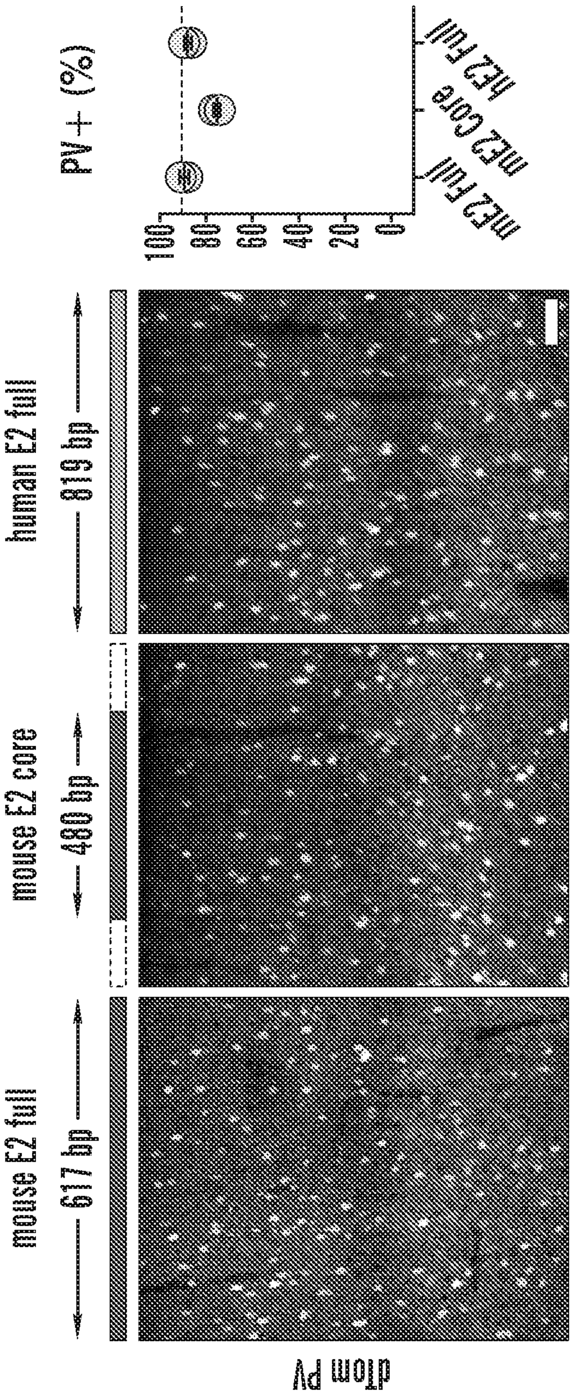
FIG. 14 presents images and a graph related to studies in which adult mice were injected with the indicated modified rAAV-E2-dTomato construct and analyzed 3 weeks post-injection with IHC for the viral reporter and PV. The corresponding specificity is shown in the graph at the right. Scale bars represent 2 μm. On the graphs, dots represent individual measurements and the lines represent average+/−s.e.m.

Notably, the human E2 enhancer showed the same degree of specificity for PV cINs upon injection in mice, further demonstrating that non-coding regions of the genome characterized by a high degree of sequence conservation are likely to retain their functional properties across species. Finally, truncation of both the 5' and 3' ends of the human E2 enhancer resulted in a drastic reduction of specificity, suggesting that the functional boundaries of the E2 enhancer have been optimally identified (FIG. 14). Together, these results indicate that the E2 vector provides an effective tool for targeting and manipulating PV cINs across mammals, including humans.

Example 5—Identification of Viral Enhancers with Regional Specificity

To demonstrate that the enhancer selection method described herein was generalizable, 25 additional enhancer/regulatory element candidates (E11-E35 herein were identified in the vicinity of seven genes whose expression was enriched in PV cINs across species (FIGS. 1A-1 to 1A-3; FIGS. 15A-1 and 15A-2; FIGS. 16A-1 and 16A-2). (see, Methods, infra). Systemic injection of AAVs containing these sequences revealed that four of them displayed greater than 90% selectivity for PV cINs. Notably, among these enhancers, the relatively few virally-labeled neurons that did not express PV were positive for the pan-interneuron marker Gad1. In FIGS. 1A-1 to 1A-3, Pvalb (UniProtKB—P20472) refers to the gene that encodes calcium-binding parvalbumin alpha protein; ACAN (NCBI Gene ID: 176; UniProt P16112) refers to the gene that encodes the aggrecan core protein (also called cartilage-specific proteoglycan core protein), which may be involved in the disease spondyloepimetaphyseal dysplasia; Tmem132c (NCBI Gene ID: 92293) refers to the gene that encodes the transmembrane protein 132c, a type of protein that spans a biological membrane of a cell or organelle; Lrrc38 (UniProtKB—Q5VT99) refers to the leucine rich repeat containing 38 gene, which shows relatively high expression in adrenal and prostate tissues; InppSj (UniProtKB—Q15735) refers to the gene that encodes phosphatidylinositol 4,5-bisphosphate 5-phosphatase A, which may be involved in the modulation of the function of inositol and phosphatidylinositol phosphate binding proteins in membrane ruffles; Mef2c (UniProtKB—Q06413) refers to the gene that encodes myocyte-specific enhancer factor 2C, a transcription factor in the Mef2 family, involved in cardiac morphogenesis and myogenesis and vascular development, as well as in neurogenesis and in the development of cortical architecture. In humans, mutations in the Mef2c gene result in autosomal dominant mental retardation 20 (MRD20), which is characterised by severe psychomotor impairment, periodic tremor as well as abnormal EEG and epilepsy. Pth1h (NCBI Gene ID: 5744) refers to the gene that encodes parathyroid hormone-like peptide, which is secreted by cancer cells, e.g., breast, lung, ovarian, pancreatic, prostate, liver, or colorectal cancer cells, causing humoral hypercalcmia of malignancy by activating the type 1 PTH/PTHrP receptor in kidney and bone. Similar to SCN1A, the above-noted genes are highly enriched in PV-interneurons compared with all other cells in the brain. As such, these genes were selected as candidates for targeting by enhancer elements, and the enhancers as described were identified and located in the vicinity of the coding sequences of these genes.

Figure 13A:
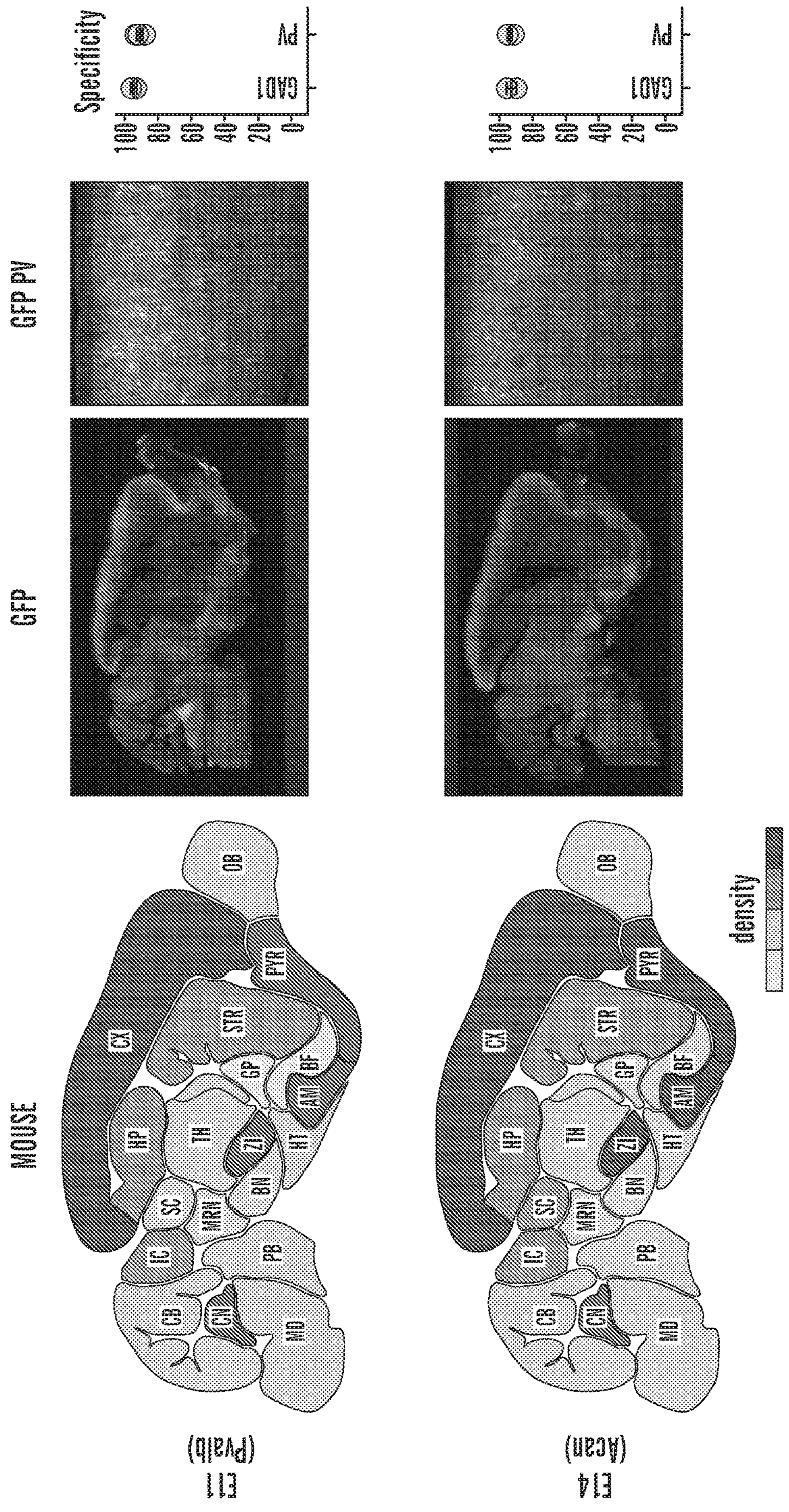
FIGS. 13A and 13B present slices, images and graphs related to the identification of viral enhancers with regional specificity.
Figure 13A:
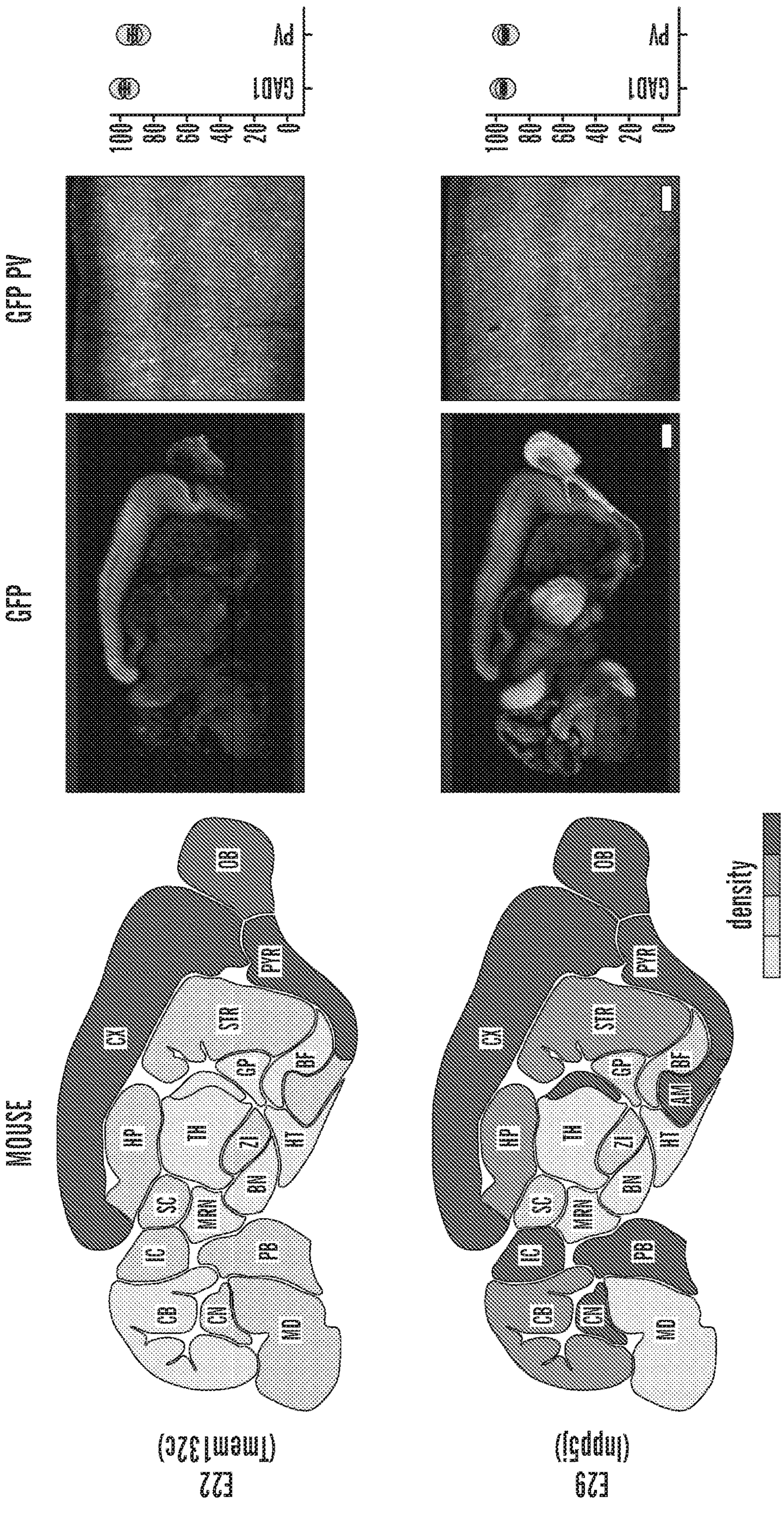
Figure 13B:
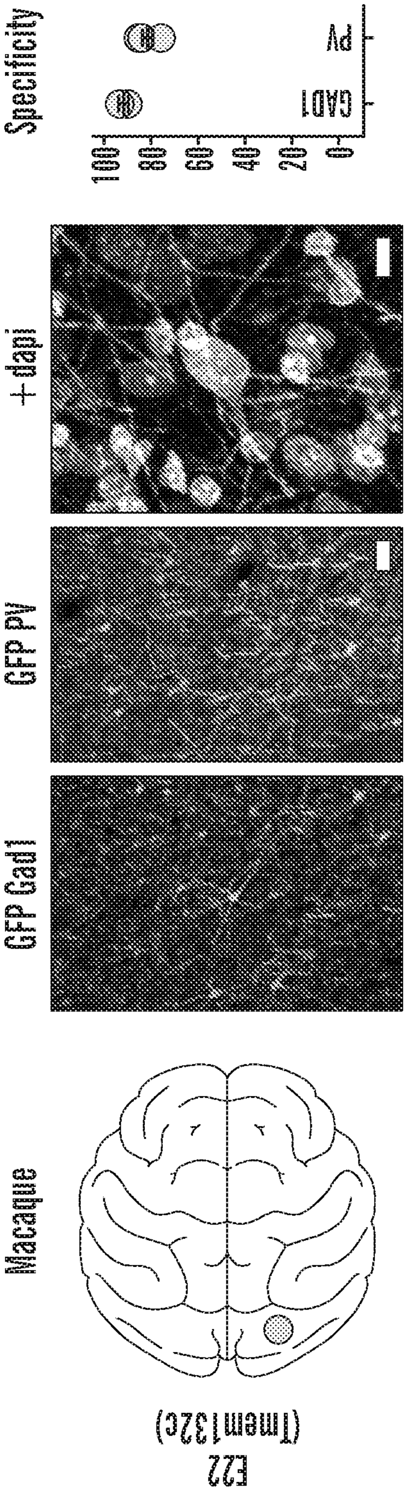

In particular, four PV-specific regulatory elements, namely, E11 (SEQ ID NO: 25, human), E14 (SEQ ID NO: 28, human), E22 (SEQ ID NO: 36, human) and E29 (SEQ ID NO: 43, human) were identified as having highly selective expression within specific brain regions. (FIGS. 13A and 13B). Each of these four enhancers was specific for distinct but overlapping subsets of the PV-expressing neurons. Specifically, while E11 and E14 showed a bias for targeting PV cINs in the upper layers of the cortex, the E22 enhancer showed restricted expression almost exclusively to the cortex, with only a few neurons showing low levels of expression elsewhere. By contrast, the E29 enhancer showed the most global expression, as it targeted the entire population of PV-expressing neurons throughout the central nervous system. All of these enhancers exhibit a high degree of sequence conservation and were selected from genes whose expression profile is similar across species. To directly test that the cross-species similarity among the enhancers results in similar functionality across species, AAV-E22-dTomato was locally injected in V1 of a macaque. This showed that, in a manner similar to that of mouse, the expression of the viral reporter was restricted to PV cINs. The combination of regional selectivity and conservation of expression across species provides a utility for these viral agents in targeted therapies to correct abnormal brain function in different mammalian species.

Example 6—SCN1A Expression is Restored to Normal Levels by Delivering a Functional Copy of the SCN1A Gene within the SCN1A-Expressing Population in a Mouse Model of DS To restore SCN1A gene expression to normal levels by delivering a functional copy of the SCN1A gene to an SCN1A-expressing interneuron cell population, e.g., in a mouse model of DS, the 'limited nucleic acid (DNA) payload' (i.e., the size of exogenous nucleic acid (DNA), e.g., a transgene and associated nucleic acid sequences, that is contained or carried within the rAAV vector) is increased using one or more approaches that result in an rAAV vector that can accommodate the size of the SCN1A gene. As noted supra, the AAV DNA is on the order of 4.7-5 kb, while genes desired for insertion within an rAAV vector and delivery by the vector are often twice that size or larger. The delivery of larger genes using rAAVs has been demonstrated in other contexts using multiple vectors that re-assemble by homologous recombination or by splicing mediated by acceptor-sites. (See, e.g., Hirsch, M. L. et al., 2016, *Methods Mol Biol,* 1382:21-39). Both of these approaches are available to overcome the packaging limits of rAAV.

As both DS animal models and human patients have demonstrated, the requirement for SCN1A is dose-dependent. Therefore, the level of expression of rAAV-driven SCN1A is appropriately titered as known and practiced in the art to match, or to match as closely as possible, the normal endogenous level of SCN1A expression. Several methods can be used to precisely modulate the levels of SCN1A gene expression. Various strategies are used to modulate the levels of SCN1A expression, using amelioration of seizures as a direct readout of the effectiveness of the treatment.

Example 7—a Pharmacogenetic Approach to Selectively Normalize the Excitability of an SCN1A-Deficient Neuronal Population in a Mouse Model of DS As an alternative to direct gene therapy using rAAV vectors harboring specific enhancer and gene nucleic acid sequences for delivery and restricted expression in interneuron cells, pharmacogenetic methods may be employed to directly correct neuronal activity within the SCN1A neuronal populations. To this end, a chemogenetic approach involving 'designer receptors' may be used to modulate interneuron activity. Designer receptors exclusively activated by designer drugs (DREADDs) are modified human muscarinic receptors. In addition, PSAM-PSEM chemogenetic agents are suitable for use.

Using Gq-DREADD, a receptor exclusively activated by clozapine-N4-oxide, (CNO), a pharmacologically inert and orally bioavailable drug, excitability/inhibitory balance (E/I balance) may be corrected in a mouse model of DS (DS mice). In brief, the Gq-DREADD receptor is expressed in SCN1A-deficient interneuron cells using an rAAV vector harboring an SCN1A-specific enhancer, e.g., E1-E10, as described supra and the SCN1A gene. Based on other studies using Gq-DREADD, the receptor is expected to be functional and located at the membrane of the transduced/infected cells. In addition, the rAAV vector containing a SCN1a-specific regulatory element, e.g., E1-E10 as described herein, should drive the expression of the G1-DREADD receptor exclusively within interneurons, such as GABAergic interneurons and PV-expressing, GABAergic interneurons. The functionality of the Gq-DREADD within infected cells may be assessed. Upon bath application of CNO, all interneurons expressing Gq-DREADD are expected to show membrane potential depolarization within less than a minute, consistent with the expression of a functional receptor). Moreover, voltage clamp recordings of a pyramidal cell in the vicinity of interneurons that express Gq-DREADD are expected to show an increase in inhibitory postsynaptic currents (IPSCs) upon application of clozapine-N-oxide (CNO). Such experiments demonstrate that rAAV comprising an SCN1a-specific E1-E10 enhancer sequence and a Gq-DREADD-encoding polynucleotide allows specific, functional and restricted expression of Gq-DREADD and that CNO-treatment effectively and selectively increases the activity of interneurons, thereby providing a localized and marked increase in inhibitory activity by the interneurons within neighboring excitatory neurons.

If the lack of SCN1A (loss of function of SCN1A) should impair the ability of the DREADD to increase the cells' excitability, DREADD can be delivered to all interneurons by using a pan-interneuron enhancer, such as, for example, the distinct and different Dlx enhancer, as described by Dimidschstein, J. et al. (2016, *Nature Neuroscience,* 19(12): 1743-1749) to circumvent the impairment by increasing the activity of other types of interneurons that are not affected by the loss of function of SCN1A.

Example 8—Materials and Methods of the Above-Described Examples scATAC-seq library preparation and sequencing. Male hemizygous Dlx6a-Cre mice (Jax stock #008199) were crossed with female homozygous INTACT mice (flox-Sun1-eGFP, Jax stock #021039) to yield Dlx6a-Cre::INTACT offspring for scATAC-seq experiments. Brains from P28 Dlx6aCre::INTACT mice were harvested, sectioned coronally on a mouse brain slicer (Zivic Instruments), and regions of interest were dissected in ice-cold artificial cerebrospinal fluid (ACSF). Tissue was then transferred to a dounce homogenizer containing Lysis Buffer (10 mM Tris-HCl, 10 mM NaCl, 3 mM $MgCl_2$, 0.01% Tween-20, and 0.01% IGEPAL CA-630, 0.001% Digitonin). Tissue was homogenized with 10 strokes of pestle A, 10 strokes of pestle B, and incubated for 5 minutes on ice before being filtered through a 30 m filter and centrifuged at 500×g for 10 minutes at 4° C. The pellet was resuspended in 1% BSA for sorting for GFP+ nuclei on a Sony SH800S cell sorter. Nuclei were sorted into Diluted Nuclei Buffer (10× Genomics). Single-cell ATAC-seq libraries were prepared using the Chromium Single Cell ATAC Solution (10× Genomics). Libraries were sequenced using a Nova-Seq S2 100 cycle kit (Illumina). (FIGS. 3A-3C)

scATAC analysis. Raw sequencing data were passed through the Cell Ranger ATAC pipeline (10× Genomics). The fragments files were then used to generate snap files for analysis using the snapATAC package, electronically available via the digital object identifier number 10.1101/615179. Cells were clustered using graph-based clustering (k=15, 24 principal components). Gene activity scores were generated as described in the snapATAC package and used to determine clusters corresponding to interneuron cardinal classes. For each cardinal class, bigwig files were generated and peaks were called using macs2 for input into the Integrated Genome Browser and enhancer selection. Peaks across cardinal classes were compared using bedtools Jaccard.

Enhancer selection. All enhancers presented herein (S5E1-E10 and E11-E35) were selected based on the co-presence of ATACseq data (for DNA accessibility) and conservation across species (using UCSC genome browser vertebrate conservation track). The genomic coordinates for mice and their human orthologs are presented in FIGS. 1A-1 to 1A-3.

For Selection, candidate regulatory elements were manually curated from a list of elements generated by intersecting the "context" region (SCN1A intergenic region+intron1) with both the "ATAseq peak union" file and the "Phastcons 60-way" file—see below. Accessibility. ATAC-seq data (Mo et al., 2015, *Neuron,* 86:1369-1384) were downloaded on the GEO repository and discretized as peaks using MACS2 ran with default parameters, electronically accessible via github/taoliu/MACS. Using a custom R script, a file containing the union of all peaks across datasets was generated and used for enhancer selection as described below. The final selection relied on the inspection of the peaks for individual cell-types rather than on the union of all peaks. Methylation. Mouse mCH levels for non-overlapping 100 kb bins across the entire genome for mouse (Luo et al., 2018, *Nat Commun,* 9(1):3824) were downloaded from Brainome portal, which is electronically accessible via brainome dot org. These data were used as a confirmation for the positioning of the candidates selected using the ATAC-seq dataset described above. Conservation. The "phascons 60-way" track was downloaded from the UCSC portal, which is electronically accessible via genome dot ucsc dot edu in BED file format and filtered using a custom R script to remove any element smaller than 10 bp and fuse any element separated by less than 50 bp using Bedtools/Interesct.

rAAV cloning and viral production. All viral constructs were generated using standard cloning methods and protocols in molecular biology. The plasmid pAAV-mDlx-GFP (Addgene #83900; Addgene, Watertown, MA), (Dimidschstein, J. et al., 2016, *Nat. Neuroscience,* 19(12):1743-1749) was used to create a standard backbone containing the elements necessary for the production of AAVs (internal terminal repeats, minimal promoter, woodchuck posttranscriptional response element).

The enhancer sequences (necessary for restricting expression to specific types of neurons) were synthesized de novo by Genewiz (Cambridge, MA) and the reporters and effectors were amplified by PCR. In particular, the enhancer sequences were amplified by PCR from mouse genomic DNA using the following primers: E1: caaagtggacagagggg-gagg (SEQ ID) NO: 50) and gtgctgttgggagtggtgga (1280 bp), (SEQ ID NO: 51); E2: aatctaacatggctgctata (SEQ ID NO: 52) and caattgctcagagttatttt (618 bp), (SEQ ID NO: 53); E3: ataaaattttattttcctaa (SEQ ID NO: 54) and gaggaaatcagc-tacggggc (832 bp), (SEQ ID NO: 55); E4: tctgacagagcaagtcttga (SEQ ID NO: 56) and tatcaaaattgtat-attcag (261 bp), (SEQ ID NO: 57); E5: aatgttttgatatttaggag (SEQ ED NO: 58) and ttgactcttaaaatttaata (663 bp), (SEQ ID NO: 59); E6: ttgtcactttgttactctac (SEQ ID NO: 60) and ttaaatcttaaaattttcct (606 bp), (SEQ ID NO: 61); E7: gatactgtataattaattag (SEQ ID NO: 62) and cttccttctggttcctttt (2430 bp), (SEQ ID NO: 63); E8: attgatctccaactttttaa (SEQ ID NO: 64) and gttcatccaagtaataagag (1644 bp), (SEQ ID NO: 65); E9: atctcaagtgtatgtaacat (SEQ ID NO: 66) and gtctttttgttttttttttt (521 bp), (SEQ ID NO: 67); E10: tat-tgcaaaaggaaggaatg (SEQ ID NO: 68) and tcatg-gaaaaagaaaaaatc (547 bp), (SEQ ID NO: 69). The enhancers, reporters and effectors were cloned using the Gibson Cloning Assembly Kit (NEB-E5510S) following standard procedures. Specifically, for AAV-E1:10-dTomato, the dTomato coding sequence was amplified from the plasmid Addgene #83897; for AAV-E2-SYP-dTomato, the Synaptophysin-td-Tomato coding sequence was amplified from the plasmid Addgene #34881; for AAV-E2-GCaMP6f, the GCaMP6f coding sequence was amplified from the plasmid Addgene #83899; for AAV-E2-C1V1-eYFP, the CIV1-eYFP coding sequence was amplified from the plasmid Addgene #35499.

Final plasmids were assembled using the Gibson Assembly® Cloning Kit (NEB-E5510S), (New England BioLabs, Ipswich, MA), following the manufacturer's instructions and standard protocol. The rAAVs were produced using standard production methods. Polyethylenimine (PEI) was used for transfection (see, e.g., Longo, P. A. et al., 2013, *Methods Enzymol.,* 529:227-240) and OptiPrep™ density gradient (Sigma-Aldrich, St. Louis, MO) was used for viral particle purification and isolation. Serotype 1 was used to produce the AAVs for local injections in mice and rats. Serotype 9 was used for systemic injection in marmosets and serotype PHPeB was used for both local injection in macaques and systemic injections in mice. Viral titer was estimated by qPCR with primers annealing via the WPRE sequence that is common to all constructs. All batches produced were in the range of $10^{10}$ to $10^{12}$ viral genomes per ml. In particular, Woodchuck Hepatitis Virus (WHP) Post-transcriptional Regulatory Element (WPRE) is a DNA sequence, which, when transcribed, creates a tertiary structure enhancing expression. WPRE, a tripartite regulatory element with gamma, alpha, and beta components, is commonly used in molecular biology to increase expression of genes delivered by viral vectors, e.g., rAAV-dTomato. (see, e.g., Choi, J.-H. et al., 2014, *Mol. Brain,* 7:17). All rAAV batches produced were in the range of $10^{10}$ to $10^{12}$ viral genomes per ml.

Animals. Mice: Female C57BL/6J mice (*Mus musculus;* 10 weeks old) were obtained from Jackson Labs (Bar Harbor, ME—stock #000664). Rats. Sprague Dawley rats (adult 150-250 gm) were obtained from Charles River labs, Kingston, NY. Marmosets. One female common marmoset (*Callithrix jacchus,* 6.0 years old) was obtained from the colony at Massachusetts Institute of Technology. Macaques. One male macaque (*Macaca mulatta;* 15.0 years old) was obtained from the California National Primate Research Center at the University of California, Davis. All animals were maintained in a 12 light/12 dark cycle with a maximum of five animals per cage for mice and one animal per cage for rats. Marmosets and macaques were socially housed. All animal maintenance and experimental procedures were performed according to the guidelines established by the Institutional Animal Care and Use Committee at the Broad Institute of MIT and Harvard (mice), McGovern research institute at MIT (rats and marmosets) and Salk Institute for Biological studies (Macaques) and adhered to the standards of the National Institutes of Health.

Local and systemic viral injections. Mouse local SL Local injection in adult mice were performed by stereotactically guided injections in the somatosensory cortex with the following coordinates: 1.0 mm posterior, 2.9 mm lateral, 0.7/0.45 mm ventral relative to Bregma with 150 nL of virus. Mouse systemic. For systemic injection in adult mice, approximately $10^{11}$ viral particles were injected in the retro-orbital sinus per animal. Post-operative monitoring was performed for five days post injection.

Rat local in V. Local injection in adult rats was performed by stereotactically guided injections in the primary visual cortex with the following coordinates: 5.4 mm posterior, 4.2 mm lateral, 2.0 mm ventral relative to bregma with 670 nL of virus.

Marmoset systemic injection. For systemic injection in adult marmosets, approximately $10^{12}$ viral particles in ~0.7 ml of sterile PBS were injected into the saphenous vein, followed by another infusion with ~0.5 ml of saline. After the final infusion, pressure was applied to the injection site to ensure hemostasis. The animal was returned to its home cage and monitored closely for normal behavior post anesthesia. The animal was euthanized 51 days after viral injection Macaque local in V. Local injection in an adult macaque was performed by a stereotactically guided injection in the left primary visual cortex with the following coordinates: 13 mm posterior, 19 mm lateral, 23 mm superior relative to the center of the inter-aural line (based on the animal's MRI). A total of volume of 333 nL was injected at 4 depths (i.e., 18, 13, 0.8 and 0.3 mm from the cortical surface).

Surgery. For stereotactically guided viral injection, animals were anesthetized under isoflurane (1-3% in oxygen) and placed in a stereotactic head frame on a temperature-controlled heating pad. A craniotomy and a durotomy were performed above the brain region of interest. The animals were injected with 50-500 nl of the indicated virus (rAAV) at a rate of 10-25 nl/minute using a sharp glass pipette (25-35 mm in diameter), which was left in place for 5-15 minutes after the injection to minimize backflow. The craniotomy site was covered with sterile bone wax, the surgical opening was closed with Vetbond, and the animals were returned to their home cages for at least 1 week. The injection sites were defined by the following coordinates: somatosensory cortex S1: 1.0 mm posterior, 3.0 mm lateral, 0.7/0.4 mm ventral relative to bregma; hippocampus CA1: 1.6 mm posterior, 1.8 mm lateral, 1.2 mm ventral relative to bregma; striatum: 0.5 mm posterior, 2.0 mm lateral, 3.2 mm ventral relative to bregma.

For retro-orbital vein injection, animals were anesthetized under isoflurane (1-3% in oxygen) and placed on a temperature-controlled heating pad. Intravenous (IV) injections were performed in the retro-orbital plexus. More specifically, the animal (mouse) was placed in a funnel-shaped nose cone connected to a non-rebreathing apparatus (Surgivet, Dublin, OH) and the needle was inserted, bevel down, at the medial canthus, into the retroorbital sinus. Up to 150 μL of supernatant containing replication-defective rAAV vectors were injected into the tail vein or retro-orbital plexus. Following injection, the eye was held shut for a minimum of 30 seconds to ensure homeostasis.

Electrophysiological Recordings in Mice:

Slice preparation for 2 to 6-weeks-old mice. Virally injected mice were anesthetized with isofluorane. Upon loss of reflexes, mice were transcardially perfused with ice-cold oxygenated ACSF containing the following (in mM): 87 NaCl, 75 sucrose, 2.5 KCl, 1.25 $NaH_2PO_4$, 26 $NaHCO_3$, 10 glucose, 1 $CaCl_2$ and 2 $MgCl_2$. Mice were then decapitated and 300-μm thick coronal slices were sectioned using a Leica VT-1200-S vibratome and incubated in a holding chamber at 32-35° C. for 5-30) min followed by continued incubation at room temperature 20-23.5° C. (68-74° F.) for at least 45-60 minutes before physiological recordings. Slices containing the injection site were transferred in a recording chamber submerged with oxygenated ACSF containing the following (in mM): 125 NaCl, 2.5 KCl, 1.25 $NaH_2PO_4$, 26 $NaHCO_3$, 10 glucose, 2 $CaCl_2$ and 1 $MgCl_2$ (pH:=7.4, bubbled with 95% $O_2$ and 5% $CO_2$). Slice preparation for 6-weeks-old and older mice. Acute coronal brain slices were prepared as follows: Mice were anesthetized with Avertin solution (20 mg/ml, 0.5 mg/g body weight) and transcardially perfused with 15 to 20 ml of ice-cold carbogenated (95% $O_2$, 5% $CO_2$) cutting solution containing the following: 194 mM sucrose, 30 mM NaCl, 4.5 mM KCl, 1.2 mM $NaH_2PO_4$, 0.2 mM $CaCl_2$, 2 mM $MgCl_2$, 26 mM $NaHCO_3$, and 10 mM D-(+)-glucose (with osmolarity of 340-350 mOsm). The brains were then rapidly removed and placed in ice-cold cutting solution for slice preparation. Coronal slices (300 vim) were prepared and then incubated at 32° C. with carbogenated artificial cerebral spinal fluid (aCSF) for 10 to 15 minutes. The slices were then incubated at room temperature for at least 1 hour in a CSF that contained the following: 119 mM NaCl, 2.3 mM KCl, 1.0 mM $NaH_2PO_4$, 26 mM $NaHCO_3$, 11 mM glucose, 1.3 mM $MgSO_4$, and 2.5 mM $CaCl_2$ (pH 7.4, with osmolarity of 295-305 mOsm) at room temperature for at least 1 hour.

Current clamp. For interneuron recording, 10 μM CNQX, 25 μM AP-5 and 10 μM SR-95531 were also added to block AMPA, NMDA and $GABA_A$ receptors, respectively, to measure the cell-intrinsic effect of optogenetic and chemogenetic stimulation. Whole-cell current-clamp recordings were obtained from visually-identified cells expressing the viral reporter using borosilicate pipettes (3-5 MΩ) containing (in mM): 130 K-gluconate, 6.3 KCl, 0.5 EGTA, 10 HEPES, 4 Mg-ATP, 0.3 Na-GTP and 0.3% biocytin (pH adjusted to 7.3 with KOH). Upon break-in, series resistance (typically 15-25 MΩ) was compensated and only stable recordings (<20% change) were included. Data were acquired using a MultiClamp 700B amplifier (Molecular Devices), sampled at 20 kHz and filtered at 10 kHz. All cells were held at −60 mV with a DC current, and current-step protocols were applied to obtain firing patterns and to extract basic subthreshold and supra-threshold electrophysiological properties.

Voltage clamp. Cells not expressing the viral reporter were selected according to their pyramidal-cell-shaped soma under IR-DIC visualization and recorded with pipettes containing (in mM): 130 Cs-gluconate, 0.5 EGTA, 7 KCl, 10 HEPES, 4 Mg-ATP, 0.3 Na-GTP, 5 phosphocreatine, 5 QX-314 and 0.3% biocytin (pH adjusted to 7.3 with CsOH). Cells were held continuously at 0 mV for baseline and optogenetic or chemogenetic stimulation. For both current and voltage clamp recording, a baseline of at least 2 minutes was recorded before stimulation. Small pulses (−20 pA or −5 mV, 100 ms at 0.2 Hz or 0.5 Hz) were applied throughout the baseline and CNO application to monitor series resistance changes. Data were analyzed offline using Clampfit 10.2 software (Molecular Devices).

In vivo calcium imaging. Approximately 100 nL of AAV-E2-GCaMP6 virus was injected into the barrel cortex of animals at postnatal day 10. At P27-P34, craniotomies were implanted over the injection site and widefield calcium imaging was performed after recovery from the craniotomy procedure. Briefly, anesthetized (1.5% isoflurane) mice were imaged at 3-4 Hz with 4× magnification (Thorlabs CCD camera—1501M-USB, Thorlabs LED stimulation—DC4104), while air puffs (100-200 ms duration, Picospritzer III) at specific intervals (5-20s) were directed at contralateral whiskers. Multiple recordings were performed, and afterward, the mouse was perfused for histological analysis. Recordings were analyzed in ImageJ by calculating the F/F (change in fluorescence/average fluorescence) for each recording and synched whisker stimulation. A threshold of (5%) F/F was set for both stimulated and spontaneous calcium signal response.

Electrophysiological Recordings in Humans.

Tissue preparation, culture protocol and inoculation of virus. Four participants (2 male/2 female; age range 22-57 years) underwent a surgical procedure in which brain tissue (temporal lobe and hippocampus) was resected for the treatment of drug resistant epilepsy. In all cases, each participant had previously undergone an initial surgery for placement of subdural and/or depth electrodes for intracranial monitoring to identify the location of seizure onset. The NINDS Institutional Review Board (IRB) approved the research protocol (ClinicalTrials.gov Identifier NCT01273129), and informed consent was obtained from the participants for experimental use of the resected tissue. 300 um slices from both hippocampus and temporal lobe were obtained (Leica 1200S Vibratome; Leica Microsystems, Bannockburn, IL) in ice-cold oxygenated sucrose based cutting solution (100 mM sucrose, 80 mM NaCl, 3.5 mM KCl, 24 mM $NaHCO_3$, 1.25 mM $NaH_2PO_4$, 4.5 mM $MgCl_2$, 0.5 mM $CaCl_2$, and 10 mM glucose, saturated with 95% $O_2$ and 5% $CO_2$) within 30 minutes following neurosurgical resection. Slices were then incubated in the sucrose cutting solution at 33° C. for 30 minutes and allowed to cool to room temperature for 15-30 minutes. The slices were transferred to culture medium (Eugene et al, 2014) and placed in an incubator (5% $CO_2$) at 35° C., for 15 minutes of equilibration. Each individual slice was then transferred onto a 30 mm Millicell Cell Culture Insert (Millipore; Cat No. PICMORG50) for interface culture and incubated as above. After 12 hours, the culture medium was changed and 1-2 µl of pAAV S5E2-dTomato with or without pAAV_S5E2_C1V1-eYFP was directly pipetted onto each slice and placed back into the incubator. For hippocampal slices, the virus was targeted to the subiculum subfield. Culture medium was routinely changed every 2-3 days until electrophysiological analyses.

Electrophysiological recordings.

Electrophysiological recordings from cultured human slices were performed between 7 to 14 days after viral inoculation. Cultured human slices were transferred to a recording chamber perfused with extracellular solution (130 mM NaCl, 3.5 mM KCl, 24 mM $NaHCO_3$, 1.25 mM $NaH_2PO_4$—$H_2O$, 10 mM glucose, 2.5 mM $CaCl_2$ and 1.5 mM $MgCl_2$ saturated with 95% $O_2$/5% ($CO_2$ (pH 7.4; 300-310 mOsm) at a rate of 3-4 ml/min at 33° C. Whole cell patch clamp recordings from pAAV-S5E2-dTomato or pAAV_S5E2_C1V1-eYFP infected neurons were performed with an intracellular solution of the following composition: 130 mM K-gluconate, 10 mM HEPES, 0.6 mM EGTA, 2 mM $MgCl_2$, 2 mM $Na_2ATP$, 0.3 mM NaGTP and 0.5% biocytin (pH adjusted to 7.4; osmolarity adjusted to 285-300 mOsm). In some recordings, 130 mM K-gluconate was replaced by 90 mM K-gluconate/40 KCl. Intrinsic membrane and firing properties were assayed essentially as described previously (Tricoire, L. et al., 2011, *J. Neurosci,* 31(30):10948-70). 550 nm light stimulated optogenetic activation of C1V1 was delivered to the slices via the 40× water immersion objective using a CoolLED pE-4000 Illumination system (Andover, UK).

Biocytin reconstruction and immunocytochemistry. After electrophysiological recording, slices were drop-fixed in 4% paraformaldehyde in 0.1M PB overnight. Slices were washed in 0.1M PB (3×15 minutes) and permeabilized/blocked in 0.5% Triton X-100/10% goat serum in 0.1M PB for at least 2 hours at room temperature. For combined biocytin recovery and immunocytochemistry, an initial incubation (4° C. for 40 hours) in primary antibodies diluted at 1:1000 was performed (rabbit anti-PV, Abcan Cat No: ab11427; guinea-pig anti-REP, SYSY, Cat No: 390005). Slices were washed in 0.1M PB at room temperature 4×30 minutes and incubated in secondary antibodies (1:1000 for goat anti guinea-pig Alex-flour 555, Thermofisher Cat No. A21435; 1:500 for goat anti-rabbit Alexa-flour 647, Thermofisher Cat No. A32733 and 1:1000 Streptavidin Alexa Fluor™ 488; Thermofisher S1123) overnight at 4° C. After a final wash procedure (4×30 minutes) the slices were mounted on microscope slides with Prolong Gold antifade (Thermofisher; Cat No. P36930) for subsequent confocal microscopy analysis.

Immunohistochemistry (IHC). Animals injected with the virus were euthanized with Euthasol (Virbac, USA) and transcardially perfused with 4% paraformaldehyde (PFA). The brains were placed in 4% PFA overnight, and then were sectioned at 50-60 µm (in particular, 50 µm) using a Leica VTS1000 vibrosector. Floating brain sections were permeabilized with 0.1% Triton X-100 and phosphate buffered saline (PBS) for 30 minutes, washed three times with PBS, and incubated in blocking buffer (5% normal donkey serum in PBS) for 30 minutes. The sections were then incubated overnight in blocking buffer with the indicated combinations of the following primary antibodies at 4° C.: chicken anti-GFP at 1:1,000 (Abcam USA, ab13970); rabbit anti-DsRed at 1:1000 (Clontech USA 632496); goat anti-PV at 1:1,000 (Swant USA, PVG-213); guinea-pig anti-PV at 1:1,000 (Swant USA, GP-72); rabbit anti-SST at 1:2000 (Peninsula USA., T-4103.0050); mouse anti-Synaptotagrnin-2 at 1:250 (ZFIN USA, #ZDB-ATB-081002-25). The sections were then washed three times with PBS incubated with Alexa Fluor-conjugated secondary antibodies at 1:1000 (Invitrogen, USA), counterstained with DAPI (Sigma, ISA) and mounted on glass slides using Fluoromount-G (Sigma, USA). Images of brain regions were acquired using a Zeiss LSM800 confocal microscope or a Zeiss Axioimager A1 epifluorescence microscope. The staining of PV IHC within human brain tissues was highly variable; therefore, estimates of viral specificity were made within regions of cortex and subiculum where staining density reflected the known distribution and density of these cells. In view of the variability for human brain tissue, accurate quantification was not obtained by this method.

In situ hybridization. The in-situ hybridization probes (Gad1; product #400951, Pvalb; product #421931, VIP; product #415961) used in the studies described herein were designed by Advanced Cell Diagnostics (Newark, CA, USA). The reagents in the RNAscope® Multiplex Fluorescent Reagent Kit v2 (product #323100), RNAscope® Probe Diluent (product #300041), HIYBEZ™ oven (product #321710/321720), humidity control tray (product #310012), and HYBEZ Humidifying Paper (product #310025) were also from Advanced Cell Diagnostics. TSA Plus Fluorescein, TSA Plus Cyanine 3, and TSA Plus Cyanine 5 from PerkinElmer (#NEL741, #NEL744, and #NEL745). Brain tissue was processed as mentioned in the immunohistochemistry section supra. Brain sections were washed one time in PBS followed by three washes in 0.1% Triton X-100 and PBS, mounted on Superfrost Plus glass slides (Fisher Scientific, 12-550-15) and baked at 60° C. in the HYBEZ oven for 25 minutes. The slides were then submerged in 4% PFA for 30 minutes then washed 3 times in $H_2O$, RNAscope $H_2O_2$ was applied to each section for 5 minutes at room temperature. The slides were then washed 3 times in $H_2O$ before being submerged in pre-warmed 90° C. $H_2O$ for 15 seconds, followed by pre-warmed 90° C. RNAscope Target Retrieval for 15 minutes. Slides were washed 3 times in 120 before RNAscope Protease III was applied onto each section and then incubated for 15 minutes at 40'C in the HYBEZ oven. Slides were washed 3 times in $H_2O$ and then were incubated with probe solution diluted to 1:50 with probe diluent for 2 hours at 40° C. in HYBEZ oven. Next, the sections were washed three times in RNAscope wash buffer followed by fluorescence amplification. Of note, probes against the RNA of the reporter revealed a non-specific staining that was likely attributed to the viral DNA. To reveal the viral reporter, the RNAscope protocol was performed with an IHC amplification of the dTomato. The sections were incubated in blocking solution (0.3% Triton X-100 plus 5% normal horse serum in PBS) for 30 minutes. Following this, sections were incubated in antibody solution (0.1% Triton X-100 plus 5% normal horse serum in PBS) with rabbit anti-DsRed at 1:250 (Clontech USA 632496) at 4° C. overnight. The sections were then washed three times with PBS, incubated with Alexa Fluor-conjugated secondary antibodies at 1:500 (Invitrogen, USA), counterstained with DAPI (Sigma, USA) and mounted on glass slides using Fluoromount-G (Sigma, USA).

Quantifications and statistics. For strength of expression, fluorescence images were taken at a standardized magnification and exposure time. The average pixel intensity of the cell bodies of each cell expressing the viral reporter was recorded and reported as an average over all cells per enhancer. For quantification of co-localization, cells expressing the indicated reporter were counted using only the corresponding color channel, and then, among these cells, the number of cells co-expressing the marker of interest was counted. A cell was considered to be positive for a given marker if the corresponding signal was above background fluorescence. The ratio of cells co-expressing both markers over the total number of cells expressing only the reporter was then calculated, reported herein as mean±s.e.m (represented as bar plots in figures herein, for example). Quantifications were performed using a minimum of two independent biological replicates (the specific number of cells, animals and conditions are indicated for each individual quantification in the table presented in FIG. 11, and/or described in the figure legends. Several sections from the same animal were used when indicated. Data collection and analysis were not performed blind to the conditions of the experiments, but experimenters from different research groups performed the quantifications. No statistical methods were used to predetermine sample sizes, but the sample sizes described were similar to those reported in previous publications.

Example 9—Viral Manipulation of Functionally Distinct Neurons from Mice to Humans Described herein are methods and approaches for understanding and treating neuronal and neuropsychiatric diseases by targeting and manipulating specific neuronal cell populations and subtypes. Gaining access to these cell populations in non-human primates and humans has become paramount. While AAVs may be useful for gene delivery in the nervous system, they have a limited genomic payload and are not intrinsically selective for particular neuronal populations. Described herein is the identification of regulatory elements capable of restricting viral expression to broad neuronal classes. To focus the selection of the enhancers as described herein, the regulatory landscape of SCN1A, a gene expressed in distinct neuronal populations and whose disruption is associated with severe epilepsy, was specifically examined.

Combining single-cell ATAC-seq data with sequence conservation across species, ten candidate regulatory sequences were identified in the vicinity of the SCN1A gene. By investigating each of these elements for its ability to direct viral expression, three enhancers (E2, E5, E6) that collectively targeted the breadth of neuronal populations expressing SCN1A were identified. Among these, a particular short regulatory sequence (E2 herein) was found to be capable of restricting viral expression to parvalbumin-expressing cortical interneurons (PV cINs). To fully assess the utility of this element beyond reporter expression, the enhancer element was validated in a variety of contexts, including synaptic tagging, calcium imaging, as well as opto- and chemo-genic approaches, both ex vivo and in vivo. Moreover, this enhancer element allowed for the selective targeting of PV cINs both during development and across species, including rodents, non-human primates and humans. Demonstrating that this approach provided a generalizable strategy for enhancer discovery, twenty-five additional regulatory elements were selected in the vicinity of seven genes enriched in PV INs (FIGS. 15A-1, 15A-2, 16A-1 and 16A-2). From these, an additional four PV-specific regulatory elements (E11, E14, E22 and E29) were identified, each of which had remarkably selective expression within specific brain regions. Together, the utility of a variety of functionally-tested tools that can be utilized across animal models was demonstrated. Such "viral reagents," comprising viral delivery vectors harboring a polynucleotide encoding one or more enhancer elements as described herein, as well as one or more target polynucleotide, can be employed to interrogate how functionally distinct neuronal cell-types are affected in the context of neurological, neurodevelopmental and neurodegenerative disease in non-human primates. Ultimately, enhancer-containing viral vectors can serve as agents that therapeutically normalize pathological neuronal activity or gene expression in specific neuronal cell populations.

The enhancers identified and described herein provide access to neuronal populations with particular clinical relevance. These enhancers may be leveraged to alleviate debilitating aspects of Dravet syndrome, for example, by the use of gene therapy or by modulation of neuronal activity. As described in the Examples supra, local and systemic injections were utilized for effective viral vector delivery to the brain. With local injections, neurological conditions and pathologies such as focal epilepsy, prefrontal cortex dysfunction or hippocampal memory disorders may be treated or ameliorated. Alternatively, the systemic introduction of virus vectors could be used in contexts where global interventions are necessary, for example, to correct generalized seizures, or for psychiatric and neurodegenerative disorders. The regulatory elements described herein provide for specifically accessing specific cell types for therapeutic contexts.

Indeed, the method and approach for enhancer selection as described herein is advantageous as it is generalizable to other genes. Without intending to be limiting, a subset of seven, representative enhancers (e.g., E1, E5, E6, E11, E14, E22, E29 herein) were identified and demonstrated to have unique specificity for both distinct neuronal populations and regions of the central nervous system. Even with application of stringent criteria (>90% selectivity for the target population), the described enhancer selection method has a high (>20%) success rate. Moreover, as predicted by the high degree of sequence conservation, the representative subset of enhancers proved equally selective and effective across species, including humans. As such, the described methods provide a reliable means to identify systematically cell-type specific enhancers that are functional across species.

Other Embodiments

From the foregoing description, it will be apparent that variations and modifications may be made to the embodiments described herein to adopt them to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof, such as described in one or more sections herein. All patents and publications mentioned in this specification are herein incorporated by reference to the same extent as if each independent patent and publication was specifically and individually indicated to be incorporated by reference.

What is claimed is:

1. A viral vector comprising a polynucleotide sequence including a gene of interest and an isolated enhancer polynucleotide sequence that restricts expression of the gene of interest in interneuron or neuron cells in the brain; wherein the isolated enhancer polynucleotide sequence of the vector comprises the polynucleotide sequence of an isolated enhancer element selected from the group consisting of:

- E1 as set forth in SEQ ID NO: 5 or SEQ ID NO: 15, which restricts expression of the gene of interest in GAD1-expressing cortical interneurons in the brain;
- E2 as set forth in SEQ ID NO: 6 or SEQ ID NO: 16, which restricts expression of the gene of interest in parvalbumin (PV)-expressing cortical interneurons in the brain;
- E3 as set forth in SEQ ID NO: 7 or SEQ ID NO: 17, which restricts expression of the gene of interest in GAD1-expressing cortical interneurons in the brain;
- E4 as set forth in SEQ ID NO: 8 or SEQ ID NO: 18, which restricts expression of the gene of interest in GAD1-expressing cortical interneurons in the brain;
- E5 as set forth in SEQ ID NO: 9 or SEQ ID NO: 19, which restricts expression of the gene of interest in pyramidal (PYR) cortical neurons in the brain;
- E6 as set forth in SEQ ID NO: 10 or SEQ ID NO: 20, which restricts expression of the gene of interest in vaso-intestinal peptide (VIP)-expressing cortical interneurons in the brain;
- E7 as set forth in SEQ ID NO: 11 or SEQ ID NO: 21, which restricts expression of the gene of interest in GAD1-expressing cortical interneurons in the brain;
- E8 as set forth in SEQ ID NO: 12 or SEQ ID NO: 22, which restricts expression of the gene of interest in GAD1-expressing cortical interneurons in the brain;
- E9 as set forth in SEQ ID NO: 13 or SEQ ID NO: 23, which restricts expression of the gene of interest in GAD1-expressing cortical interneurons in the brain; and
- E10 as set forth in SEQ ID NO: 14 or SEQ ID NO: 24, which restricts expression of the gene of interest in GAD1-expressing cortical interneurons in the brain.

2. The viral vector of claim 1, wherein the gene of interest is a SCN1A gene.

3. The viral vector of claim 1, wherein the gene of interest is a reporter gene, a Designer receptor exclusively activated by a designer receptor exclusively activated by a designer drug (DREADD)-encoding gene, pharmacologically selective actuator molecule (PSAM)-encoding therapeutic gene, or a therapeutic gene.

4. The viral vector of claim 1, wherein the gene of interest is an SCN1A gene, a DREADD-encoding gene, or a pharmacologically selective actuator molecule (PSAM)-encoding therapeutic gene.

5. The viral vector of claim 4, wherein the DREADD-encoding gene is an hM3Dq modified muscarinic receptor (Gq-DREADD)-encoding gene that is activated by the chemogen clozapine-N4-oxide (CNO).

6. The viral vector of claim 1, wherein the viral vector is recombinant adeno-associated virus (rAAV) vector.

7. The viral vector of claim 1, wherein the PV-expressing or VIP-expressing cortical interneurons are within the brain telencephalon.

8. The viral vector of claim 1, wherein the isolated enhancer polynucleotide sequence of the vector is the polynucleotide sequence of isolated enhancer element E2 as set forth in SEQ ID NO: 6 or in SEQ ID NO: 16.

9. The viral vector of claim 1, wherein the interneuron or neuron cells are in the brain of a subject who is a human patient, optionally wherein the human patient is an infant suffering from Dravet syndrome (DS).

10. A viral particle or virus-like particle comprising the viral vector of claim 1.

11. A cell comprising the viral particle or virus-like particle of claim 10.

12. A pharmaceutical composition comprising the viral particle or virus-like particle of claim 10, and a pharmaceutically acceptable vehicle, carrier, or diluent.

13. The viral vector of claim 1, wherein the isolated enhancer polynucleotide sequence of the vector comprises:

E2 as set forth in SEQ ID NO: 6 or SEQ ID NO: 16, which restricts expression of the gene of interest in parvalbumin (PV)-expressing interneurons in the brain cortex;

E5 as set forth in SEQ ID NO: 9 or SEQ ID NO: 19, which restricts expression of the gene of interest in pyramidal (PYR) neurons in the brain cortex; or E6 as set forth in SEQ ID NO: 10 or SEQ ID NO: 20, which restricts expression of the gene of interest in vaso-intestinal peptide (VIP)-expressing interneurons in the brain cortex.

14. The viral vector of claim 1, wherein the isolated enhancer element E5 restricts expression of the gene of interest in PYR neurons in cortical layer 5 in the brain.

* * * * *